(12) United States Patent
Georgiou et al.

(10) Patent No.: US 10,725,037 B2
(45) Date of Patent: *Jul. 28, 2020

(54) IMMUNOGLOBULIN FC LIBRARIES

(71) Applicant: Research Development Foundation, Carson City, NV (US)

(72) Inventors: George Georgiou, Austin, TX (US); Sang Taek Jung, Seoul (KR)

(73) Assignee: Research Development Foundation, Carson City, NV (US)

( * ) Notice: Subject to any disclaimer, the term of this patent is extended or adjusted under 35 U.S.C. 154(b) by 921 days.

This patent is subject to a terminal disclaimer.

(21) Appl. No.: 14/105,642

(22) Filed: Dec. 13, 2013

(65) Prior Publication Data

US 2014/0179550 A1 Jun. 26, 2014

Related U.S. Application Data

(62) Division of application No. 12/112,971, filed on Apr. 30, 2008, now Pat. No. 8,629,245.

(60) Provisional application No. 60/982,652, filed on Oct. 25, 2007, provisional application No. 60/915,183, filed on May 1, 2007.

(51) Int. Cl.
*G01N 33/569* (2006.01)
*C07K 16/32* (2006.01)
*C07K 16/00* (2006.01)

(52) U.S. Cl.
CPC ........ *G01N 33/56911* (2013.01); *C07K 16/00* (2013.01); *C07K 16/32* (2013.01); *C07K 2317/52* (2013.01); *C07K 2317/72* (2013.01); *C07K 2319/035* (2013.01); *C07K 2319/30* (2013.01)

(58) Field of Classification Search
None
See application file for complete search history.

(56) References Cited

U.S. PATENT DOCUMENTS

| | | |
|---|---|---|
| 5,576,195 A | 11/1996 | Robinson et al. |
| 5,578,464 A | 11/1996 | Lunn et al. |
| 5,595,898 A | 1/1997 | Robinson et al. |
| 5,618,920 A | 4/1997 | Robinson et al. |
| 5,648,260 A | 7/1997 | Winter et al. |
| 5,693,493 A | 12/1997 | Robinson et al. |
| 5,698,417 A | 12/1997 | Robinson et al. |
| 5,698,435 A | 12/1997 | Robinson et al. |
| 5,824,520 A | 10/1998 | Mulligan-Kehoe |
| 5,846,818 A | 12/1998 | Robinson et al. |
| 5,858,657 A | 1/1999 | Winter et al. |
| 5,939,317 A | 8/1999 | Fayard et al. |
| 5,994,514 A | 11/1999 | Jardieu et al. |
| 6,165,745 A | 12/2000 | Ward et al. |
| 6,172,197 B1 | 1/2001 | McCafferty et al. |
| 6,194,551 B1 | 2/2001 | Idusogie et al. |
| 6,204,023 B1 | 3/2001 | Robinson et al. |
| 6,248,516 B1 | 6/2001 | Winter et al. |
| 6,331,415 B1 | 12/2001 | Cabilly et al. |
| 6,455,279 B1 | 9/2002 | Ambrosius et al. |
| 6,500,641 B1 | 12/2002 | Chen et al. |
| 6,528,624 B1 | 3/2003 | Idusogie et al. |
| 6,538,124 B1 | 3/2003 | Idusogie et al. |
| 6,545,142 B1 | 4/2003 | Winter et al. |
| 6,555,313 B1 | 4/2003 | Griffiths et al. |
| 6,667,150 B1 | 12/2003 | Rudert et al. |
| 6,696,248 B1 | 2/2004 | Knappik et al. |
| 6,737,056 B1 | 5/2004 | Presta |
| 6,806,079 B1 | 10/2004 | McCafferty et al. |
| 6,846,653 B2 | 1/2005 | Kolkman |
| 6,979,538 B2 | 12/2005 | Ladner et al. |
| 6,979,556 B2 | 12/2005 | Simmons et al. |
| 6,989,250 B2 | 1/2006 | Soderlind et al. |
| 7,094,571 B2 | 8/2006 | Harvey et al. |
| 7,118,879 B2 | 10/2006 | Ladner et al. |
| 7,183,387 B1 | 2/2007 | Presta |
| 7,202,055 B2 | 4/2007 | Schafer et al. |
| 7,217,798 B2 | 5/2007 | Hinton et al. |
| 7,229,792 B2 | 6/2007 | Pandiripally |
| 7,264,963 B1 | 9/2007 | Knappik et al. |
| 7,317,091 B2 | 1/2008 | Lazar et al. |
| 7,371,826 B2 | 5/2008 | Presta |
| 7,662,925 B2 | 2/2010 | Lazar et al. |
| 2003/0158389 A1 | 8/2003 | Idusogie et al. |

(Continued)

FOREIGN PATENT DOCUMENTS

| | | |
|---|---|---|
| WO | WO 2005-037867 | 4/2005 |
| WO | WO 2006-076594 | 7/2006 |

OTHER PUBLICATIONS

Andersen et al., "The conserved histidine 166 residue of the human neonatal Fc receptor heavy chain is critical for the pH-dependent binding to albumin," *Eur. J. Immunol.*, 36:3044-3051, 2006.
Better et al., "*Escherichia coli* secretion of an active chimeric antibody fragment," *Science*, 240: 1041-1043, 1988.
Boeke et al., "Effects of bacteriophage f1 gene III protein on the host cell membrane ," *Mol. Gen. Genet.*, 186(2):185-92, 1982.
Boss et al., "Assembly of functional antibodies from immunoglobulin heavy and light chains synthesised in *E. coli*," *Nucleic Acids Res.*, 12:3791-3806, 1984.
Bowden and Georgiou, "Folding and aggregation of beta-lactamase in the periplasmic space of *Escherichia coli*," *J. Biol. Chem.*, 265:16760-16766, 1990.
Bukau et al., "Ca2+-induced permeabilization of the *Escherichia coli* outer membrane: comparison of transformation and reconstitution of binding-protein-dependent transport," *J. Bacteriol.*, 163:61, 1985.

(Continued)

*Primary Examiner* — Robert A Zeman
(74) *Attorney, Agent, or Firm* — Parker Highlander PLLC

(57) ABSTRACT

Methods and composition for the screening and isolation of aglycosylated antibody Fc domain polypeptides. For example, in certain aspects methods for identifying aglycosylated Fc domains that bind to Fc receptors or preferentially bind to particular Fc receptors are described. Furthermore, the invention provides aglycosylated Fc domains that bind to Fc receptors with high affinity. Enhanced methods and media for prokaryotic based interaction screening are also provided.

39 Claims, 54 Drawing Sheets

Specification includes a Sequence Listing.

(56) References Cited

U.S. PATENT DOCUMENTS

| | | |
|---|---|---|
| 2003/0166868 A1 | 9/2003 | Presta et al. |
| 2004/0002587 A1 | 1/2004 | Watkins et al. |
| 2004/0132101 A1 | 7/2004 | Lazar et al. |
| 2004/0228856 A1 | 11/2004 | Presta |
| 2005/0037000 A1 | 2/2005 | Stavenhagen et al. |
| 2005/0054832 A1 | 3/2005 | Lazar et al. |
| 2005/0064514 A1 | 3/2005 | Stavenhagen et al. |
| 2005/0118174 A1 | 6/2005 | Presta |
| 2005/0233382 A1 | 10/2005 | Presta |
| 2005/0244403 A1 | 11/2005 | Lazar et al. |
| 2005/0249723 A1 | 11/2005 | Lazar |
| 2006/0024298 A1 | 2/2006 | Lazar et al. |
| 2006/0121032 A1 | 6/2006 | Dahiyat et al. |
| 2006/0134709 A1 | 6/2006 | Stavenhagen et al. |
| 2006/0153838 A1 | 7/2006 | Watkins et al. |
| 2006/0160996 A9 | 7/2006 | Lazar et al. |
| 2006/0173170 A1 | 8/2006 | Chamberlain et al. |
| 2006/0194290 A1 | 8/2006 | Presta |
| 2006/0194291 A1 | 8/2006 | Presta |
| 2006/0194954 A1 | 8/2006 | Idusogie et al. |
| 2006/0194957 A1 | 8/2006 | Presta |
| 2006/0235208 A1 | 10/2006 | Lazar et al. |
| 2007/0003546 A1 | 1/2007 | Lazar et al. |
| 2007/0036799 A1 | 2/2007 | Stavenhagen et al. |
| 2007/0048300 A1* | 3/2007 | Taylor .............. A61K 47/48215 424/133.1 |
| 2007/0053901 A1 | 3/2007 | Lazar et al. |

OTHER PUBLICATIONS

Cabilly et al., "Generation of antibody activity from immunoglobulin polypeptide chains produced in *Escherichia coli,*" *Proc. Natl. Acad. Sci. USA*, 81:3273-3277, 1984.

Canfield et al., "The binding affinity ofh uman IGG for its high affinity FC receptor is determined by multiple amino acids in the C-H2 domain and is modulated by the hinge region," *Journal of Experimental Medicine*, 173(6): 1483-1492, 1991.

Daughtery et al., "Development of an optimized expression system for the screening of antibody libraries displayed on the *Escherichia coli* surface," *Protein Eng.*, 12:613-621, 1999.

De Kruif and Logtenberg, "Leucine zipper dimerized bivalent and bispecific scFv antibodies from a semi-synthetic antibody phage display library," *J. Biol. Chem.*, 271:7630-7634, 1996.

Eigenbrot et al., "X-ray structures of the antigen-binding domains from three variants of humanized anti-p185HER2 antibody 4D5 and comparison with molecular modeling," *J. Molec. Biol.*, 229:969-995, 1993.

Elbein et al., "New insights on trehalose: a multifunctional molecule," *Glycobiology*, 13:17R-27R, 2003.

Farmer et al, "Penetration of beta-lactamase inhibitors into the periplasm of gram-negative bacteria," *FEMS Microbiol. Lett.*, 176:11, 1999.

Francisco et al., "Production and fluorescence-activated cell sorting of *Escherichia coli* expressing a functional antibody fragment on the external surface," *Proc. Natl. Acad. Sci. USA*, 90:10444-10448, 1993.

Friend et al., "Phase I study of an engineered aglycosylated humanized CD3 antibody in renal transplant rejection," *Transplantation*, 68(110):1632-1637, 1999.

Garinot-Schneider et al., "Identification of putative active-site residues in the DNase domain of colicin E9 by random mutagenesis," *J. Mol. Biol.*, 260:731-742, 1996.

Georgiou and Segatori, "Preparative expression of secreted proteins in bacteria: status report and future prospects," *Current Opin. Biotech.*, 16:538-545, 2005.

Ghetie and Ward, "Multiple roles for the major histocompatibility complex class I-related receptor FcRn," *Annu. Rev. Immunol.*, 18:739-766, 2000.

Greenspan et al., "Defining epitopes: It's not as easy as it seems," *Nature Biotechnology*, 17:936-937, 1999.

Griffiths and Duncan, "Strategies for selection of antibodies by phage display," *Curr. Opin. Biotechnol.*, 9:102-108, 1998.

Harvey et al., "Anchored periplasmic expression, a versatile technology for the isolation of high-affinity antibodies from *Escherichia coli*-expressed libraries," *Proc. Natl. Acad. Sci. USA*, 101, 9193-9198, 2004.

Harvey et al., "Engineering of recombinant antibody fragments to methamphetamine by anchored periplasmic expression," *J. Immunol. Methods*, 308:43-52, 2006.

Hoogenboom et al., "Antibody phage display technology and its applications," *Immunotechnology.*, 4:1-20, 1998.

Hoover and Lubkowski, "DNAWorks: an automated method for designing oligonucleotides for PCR-based gene synthesis," *Nucl. Acids Res.*, 30:e43, 2002.

Irvin et al., "Tris(hydroxymethyl)aminomethane buffer modification of *Escherichia coli* outer membrane permeability," *J. Bacteriol.*, 145:1397, 1981.

Jefferis et al., "Recognition sites on human IgG for Fc gamma receptors: the role of glycosylation," *Immunology Letters*, 44(2-3):111-117, 1995.

Jefferis, "Glycosylation of recombinant antibody therapeutics," *Biotechnol. Prog.*, 21:11-16, 2005.

Jouenne and Junter, "Do beta-lactam antibiotics permeabilize the outer membrane of gram-negative bacteria? An electrochemical investigation," *FEMS Microbiol. Lett.*, 68(3):313-318, 1990.

Jung et al., "Purification of enzymatically active human lysyl oxidase and lysyl oxidase-like protein from *Escherichia coli* inclusion bodies," *Protein Expr. Purif.*, 31:240-246, 2003.

Kabat et al., In: *Sequences of Proteins of Immunological Interest*, U.S. Dept. Health and Hum. Serv., Bethesda, Md., 1991.

Kawarasaki et al., "Enhanced crossover SCRATCHY: construction and high-throughput screening of a combinatorial library containing multiple non-homologous crossovers," *Nucleic Acids Res.*, 31:e126, 2003.

Kipriyanov and Little, "Generation of recombinant antibodies," *Mol. Biotechnol.*, 12:173-201, 1999.

Knight et al., "The immunogenicity of the 7E3 murine monoclonal Fab antibody fragment variable region is dramatically reduced in humans by substitution of human for murine constant regions," *Mol. Immunol.*, 32:1271-1281, 1995.

Kohler and Milstein, "Continuous cultures of fused cells secreting antibody of predefined specificity," *Nature*, 256:495-497, 1975.

Kouzarides and Ziff, "The role of the leucine zipper in the fos—jun interaction," *Nature*, 336:646-6451, 1988.

Landschulz et al., "The leucine zipper: a hypothetical structure common to a new class of DNA binding proteins," *Science*, 240:1759-1764, 1988.

Lazar et al., "Engineered antibody Fc variants with enhanced effector function," *Proc. Natl. Acad. Sci. USA*, 103:4005-4010, 2006.

Lei et al., "Characterization of the Erwinia carotovora pelB gene and its product pectate lyase," *J. Bacteriol.*, 169:4379-4383, 1987.

Mazor et al., "Isolation of engineered, full-length antibodies from libraries expressed in *Escherichia coli,*" *Nat. Biotech.*, 25:563-5, 2007.

Munson and Robard, "Ligand: a versatile computerized approach for characterization of ligand-binding systems," *Anal. Biochem.*, 107:220-239, 1980.

O'Brien et al., "Bacterial expression and purification of recombinant bovine Fab fragments," *Protein Expr. Purif.*, 24:43-50, 2002.

Office Action issued in Australian Application No. 2008247819, dated May 16, 2012.

Office Action issued in Australian Application No. 2008247819, dated Jul. 19, 2012.

Office Action issued in European Application No. 08747239.5, dated May 16, 2011.

Office Action issued in European Application No. 08747239.5, dated Jul. 21, 2011.

Office Action issued in European Application No. 08747239.5, dated Oct. 21, 2011.

Office Action issued in European Application No. 08747239.5, dated Mar. 19, 2012.

(56) References Cited

OTHER PUBLICATIONS

Office Action issued in European Application No. 08747239.5, dated Sep. 3, 2012.
Office Action issued in U.S. Appl. No. 12/112,971, dated Jul. 20, 2012.
Office Action issued in U.S. Appl. No. 12/112,971, dated May 20, 2013.
Office Action issued in U.S. Appl. No. 12/112,971, dated May 26, 2011.
Office Action issued in U.S. Appl. No. 12/112,971, dated Nov. 9, 2010.
Office Action issued in U.S. Appl. No. 12/112,971, dated Nov. 29, 2012.
Orlandi et al., "Cloning immunoglobulin variable domains for expression by the polymerase chain reaction," *Proc. Natl. Acad. Sci. USA*, 86:3833-3837, 1989.
Osborn et al., "Mechanism of assembly of the outer membrane of *Salmonella typhimurium*. Site of synthesis of lipopolysaccharide," *J. Biol. Chem*, 247:3973-3986, 1972.
PCT International Preliminary Report on Patentability issued in International Application No. PCT/US2008/062090, dated May 8, 2009.
PCT International Search Report issued in International Application No. PCT/US2008/062090, dated Nov. 24, 2008.
PCT Invitation to Pay Additional Fees and Communication Relating to the Results of the Partial International Search Report, issued in International Application No. PCT/US2008/062090, dated Aug. 26, 2008.
Purvis et al., "Enhanced trehalose production improves growth of *Escherichia coli* under osmotic stress," *Appl. Environ. Microbiol.*, 71:3761-3769, 2005.
Rao and Torriani, "Utilization by *Escherichia coli* of a high-molecular-weight, linear polyphosphate: Roles of phosphatases and pore proteins," *J. Bacteriol.*, 170, 5216-5223, 1988.
Schierle et al., "The DsbA signal sequence directs efficient, cotranslational export of passenger proteins to the *Escherichia coli* periplasm via the signal recognition particle pathway," *J. Bacteriol.*, 185:5706-5713, 2003.
Sergina, and Moasser, "The HER family and cancer: emerging molecular mechanisms and therapeutic targets," *Trends in Molec. Med.*, 13:527-534, 2007.
Simmons et al., "Expression of full-length immunoglobulins in *Escherichia coli*: rapid and efficient production of aglycosylated antibodies," *Journal of Immunological Methods*, 263(1-2): 133-147, 2002.
Sondermann et al., "Molecular basis for immune complex recognition: a comparison of Fc-receptor structures," *J. Mol. Biol.*, 309:737-749, 2001.
Stengelin et al., "Isolation of cDNAs for two distinct human Fc receptors by ligand affinity cloning," *EMBO J*, 7:1053-1059, 1988.
U.S. Appl. No. 60/915,183, by Georgiou et al., filed May 1, 2007.
U.S. Appl. No. 60/982,652, by Georgiou et al., filed Oct. 25, 2007.
Wada et al., "A novel labeling approach supports the five-transmembrane model of subunit a of the *Escherichia coli* ATP synthase," *J. Biol. Chem.*, 274:17353-17357, 1999.
Wright and Morrison, "Effect of glycosylation on antibody function: implications for genetic engineering," *Trends Biotech.*, 15:26-32, 1997.

\* cited by examiner

Lane 1: PelB-Fc-FLAG (No Trehalose)
Lane 2: PelB-Fc-FLAG (Trehalose)
Lane 3: PelB-M18 scFv-FLAG (No Trehalose)
Lane 4: PelB-M18 scFv-FLAG (Trehalose)

Lane 1,3: Reduced sample after spheroplasting
Lane 2,4: Not reduced sample after spheroplasting 12.5µl/OD600 equivalent culture volume loading for each well

FIG. 18C

```
            390        400        410        420        430        440
FcWT   (16.39)  ENNYKTTPPVLDSDGSFFLYSKLTVDSKRWQQGNVFSCSVMHEALHNHYTQKSLSLSPGK
Fc104  (87.17)  ------------------------------------------------------------
Fc107  (316.58) ------------------------------------------------------------
Fc101  (521.92) ------------I-----------------------------------------------
Fc147  (464.35) ------------I-----------------------------------------------
Fc102  (373.63) ------------I-----------------------------------------------
Fc114  (370.26) ------------I-----------------------------------------------
Fc117  (390.62) ------------I-----------------------A-----------------------
Fc151  (325.53) ------------------------------------I-L-S------------------
Fc143  (211.23) ------------------------------------V-L-H------------------
Fc152  (172.61) ------------------------------------T-S-P------------------
Fc149  (139.57) ------------------------------------V-L-D------------------
Fc106  (268.78) ------------I-----------------------------------------------
Fc100  (137.93) ------------------------------------------------------------
```

1) Fc101 = Fc103, 111, 115, 116, 125, 136, 141, 146, 148; FACS mean values are indicated in the parenthesis Lane M: Molecular weight marker
Lane 1: Purified FcrRIIIa (23.45 kDa)

SEQUENCE LISTING

<160> NUMBER OF SEQ ID NOS: 131

<210> SEQ ID NO 1
<211> LENGTH: 227
<212> TYPE: PRT
<213> ORGANISM: Homo sapiens
<220> FEATURE:
<221> NAME/KEY: MISC_FEATURE
<223> OTHER INFORMATION: Fc IgG1

<400> SEQUENCE: 1

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met

```
                    20                  25                  30
Ile Ser Arg Thr Pro Glu Val Thr Cys Val Val Val Asp Val Ser His
        35                  40                  45
Glu Asp Pro Glu Val Lys Phe Asn Trp Tyr Val Asp Gly Val Glu Val
 50                  55                  60
His Asn Ala Lys Thr Lys Pro Arg Glu Glu Gln Tyr Asn Ser Thr Tyr
 65                  70                  75                  80
Arg Val Val Ser Val Leu Thr Val Leu His Gln Asp Trp Leu Asn Gly
                    85                  90                  95
Lys Glu Tyr Lys Cys Lys Val Ser Asn Lys Ala Leu Pro Ala Pro Ile
                100                 105                 110
Glu Lys Thr Ile Ser Lys Ala Lys Gly Gln Pro Arg Glu Pro Gln Val
                115                 120                 125
Tyr Thr Leu Pro Pro Ser Arg Asp Glu Leu Thr Lys Asn Gln Val Ser
            130                 135                 140
Leu Thr Cys Leu Val Lys Gly Phe Tyr Pro Ser Asp Ile Ala Val Glu
145                 150                 155                 160
Trp Glu Ser Asn Gly Gln Pro Glu Asn Asn Tyr Lys Thr Thr Pro Pro
                165                 170                 175
Val Leu Asp Ser Asp Gly Ser Phe Phe Leu Tyr Ser Lys Leu Thr Val
                180                 185                 190
Asp Lys Ser Arg Trp Gln Gln Gly Asn Val Phe Ser Cys Ser Val Met
                195                 200                 205
His Glu Ala Leu His Asn His Tyr Thr Gln Lys Ser Leu Ser Leu Ser
            210                 215                 220
Pro Gly Lys
225

<210> SEQ ID NO 2
<211> LENGTH: 227
<212> TYPE: PRT
<213> ORGANISM: Homo sapiens
<220> FEATURE:
<221> NAME/KEY: MISC_FEATURE
<223> OTHER INFORMATION: Fc 11

<400> SEQUENCE: 2

Asp Lys Thr His Thr Cys Pro Pro Cys Pro Ala Pro Glu Leu Leu Gly
 1               5                  10                  15
Gly Pro Ser Val Phe Leu Phe Pro Pro Lys Pro Lys Asp Thr Leu Met
                20                  25                  30
Ile Ser Arg Thr Pro Glu Val Thr Cys Val Val Val Asp Val Ser His
        35                  40                  45
Glu Asp Pro Glu Val Lys Phe Asn Trp Tyr Val Asp Gly Val Glu Val
 50                  55                  60
His Asn Ala Lys Thr Lys Pro Arg Glu Glu Gln Tyr Asn Ser Thr Tyr
 65                  70                  75                  80
Arg Val Val Ser Val Leu Thr Val Leu His Gln Asp Trp Leu Asn Gly
                    85                  90                  95
Lys Glu Tyr Lys Cys Lys Val Ser Asn Lys Ala Leu Pro Ala Pro Ile
                100                 105                 110
Glu Lys Thr Ile Ser Lys Ala Lys Gly Gln Pro Arg Glu Pro Gln Val
                115                 120                 125
Tyr Thr Leu Pro Pro Ser Arg Asp Glu Leu Thr Lys Asn Gln Val Ser
            130                 135                 140
```

```
Leu Thr Cys Leu Val Lys Gly Phe Tyr Pro Ser Asp Ile Ala Val Glu
145                 150                 155                 160

Trp Val Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
            210                 215                 220

Pro Gly Lys
225

<210> SEQ ID NO 3
<211> LENGTH: 227
<212> TYPE: PRT
<213> ORGANISM: Homo sapiens
<220> FEATURE:
<221> NAME/KEY: MISC_FEATURE
<223> OTHER INFORMATION: Fc 5

<400> SEQUENCE: 3

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Val Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Ile
            195                 200                 205

His Glu Ala Leu His Asn His Tyr Thr Gln Lys Ser Leu Ser Leu Ser
            210                 215                 220

Pro Gly Lys
225

<210> SEQ ID NO 4
<211> LENGTH: 227
<212> TYPE: PRT
<213> ORGANISM: Homo sapiens
```

```
<220> FEATURE:
<221> NAME/KEY: MISC_FEATURE
<223> OTHER INFORMATION: Fc 12

<400> SEQUENCE: 4

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asp Gln Val Ser
    130                 135                 140

Leu Thr Cys Leu Val Lys Gly Phe Tyr Pro Ser Asp Ile Ala Val Glu
145                 150                 155                 160

Trp Val Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Ile
        195                 200                 205

His Glu Ala Leu His Asn His Tyr Thr Gln Lys Ser Leu Ser Leu Ser
    210                 215                 220

Pro Gly Lys
225

<210> SEQ ID NO 5
<211> LENGTH: 227
<212> TYPE: PRT
<213> ORGANISM: Homo sapiens
<220> FEATURE:
<221> NAME/KEY: MISC_FEATURE
<223> OTHER INFORMATION: Fc 20

<400> SEQUENCE: 5

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95
```

```
Lys Glu Tyr Lys Cys Lys Val Ser Asn Lys Ala Leu Pro Ala Pro Ile
                100                 105                 110
Glu Lys Thr Ile Ser Lys Ala Lys Gly Gln Pro Arg Glu Pro Gln Val
            115                 120                 125
Tyr Thr Leu Pro Pro Ser Arg Asp Glu Leu Thr Lys Asp Gln Val Ser
        130                 135                 140
Leu Thr Cys Leu Val Lys Gly Leu Tyr Pro Ser Asp Ile Ala Val Glu
145                 150                 155                 160
Trp Val Ser Asn Gly Gln Pro Glu Asn Asn Tyr Lys Thr Thr Pro Pro
                165                 170                 175
Val Leu Asp Ser Asp Gly Ser Phe Phe Leu Tyr Ser Lys Leu Thr Val
            180                 185                 190
Asp Lys Ser Arg Trp Gln Gln Gly Asn Val Phe Ser Cys Ser Val Ile
        195                 200                 205
His Glu Ala Leu His Asn His Tyr Thr Gln Lys Ser Leu Ser Leu Ser
    210                 215                 220
Pro Gly Lys
225

<210> SEQ ID NO 6
<211> LENGTH: 227
<212> TYPE: PRT
<213> ORGANISM: Homo sapiens
<220> FEATURE:
<221> NAME/KEY: MISC_FEATURE
<223> OTHER INFORMATION: Fc 49

<400> SEQUENCE: 6

Asp Lys Thr His Thr Cys Pro Pro Arg Pro Ala Pro Glu Leu Leu Gly
1               5                   10                  15
Gly Pro Ser Val Phe Leu Phe Pro Pro Lys Pro Lys Asp Thr Leu Met
                20                  25                  30
Ile Ser Arg Thr Pro Glu Val Thr Cys Val Val Val Asp Val Ser His
            35                  40                  45
Glu Asp Pro Glu Val Lys Phe Asn Trp Tyr Val Asp Gly Val Glu Val
        50                  55                  60
His Asn Ala Lys Thr Lys Pro Arg Glu Glu Gln Tyr Asn Ser Thr Tyr
65                  70                  75                  80
Arg Val Val Ser Val Leu Thr Val Leu His Gln Asp Trp Leu Asn Gly
                85                  90                  95
Lys Glu Tyr Lys Cys Lys Val Ser Asn Lys Ala Leu Pro Ala Pro Ile
                100                 105                 110
Glu Lys Thr Ile Ser Lys Ala Lys Gly Gln Pro Arg Glu Pro Gln Val
            115                 120                 125
Tyr Thr Leu Pro Pro Ser Arg Asp Glu Leu Thr Lys Asn Gln Val Ser
        130                 135                 140
Leu Thr Cys Leu Val Lys Gly Phe Tyr Pro Ser Asp Ile Ala Val Glu
145                 150                 155                 160
Trp Val Ser Asn Gly Gln Pro Glu Asn Asn Tyr Lys Thr Thr Pro Pro
                165                 170                 175
Val Leu Asp Ser Asp Gly Ser Phe Phe Leu Tyr Ser Lys Leu Thr Val
            180                 185                 190
Asp Lys Ser Arg Trp Gln Gln Gly Asn Val Phe Ser Cys Ser Val Ile
        195                 200                 205
His Glu Ala Leu His Asn His Tyr Thr Gln Lys Ser Leu Ser Leu Ser
```

Pro Gly Lys
225

<210> SEQ ID NO 7
<211> LENGTH: 227
<212> TYPE: PRT
<213> ORGANISM: Homo sapiens
<220> FEATURE:
<221> NAME/KEY: MISC_FEATURE
<223> OTHER INFORMATION: Fc 23

<400> SEQUENCE: 7

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu Tyr Gln Asp Trp Leu Asn Gly
                85                  90                  95

Lys Glu Tyr Lys Cys Arg Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Ala Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Val Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Thr Val Met
        195                 200                 205

His Glu Ala Leu His Asn His Tyr Thr Gln Lys Ser Leu Pro Leu Ser
    210                 215                 220

Pro Gly Lys
225

<210> SEQ ID NO 8
<211> LENGTH: 21
<212> TYPE: DNA
<213> ORGANISM: Artificial
<220> FEATURE:
<223> OTHER INFORMATION: Artificial primer

<400> SEQUENCE: 8
ttgtgagcgg ataacaattt c                                         21

<210> SEQ ID NO 9
<211> LENGTH: 41
<212> TYPE: DNA
<213> ORGANISM: Artificial
<220> FEATURE:

<223> OTHER INFORMATION: Artificial primer

<400> SEQUENCE: 9
cgaactggcc cagccggcca tcgcccggct agaggaaaaa g                41

<210> SEQ ID NO 10
<211> LENGTH: 45
<212> TYPE: DNA
<213> ORGANISM: Artificial
<220> FEATURE:
<223> OTHER INFORMATION: Artificial primer

<400> SEQUENCE: 10
cgaactggcc cccgaggccc ggtggttcat gactttctgt ttaag            45

<210> SEQ ID NO 11
<211> LENGTH: 34
<212> TYPE: DNA
<213> ORGANISM: Artificial
<220> FEATURE:
<223> OTHER INFORMATION: Artificial primer

<400> SEQUENCE: 11
gatatcgcgg ccgcactgac cgacaccctg cagg                        34

<210> SEQ ID NO 12
<211> LENGTH: 39
<212> TYPE: DNA
<213> ORGANISM: Artificial
<220> FEATURE:
<223> OTHER INFORMATION: Artificial primer

<400> SEQUENCE: 12
ttttaggggt cgactgcggc gtgtgccgcc aggatgaac                   39

<210> SEQ ID NO 13
<211> LENGTH: 47
<212> TYPE: DNA
<213> ORGANISM: Artificial
<220> FEATURE:
<223> OTHER INFORMATION: Artificial primer

<400> SEQUENCE: 13
cgcagcgagg cccagccggc catggcgcaa gctgctcccc caaaggc          47

<210> SEQ ID NO 14
<211> LENGTH: 49
<212> TYPE: DNA
<213> ORGANISM: Artificial
<220> FEATURE:
<223> OTHER INFORMATION: Artificial primer

<400> SEQUENCE: 14
cgcagcgagg cccagccggc catggcgatc cagcgtactc caaagattc        49

<210> SEQ ID NO 15
<211> LENGTH: 45
<212> TYPE: DNA
<213> ORGANISM: Artificial
<220> FEATURE:
<223> OTHER INFORMATION: Artificial primer

<400> SEQUENCE: 15
cgcaattcgg cccccgaggc cccaatgacc cccattggtg aagag            45

```
<210> SEQ ID NO 16
<211> LENGTH: 44
<212> TYPE: DNA
<213> ORGANISM: Artificial
<220> FEATURE:
<223> OTHER INFORMATION: Artificial primer

<400> SEQUENCE: 16
cgcaattcgg cccccgaggc ccccatgtct cgatcccact taac             44

<210> SEQ ID NO 17
<211> LENGTH: 54
<212> TYPE: DNA
<213> ORGANISM: Artificial
<220> FEATURE:
<223> OTHER INFORMATION: Artificial primer

<400> SEQUENCE: 17
cagcgtactc caaagattca ggtttactca cgtcatccag cagagaatgg aaag   54

<210> SEQ ID NO 18
<211> LENGTH: 54
<212> TYPE: DNA
<213> ORGANISM: Artificial
<220> FEATURE:
<223> OTHER INFORMATION: Artificial primer

<400> SEQUENCE: 18
cagcagagaa tggaaagtca aatttcctga attgctatgt gtctgggttt catc   54

<210> SEQ ID NO 19
<211> LENGTH: 54
<212> TYPE: DNA
<213> ORGANISM: Artificial
<220> FEATURE:
<223> OTHER INFORMATION: Artificial primer

<400> SEQUENCE: 19
ctatgtgtct gggtttcatc catccgacat tgaagttgac ttactgaaga atgg   54

<210> SEQ ID NO 20
<211> LENGTH: 54
<212> TYPE: DNA
<213> ORGANISM: Artificial
<220> FEATURE:
<223> OTHER INFORMATION: Artificial primer

<400> SEQUENCE: 20
gttgacttac tgaagaatgg agagagaatt gaaaaagtgg agcattcaga cttg   54

<210> SEQ ID NO 21
<211> LENGTH: 54
<212> TYPE: DNA
<213> ORGANISM: Artificial
<220> FEATURE:
<223> OTHER INFORMATION: Artificial primer

<400> SEQUENCE: 21
gtacaagaga tagaaagacc agtccttgct gaaagacaag tctgaatgct ccac   54

<210> SEQ ID NO 22
<211> LENGTH: 54
<212> TYPE: DNA
<213> ORGANISM: Artificial
<220> FEATURE:
<223> OTHER INFORMATION: Artificial primer
```

<400> SEQUENCE: 22
actcatcttt ttcagtgggg gtgaattcag tgtagtacaa gagatagaaa gacc        54

<210> SEQ ID NO 23
<211> LENGTH: 54
<212> TYPE: DNA
<213> ORGANISM: Artificial
<220> FEATURE:
<223> OTHER INFORMATION: Artificial primer

<400> SEQUENCE: 23
ctgtgacaaa gtcacatggt tcacacggca ggcatactca tcttttttcag tggg       54

<210> SEQ ID NO 24
<211> LENGTH: 49
<212> TYPE: DNA
<213> ORGANISM: Artificial
<220> FEATURE:
<223> OTHER INFORMATION: Artificial primer

<400> SEQUENCE: 24
catgtctcga tcccacttaa ctatcttggg ctgtgacaaa gtcacatgg              49

<210> SEQ ID NO 25
<211> LENGTH: 54
<212> TYPE: DNA
<213> ORGANISM: Artificial
<220> FEATURE:
<223> OTHER INFORMATION: Artificial primer

<400> SEQUENCE: 25
cgaactggcc cagccggcca tggcgtgcgg cggcatcgcc cggctagagg aaaa        54

<210> SEQ ID NO 26
<211> LENGTH: 54
<212> TYPE: DNA
<213> ORGANISM: Artificial
<220> FEATURE:
<223> OTHER INFORMATION: Artificial primer

<400> SEQUENCE: 26
cgaactggcc cccgaggccc ggcagccgcc gtggttcatg actttctgtt taag        54

<210> SEQ ID NO 27
<211> LENGTH: 43
<212> TYPE: DNA
<213> ORGANISM: Artificial
<220> FEATURE:
<223> OTHER INFORMATION: Artificial primer

<400> SEQUENCE: 27
gatatcgcgg ccgcatgcgg cggcctgacc gacaccctgc agg                   43

<210> SEQ ID NO 28
<211> LENGTH: 47
<212> TYPE: DNA
<213> ORGANISM: Artificial
<220> FEATURE:
<223> OTHER INFORMATION: Artificial primer

<400> SEQUENCE: 28
ttttaggggt cgactgcggc gcagcgccgt gtgccgccag gatgaac               47

<210> SEQ ID NO 29
<211> LENGTH: 54

```
<212> TYPE: DNA
<213> ORGANISM: Artificial
<220> FEATURE:
<223> OTHER INFORMATION: Artificial primer

<400> SEQUENCE: 29
gacgaactgg cccagccggc catggcggag agtaaacgga ataagccagg gaag        54

<210> SEQ ID NO 30
<211> LENGTH: 54
<212> TYPE: DNA
<213> ORGANISM: Artificial
<220> FEATURE:
<223> OTHER INFORMATION: Artificial primer

<400> SEQUENCE: 30
gcgaactggc cccgaggcc cccttacccc gatgaatatc aatatgtcgc ttag         54

<210> SEQ ID NO 31
<211> LENGTH: 54
<212> TYPE: DNA
<213> ORGANISM: Artificial
<220> FEATURE:
<223> OTHER INFORMATION: Artificial primer

<400> SEQUENCE: 31
cgagatatcg cggccgcaat ggaactgaaa catagtatta gtgattatac cgag        54

<210> SEQ ID NO 32
<211> LENGTH: 51
<212> TYPE: DNA
<213> ORGANISM: Artificial
<220> FEATURE:
<223> OTHER INFORMATION: Artificial primer

<400> SEQUENCE: 32
gttttagggg tcgactgcgg cgccctgttt aaatcctgac ttaccgttag c           51

<210> SEQ ID NO 33
<211> LENGTH: 54
<212> TYPE: DNA
<213> ORGANISM: Artificial
<220> FEATURE:
<223> OTHER INFORMATION: Artificial primer

<400> SEQUENCE: 33
cttaccccga tgaatatcaa tcgctcgctt aggtgtggtc actctgatat tatt        54

<210> SEQ ID NO 34
<211> LENGTH: 54
<212> TYPE: DNA
<213> ORGANISM: Artificial
<220> FEATURE:
<223> OTHER INFORMATION: Artificial primer

<400> SEQUENCE: 34
gcgaactggc cccgaggcc cccttacccc gatgaatatc aatcgctcgc ttag         54

<210> SEQ ID NO 35
<211> LENGTH: 44
<212> TYPE: DNA
<213> ORGANISM: Artificial
<220> FEATURE:
<223> OTHER INFORMATION: Artificial primer

<400> SEQUENCE: 35
```

```
cttaccccgc gcaatatcaa tatgtcgctt aggtgtggtc actc                44
```

<210> SEQ ID NO 36
<211> LENGTH: 54
<212> TYPE: DNA
<213> ORGANISM: Artificial
<220> FEATURE:
<223> OTHER INFORMATION: Artificial primer

<400> SEQUENCE: 36

```
gcgaactggc ccccgaggcc cccttacccc gcgcaatatc aatatgtcgc ttag      54
```

<210> SEQ ID NO 37
<211> LENGTH: 54
<212> TYPE: DNA
<213> ORGANISM: Artificial
<220> FEATURE:
<223> OTHER INFORMATION: Artificial primer

<400> SEQUENCE: 37

```
cttaccccgc gcaatatcaa tcgctcgctt aggtgtggtc actctgatat tatt      54
```

<210> SEQ ID NO 38
<211> LENGTH: 54
<212> TYPE: DNA
<213> ORGANISM: Artificial
<220> FEATURE:
<223> OTHER INFORMATION: Artificial primer

<400> SEQUENCE: 38

```
gcgaactggc ccccgaggcc cccttacccc gcgcaatatc aatcgctcgc ttag      54
```

<210> SEQ ID NO 39
<211> LENGTH: 36
<212> TYPE: DNA
<213> ORGANISM: Artificial
<220> FEATURE:
<223> OTHER INFORMATION: Artificial primer

<400> SEQUENCE: 39

```
ttttaggggt cgaccaagct gctcccccaa aggctg                          36
```

<210> SEQ ID NO 40
<211> LENGTH: 44
<212> TYPE: DNA
<213> ORGANISM: Artificial
<220> FEATURE:
<223> OTHER INFORMATION: Artificial primer

<400> SEQUENCE: 40

```
tttaagggaa gcttctatca atggtggtgg tggtggtggt gatg                 44
```

<210> SEQ ID NO 41
<211> LENGTH: 40
<212> TYPE: DNA
<213> ORGANISM: Artificial
<220> FEATURE:
<223> OTHER INFORMATION: Artificial primer

<400> SEQUENCE: 41

```
ttttaggggt cgacgacaaa actcacacat gcccaccgtg                      40
```

<210> SEQ ID NO 42
<211> LENGTH: 39
<212> TYPE: DNA
<213> ORGANISM: Artificial

```
<220> FEATURE:
<223> OTHER INFORMATION: Artificial primer

<400> SEQUENCE: 42
tttaagggaa gcttctatta ggcgcgccct ttgtcatcg                          39

<210> SEQ ID NO 43
<211> LENGTH: 81
<212> TYPE: DNA
<213> ORGANISM: Artificial
<220> FEATURE:
<223> OTHER INFORMATION: Artificial primer
<220> FEATURE:
<221> NAME/KEY: misc_feature
<222> LOCATION: (30)..(31)
<223> OTHER INFORMATION: n is a, c, g, or t
<220> FEATURE:
<221> NAME/KEY: misc_feature
<222> LOCATION: (33)..(34)
<223> OTHER INFORMATION: n is a, c, g, or t
<220> FEATURE:
<221> NAME/KEY: misc_feature
<222> LOCATION: (36)..(37)
<223> OTHER INFORMATION: n is a, c, g, or t
<220> FEATURE:
<221> NAME/KEY: misc_feature
<222> LOCATION: (39)..(40)
<223> OTHER INFORMATION: n is a, c, g, or t
<220> FEATURE:
<221> NAME/KEY: misc_feature
<222> LOCATION: (42)..(43)
<223> OTHER INFORMATION: n is a, c, g, or t
<220> FEATURE:
<221> NAME/KEY: misc_feature
<222> LOCATION: (45)..(46)
<223> OTHER INFORMATION: n is a, c, g, or t
<220> FEATURE:
<221> NAME/KEY: misc_feature
<222> LOCATION: (48)..(49)
<223> OTHER INFORMATION: n is a, c, g, or t
<220> FEATURE:
<221> NAME/KEY: misc_feature
<222> LOCATION: (51)..(52)
<223> OTHER INFORMATION: n is a, c, g, or t
<220> FEATURE:
<221> NAME/KEY: misc_feature
<222> LOCATION: (54)..(55)
<223> OTHER INFORMATION: n is a, c, g, or t
<220> FEATURE:
<221> NAME/KEY: misc_feature
<222> LOCATION: (57)..(58)
<223> OTHER INFORMATION: n is a, c, g, or t

<400> SEQUENCE: 43
ctagggagcc gcgggaggag cagtacaacn nsnnsnnsnn snnsnnsnns nnsnnsnnsa   60
gcacgtaccg tgtggtcagc g                                            81

<210> SEQ ID NO 44
<211> LENGTH: 32
<212> TYPE: DNA
<213> ORGANISM: Artificial
<220> FEATURE:
<223> OTHER INFORMATION: Artificial primer

<400> SEQUENCE: 44
ctagaggaat tcggcccccg aggccccttt ac                                32

<210> SEQ ID NO 45
<211> LENGTH: 27
<212> TYPE: DNA
<213> ORGANISM: Artificial
<220> FEATURE:
```

```
<223> OTHER INFORMATION: Artificial primer

<400> SEQUENCE: 45
cgcagcgagg cccagccggc catggcg                                     27

<210> SEQ ID NO 46
<211> LENGTH: 29
<212> TYPE: DNA
<213> ORGANISM: Artificial
<220> FEATURE:
<223> OTHER INFORMATION: Artificial primer

<400> SEQUENCE: 46
cgcaattcga attcggcccc cgaggcccc                                   29

<210> SEQ ID NO 47
<211> LENGTH: 27
<212> TYPE: DNA
<213> ORGANISM: Artificial
<220> FEATURE:
<223> OTHER INFORMATION: Artificial primer

<400> SEQUENCE: 47
caattttgtc agccgcctga gcagaag                                     27

<210> SEQ ID NO 48
<211> LENGTH: 64
<212> TYPE: DNA
<213> ORGANISM: Artificial
<220> FEATURE:
<223> OTHER INFORMATION: Artificial primer
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (32)..(33)
<223> OTHER INFORMATION: n is a, c, g, or t
<220> FEATURE:
<221> NAME/KEY: misc_feature
<222> LOCATION: (38)..(39)
<223> OTHER INFORMATION: n is a, c, g, or t

<400> SEQUENCE: 48
cttctatccc agcgacatcg ccgtgnnstg gnnsagcnns gggcagccgg agaacaacta   60
caag                                                              64

<210> SEQ ID NO 49
<211> LENGTH: 64
<212> TYPE: DNA
<213> ORGANISM: Artificial
<220> FEATURE:
<223> OTHER INFORMATION: Artificial primer

<400> SEQUENCE: 49
gaccaagaac caggtcagcc tgacctgcct ggtcaaaggc ttctatccca gcgacatcgc   60
cgtg                                                              64

<210> SEQ ID NO 50
<211> LENGTH: 77
<212> TYPE: DNA
<213> ORGANISM: Artificial
<220> FEATURE:
<223> OTHER INFORMATION: Artificial primer
<220> FEATURE:
<221> NAME/KEY: misc_feature
```

```
<222> LOCATION: (40)..(41)
<223> OTHER INFORMATION: n is a, c, g, or t
<220> FEATURE:
<221> NAME/KEY: misc_feature
<222> LOCATION: (46)..(47)
<223> OTHER INFORMATION: n is a, c, g, or t
<220> FEATURE:
<221> NAME/KEY: misc_feature
<222> LOCATION: (52)..(53)
<223> OTHER INFORMATION: n is a, c, g, or t

<400> SEQUENCE: 50
agggagaggc tcttctgcgt gtagtggttg tgcagagcwn natgwnncac wnngcatgag    60
aagacgttcc cctgctg                                                  77

<210> SEQ ID NO 51
<211> LENGTH: 80
<212> TYPE: DNA
<213> ORGANISM: Artificial
<220> FEATURE:
<223> OTHER INFORMATION: Artificial primer
<220> FEATURE:
<221> NAME/KEY: misc_feature
<222> LOCATION: (46)..(47)
<223> OTHER INFORMATION: n is a, c, g, or t
<220> FEATURE:
<221> NAME/KEY: misc_feature
<222> LOCATION: (49)..(50)
<223> OTHER INFORMATION: n is a, c, g, or t

<400> SEQUENCE: 51
agggagaggc tcttctgcgt gtagtggttg tgcagagcct catgwnnwnn cacggagcat    60
gagaagacgt tcccctgctg                                               80

<210> SEQ ID NO 52
<211> LENGTH: 83
<212> TYPE: DNA
<213> ORGANISM: Artificial
<220> FEATURE:
<223> OTHER INFORMATION: Artificial primer
<220> FEATURE:
<221> NAME/KEY: misc_feature
<222> LOCATION: (46)..(47)
<223> OTHER INFORMATION: n is a, c, g, or t
<220> FEATURE:
<221> NAME/KEY: misc_feature
<222> LOCATION: (49)..(50)
<223> OTHER INFORMATION: n is a, c, g, or t
<220> FEATURE:
<221> NAME/KEY: misc_feature
<222> LOCATION: (52)..(53)
<223> OTHER INFORMATION: n is a, c, g, or t

<400> SEQUENCE: 52
agggagaggc tcttctgcgt gtagtggttg tgcagagcct catgwnnwnn wnncacggag    60
catgagaaga cgttcccctg ctg                                           83

<210> SEQ ID NO 53
<211> LENGTH: 33
<212> TYPE: DNA
<213> ORGANISM: Artificial
<220> FEATURE:
<223> OTHER INFORMATION: Artificial primer

<400> SEQUENCE: 53
gcggaattcc catggcggat attcaaatga ccc                                33

<210> SEQ ID NO 54
```

```
<211> LENGTH: 50
<212> TYPE: DNA
<213> ORGANISM: Artificial
<220> FEATURE:
<223> OTHER INFORMATION: Artificial primer

<400> SEQUENCE: 54
cagacgcgct taaagaagac gggctttggg tcatttgaat atccgccatg                50

<210> SEQ ID NO 55
<211> LENGTH: 50
<212> TYPE: DNA
<213> ORGANISM: Artificial
<220> FEATURE:
<223> OTHER INFORMATION: Artificial primer

<400> SEQUENCE: 55
cgtcttcttt aagcgcgtct gtcggtgatc gcgtgaccat cacgtgtcgt                50

<210> SEQ ID NO 56
<211> LENGTH: 50
<212> TYPE: DNA
<213> ORGANISM: Artificial
<220> FEATURE:
<223> OTHER INFORMATION: Artificial primer

<400> SEQUENCE: 56
aggccaccgc cgtattaaca tcttggctcg cacgacacgt gatggtcacg                50

<210> SEQ ID NO 57
<211> LENGTH: 50
<212> TYPE: DNA
<213> ORGANISM: Artificial
<220> FEATURE:
<223> OTHER INFORMATION: Artificial primer

<400> SEQUENCE: 57
gttaatacgg cggtggcctg gtatcaacaa aaaccgggta agcccccgaa                50

<210> SEQ ID NO 58
<211> LENGTH: 50
<212> TYPE: DNA
<213> ORGANISM: Artificial
<220> FEATURE:
<223> OTHER INFORMATION: Artificial primer

<400> SEQUENCE: 58
gagtacagaa agctggcgct gtagattaac agcttcgggg ctttacccgg                50

<210> SEQ ID NO 59
<211> LENGTH: 50
<212> TYPE: DNA
<213> ORGANISM: Artificial
<220> FEATURE:
<223> OTHER INFORMATION: Artificial primer

<400> SEQUENCE: 59
cagcgccagc tttctgtact ctggcgtccc gagccgcttt tctggcagcc                50

<210> SEQ ID NO 60
<211> LENGTH: 10
<212> TYPE: PRT
<213> ORGANISM: Artificial
<220> FEATURE:
<223> OTHER INFORMATION: Artificial peptide

<400> SEQUENCE: 60
```

```
Arg Thr Glu Thr Pro Val Tyr Met Val Met
1               5                   10

<210> SEQ ID NO 61
<211> LENGTH: 10
<212> TYPE: PRT
<213> ORGANISM: Artificial
<220> FEATURE:
<223> OTHER INFORMATION: Artificial peptide

<400> SEQUENCE: 61

Trp Gln Val Phe Asn Lys Tyr Thr Lys Pro
1               5                   10

<210> SEQ ID NO 62
<211> LENGTH: 10
<212> TYPE: PRT
<213> ORGANISM: Artificial
<220> FEATURE:
<223> OTHER INFORMATION: Artificial peptide

<400> SEQUENCE: 62

Leu Gly Asp Gly Ser Pro Cys Lys Ala Asn
1               5                   10

<210> SEQ ID NO 63
<211> LENGTH: 10
<212> TYPE: PRT
<213> ORGANISM: Artificial
<220> FEATURE:
<223> OTHER INFORMATION: Artificial peptide

<400> SEQUENCE: 63

Glu Val Pro Leu Val Trp Met Trp Val Ser
1               5                   10

<210> SEQ ID NO 64
<211> LENGTH: 10
<212> TYPE: PRT
<213> ORGANISM: Artificial
<220> FEATURE:
<223> OTHER INFORMATION: Artificial peptide

<400> SEQUENCE: 64

Glu Gln Trp Gly Ser Gln Phe Gly Cys Gly
1               5                   10

<210> SEQ ID NO 65
<211> LENGTH: 227
<212> TYPE: PRT
<213> ORGANISM: Homo sapiens

<400> SEQUENCE: 65

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
        50                  55                  60

His Asn Ala Lys Thr Lys Pro Arg Glu Glu Gln Tyr Asn Ser Thr Tyr
65                  70                  75                  80
```

-continued

Arg Val Val Ser Val Leu Thr Val Leu His Gln Asp Arg Leu Asn Gly
              85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Ile
        195                 200                 205

His Glu Ala Leu His Asn His Tyr Thr Gln Lys Ser Leu Ser Leu Ser
    210                 215                 220

Pro Gly Lys
225

<210> SEQ ID NO 66
<211> LENGTH: 227
<212> TYPE: PRT
<213> ORGANISM: Homo sapiens

<400> SEQUENCE: 66

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
              85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Thr Ser Asp Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Ile
        195                 200                 205

His Glu Ala Leu His Asn His Tyr Thr Gln Lys Ser Leu Ser Leu Ser
    210                 215                 220

Pro Gly Lys
225

<210> SEQ ID NO 67
<211> LENGTH: 227
<212> TYPE: PRT
<213> ORGANISM: Homo sapiens

<400> SEQUENCE: 67

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Thr
145                 150                 155                 160

Trp Met Ser Glu Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 68
<211> LENGTH: 227
<212> TYPE: PRT
<213> ORGANISM: Artificial
<220> FEATURE:
<223> OTHER INFORMATION: Artificial peptide

<400> SEQUENCE: 68

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

```
His Asn Ala Lys Thr Lys Pro Arg Glu Glu Gln Tyr Asn Ser Thr Tyr
 65                  70                  75                  80

Arg Val Val Ser Val Leu Thr Val Leu His Gln Asp Trp Leu Asn Gly
                 85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Ser Gln Val Ser
    130                 135                 140

Leu Thr Cys Leu Val Lys Gly Phe Tyr Pro Ser Asp Ile Ala Val Glu
145                 150                 155                 160

Trp Val Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Ile
        195                 200                 205

His Glu Ala Leu His Asn His Tyr Thr Gln Lys Ser Leu Ser Leu Ser
210                 215                 220

Pro Gly Lys
225

<210> SEQ ID NO 69
<211> LENGTH: 227
<212> TYPE: PRT
<213> ORGANISM: Homo sapiens

<400> SEQUENCE: 69

Asp Lys Thr His Thr Cys Pro Pro Cys Pro Ala Pro Glu Leu Leu Gly
  1               5                  10                  15

Gly Pro Ser Val Phe Leu Phe Pro Pro Lys Pro Lys Asp Thr Leu Met
             20                  25                  30

Ile Ser Arg Thr Pro Glu Val Thr Cys Val Val Val Asp Val Ser His
         35                  40                  45

Glu Asp Pro Glu Val Lys Phe Asn Trp Tyr Val Asp Gly Val Glu Val
 50                  55                  60

His Asn Ala Lys Thr Lys Pro Arg Glu Glu Gln Tyr Asn Ser Thr Tyr
 65                  70                  75                  80

Arg Val Val Ser Val Leu Thr Val Leu His Gln Asp Trp Leu Asn Gly
                 85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Val Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Ile
        195                 200                 205
```

His Glu Ala Leu His Asn His Ala Thr Gln Lys Ser Leu Ser Leu Ser
     210                 215                 220

Pro Gly Lys
225

<210> SEQ ID NO 70
<211> LENGTH: 227
<212> TYPE: PRT
<213> ORGANISM: Homo sapiens

<400> SEQUENCE: 70

Asp Lys Thr His Thr Cys Pro Pro Cys Pro Ala Pro Glu Leu Leu Gly
1               5                   10                  15

Gly Ser Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Val Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Val Val Leu
        195                 200                 205

His His Ala Leu His Asn His Tyr Thr Gln Lys Ser Leu Ser Leu Ser
    210                 215                 220

Pro Gly Lys
225

<210> SEQ ID NO 71
<211> LENGTH: 227
<212> TYPE: PRT
<213> ORGANISM: Homo sapiens

<400> SEQUENCE: 71

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Asp
145                 150                 155                 160

Trp Val Ser Arg Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Val Val Leu
        195                 200                 205

His Asp Ala Leu His Asn His Tyr Thr Gln Lys Ser Leu Ser Leu Ser
    210                 215                 220

Pro Gly Lys
225

<210> SEQ ID NO 72
<211> LENGTH: 227
<212> TYPE: PRT
<213> ORGANISM: Homo sapiens

<400> SEQUENCE: 72

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Val Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ile Val Leu

His Ser Ala Leu His Asn His Tyr Thr Gln Lys Ser Leu Ser Leu Ser
        210                 215                 220

Pro Gly Lys
225

<210> SEQ ID NO 73
<211> LENGTH: 227
<212> TYPE: PRT
<213> ORGANISM: Homo sapiens

<400> SEQUENCE: 73

Asp Lys Thr Arg Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Val Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Thr Val Ser
        195                 200                 205

His Pro Ala Leu His Asn His Tyr Thr Gln Lys Ser Leu Ser Leu Ser
    210                 215                 220

Pro Gly Lys
225

<210> SEQ ID NO 74
<211> LENGTH: 237
<212> TYPE: PRT
<213> ORGANISM: Homo sapiens

<400> SEQUENCE: 74

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val

```
                50                  55                  60
His Asn Ala Lys Thr Lys Pro Arg Glu Glu Gln Tyr Asn Gln Leu Ile
 65                  70                  75                  80

Ser His Tyr Arg His Leu Thr Ser Thr Tyr Arg Val Val Ser Val Leu
                 85                  90                  95

Thr Val Leu His Gln Asp Trp Leu Asn Gly Lys Glu Tyr Lys Cys Lys
                100                 105                 110

Val Ser Asn Lys Ala Leu Pro Ala Pro Ile Glu Lys Thr Ile Ser Lys
            115                 120                 125

Ala Lys Gly Gln Pro Arg Glu Pro Gln Val Tyr Thr Leu Pro Pro Ser
        130                 135                 140

Arg Asp Glu Leu Thr Lys Asn Gln Val Ser Leu Thr Cys Leu Val Lys
145                 150                 155                 160

Gly Phe Tyr Pro Ser Asp Ile Ala Val Glu Trp Glu Ser Asn Gly Gln
                165                 170                 175

Pro Glu Asn Asn Tyr Lys Thr Thr Pro Pro Val Leu Asp Ser Asp Gly
            180                 185                 190

Ser Phe Phe Leu Tyr Ser Lys Leu Thr Val Asp Lys Ser Arg Trp Gln
        195                 200                 205

Gln Gly Asn Val Phe Ser Cys Ser Val Met His Glu Ala Leu His Asn
    210                 215                 220

His Tyr Thr Gln Lys Ser Leu Ser Leu Ser Pro Gly Lys
225                 230                 235

<210> SEQ ID NO 75
<211> LENGTH: 237
<212> TYPE: PRT
<213> ORGANISM: Homo sapiens

<400> SEQUENCE: 75

Asp Lys Thr His Thr Cys Pro Pro Cys Pro Ala Pro Glu Leu Leu Gly
 1               5                  10                  15

Gly Pro Ser Val Leu Leu Phe Pro Pro Lys Pro Lys Asp Thr Leu Met
                 20                  25                  30

Ile Ser Arg Thr Pro Glu Val Thr Cys Val Val Val Asp Val Ser His
             35                  40                  45

Glu Asp Pro Glu Val Lys Phe Asn Trp Tyr Val Asp Gly Val Glu Val
 50                  55                  60

His Asn Ala Lys Thr Lys Pro Arg Glu Glu Gln Tyr Asn Glu Val Pro
 65                  70                  75                  80

Leu Val Trp Met Trp Val Ser Ser Thr Tyr Arg Val Val Ser Val Leu
                 85                  90                  95

Thr Val Leu His Gln Asp Trp Leu Asn Gly Lys Glu Tyr Lys Cys Lys
                100                 105                 110

Val Ser Asn Glu Ala Leu Pro Ala Pro Ile Glu Lys Thr Ile Ser Lys
            115                 120                 125

Ala Lys Gly Gln Pro Arg Glu Pro Gln Val Tyr Thr Leu Pro Pro Ser
        130                 135                 140

Arg Asp Glu Leu Thr Lys Asn Gln Val Ser Leu Thr Cys Leu Val Lys
145                 150                 155                 160

Gly Phe Tyr Pro Ser Asp Ile Ala Val Glu Trp Glu Ser Asn Gly Gln
                165                 170                 175

Pro Glu Asn Asn Tyr Lys Thr Thr Pro Pro Val Leu Asp Ser Asp Gly
            180                 185                 190
```

Ser Phe Phe Leu Tyr Ser Lys Leu Thr Val Asp Lys Ser Arg Trp Gln
            195                 200                 205

Gln Gly Asn Val Phe Ser Cys Ser Val Met His Glu Ala Leu His Asn
            210                 215                 220

His Tyr Thr Gln Lys Ser Leu Ser Leu Ser Pro Gly Lys
225                 230                 235

<210> SEQ ID NO 76
<211> LENGTH: 237
<212> TYPE: PRT
<213> ORGANISM: Artificial
<220> FEATURE:
<223> OTHER INFORMATION: Artificial peptide

<400> SEQUENCE: 76

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Trp Gln Val
65                  70                  75                  80

Phe Asn Lys Tyr Thr Lys Pro Ser Thr Tyr Arg Val Val Ser Val Leu
                85                  90                  95

Thr Val Leu His Gln Asp Trp Leu Asn Gly Lys Glu Tyr Lys Cys Lys
            100                 105                 110

Val Ser Asn Lys Ala Leu Pro Ala Pro Ile Glu Lys Thr Ile Ser Lys
        115                 120                 125

Ala Lys Gly Gln Pro Arg Glu Pro Gln Val Tyr Thr Leu Pro Pro Ser
    130                 135                 140

Arg Asp Glu Leu Thr Lys Asn Gln Val Ser Leu Thr Cys Leu Val Lys
145                 150                 155                 160

Gly Phe Tyr Pro Ser Asp Ile Ala Val Glu Trp Glu Ser Asn Gly Gln
                165                 170                 175

Pro Glu Asn Asn Tyr Lys Thr Thr Pro Pro Val Leu Asp Ser Asp Gly
            180                 185                 190

Ser Phe Phe Leu Tyr Ser Lys Leu Thr Val Asp Lys Ser Arg Trp Gln
        195                 200                 205

Gln Gly Asn Val Phe Ser Cys Ser Val Met His Glu Ala Leu His Asn
    210                 215                 220

His Tyr Thr Gln Lys Ser Leu Ser Leu Ser Pro Gly Lys
225                 230                 235

<210> SEQ ID NO 77
<211> LENGTH: 237
<212> TYPE: PRT
<213> ORGANISM: Homo sapiens

<400> SEQUENCE: 77

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His

```
                35                  40                  45
Glu Asp Pro Glu Val Lys Phe Asn Trp Tyr Val Asp Gly Val Glu Val
 50                  55                  60
His Asn Ala Lys Thr Lys Pro Arg Glu Glu Gln Tyr Asn Leu Gly Asp
 65                  70                  75                  80
Gly Ser Pro Cys Lys Ala Asn Ser Thr Tyr Arg Val Val Ser Val Leu
                 85                  90                  95
Thr Val Leu His Gln Asp Trp Leu Asn Gly Lys Glu Tyr Lys Cys Lys
                100                 105                 110
Val Ser Asn Lys Ala Leu Pro Ala Pro Ile Glu Lys Thr Ile Ser Lys
            115                 120                 125
Ala Lys Gly Gln Pro Arg Glu Pro Gln Val Tyr Thr Leu Pro Pro Ser
130                 135                 140
Arg Asp Glu Leu Thr Lys Asn Gln Val Ser Leu Thr Cys Leu Val Lys
145                 150                 155                 160
Gly Phe Tyr Pro Ser Asp Ile Ala Val Glu Trp Glu Ser Asn Gly Gln
                165                 170                 175
Pro Glu Asn Asn Tyr Lys Thr Thr Pro Pro Val Leu Asp Ser Asp Gly
            180                 185                 190
Ser Phe Phe Leu Tyr Ser Lys Leu Thr Val Asp Lys Ser Arg Trp Gln
        195                 200                 205
Gln Gly Asn Val Phe Ser Cys Ser Val Met His Glu Ala Leu His Asn
210                 215                 220
His Tyr Thr Gln Lys Ser Leu Ser Leu Ser Pro Gly Lys
225                 230                 235

<210> SEQ ID NO 78
<211> LENGTH: 237
<212> TYPE: PRT
<213> ORGANISM: Homo sapiens

<400> SEQUENCE: 78

Asp Lys Thr His Thr Cys Pro Pro Cys Pro Ala Pro Glu Leu Leu Gly
 1               5                  10                  15
Gly Pro Ser Val Phe Leu Phe Pro Pro Lys Pro Lys Asp Thr Leu Met
                 20                  25                  30
Ile Ser Arg Thr Pro Glu Val Thr Cys Val Val Val Asp Val Ser His
             35                  40                  45
Glu Asp Pro Glu Val Lys Phe Asn Trp Tyr Val Asp Gly Ala Glu Val
 50                  55                  60
His Asn Ala Lys Thr Lys Pro Arg Glu Glu Gln Tyr Asn Glu Gln Trp
 65                  70                  75                  80
Gly Ser Gln Phe Gly Cys Gly Ser Thr Tyr Arg Val Val Ser Val Leu
                 85                  90                  95
Thr Val Leu His Gln Asp Trp Leu Asn Gly Lys Glu Tyr Lys Cys Lys
                100                 105                 110
Val Ser Asn Lys Ala Leu Pro Ala Pro Ile Glu Lys Thr Ile Ser Lys
            115                 120                 125
Ala Lys Gly Gln Pro Arg Glu Pro Gln Val Tyr Thr Leu Pro Pro Ser
130                 135                 140
Arg Asp Glu Leu Thr Lys Asn Gln Val Ser Leu Thr Cys Leu Val Lys
145                 150                 155                 160
Gly Phe Tyr Pro Ser Asp Ile Ala Val Glu Trp Glu Ser Asn Gly Gln
                165                 170                 175
```

```
Pro Glu Asn Asn Tyr Lys Thr Thr Pro Val Leu Asp Ser Asp Gly
            180                 185                 190

Ser Phe Phe Leu Tyr Ser Lys Leu Thr Val Asp Lys Ser Arg Trp Gln
        195                 200                 205

Gln Gly Asn Val Phe Ser Cys Ser Val Met His Glu Ala Leu His Asn
    210                 215                 220

His Tyr Thr Gln Lys Ser Leu Ser Leu Ser Pro Gly Lys
225                 230                 235

<210> SEQ ID NO 79
<211> LENGTH: 227
<212> TYPE: PRT
<213> ORGANISM: Artificial
<220> FEATURE:
<223> OTHER INFORMATION: Artificial peptide

<400> SEQUENCE: 79

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Val Ser Asn Gly Gln Pro Glu Asn Asn Tyr Lys Thr Thr Pro Pro
                165                 170                 175

Val Leu Asp Ser Asp Ser Phe Phe Leu Tyr Ser Lys Leu Thr Val
            180                 185                 190

Asp Lys Ser Arg Trp Gln Gln Gly Asn Val Phe Ser Cys Ser Val Ile
        195                 200                 205

His Glu Ala Leu His Asn His Tyr Thr Gln Lys Ser Leu Ser Leu Ser
    210                 215                 220

Pro Gly Lys
225

<210> SEQ ID NO 80
<211> LENGTH: 227
<212> TYPE: PRT
<213> ORGANISM: Homo sapiens

<400> SEQUENCE: 80

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
```

```
            20                  25                  30
Ile Ser Arg Thr Pro Glu Val Thr Cys Val Val Asp Val Ser His
        35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Leu Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Val Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Ile
        195                 200                 205

His Glu Ala Leu His Asn His Tyr Thr Gln Lys Ser Leu Ser Leu Ser
    210                 215                 220

Pro Gly Lys
225

<210> SEQ ID NO 81
<211> LENGTH: 227
<212> TYPE: PRT
<213> ORGANISM: Homo sapiens

<400> SEQUENCE: 81

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Asp Val Ser His
        35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Leu Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160
```

```
Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 82
<211> LENGTH: 227
<212> TYPE: PRT
<213> ORGANISM: Homo sapiens

<400> SEQUENCE: 82

Asp Lys Thr His Thr Cys Pro Pro Cys Pro Ala Pro Glu Leu Leu Gly
1               5                   10                  15

Gly Pro Leu Val Phe Leu Phe Pro Pro Lys Pro Lys Asp Thr Leu Met
            20                  25                  30

Thr Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
            85                  90                  95

Lys Glu Tyr Lys Cys Lys Val Ser Asn Lys Ala Leu Pro Ala Pro Ile
        100                 105                 110

Glu Lys Thr Ile Ser Lys Ala Lys Gly Gln Pro Arg Glu Pro Leu Val
    115                 120                 125

Tyr Thr Leu Pro Pro Ser Arg Asp Glu Leu Thr Lys Asn Gln Val Ser
130                 135                 140

Leu Thr Cys Leu Val Lys Gly Phe Tyr Pro Ser Asp Ile Ala Val Glu
145                 150                 155                 160

Trp Val Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 83
<211> LENGTH: 1827
<212> TYPE: DNA
<213> ORGANISM: Homo sapiens
<220> FEATURE:
<221> NAME/KEY: misc_feature
<222> LOCATION: (1778)..(1778)
<223> OTHER INFORMATION: n is a, c, g, or t
<220> FEATURE:
<221> NAME/KEY: misc_feature
```

<222> LOCATION: (1798)..(1798)
<223> OTHER INFORMATION: n is a, c, g, or t

<400> SEQUENCE: 83

```
cctccaccaa gggcccatcg gtcttccccc tggcaccctc ctccaagagc acctctgggg      60
gcacagcggc cctgggctgc ctggtcaagg actacttccc cgaaccggtg acggtgtcgt     120
ggaactcagg cgccctgacc agcggcgtgc acaccttccc ggctgtccta cagtcctcag     180
gactctactc cctcagcagc gtggtgaccg tgccctccag cagcttgggc acccagacct     240
acatctgcaa cgtgaatcac aagcccagca acaccaaggt ggacaagaga gttggtgaga     300
ggccagcaca gggagggagg gtgtctgctg gaagccaggc tcagcgctcc tgcctggacg     360
catcccggct atgcagtccc agtccagggc agcaaggcag ccccgtctg cctcttcacc      420
cggaggcctc tgcccgcccc actcatgctc agggagaggg tcttctggct ttttccccag     480
gctctgggca ggcacaggct aggtgcccct aacccaggcc ctgcacacaa aggggcaggt     540
gctgggctca gacctgccaa gagccatatc cggaggacc ctgcccctga cctaagccca      600
ccccaaaggc caaactctcc actccctcag ctcggacacc ttctctcctc ccagattcca     660
gtaactccca atcttctctc tgcagagccc aaatcttgtg acaaaactca cacatgccca     720
ccgtgcccag gtaagccagc ccaggcctcg ccctccagct caaggcggga caggtgccct     780
agagtagcct gcatccaggg acaggcccca gccgggtgct gacacgtcca cctccatctc     840
ttcctcagca cctgaactcc tggggggacc gtcagtcttc ctcttccccc caaaacccaa     900
ggacaccctc atgatctccc ggaccccctga ggtcacatgc gtggtggtgg acgtgagcca    960
cgaagaccct gaggtcaagt tcaactggta cgtggacggc gtggaggtgc ataatgccaa    1020
gacaaagccg cgggaggagc agtacaacag cacgtaccgt gtggtcagcg tcctcaccgt    1080
cctgcaccag gactggctga atggcaagga gtacaagtgc aaggtctcca acaaagccct    1140
cccagccccc atcgagaaaa ccatctccaa agccaaaggt gggacccgtg gggtgcgagg    1200
gccacatgga cagaggccgg ctcggcccac cctctgccct gagagtgacc gctgtaccaa    1260
cctctgtccc tacagggcag ccccgagaac acaggtgta cccctgccc catcccggg       1320
aggagatgac caagaaccag gtcagcctga cctgcctggt caaaggcttc tatcccagcg    1380
acatcgccgt ggagtgggag agcaatgggc agccggagaa caactacaag accacgcctc    1440
ccgtgctgga ctccgacggc tccttcttcc tctatagcaa gctcaccgtg gacaagagca    1500
ggtggcagca ggggaacgtc ttctcatgct ccgtgatgca tgaggctctg cacaaccact    1560
acacgcagaa gagcctctcc ctgtccccgg gtaaatgagt gcggtacccg ggtggcatcc    1620
ctgtgacccc tccccagtgc ctctcctggc cctggaagtt gccactccag tgcccaccag    1680
ccttgtccta ataaaattaa gttgcatcat tttgtctgac taggtggcct tctataatat    1740
tatggggtgg aggggggtgg gatggagcaa ggggcaangt tgggaagaca acctgtangg    1800
cctgcggggt ctattgggaa cccaact                                         1827
```

<210> SEQ ID NO 84
<211> LENGTH: 6
<212> TYPE: PRT
<213> ORGANISM: Artificial
<220> FEATURE:
<223> OTHER INFORMATION: Artificial peptide

<400> SEQUENCE: 84

Cys Asp Gln Ser Ser Ser
1               5

```
<210> SEQ ID NO 85
<211> LENGTH: 8
<212> TYPE: PRT
<213> ORGANISM: Artificial
<220> FEATURE:
<223> OTHER INFORMATION: Artificial peptide

<400> SEQUENCE: 85

Ala Val Ala Trp Asp Ser Arg Gly
1               5

<210> SEQ ID NO 86
<211> LENGTH: 8
<212> TYPE: PRT
<213> ORGANISM: Artificial
<220> FEATURE:
<223> OTHER INFORMATION: Artificial peptide

<400> SEQUENCE: 86

Ala Val Tyr Trp Ser Ser Leu Gly
1               5

<210> SEQ ID NO 87
<211> LENGTH: 8
<212> TYPE: PRT
<213> ORGANISM: Artificial
<220> FEATURE:
<223> OTHER INFORMATION: Artificial peptide

<400> SEQUENCE: 87

Ala Val Leu Trp Gly Ser Leu Gly
1               5

<210> SEQ ID NO 88
<211> LENGTH: 8
<212> TYPE: PRT
<213> ORGANISM: Artificial
<220> FEATURE:
<223> OTHER INFORMATION: Artificial peptide

<400> SEQUENCE: 88

Ala Val Val Cys Tyr Ser Tyr Gly
1               5

<210> SEQ ID NO 89
<211> LENGTH: 8
<212> TYPE: PRT
<213> ORGANISM: Artificial
<220> FEATURE:
<223> OTHER INFORMATION: Artificial peptide

<400> SEQUENCE: 89

Ala Val Ser Trp Ile Ser Gln Gly
1               5

<210> SEQ ID NO 90
<211> LENGTH: 8
<212> TYPE: PRT
<213> ORGANISM: Artificial
<220> FEATURE:
<223> OTHER INFORMATION: Artificial peptide

<400> SEQUENCE: 90

Ala Val Asn Trp Glu Ser Lys Gly
1               5
```

```
<210> SEQ ID NO 91
<211> LENGTH: 8
<212> TYPE: PRT
<213> ORGANISM: Artificial
<220> FEATURE:
<223> OTHER INFORMATION: Artificial peptide

<400> SEQUENCE: 91

Ala Val Thr Trp Arg Ser Trp Gly
1               5

<210> SEQ ID NO 92
<211> LENGTH: 7
<212> TYPE: PRT
<213> ORGANISM: Artificial
<220> FEATURE:
<223> OTHER INFORMATION: Artificial peptide

<400> SEQUENCE: 92

Ala Val Trp Ser Ser Gln Gly
1               5

<210> SEQ ID NO 93
<211> LENGTH: 8
<212> TYPE: PRT
<213> ORGANISM: Artificial
<220> FEATURE:
<223> OTHER INFORMATION: Artificial peptide

<400> SEQUENCE: 93

Ala Val Asn Trp Asn Ser Trp Gly
1               5

<210> SEQ ID NO 94
<211> LENGTH: 8
<212> TYPE: PRT
<213> ORGANISM: Artificial
<220> FEATURE:
<223> OTHER INFORMATION: Artificial peptide

<400> SEQUENCE: 94

Ala Val Asp Trp Arg Ser Val Gly
1               5

<210> SEQ ID NO 95
<211> LENGTH: 9
<212> TYPE: PRT
<213> ORGANISM: Artificial
<220> FEATURE:
<223> OTHER INFORMATION: Artificial peptide

<400> SEQUENCE: 95

Cys Ser Val Ala Leu His Glu Ala Leu
1               5

<210> SEQ ID NO 96
<211> LENGTH: 8
<212> TYPE: PRT
<213> ORGANISM: Artificial
<220> FEATURE:
<223> OTHER INFORMATION: Artificial peptide

<400> SEQUENCE: 96

Cys Leu Val Cys His Ser Ala Leu
1               5
```

```
<210> SEQ ID NO 97
<211> LENGTH: 8
<212> TYPE: PRT
<213> ORGANISM: Artificial
<220> FEATURE:
<223> OTHER INFORMATION: Artificial peptide

<400> SEQUENCE: 97

Cys Leu Val Leu His Gly Ala Leu
1               5

<210> SEQ ID NO 98
<211> LENGTH: 7
<212> TYPE: PRT
<213> ORGANISM: Artificial
<220> FEATURE:
<223> OTHER INFORMATION: Artificial peptide

<400> SEQUENCE: 98

Cys Arg Val His Pro Ala Leu
1               5

<210> SEQ ID NO 99
<211> LENGTH: 9
<212> TYPE: PRT
<213> ORGANISM: Artificial
<220> FEATURE:
<223> OTHER INFORMATION: Artificial peptide

<400> SEQUENCE: 99

Cys Ser Val Gly Gly His Glu Ala Leu
1               5

<210> SEQ ID NO 100
<211> LENGTH: 10
<212> TYPE: PRT
<213> ORGANISM: Artificial
<220> FEATURE:
<223> OTHER INFORMATION: Artificial peptide

<400> SEQUENCE: 100

Cys Ser Val Leu Leu Ser His Glu Ala Leu
1               5                   10

<210> SEQ ID NO 101
<211> LENGTH: 9
<212> TYPE: PRT
<213> ORGANISM: Artificial
<220> FEATURE:
<223> OTHER INFORMATION: Artificial peptide

<400> SEQUENCE: 101

Cys Ser Val Pro Val His Glu Ala Leu
1               5

<210> SEQ ID NO 102
<211> LENGTH: 9
<212> TYPE: PRT
<213> ORGANISM: Artificial
<220> FEATURE:
<223> OTHER INFORMATION: Artificial peptide

<400> SEQUENCE: 102

Cys Ser Val His Leu His Glu Ala Leu
1               5

<210> SEQ ID NO 103
```

```
<211> LENGTH: 9
<212> TYPE: PRT
<213> ORGANISM: Artificial
<220> FEATURE:
<223> OTHER INFORMATION: Artificial peptide

<400> SEQUENCE: 103

Cys Ser Val Arg Asp His Glu Ala Leu
1               5

<210> SEQ ID NO 104
<211> LENGTH: 8
<212> TYPE: PRT
<213> ORGANISM: Artificial
<220> FEATURE:
<223> OTHER INFORMATION: Artificial peptide

<400> SEQUENCE: 104

Cys Thr Val Cys His Ile Ala Leu
1               5

<210> SEQ ID NO 105
<211> LENGTH: 576
<212> TYPE: DNA
<213> ORGANISM: Homo sapiens

<400> SEQUENCE: 105
ggcatgcgta ccgaagatct gcccaaagcg gtggtgtttc tggaaccgca gtggtatcgt      60
gtgctggaga agatagcgt cacactgaaa tgccagggcg cgtatagccc tgaggataat     120
tctacccagt ggtttcataa tgaaagcctg attagcagcc aggcgagctc ttactttatc     180
gatgcggcga ccgtggatga cagcggcgaa tatcgttgtc agaccaatct gagcaccttg     240
agcgatccgg tgcagttaga agtgcatatt ggctggttac tgctgcaagc gcctcgttgg     300
gtgtttaaag aagaagatcc gattcatctg cgttgccata gctggaaaaa taccgcgctg     360
cataaagtga cctatttaca gaatggcaaa ggccgtaagt attttcatca taatagcgat     420
ttctatattc cgaaagcgac cttgaaggat tctggcagct atttctgtcg tgggcttgtc     480
ggaagcaaaa atgtgagcag cgaaaccgtg aatattacca ttacccaggg cctgagcgtt     540
agcaccataa gcagcttttt tcctccgggg tatcag                              576

<210> SEQ ID NO 106
<211> LENGTH: 555
<212> TYPE: DNA
<213> ORGANISM: Homo sapiens

<400> SEQUENCE: 106
caggctgccc caccgaaagc cgtgctgaaa ctggaaccgc cgtggattaa tgtgttgcag      60
gaagatagcg tgaccctgac ctgtcaggga gcgcgtagcc ctgaaagcga ttctattcag     120
tggtttcaca tggaaatctc gattccgacc cataccccagc cgagctatcg ttttaaagcg     180
aacaataatg atagcggcga atacacctgc cagacgggcc agaccagcct gagcgatccg     240
gtgcatctga ccgtgcttag cgaatggctg gtgctgcaaa ccccgcatct ggaatttcag     300
gaaggcgaaa ccattatgct gcgttgccat agctggaaag ataaaccgct ggtgaaagtg     360 acctttttt agaatggcaa aagccagaaa ttttctcacc tggatccgac ctttagcatt     420
ccgcaggcga atcattctca ctccggcgat taccattgta ccggcaatat aggctatacc     480
ctgtttagca gcaaaccggt gacaattacc gtgcaggtgc cgagcatggg cagcagctca     540
ccgatgggcg tgatt                                                     555
```

<210> SEQ ID NO 107
<211> LENGTH: 681
<212> TYPE: DNA
<213> ORGANISM: Homo sapiens

<400> SEQUENCE: 107
gacaaaactc acacatgccc accgtgccca gcacctgaac tcctgggggg accgtcagtc      60
ttcctcttcc ccccaaaacc caaggacacc ctcatgatct cccggacccc tgaggtcaca     120
tgcgtggtgg tggacgtgag ccacgaagac cctgaggtca agttcaactg gtacgtggac     180
ggcgtggagg tgcataatgc caagacaaag ccgcgggagg agcagtacaa cagcacgtac     240
cgtgtggtca gcgtcctcac cgtcctgcac caggactggc tgaatggcaa ggagtacaag     300
tgcaaggtct ccaacaaagc cctcccagcc cccatcgaga aaccatctc caaagccaaa      360
gggcagcccc gagaaccaca ggtgtacacc ctgcccccat cccgggatga gctgaccaag     420
aaccaggtca gcctgacctg cctggtcaaa ggcttctatc ccagcgacat cgccgtggag     480
tgggagagca atgggcagcc ggagaacaac tacaagacca cacctcccgt gctggactcc     540
gacggctcct tcttcctcta cagcaagctc accgtggaca agagcaggtg gcagcagggg     600
aacgtcttct catgctccgt gatgcatgag gctctgcaca accactacac gcagaagagc     660
ctctccctgt ccccgggtaa a                                               681

<210> SEQ ID NO 108
<211> LENGTH: 10
<212> TYPE: PRT
<213> ORGANISM: Artificial
<220> FEATURE:
<223> OTHER INFORMATION: Artificial peptide

<400> SEQUENCE: 108

Gln Leu Ile Ser His Tyr Arg His Leu Thr
1               5                   10

<210> SEQ ID NO 109
<211> LENGTH: 57
<212> TYPE: DNA
<213> ORGANISM: Artificial
<220> FEATURE:
<223> OTHER INFORMATION: Artificial primer

<400> SEQUENCE: 109
atgaaaaaga tttggctggc gctggctggt ttagttttag cgtttagcgc atcggcg        57

<210> SEQ ID NO 110
<211> LENGTH: 218
<212> TYPE: PRT
<213> ORGANISM: Homo sapiens

<400> SEQUENCE: 110

Pro Ala Pro Glu Leu Leu Gly Gly Pro Ser Val Phe Leu Phe Pro Pro
1               5                   10                  15

Lys Pro Lys Asp Thr Leu Met Ile Ser Arg Thr Pro Glu Val Thr Cys
            20                  25                  30

Val Val Val Asp Val Ser His Glu Asp Pro Glu Val Lys Phe Asn Trp
        35                  40                  45

Tyr Val Asp Gly Val Glu Val His Asn Ala Lys Thr Lys Pro Arg Glu
    50                  55                  60

Glu Gln Tyr Asn Ser Thr Tyr Arg Val Val Ser Val Leu Thr Val Leu 65                  70                  75                  80
His Gln Asp Trp Leu Asn Gly Lys Glu Tyr Lys Cys Lys Val Ser Asn
                    85                  90                  95

Lys Ala Leu Pro Ala Pro Ile Glu Lys Thr Ile Ser Lys Ala Lys Gly
                100                 105                 110

Gln Pro Arg Glu Pro Gln Val Tyr Thr Leu Pro Pro Ser Arg Asp Glu
            115                 120                 125

Leu Thr Lys Asn Gln Val Ser Leu Thr Cys Leu Val Lys Gly Phe Tyr
        130                 135                 140

Pro Ser Asp Ile Ala Val Glu Trp Glu Ser Asn Gly Gln Pro Glu Asn
145                 150                 155                 160

Asn Tyr Lys Thr Thr Pro Pro Val Leu Asp Ser Asp Gly Ser Phe Phe
                165                 170                 175

Leu Tyr Ser Lys Leu Thr Val Asp Lys Ser Arg Trp Gln Gln Gly Asn
            180                 185                 190

Val Phe Ser Cys Ser Val Met His Glu Ala Leu His Asn His Tyr Thr
        195                 200                 205

Gln Lys Ser Leu Ser Leu Ser Pro Gly Lys
    210                 215

<210> SEQ ID NO 111
<211> LENGTH: 218
<212> TYPE: PRT
<213> ORGANISM: Homo sapiens

<400> SEQUENCE: 111

Pro Ala Pro Pro Val Ala Gly Gly Pro Ser Val Phe Leu Phe Pro Pro
1               5                   10                  15

Lys Pro Lys Asp Thr Leu Met Ile Ser Arg Thr Pro Glu Val Thr Cys
            20                  25                  30

Val Val Val Asp Val Ser His Glu Asp Pro Glu Val Gln Phe Asn Trp
        35                  40                  45

Tyr Val Asp Gly Val Glu Val His Asn Ala Lys Thr Lys Pro Arg Glu
    50                  55                  60

Glu Gln Phe Asn Ser Thr Phe Arg Val Val Ser Val Leu Thr Val Val
65                  70                  75                  80

His Gln Asp Trp Leu Asn Gly Lys Glu Tyr Lys Cys Lys Val Ser Asn
                    85                  90                  95

Lys Gly Leu Pro Ala Pro Ile Glu Lys Thr Ile Ser Lys Thr Lys Gly
                100                 105                 110

Gln Pro Arg Glu Pro Gln Val Tyr Thr Leu Pro Pro Ser Arg Glu Glu
            115                 120                 125

Leu Met Lys Asn Gln Val Ser Leu Thr Cys Leu Val Lys Gly Phe Tyr
        130                 135                 140

Pro Ser Asp Ile Ala Val Glu Trp Glu Ser Asn Gly Gln Pro Glu Asn
145                 150                 155                 160

Asn Tyr Lys Thr Thr Pro Pro Met Leu Asp Ser Asp Gly Ser Phe Phe
                165                 170                 175

Leu Tyr Ser Lys Leu Thr Val Asp Lys Ser Arg Trp Gln Gln Gly Asn
            180                 185                 190

Val Phe Ser Cys Ser Val Met His Glu Ala Leu His Asn His Tyr Thr
        195                 200                 205

Gln Lys Ser Leu Ser Leu Ser Pro Gly Lys
    210                 215

<210> SEQ ID NO 112
<211> LENGTH: 218
<212> TYPE: PRT
<213> ORGANISM: Homo sapiens

<400> SEQUENCE: 112

```
Pro Ala Pro Glu Leu Gly Gly Pro Ser Val Phe Leu Phe Pro Pro
1               5                   10                  15

Lys Pro Lys Asp Thr Leu Met Ile Ser Arg Thr Pro Glu Val Thr Cys
            20                  25                  30

Val Val Val Asp Val Ser His Glu Asp Pro Glu Val Gln Phe Lys Trp
        35                  40                  45

Tyr Val Asp Gly Val Glu Val His Asn Ala Lys Thr Lys Pro Arg Glu
    50                  55                  60

Glu Gln Tyr Asn Ser Thr Phe Arg Val Val Ser Val Leu Thr Val Leu
65                  70                  75                  80

His Gln Asp Trp Leu Asn Gly Lys Glu Tyr Lys Cys Lys Val Ser Asn
                85                  90                  95

Lys Ala Leu Pro Ala Pro Ile Glu Lys Thr Ile Ser Lys Thr Lys Gly
            100                 105                 110

Gln Pro Arg Glu Pro Gln Val Tyr Thr Leu Pro Pro Ser Arg Glu Glu
        115                 120                 125

Leu Met Lys Asn Gln Val Ser Leu Thr Cys Leu Val Lys Gly Phe Tyr
    130                 135                 140

Pro Ser Asp Ile Ala Val Glu Trp Glu Ser Ser Gly Gln Pro Glu Asn
145                 150                 155                 160

Asn Tyr Asn Thr Thr Pro Pro Met Leu Asp Ser Asp Gly Ser Phe Phe
                165                 170                 175

Leu Tyr Ser Lys Leu Thr Val Asp Lys Ser Arg Trp Gln Gln Gly Asn
            180                 185                 190

Ile Phe Ser Cys Ser Val Met His Glu Ala Leu His Asn Arg Phe Thr
        195                 200                 205

Gln Lys Ser Leu Ser Leu Ser Pro Gly Lys
    210                 215
```

<210> SEQ ID NO 113
<211> LENGTH: 218
<212> TYPE: PRT
<213> ORGANISM: Homo sapiens

<400> SEQUENCE: 113

```
Pro Ala Pro Glu Phe Leu Gly Gly Pro Ser Val Phe Leu Phe Pro Pro
1               5                   10                  15

Lys Pro Lys Asp Thr Leu Met Ile Ser Arg Thr Pro Glu Val Thr Cys
            20                  25                  30

Val Val Val Asp Val Ser Gln Glu Asp Pro Glu Val Gln Phe Asn Trp
        35                  40                  45

Tyr Val Asp Gly Val Glu Val His Asn Ala Lys Thr Lys Pro Arg Glu
    50                  55                  60

Glu Gln Phe Asn Ser Thr Tyr Arg Val Val Ser Val Leu Thr Val Leu
65                  70                  75                  80

His Gln Asp Trp Leu Asn Gly Lys Glu Tyr Lys Cys Lys Val Ser Asn
                85                  90                  95

Lys Gly Leu Pro Ser Ser Ile Glu Lys Thr Ile Ser Lys Ala Lys Gly
            100                 105                 110
```

```
Gln Pro Arg Glu Pro Gln Val Tyr Thr Leu Pro Ser Gln Glu Glu
            115                 120                 125

Leu Met Lys Asn Gln Val Ser Leu Thr Cys Leu Val Lys Gly Phe Tyr
    130                 135                 140

Pro Ser Asp Ile Ala Val Glu Trp Glu Ser Asn Gly Gln Pro Glu Asn
145                 150                 155                 160

Asn Tyr Lys Thr Thr Pro Pro Val Leu Asp Ser Asp Gly Ser Phe Phe
                165                 170                 175

Leu Tyr Ser Arg Leu Thr Val Asp Lys Ser Arg Trp Gln Glu Gly Asn
            180                 185                 190

Val Phe Ser Cys Ser Val Met His Glu Ala Leu His Asn His Tyr Thr
    195                 200                 205

Gln Lys Ser Leu Ser Leu Ser Leu Gly Lys
    210                 215

<210> SEQ ID NO 114
<211> LENGTH: 8
<212> TYPE: PRT
<213> ORGANISM: Artificial
<220> FEATURE:
<223> OTHER INFORMATION: Artificial peptide

<400> SEQUENCE: 114

Asp Tyr Lys Asp Asp Asp Asp Lys
1               5

<210> SEQ ID NO 115
<211> LENGTH: 270
<212> TYPE: PRT
<213> ORGANISM: Homo sapiens

<400> SEQUENCE: 115

Met Lys Ser Leu Leu Pro Thr Ala Ala Ala Gly Leu Leu Leu Leu Ala
1               5                   10                  15

Ala Gln Pro Ala Met Ala Asp Lys Thr His Thr Cys Pro Pro Cys Pro
            20                  25                  30

Ala Pro Glu Leu Leu Gly Gly Pro Ser Val Phe Leu Phe Pro Pro Lys
        35                  40                  45

Pro Lys Asp Thr Leu Met Ile Ser Arg Thr Pro Glu Val Thr Cys Val
50                  55                  60

Val Val Asp Val Ser His Glu Asp Pro Glu Val Lys Phe Asn Trp Tyr
65                  70                  75                  80

Val Asp Gly Val Glu Val His Asn Ala Lys Thr Lys Pro Arg Glu Glu
                85                  90                  95

Gln Tyr Asn Ser Thr Tyr Arg Val Val Ser Val Leu Thr Val Leu His
            100                 105                 110

Gln Asp Trp Leu Asn Gly Lys Glu Tyr Lys Cys Lys Val Ser Asn Lys
        115                 120                 125

Ala Leu Pro Ala Pro Ile Glu Lys Thr Ile Ser Lys Ala Lys Gly Gln
    130                 135                 140

Pro Arg Glu Pro Gln Val Tyr Thr Leu Pro Pro Ser Arg Asp Glu Leu
145                 150                 155                 160

Thr Lys Asn Gln Val Ser Leu Thr Cys Leu Val Lys Gly Phe Tyr Pro
                165                 170                 175

Ser Asp Ile Ala Val Glu Trp Glu Ser Asn Gly Gln Pro Glu Asn Asn
            180                 185                 190

Tyr Lys Thr Thr Pro Pro Val Leu Asp Ser Asp Gly Ser Phe Phe Leu
```

```
                195                 200                 205
Tyr Ser Lys Leu Thr Val Asp Lys Ser Arg Trp Gln Gln Gly Asn Val
    210                 215                 220

Phe Ser Cys Ser Val Met His Glu Ala Leu His Asn His Tyr Thr Gln
225                 230                 235                 240

Lys Ser Leu Ser Leu Ser Pro Gly Lys Gly Ala Ser Gly Ala Glu Phe
                245                 250                 255

Ala Ala Ala Asp Tyr Lys Asp Asp Asp Lys Gly Arg Ala
        260                 265                 270

<210> SEQ ID NO 116
<211> LENGTH: 270
<212> TYPE: PRT
<213> ORGANISM: Homo sapiens

<400> SEQUENCE: 116

Met Lys Ser Leu Leu Pro Thr Ala Ala Ala Gly Leu Leu Leu Leu Ala
1               5                   10                  15

Ala Gln Pro Ala Met Ala Asp Lys Thr His Thr Cys Pro Pro Cys Pro
                20                  25                  30

Ala Pro Glu Leu Leu Gly Gly Pro Ser Val Phe Leu Phe Pro Pro Lys
            35                  40                  45

Pro Lys Asp Thr Leu Met Ile Ser Arg Thr Pro Glu Val Thr Cys Val
50                  55                  60

Val Val Asp Val Ser His Glu Asp Pro Glu Val Lys Phe Asn Trp Tyr
65                  70                  75                  80

Val Asp Gly Val Glu Val His Asn Ala Lys Thr Lys Pro Arg Glu Glu
                85                  90                  95

Gln Tyr Asn Ser Thr Tyr Arg Val Val Ser Val Leu Thr Val Leu His
            100                 105                 110

Gln Asp Trp Leu Asn Gly Lys Glu Tyr Lys Cys Lys Val Ser Asn Lys
        115                 120                 125

Ala Leu Pro Ala Pro Ile Glu Lys Thr Ile Ser Lys Ala Lys Gly Gln
    130                 135                 140

Pro Arg Glu Pro Gln Val Tyr Thr Leu Pro Pro Ser Arg Asp Glu Leu
145                 150                 155                 160

Thr Lys Asn Gln Val Ser Leu Thr Cys Leu Val Lys Gly Phe Tyr Pro
                165                 170                 175

Ser Asp Ile Ala Val Glu Trp Val Ser Asn Gly Gln Pro Glu Asn Asn
            180                 185                 190

Tyr Lys Thr Thr Pro Pro Val Leu Asp Ser Asp Gly Ser Phe Phe Leu
        195                 200                 205

Tyr Ser Lys Leu Thr Val Asp Lys Ser Arg Trp Gln Gln Gly Asn Val
    210                 215                 220

Phe Ser Cys Ser Val Met His Glu Ala Leu His Asn His Tyr Thr Gln
225                 230                 235                 240

Lys Ser Leu Ser Leu Ser Pro Gly Lys Gly Ala Ser Gly Ala Glu Phe
                245                 250                 255

Ala Ala Ala Asp Tyr Lys Asp Asp Asp Lys Gly Arg Ala
        260                 265                 270

<210> SEQ ID NO 117
<211> LENGTH: 270
<212> TYPE: PRT
<213> ORGANISM: Homo sapiens
```

<400> SEQUENCE: 117

Met Lys Ser Leu Leu Pro Thr Ala Ala Gly Leu Leu Leu Ala
1               5                   10                  15

Ala Gln Pro Ala Met Ala Asp Lys Thr His Thr Cys Pro Cys Pro
            20                  25                  30

Ala Pro Glu Leu Leu Gly Gly Pro Ser Val Phe Leu Phe Pro Pro Lys
        35                  40                  45

Pro Lys Asp Thr Leu Met Ile Ser Arg Thr Pro Glu Val Thr Cys Val
    50                  55                  60

Val Val Asp Val Ser His Glu Asp Pro Glu Val Lys Phe Asn Trp Tyr
65                  70                  75                  80

Val Asp Gly Val Glu Val His Asn Ala Lys Thr Lys Pro Arg Glu Glu
                85                  90                  95

Gln Tyr Asn Ser Thr Tyr Arg Val Val Ser Val Leu Thr Val Leu His
            100                 105                 110

Gln Asp Trp Leu Asn Gly Lys Glu Tyr Lys Cys Lys Val Ser Asn Lys
        115                 120                 125

Ala Leu Pro Ala Pro Ile Glu Lys Thr Ile Ser Lys Ala Lys Gly Gln
    130                 135                 140

Pro Arg Glu Pro Gln Val Tyr Thr Leu Pro Pro Ser Arg Asp Glu Leu
145                 150                 155                 160

Thr Lys Asn Gln Val Ser Leu Thr Cys Leu Val Lys Gly Phe Tyr Pro
                165                 170                 175

Ser Asp Ile Ala Val Glu Trp Val Ser Asn Gly Gln Pro Glu Asn Asn
            180                 185                 190

Tyr Lys Thr Thr Pro Pro Val Leu Asp Ser Asp Gly Ser Phe Phe Leu
        195                 200                 205

Tyr Ser Lys Leu Thr Val Asp Lys Ser Arg Trp Gln Gln Gly Asn Val
    210                 215                 220

Phe Ser Cys Ser Val Ile His Glu Ala Leu His Asn His Tyr Thr Gln
225                 230                 235                 240

Lys Ser Leu Ser Leu Ser Pro Gly Lys Gly Ala Ser Gly Ala Glu Phe
                245                 250                 255

Ala Ala Ala Asp Tyr Lys Asp Asp Asp Lys Gly Arg Ala
            260                 265                 270

<210> SEQ ID NO 118
<211> LENGTH: 270
<212> TYPE: PRT
<213> ORGANISM: Homo sapiens

<400> SEQUENCE: 118

Met Lys Ser Leu Leu Pro Thr Ala Ala Gly Leu Leu Leu Ala
1               5                   10                  15

Ala Gln Pro Ala Met Ala Asp Lys Thr His Thr Cys Pro Cys Pro
            20                  25                  30

Ala Pro Glu Leu Leu Gly Gly Pro Ser Val Phe Leu Phe Pro Pro Lys
        35                  40                  45

Pro Lys Asp Thr Leu Met Ile Ser Arg Thr Pro Glu Val Thr Cys Val
    50                  55                  60

Val Val Asp Val Ser His Glu Asp Pro Glu Val Lys Phe Asn Trp Tyr
65                  70                  75                  80

Val Asp Gly Val Glu Val His Asn Ala Lys Thr Lys Pro Arg Glu Glu
                85                  90                  95

```
Gln Tyr Asn Ser Thr Tyr Arg Val Val Ser Val Leu Thr Val Leu His
                100                 105                 110

Gln Asp Trp Leu Asn Gly Lys Glu Tyr Lys Cys Lys Val Ser Asn Lys
            115                 120                 125

Ala Leu Pro Ala Pro Ile Glu Lys Thr Ile Ser Lys Ala Lys Gly Gln
        130                 135                 140

Pro Arg Glu Pro Gln Val Tyr Thr Leu Pro Pro Ser Arg Asp Glu Leu
145                 150                 155                 160

Thr Lys Asp Gln Val Ser Leu Thr Cys Leu Val Lys Gly Phe Tyr Pro
                165                 170                 175

Ser Asp Ile Ala Val Glu Trp Val Ser Asn Gly Gln Pro Glu Asn Asn
            180                 185                 190

Tyr Lys Thr Thr Pro Pro Val Leu Asp Ser Asp Gly Ser Phe Phe Leu
        195                 200                 205

Tyr Ser Lys Leu Thr Val Asp Lys Ser Arg Trp Gln Gln Gly Asn Val
210                 215                 220

Phe Ser Cys Ser Val Ile His Glu Ala Leu His Asn His Tyr Thr Gln
225                 230                 235                 240

Lys Ser Leu Ser Leu Ser Pro Gly Lys Gly Ala Ser Gly Ala Glu Phe
                245                 250                 255

Ala Ala Ala Asp Tyr Lys Asp Asp Asp Lys Gly Arg Ala
            260                 265                 270

<210> SEQ ID NO 119
<211> LENGTH: 270
<212> TYPE: PRT
<213> ORGANISM: Homo sapiens

<400> SEQUENCE: 119

Met Lys Ser Leu Leu Pro Thr Ala Ala Ala Gly Leu Leu Leu Leu Ala
1               5                   10                  15

Ala Gln Pro Ala Met Ala Asp Lys Thr His Thr Cys Pro Pro Cys Pro
            20                  25                  30

Ala Pro Glu Leu Leu Gly Gly Pro Ser Val Phe Leu Phe Pro Pro Lys
        35                  40                  45

Pro Lys Asp Thr Leu Met Ile Ser Arg Thr Pro Glu Val Thr Cys Val
50                  55                  60

Val Val Asp Val Ser His Glu Asp Pro Glu Val Lys Phe Asn Trp Tyr
                65                  70                  75                  80

Val Asp Gly Val Glu Val His Asn Ala Lys Thr Lys Pro Arg Glu Glu
            85                  90                  95

Gln Tyr Asn Ser Thr Tyr Arg Val Val Ser Val Leu Thr Val Leu His
        100                 105                 110

Gln Asp Trp Leu Asn Gly Lys Glu Tyr Lys Cys Lys Val Ser Asn Lys
            115                 120                 125

Ala Leu Pro Ala Pro Ile Glu Lys Thr Ile Ser Lys Ala Lys Gly Gln
        130                 135                 140

Pro Arg Glu Pro Gln Val Tyr Thr Leu Pro Pro Ser Arg Asp Glu Leu
145                 150                 155                 160

Thr Lys Asp Gln Val Ser Leu Thr Cys Leu Val Lys Gly Leu Tyr Pro
                165                 170                 175

Ser Asp Ile Ala Val Glu Trp Val Ser Asn Gly Gln Pro Glu Asn Asn
            180                 185                 190

Tyr Lys Thr Thr Pro Pro Val Leu Asp Ser Asp Gly Ser Phe Phe Leu
        195                 200                 205
```

```
Tyr Ser Lys Leu Thr Val Asp Lys Ser Arg Trp Gln Gln Gly Asn Val
        210                 215                 220

Phe Ser Cys Ser Val Ile His Glu Ala Leu His Asn His Tyr Thr Gln
225                 230                 235                 240

Lys Ser Leu Ser Leu Ser Pro Gly Lys Gly Ala Ser Gly Ala Glu Phe
                245                 250                 255

Ala Ala Ala Asp Tyr Lys Asp Asp Asp Lys Gly Arg Ala
        260                 265                 270

<210> SEQ ID NO 120
<211> LENGTH: 270
<212> TYPE: PRT
<213> ORGANISM: Artificial
<220> FEATURE:
<223> OTHER INFORMATION: Artificial peptide

<400> SEQUENCE: 120

Met Lys Ser Leu Leu Pro Thr Ala Ala Ala Gly Leu Leu Leu Leu Ala
1               5                   10                  15

Ala Gln Pro Ala Met Ala Asp Lys Thr His Thr Cys Pro Pro Arg Pro
            20                  25                  30

Ala Pro Glu Leu Leu Gly Gly Pro Ser Val Phe Leu Phe Pro Pro Lys
        35                  40                  45

Pro Lys Asp Thr Leu Met Ile Ser Arg Thr Pro Glu Val Thr Cys Val
50                  55                  60

Val Val Asp Val Ser His Glu Asp Pro Glu Val Lys Phe Asn Trp Tyr
65                  70                  75                  80

Val Asp Gly Val Glu Val His Asn Ala Lys Thr Lys Pro Arg Glu Glu
                85                  90                  95

Gln Tyr Asn Ser Thr Tyr Arg Val Val Ser Val Leu Thr Val Leu His
            100                 105                 110

Gln Asp Trp Leu Asn Gly Lys Glu Tyr Lys Cys Lys Val Ser Asn Lys
        115                 120                 125

Ala Leu Pro Ala Pro Ile Glu Lys Thr Ile Ser Lys Ala Lys Gly Gln
    130                 135                 140

Pro Arg Glu Pro Gln Val Tyr Thr Leu Pro Pro Ser Arg Asp Glu Leu
145                 150                 155                 160

Thr Lys Asn Gln Val Ser Leu Thr Cys Leu Val Lys Gly Phe Tyr Pro
                165                 170                 175

Ser Asp Ile Ala Val Glu Trp Val Ser Asn Gly Gln Pro Glu Asn Asn
            180                 185                 190

Tyr Lys Thr Thr Pro Pro Val Leu Asp Ser Asp Gly Ser Phe Phe Leu
        195                 200                 205

Tyr Ser Lys Leu Thr Val Asp Lys Ser Arg Trp Gln Gln Gly Asn Val
    210                 215                 220

Phe Ser Cys Ser Val Ile His Glu Ala Leu His Asn His Tyr Thr Gln
225                 230                 235                 240

Lys Ser Leu Ser Leu Ser Pro Gly Lys Gly Ala Ser Gly Ala Glu Phe
                245                 250                 255

Ala Ala Ala Asp Tyr Lys Asp Asp Asp Lys Gly Arg Ala
        260                 265                 270

<210> SEQ ID NO 121
<211> LENGTH: 270
<212> TYPE: PRT
<213> ORGANISM: Homo sapiens
```

<400> SEQUENCE: 121

```
Met Lys Ser Leu Leu Pro Thr Ala Ala Ala Gly Leu Leu Leu Leu Ala
1               5                   10                  15
Ala Gln Pro Ala Met Ala Asp Lys Thr His Thr Cys Pro Pro Cys Pro
            20                  25                  30
Ala Pro Glu Leu Leu Gly Gly Pro Ser Val Phe Leu Phe Pro Pro Lys
        35                  40                  45
Pro Lys Asp Thr Leu Met Ile Ser Arg Thr Pro Glu Val Thr Cys Val
50                  55                  60
Val Val Asp Val Ser His Glu Asp Pro Glu Val Lys Phe Asn Trp Tyr
65                  70                  75                  80
Val Asp Gly Val Glu Val His Asn Ala Lys Thr Lys Pro Arg Glu Glu
                85                  90                  95
Gln Tyr Asn Ser Thr Tyr Arg Val Val Ser Val Leu Thr Val Leu Tyr
            100                 105                 110
Gln Asp Trp Leu Asn Gly Lys Glu Tyr Lys Cys Arg Val Ser Asn Lys
        115                 120                 125
Ala Leu Pro Ala Pro Ile Glu Lys Thr Ile Ser Lys Ala Lys Gly Gln
130                 135                 140
Pro Arg Glu Pro Gln Val Tyr Ala Leu Pro Pro Ser Arg Asp Glu Leu
145                 150                 155                 160
Thr Lys Asn Gln Val Ser Leu Thr Cys Leu Val Lys Gly Phe Tyr Pro
                165                 170                 175
Ser Asp Ile Ala Val Glu Trp Val Ser Asn Gly Gln Pro Glu Asn Asn
            180                 185                 190
Tyr Lys Thr Thr Pro Pro Val Leu Asp Ser Asp Gly Ser Phe Phe Leu
        195                 200                 205
Tyr Ser Lys Leu Thr Val Asp Lys Ser Arg Trp Gln Gln Gly Asn Val
210                 215                 220
Phe Ser Cys Thr Val Met His Glu Ala Leu His Asn His Tyr Thr Gln
225                 230                 235                 240
Lys Ser Leu Pro Leu Ser Pro Gly Lys Gly Ala Ser Gly Ala Glu Phe
                245                 250                 255
Ala Ala Ala Asp Tyr Lys Asp Asp Asp Lys Gly Arg Ala
            260                 265                 270
```

<210> SEQ ID NO 122
<211> LENGTH: 237
<212> TYPE: PRT
<213> ORGANISM: Homo sapiens

<400> SEQUENCE: 122

```
Asp Lys Thr His Thr Cys Pro Pro Cys Pro Ala Pro Glu Leu Leu Gly
1               5                   10                  15
Gly Pro Ser Val Phe Leu Phe Pro Pro Lys Pro Lys Asp Thr Leu Met
            20                  25                  30
Ile Ser Arg Thr Pro Glu Val Thr Cys Val Val Val Asp Val Ser His
        35                  40                  45
Glu Asp Pro Glu Val Lys Phe Asn Trp Tyr Val Asp Gly Val Glu Val
50                  55                  60
His Asn Ala Lys Thr Lys Pro Arg Glu Glu Gln Tyr Asn Arg Thr Glu
65                  70                  75                  80
Thr Pro Val Tyr Met Val Met Ser Thr Tyr Arg Val Val Ser Val Leu
                85                  90                  95
```

-continued

Thr Val Leu His Gln Asp Trp Leu Asn Gly Lys Glu Tyr Lys Cys Lys
            100                 105                 110

Val Ser Asn Lys Ala Leu Pro Ala Pro Ile Glu Lys Thr Ile Ser Lys
        115                 120                 125

Ala Lys Gly Gln Pro Arg Glu Pro Gln Val Tyr Thr Leu Pro Pro Ser
130                 135                 140

Arg Asp Glu Leu Thr Lys Asn Gln Val Ser Leu Thr Cys Leu Val Lys
145                 150                 155                 160

Gly Phe Tyr Pro Ser Asp Ile Ala Val Glu Trp Glu Ser Asn Gly Gln
                165                 170                 175

Pro Glu Asn Asn Tyr Lys Thr Thr Pro Pro Val Leu Asp Ser Asp Gly
            180                 185                 190

Ser Phe Phe Leu Tyr Ser Lys Leu Thr Val Asp Lys Ser Arg Trp Gln
        195                 200                 205

Gln Gly Asn Val Phe Ser Cys Ser Val Met His Glu Ala Leu His Asn
210                 215                 220

His Tyr Thr Gln Lys Ser Leu Ser Leu Ser Pro Gly Lys
225                 230                 235

<210> SEQ ID NO 123
<211> LENGTH: 8
<212> TYPE: PRT
<213> ORGANISM: Artificial Sequence
<220> FEATURE:
<223> OTHER INFORMATION: Synthetic peptide

<400> SEQUENCE: 123

Ala Val Glu Trp Glu Ser Asn Gly
1               5

<210> SEQ ID NO 124
<211> LENGTH: 8
<212> TYPE: PRT
<213> ORGANISM: Artificial Sequence
<220> FEATURE:
<223> OTHER INFORMATION: Synthetic peptide

<400> SEQUENCE: 124

Cys Ser Val Met His Glu Ala Leu
1               5

<210> SEQ ID NO 125
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 125

Ala Val Xaa Trp Xaa Ser Xaa Gly
1               5

```
<210> SEQ ID NO 126
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 126

Cys Xaa Val Xaa His Xaa Ala
 1               5

<210> SEQ ID NO 127
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (4)..(5)
<223> OTHER INFORMATION: Xaa can be any naturally occurring amino acid

<400> SEQUENCE: 127

Cys Ser Val Xaa Xaa His Glu Ala
 1               5

<210> SEQ ID NO 128
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (4)..(6)
<223> OTHER INFORMATION: Xaa can be any naturally occurring amino acid

<400> SEQUENCE: 128

Cys Ser Val Xaa Xaa Xaa His Glu Ala
 1               5

<210> SEQ ID NO 129
<211> LENGTH: 227
<212> TYPE: PRT
<213> ORGANISM: Homo sapiens

<400> SEQUENCE: 129

Asp Lys Thr His Thr Cys Pro Pro Cys Pro Ala Pro Glu Leu Leu Gly
 1               5                  10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
        50                  55                  60
```

```
His Asn Ala Lys Thr Lys Pro Arg Glu Glu Gln Tyr Asn Ser Thr Tyr
 65                  70                  75                  80

Arg Val Val Ser Val Leu Thr Val Leu His Gln Asp Trp Leu Asn Gly
                 85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Val Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 130
<211> LENGTH: 227
<212> TYPE: PRT
<213> ORGANISM: Homo sapiens

<400> SEQUENCE: 130

Asp Lys Thr His Thr Cys Pro Pro Cys Pro Ala Pro Glu Leu Leu Gly
  1               5                  10                  15

Gly Pro Ser Val Phe Leu Phe Pro Pro Lys Pro Lys Asp Thr Leu Met
             20                  25                  30

Ile Ser Arg Thr Pro Glu Val Thr Cys Val Val Val Asp Val Ser His
         35                  40                  45

Glu Asp Pro Glu Val Lys Phe Asn Trp Tyr Val Asp Gly Val Glu Val
     50                  55                  60

His Asn Ala Lys Thr Lys Pro Arg Glu Glu Gln Tyr Asn Ser Thr Tyr
 65                  70                  75                  80

Arg Val Val Ser Val Leu Thr Val Leu His Gln Asp Trp Leu Asn Gly
                 85                  90                  95

Lys Glu Tyr Lys Cys Lys Val Ser Asn Lys Ala Leu Pro Ala Leu Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Val Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205
```

```
His Glu Ala Leu His Asn His Tyr Thr Gln Lys Ser Leu Ser Leu Ser
    210                 215                 220

Pro Gly Lys
225

<210> SEQ ID NO 131
<211> LENGTH: 227
<212> TYPE: PRT
<213> ORGANISM: Homo sapiens

<400> SEQUENCE: 131

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
        50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Val Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Asp Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225
```

IMMUNOGLOBULIN FC LIBRARIES

This application is a divisional of U.S. application Ser. No. 12/112,971, filed Apr. 30, 2008, now U.S. Pat. No. 8,629,245, which claims priority to U.S. Provisional Application No. 60/915,183, filed May 1, 2007 and U.S. Provisional Application No. 60/982,652, filed Oct. 25, 2007, the entire disclosure of each of which is specifically incorporated herein by reference in its entirety without disclaimer.

BACKGROUND OF THE INVENTION

1. Field of the Invention

The present invention relates generally to the field of protein engineering. More particularly, it concerns improved methods and compositions for the screening of combinatorial antibody Fc libraries expressed in bacteria.

2. Description of Related Art

Currently recombinant therapeutic antibodies have sales of well over $10 bn/yr and with a forecast of annual growth rate of 20.9%, they are projected to increase to $25 bn/yr by 2010. Monoclonal antibodies (mAbs) comprise the majority of recombinant proteins currently in the clinic, with more than 150 products in studies sponsored by companies located worldwide (Pavlou and Belsey, 2005). In terms of therapeutic focus, the mAb market is heavily focused on oncology and arthritis, immune and inflammatory disorders, and products within these therapeutic areas are set to continue to be the key growth drivers over the forecast period. As a group, genetically engineered mAbs generally have higher probability of FDA approval success than small-molecule drugs. At least 50 biotechnology companies and all the major pharmaceutical companies have active antibody discovery programs in place.

The original method for isolation and production of mAbs was first reported at 1975 by Milstein and Kohler (Kohler and Milstein, 1975), and it involved the fusion of mouse lymphocyte and myeloma cells, yielding mouse hybridomas. Therapeutic murine mAbs entered clinical study in the early 1980s; however, problems with lack of efficacy and rapid clearance due to patients' production of human anti-mouse antibodies (HAMA) became apparent. These issues, as well as the time and cost consuming related to the technology became driving forces for the evolution of mAb production technology. Polymerase Chain Reaction (PCR) facilitated the cloning of monoclonal antibodies genes directly from lymphocytes of immunized animals and the expression of combinatorial library of fragments antibodies in bacteria (Orlandi et al., 1989). Later libraries were created entirely by in vitro cloning techniques using naïve genes with rearranged complementarity determining region 3 (CDR3) (Griffiths and Duncan, 1998; Hoogenboom et al., 1998). As a result, the isolation of antibody fragments with the desired specificity was no longer dependent on the immunogenicity of the corresponding antigen. Moreover, the range of antigen specificities in synthetic combinatorial libraries was greater than that found in a panel of hybridomas generated from an immunized mouse. These advantages have facilitated the development of antibody fragments to a number of unique antigens including small molecular compounds (haptens) (Hoogenboom and Winter, 1992), molecular complexes (Chames et al., 2000), unstable compounds (Kjaer et al., 1998) and cell surface proteins (Desai et al., 1998).

In microbial cells, display screening may be carried out by flow cytometry. In particular, Anchored Periplasmic Expression (APEx) is based on anchoring the antibody fragment on the periplasmic face of the inner membrane of *E. coli* followed by disruption of the outer membrane, incubation with fluorescently labeled target and sorting of the spheroplasts (U.S. Pat. No. 7,094,571). APEx was used for the affinity maturation of antibody fragments (Harvey et al., 2004; Harvey et al., 2006). In one study over 200-fold affinity improvement was obtained after only two rounds of screening.

One important mechanism underlying the potency of antibody therapeutics is the ability of antibody to recruit immune cells to a target antigen (or cell). Thus, the Fc region of an antibody is crucial for recruitment of immunological cells and antibody dependent cytotoxicity (ADCC). In particular, the nature of the ADCC response elicited by antibodies depends on the interaction of the Fc region with receptors (FcRs) located on the surface of many cell types. Humans contain five different classes of Fc receptors. In addition haplotypes, or genetic variants of different FcRs belonging to a particular class are known. The binding of an antibody to FcRs determines its ability to recruit other immunological cells and the type of cell recruited. Hence, the ability to engineer antibodies that can recruit only certain kinds of cells can be critically important for therapy.

However, to the inventors' knowledge, previous attempts to engineer Fc domains have been performed using mammalian-expressed IgG molecules. Mammalian antibodies are glycosylated. The carbohydrate chain is attached to the Fc region and alters the conformation of the protein and enables the antibody to bind to FcRs. In contrast, aglycosylated antibodies produced in bacteria cannot bind to FcRs and therefore are unable to elicit ADCC. It is desirable to engineer aglycosylated antibodies that are capable of eliciting ADCC and thus benefit from the lower production costs that are derived from bacterial expression.

Second, and most importantly, mammalian antibodies with engineered Fc regions display increased binding to a particular FcR of interest but in addition they are still capable of binding to other FcRs with normal affinity. Thus, while such antibodies are more selective than the molecules naturally produced by the immune system they can nonetheless still mediate undesirable immunological responses.

Nonetheless, all high throughput antibody screening technologies available to-date rely on microbial expression of antibody fragments. The use of antibody fragments rather than intact or full length IgGs, in the construction and screening of libraries has been dictated by limitations related to the expression of the much larger IgGs in microorganisms. IgG libraries have never before been expressed or screened using microorganisms such as bacteria or yeasts. As a result the isolation of antigen binding proteins has been carried out exclusively using antibody fragments that are smaller and much easier to produce. Once isolated, such antibody fragments have to then be fused to vectors that express full length immunoglobulins which in turn are expressed preferentially in mammalian cells such as CHO cells.

*E. coli* possesses a reducing cytoplasm that is unsuitable for the folding of proteins with disulfide bonds which accumulate in an unfolded or incorrectly folded state (Baneyx and Mujacic, 2004). In contrast to the cytoplasm, the periplasm of *E. coli* is maintained in an oxidized state that allows the formation of protein disulfide bonds. Notably, periplasmic expression has been employed successfully for the expression of antibody fragments such as Fvs, scFvs, Fabs or F(ab')2s (Kipriyanov and Little, 1999). These fragments can be made relatively quickly in large quantities with the retention of antigen binding activity. However, because antibody fragments lack the Fc domain, they do not bind the FcRn receptor and are cleared quickly; thus, they are only occasionally suitable as therapeutic proteins (Knight et al., 1995). Until recently, full-length antibodies could only be expressed in *E. coli* as insoluble aggregates and then refolded in vitro (Boss et al., 1984; Cabilly et al., 1984). Clearly this approach is not amenable to the high throughput screening of antibody libraries since with the current technology it is not possible to refold millions or tens of millions of antibodies individually. A further problem is that since *E. coli* expressed antibodies are not glycosylated, they fail to bind to complement factor 1q (C1q) or Fc and many other Fc receptors. However, aglycosylated Fc domains can bind to the neonatal Fc receptor efficiently (FcRn). Consequently bacterially expressed aglycosylated antibodies do exhibit serum persistence and pharmacokinetics similar to those of fully glycosylated IgGs produced in human cells. Nonetheless, since the aglycosylated antibodies fail to elicit complement activation and can not mediate the recruitment of immune cells such as macrophages, they have previously been ineffective for many therapeutic applications.

SUMMARY OF THE INVENTION

The present invention overcomes a major deficiency in the art in providing aglycosylated antibody Fc domains that bind to Fc receptors and providing methods for the screening and production thereof. In a first embodiment there is provided a method of selecting a bacterial cell comprising an aglycosylated antibody Fc domain having specific affinity for an Fc receptor (FcR) polypeptide comprising the steps of: (a) obtaining a population of Gram negative bacterial cells, cells of which population express an aglycosylated antibody Fc domain in their periplasm, wherein the population expresses a plurality of different Fc domains; (b) contacting the bacterial cells with an FcR polypeptide under conditions wherein the FcR polypeptide contacts the aglycosylated Fc domains; and (c) selecting at least one bacterial cell based on binding of the aglycosylated Fc domain to the FcR polypeptide. Method for expressing polypeptides and in particular antibodies in the periplasmic space are known in the art for example see U.S. Pat. No. 7,094,571 and U.S. Patent Publ. 20030180937 and 20030219870 each incorporated herein by reference. In some cases, a gram negative bacterial cell of the invention may be defined as an *E. coli* cell. Furthermore, in some preferred aspects a Gram negative bacterial cell of the invention may defined as a genetically engineered bacterial cell such as a Jude-1 strain of *E. coli*. Preferably, Gram negative bacterial cells of the invention are viable bacterial cells.

In certain further embodiments, the invention involves disrupting, permeablizing or removing the outer membrane of bacteria are well known in the art, for example, see U.S. Pat. No. 7,094,571. For instance, prior to contacting the bacterial cells with an FcR polypeptide the outer membrane of the bacterial cell may be treated with hyperosmotic conditions, physical stress, lysozyme, EDTA, a digestive enzyme, a chemical that disrupts the outer membrane, or by infecting the bacterium with a phage or a combination of the foregoing methods. Thus, in some cases, the outer membrane may be disrupted by lysozyme and EDTA treatment. Furthermore, in certain aspects of the invention the bacterial outer membrane may be removed entirely.

In still further aspects of the invention, an antibody Fc domain that is comprised in the bacterial periplasm may be defined as comprising a hinge, CH2 and CH3 region. However, in some aspects, Fc domains of the invention comprise a functional domain fragment. As used herein the term functional domain fragment means that antibody Fc domain that comprises amino acid deletions relative to wild-type sequence but nonetheless is able to bind to an FcR polypeptide. A skilled artisan will recognize that an antibody Fc domain for use in the invention may be an IgA, IgM, IgE, IgD or IgG antibody Fc domain or a variant thereof. Preferably, an antibody of the invention is an IgG antibody Fc domain such as an IgG1, IgG2a, IgG2b, IgG3 or IgG4 antibody Fc domain. Furthermore, the antibody Fc domain may be defined as a human Fc domain. In certain aspects, the Fc domain may be an IgG1 Fc domain, specifically, the Fc domain of an anti-HER2 antibody, more specifically, the Fc domain of trastuzumab.

In some further aspects, a Gram negative bacterial cell of the invention further comprises a nucleic acid sequence encoding an antibody Fc domain. The encoded antibody may be any of the antibody Fc domains defined herein. In further aspects, a nucleic acid of the invention comprises sequences that facilitate Fc export into the periplasmic space. Such sequences are well known in the art and may comprise a secretion signal fused to the Ig chain (U.S. Patent Publ. 20030180937 and 20030219870). Furthermore, an antibody Fc domain encoding nucleic acid may comprise additional elements such as an origin of replication or a selectable marker gene. In some preferred aspects the Fc domain encoding sequences are flanked by known sequences such that the Ig sequence may be amplified by PCR using primers that anneal to the known sequence. Furthermore, the skilled artisan will recognize that a nucleic acid sequence encoding an Fc domain of the invention will comprise sequences that mediate periplasmic expression, such as a secretion signal. For example, in some cases a dual arginine secretion signal may be used. In some highly preferred embodiments the secretion signal is from PelB. In a other embodiments, the dsbA secretion signal or any other signal peptide capable of co-translational secretion may be used in order to achieve higher expression.

Furthermore, in highly preferred aspects of the invention Gram negative bacterial cells for use in the invention comprise a plurality of distinct Fc domain sequences. As used herein a "distinct Fc domain" may be defined as a domain that differs from another Fc by as little as one amino acid. Methods for making a library of distinct antibody Fc domains or nucleic acids that encode antibodies are well known in the art and exemplified herein. For example, in some cases Fc domains may be amplified by error prone PCR as exemplified herein. Furthermore, in certain cases a plurality of antibody Fc domains may comprise a stretch (1, 2, 3, 4, 5, 6, 7, 8, 9, 10 or more) amino acids that have been randomized. In certain cases specific mutations may be engineered into Fc domains. For example, in some aspects, residues that are normally glycosylated in an antibody Fc domain may be mutated. Furthermore, in certain aspects, residues that are normally glycosylated (or adjacent residues) may be used as a site for an insertion of 1, 2, 3, 4, 5, 6, 7, 8, 9, 10 or more amino acids. In still further embodiments, an amino acid insertion may be made at, or adjacent to, a residue corresponding to amino acid 384 of the IgG1 Fc (SEQ ID NO:1). In still further cases, a population of gram negative bacteria according to the invention may be defined as comprising at least about $1 \times 10^3$, $1 \times 10^4$, $1 \times 10^5$, $1 \times 10^6$, $1 \times 10^7$, $1 \times 10^8$, or more distinct antibodies Fc domains. In some specific cases, a population of Gram negative bacterial cells may be produced by a method comprising the steps of: (a) preparing a plurality of nucleic acid sequences encoding a plurality of distinct antibody Fc domains; and (b) transforming a population of Gram negative bacteria with said nucleic acids wherein the Gram negative bacteria comprise a plurality of antibody Fc domains expressed in the periplasm.

A variety of antibody-binding domains (e.g., FcR polypeptides) are known in the art and may be used in the methods and compositions of the invention. For example, in some aspects, an FcR may have specificity for a particular type or subtype of Ig, such as IgA, IgM, IgE or IgG (e.g., IgG1, IgG2a, IgG2b, IgG3 or IgG4). Thus, in some preferred cases the antibody-binding domain may be defined as an IgG binding domain. The FcR polypeptide may comprises an eukaryotic, prokaryotic, or synthetic FcR domain. For instance, an antibody Fc-binding domain may be defined as a mammalian, bacterial or synthetic binding domain. Some Fc-binding domains for use in the invention include but are not limited to a binding domain from one of the polypeptides of Table 1. For example, an Fc-binding polypeptide may be encoded by an FCGR2A, FCGR2B, FCGR2c, FCGR3A, FCGR3B, FCGR1A, Fcgr1, FCGR2, FCGR2, Fcgr2, Fcgr2, FCGR3, FCGR3, Fcgr3, FCGR3, Fcgr3, FCGRT, mrp4, spa or spg gene. Preferably, an FcR polypeptide for use according to the invention may be an Fc binding region from human FcγRIa, FcγRIIa, FcγRIIb, FcγRIIc, FcγRIIIa, FcγRIIIb, FcαRI or C1q.

In still further embodiments of the invention an Fc polypeptide may be anchored to the inner membrane of a Gram negative bacteria. Methods and compositions for the anchoring of polypeptides to the inner membrane of Gram negative bacterial have previously been described (U.S. Pat. No. 7,094,571 and U.S. Patent Publ. 20050260736). Thus, in some aspects, an Fc domain may be fused to a polypeptide that is associated with or integrated in a bacterial inner membrane. Such a fusion protein may comprise an N terminal or C terminal fusion with an Fc domain and in some case may comprise additional linker amino acids between the membrane anchoring polypeptide and the Fc domain. In certain specific cases, a membrane anchoring polypeptide may be the first six amino acids encoded by the *E. coli* NlpA gene, one or more transmembrane α-helices from an *E. coli* inner membrane protein, a gene III protein of filamentous phage or a fragment thereof, or an inner membrane lipoprotein or fragment thereof. Thus, as an example, a membrane anchoring polypeptide may be an inner membrane lipoprotein or fragment thereof such as from AraH, MglC, MalF, MalG, MalC, MalD, RbsC, RbsC, ArtM, ArtQ, GlnP, ProW, HisM, HisQ, LivH, LivM, LivA, LivE, DppB, DppC, OppB, AmiC, AmiD, BtuC, ThuD, FecC, FecD, FecR, FepD, NikB, NikC, CysT, CysW, UgpA, UgpE, PstA, PstC, PotB, PotC, PotH, Pod, ModB, NosY, PhnM, LacY, SecY, TolC, Dsb, B, DsbD, TouB, TatC, CheY, TraB, ExbD, ExbB or Aas.

The skilled artisan will understand that methods for selecting cells based upon their interaction (binding) with an FcR are well known in the art. For example, an FcR may be immobilized on a column or bead (e.g., a magnetic bead) and the bacterial cell binding to the FcR separated by repeated washing of the bead (e.g., magnetic separation) or column. Furthermore, in some aspects a target ligand may be labeled such as with a fluorophor, a radioisotope or an enzyme. Thus, bacterial cells may, in some cases, be selected by detecting a label on a bound FcR. For example, a fluorophore may be used to select cells using fluorescence activated cell sorting (FACS). Furthermore, in some aspects, bacterial cells may be selected based on binding or lack of binding two or more FcR polypeptides. For instance, bacteria may be selected that display antibodies that bind to two FcR polypeptides, wherein each FcR is used to select the bacterial sequentially. Conversely, in certain aspects, bacteria may be selected that display antibody Fc domains that bind to one FcR (such as an FcR comprising a first label) but not to a second FcR (e.g., comprising a second label). The foregoing method maybe used, for example, to identify antibody Fc domains that bind to a specific FcR but not a second specific FcR.

In further embodiments, methods for producing bacteria of the invention, may comprise at least two rounds of selection (step c) wherein the sub-population of bacterial cells obtained in the first round of selection is subjected to at least a second round of selection based on the binding of the candidate antibody Fc domain to an FcR. Furthermore in some aspects the sub-population of bacterial cells obtained in the first round of selection may be grown under permissive conditions prior to a second selection (to expand the total number of cells). Thus, in some aspects, methods of the invention may comprise 2, 3, 4, 5, 6, 7, 8, 9, 10 or more rounds of selection. Furthermore, in some aspects, a sub-population of bacterial cells obtained from each round of selection will be grown under permissive conditions before a subsequent round of selection. Cells isolated following one or more such rounds of selection may be subjected to additional rounds of mutagenesis. In some cases, selection will be performed after removing FcR polypeptide that is not bound to the antibody. Furthermore, in some cases the stringency of selection may be modified by adjusting the pH, salt concentration, or temperature of a solution comprising bacteria that display antibodies. Thus, in some aspects, it may be preferred that a bacterial cell of the invention is grown at a sub-physiological temperature such as at about 25° C.

In still further aspects, a method of producing a bacterial cell according to the invention may be further defined as a method of producing a nucleic acid sequence encoding an Fc domain that binds to at least a first FcR. Thus, a bacterial cell produced by the methods herein may be used to clone a nucleic acid sequence encoding the Fc domain having a specific affinity for an FcR polypeptide. Methods for isolating and amplifying such a nucleic acid from a cell for example by PCR are well known in the art and further described below. Thus, a nucleic acid sequence produced by the forgoing methods is included as part of the instant invention. Furthermore, such a sequence maybe expressed in a cell to produce an Fc domain having a specific affinity for an FcR. Thus, in some aspects, the invention provides a method for producing an Fc domain having a specific affinity for an FcR. Furthermore, the invention includes antibody Fc domains produced by the methods of the invention. It will be understood however that the antibody Fc domains produced by such a screen may be combine with antibody variable regions that have an affinity for a particular target ligand and these antibodies are also included as part of the invention.

In yet a further embodiment the invention provides a polypeptide comprising an aglycosylated antibody Fc domain capable of binding an FcR polypeptide. In some aspects, the aglycosylated Fc domain may be further defined as having a specific affinity for an FcR polypeptide under physiological conditions. For instance an Fc domain may have an equilibrium dissociation constant between about $10^{-6}$ M to about $10^{-9}$ M under physiological conditions. Furthermore in some aspects an aglycosylated Fc domain may be defined as comprising one or more amino acid substitution or insertion relative to a wild type human sequence.

Of course, it is contemplated that a preferred means of preparing such a polypeptide is through the practice of the methods discussed above. However, one can alternatively prepare such polypeptides directly by genetic engineering techniques such as, for example, by introducing selected amino acid substitutions or insertions into a known Fc background, wherein the insertion or substitution provides an improved FcR binding capability to aglycosylated Fc regions. The inventors have identified as particularly preferred substitutions for achieving such improved FcR binding as those at positions 331, 382 and/or 428 of the Fc domain (for example, see Nagaoka and Akaike 2003; such as P331, E382 and/or M428 of the human IgG Fc domain sequence as shown in FIG. 46 and also in, e.g., U.S. Patent Publ. US20060173170, incorporated herein by reference), and still more preferred are one or more substations defined by P331L, E382V, M428I or M428L.

Preferred substitutions may further include one or more of 426, 229, 322, 350, 361, 372, 442, 402, 224, 430, 238, 436, 310, 313, 384, 372, 380 or 331 of the Fc domain, such as S426, C229, K322, T350, N361, F372, 5442, G402, H224, E430, P238, Y436, H310, W313, N384, F372, E380 or P331 of the human IgG Fc domain, with the specific preferred examples being a) E382 and M428; b) N361, E382 and M428; c) N361, F372, E382 and M428; d) H310, K322, T350, E382, S426 and S442; e) C229R, E382 and M428; f) W313 and M428; g) E382, N384 and M428; h) E380, E382 and N384; i) N361, E382 and M428; j) E382, M428 and Y436; k) P238, E382, S426, M428 and E430; l) E380, E382, N384, S426, M428 and E430; m) E382, S426, M428 and E430; n) H224, E382, S426, M428 and E430; o) P331; p) 5239, 1253, Q347, E382; q) E382, G402 and M428; and r) E382, P331 and M428. Of these, the most preferred include a) E382V and M428I; b) E382V; c) N361D, E382V and M428I; d) N361D, F372L, E382V and M428I; e) H310Y, K322R, T350A, E382V, S426T and S442P; f) C229R, E382V and M428I; g) W313R and M428I; h) E382T, N384D and M428I; i) E380R, E382M and N384E; j) N361S, E382V and M428I; k) E382V, M428I and Y436A; l) P238S, E382V, S426V, M428L and E430H; m) E380D, E382V, N384R, S426V, M428L and E430D; n) E382V, S426I, M428L and E430S; o) H224R, E382V, S426T, M428S and E430P; p) P331L; q) S239L, 1253T, Q347L, E382V; r) E382V, G402D and M428I; and s) E382V, P331L and M428I.

The inventors have also identified various insertion points that upon insertion of additional amino acids, provide improved FcR binding capability. Most preferred in this regard are insertions of 5 to 15 amino acids, and preferably 10 amino acids, between amino acids N297 and 5298 of an Fc domain, such as a human IgG Fc domain. Particularly preferred insertions at this position (as well as substitutions) include a) RTETPVYMVM (SEQ ID NO:60); b) WQVFNKYTKP (SEQ ID NO:61); c) LGDGSPCKAN (SEQ ID NO:62); d) EVPLVWMWVS (SEQ ID NO:63) together with F241L and K326E; and e) EQWGSQFGCG (SEQ ID NO:64) together with V282A.

The Fc domain of the invention may be a human IgG Fc that comprises an amino acid substitution at an amino acid residue corresponding to E382 of the IgG Fc domain. Furthermore, an aglycosylated Fc domain may comprise an amino acid sequence insertion (e.g., about 1 to 5 amino acids) adjacent to an amino acid residue corresponding to E382 of the IgG Fc domain. Thus, in some specific aspects an Fc domain may comprise a hydrophobic amino acid substitution at E382 such as an E to V substitution. Furthermore, in some aspects an Fc domain of the invention may comprise an amino acid substitution at a residue corresponding to M428 (e.g., M428 to I), 5426, C229, H310, K322, T350, N361, F372 or 5442 of the human IgG Fc. In certain specific embodiments, an aglycosylated Fc domain may comprise an amino acid substitution corresponding to those found in the Fc11 (SEQ ID NO:2), Fc5 (SEQ ID NO:3), Fc12 (SEQ ID NO:4), Fc 20 (SEQ ID NO:5), Fc49 (SEQ ID NO:6) or Fc23 Fc (SEQ ID NO:7) domains described herein (see FIG. 14). Hence in a very specific case an aglycosylated Fc domain may comprise the amino acid sequence of Fc11 (SEQ ID NO:2), Fc5 (SEQ ID NO:3), Fc12 (SEQ ID NO:4), Fc 20 (SEQ ID NO:5), Fc49 (SEQ ID NO:6), Fc23 (SEQ ID NO:7), Fc104 (SEQ ID NO:65), Fc106 (SEQ ID NO:66), Fc110 (SEQ ID NO:67), Fc114 (SEQ ID NO:68), Fc117 (SEQ ID NO:69), Fc143 (SEQ ID NO:70), Fc149 (SEQ ID NO:71), Fc151 (SEQ ID NO:72), Fc152 (SEQ ID NO:73), Fc207 (SEQ ID NO:74), Fc209 (SEQ ID NO:75), Fc216 (SEQ ID NO:76), Fc217 (SEQ ID NO:77), Fc236 (SEQ ID NO:78), Fc331 (SEQ ID NO:79), Fc336 (SEQ ID NO:80), Fc 401 (SEQ ID NO:122); Fc402 (SEQ ID NO:81), or Fc403 (SEQ ID NO:82). As described supra the instant invention also contemplates antibodies or antibody fragments that comprise an aglycosylated Fc domain of the invention. Thus, in some cases, polypeptides described herein (Fc domains) may comprise an Ig variable domain and may be further defined as a full length antibody.

Preferably, an aglycosylated Fc domain of the invention comprises a specific binding affinity for an FcR such as human FcγRIa, FcγRIIa, FcγRIIb, FcγRIIc, FcγRIIIa, FcγRIIIb, FcαRI or C1q. Thus, in some aspects an aglycosylated Fc domain of the invention is defined as an Fc domain with a specific affinity for FcγRIa. Furthermore, such an Fc domain may be defined as having an equilibrium dissociation constant, with respect to FcγRIa binding, of about $10^{-6}$ M to about $10^{-9}$ M under physiological conditions.

Of course, a still further aspect of the invention includes isolated DNA segments encoding a polypeptide in accordance with any one of the foregoing modified Fc regions as well as antibodies, etc., incorporating such a polypeptide. Such DNA segments may preferably be positioned in an expression vector, which is preferably a bacterial expression vector.

In still a further aspect of the invention there is provided a bacterial growth media that comprises trehalose. In certain aspects such a media may be used in a method A method of identifying a bacteria cell comprising a first binding partner associated with an inner membrane comprised in the bacteria cell, wherein the binding partner having specific affinity for a second binding partner, comprising the steps of: a) obtaining a population of bacteria cells, cells of which population comprise the first binding partner associated with the inner membrane in the periplasm of the bacteria cells, wherein the population comprises a plurality of different such first binding partners; b) contacting the bacteria cells with the second binding partner, wherein the first binding partner or the second binding partner comprises a label, wherein a signal is elicited when the first binding partner binds to the second binding partner; and c) selecting at least one bacterial cell by detecting such a signal from at least such a first binding partner binding to at least such second binding partner. Preferably, the signal may be a fluorescent signal. In this respect a media comprising trehalose, as demonstrated herein, provides enhanced fluorescence signal and greatly improves the screening process. Thus, methods for the used of the trehalose bacterial media in screening such binding partners are included as part of the instant invention. Any of the fluorescence screening methods known in the art or described herein may be used in combination with a trehalose bacterial media of the invention. For example, a fluorescence signal may be detected by flow cytometry. Furthermore, bacteria comprising binding partners for detection may have their outer r membrane disrupted or partially disrupted. Furthermore, in certain preferred aspects of the one of the binding partners for use in the instant methods may be defined as an antibody or an antibody domain. In some very aspects a bacterial growth media comprising trehalose may be further defined based upon the trehalose concentration in the media. For example a media comprising about between about 0.05 and 1.5M trehalose or preferably between about 0.1 and 1.0 M trehalose is specifically contemplated herein. Thus, in a very specific aspect, bacterial media comprising about 0.5 M trehalose is provided.

Embodiments discussed in the context of a methods and/or composition of the invention may be employed with respect to any other method or composition described herein. Thus, an embodiment pertaining to one method or composition may be applied to other methods and compositions of the invention as well.

As used herein the terms "encode" or "encoding" with reference to a nucleic acid are used to make the invention readily understandable by the skilled artisan however these terms may be used interchangeably with "comprise" or "comprising" respectively.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 2a, FACS signals of periplasmic displayed Fc using cJun-cFos and cJun(Cys)-cFos(Cys) were compared with a positive and a negative controls. FIG. 2b, FACS signals of periplasmic displayed Fc using cJun-cFos and cJun(Cys)-cFos(Cys) were compared with one plasmid systems not co-expressing NlpA and 6 amino acid residues (CDQSSS (SEQ ID N:84)) fused cJun or cJun (Cys). Spheroplasts were incubated with Protein A-FITC probe for detection. Mn: Mean fluorescence intensity.

FIG. 4a, Display of Im2 fused M18 scFv or 26-10 scFv co-expressed with APEx displayed ColE2(H578A) and incubated with PA-FITC. FIG. 4b, Display of Im2 fused M18 scFv or 26-10 scFv co-expressed with APEx displayed ColE2(H578A) and incubated with digoxin-BODIPY. Mn: Mean fluorescence intensity.

FIG. 9a, Western blot result from reduced gel for the periplasmic expressed Fc and M18 scFv cultured in the media with or without trehalose. FIG. 9b, Western blot result from reduced or non-reduced gel for the periplasmic expressed Fc cultured in the media with or without trehalose. Anti-ECS antibody peroxidase conjugated was used as a detection antibody for Western blot.

FIG. 10a, Comparison of FACS signals between PelB and dsbA fused proteins. PelB or dsbA signal peptide fused proteins were cultured with 0.5M trehalose. FIG. 10b, Comparison of FACS signals between with and without trehalose in the media. DsbA signal peptide fused proteins were cultured with or without 0.5M trehalose. Mn: Mean fluorescence intensity. Spheroplasts were incubated with Protein A-FITC probe for detection.

FIG. 12a, IgG-Fc was coated onto fluorescence ELISA plate. The fluorescence of serially diluted and bound FcγRIa-FITC was detected at excitation 485 nm and emission 528 nm. FIG. 12b, Fluorescence signals of serially diluted FcγRIa-FITC in the IgG-Fc coated wells compared to the signals in the BSA coated wells.

FIG. 13*a*, Histogram showing enrichment of high affinity clones sorted by FcγRIa-FITC. FIG. 13*b*, Histogram showing fluorescence signals of Fc mutants comparing with wild type Fc. Spheroplasts were incubated with FcγRIa-FITC for detection. Mn: Mean fluorescence intensity.

FIG. 15*a*, Major mutation points in full glycosylated IgG. FIG. 15*b*, Interaction of two beta sheets including 382E and 428M in the CH3 region.

FIG. 18*a-c*: Sequence of isolated Fc mutant clones exhibiting high affinity to FcγRIa. Spheroplasts were incubated with FcγRIa-FITC for detection. FACS mean values are indicated in the parenthesis. (FcWT (Seq ID NO:1); Fc104 (Seq ID NO:65); Fc107 (Seq ID NO:2); Fc101 (Seq ID NO:3); Fc147 (Seq ID NO:6); Fc102 (Seq ID NO:4); Fc114 (Seq ID NO:68); Fc117 (Seq ID NO:69); Fc151 (Seq ID NO:72); Fc143 (Seq ID NO:70); Fc152 (Seq ID NO:73); Fc149 (Seq ID NO:71); Fc106 (Seq ID NO:66); Fc100 (Seq ID NO:67).

FIG. 22: Sequences of isolated Fc mutant clones exhibiting high affinity to FcγRIIIa. (WT (Seq ID NO:1; Fc 207 (Seq ID NO:74); Fc209 (Seq ID NO:75); Fc236 (Seq ID NO:78); Fc216 (Seq ID NO:76); Fc217 (Seq ID NO:77); QLISHYRHLT (Seq ID NO:108); EVPLVWMWVS (Seq ID NO:63); EQWGSQFGCG (Seq ID NO:64); WQVFNKYTKP (Seq ID NO:61); LGDGSPCKN (Seq ID NO:62).

FIG. 25: Sequences of isolated Fc mutant clones exhibiting high affinity to FcγRIIIa. (WT (Seq ID NO:1); Fc5 (Seq ID NO:129); Fc336 (Seq ID NO:130); Fc331 (Seq ID NO:131).

DESCRIPTION OF ILLUSTRATIVE EMBODIMENTS

Figure 1:
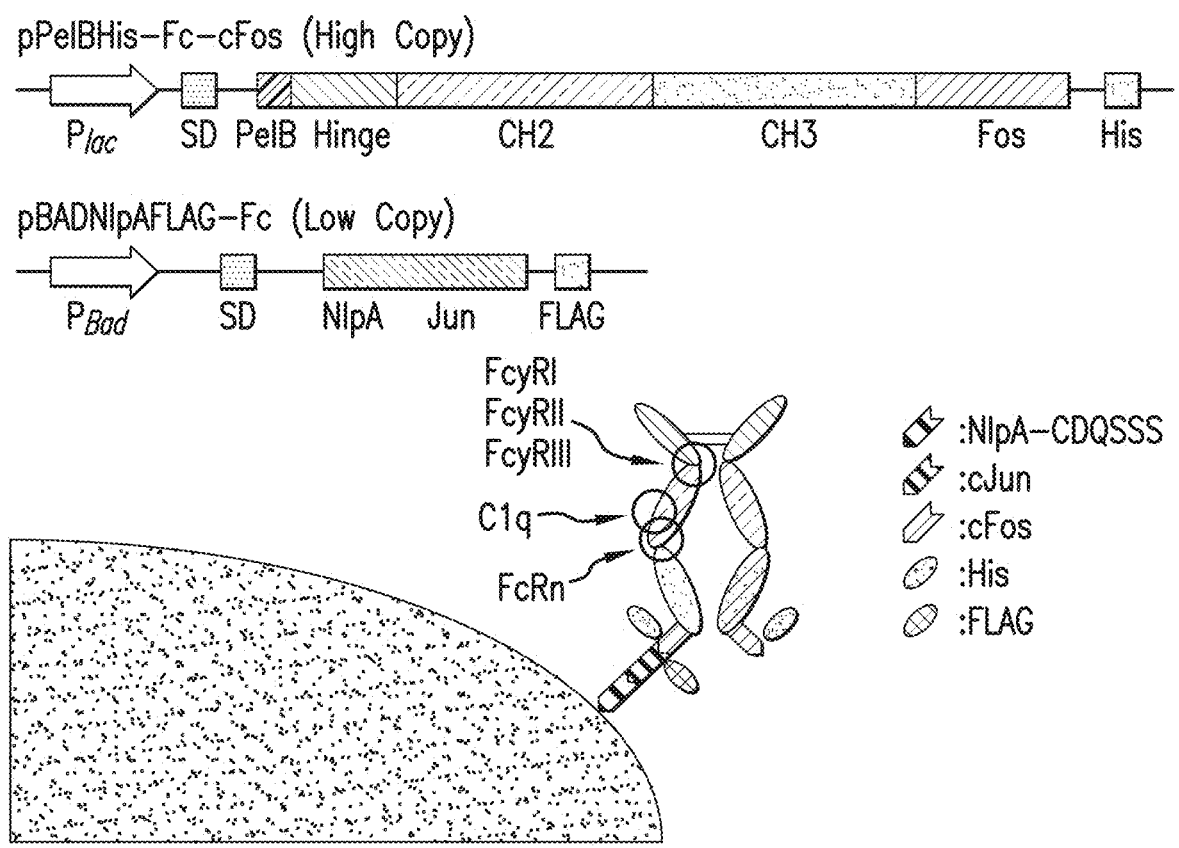
FIG. 1: Two plasmids system for the periplasmic display of Fc using cJun-cFos or cJun(Cys)-cFos(Cys) interaction.

The instant invention overcomes several major problems with current immunotherapeutic technologies in providing aglycosylated antibody Fc domains that are able to bind to Fc receptor polypeptides. Furthermore, now methods for identifying aglycosylated Fc domains capable of binding to Fc receptors are described. These methods enable isolation of antibody Fc domains that preferentially or selectively bind to specific Fc receptors. Thus, the new compositions and methods will enable manufacture of antibody therapeutics that may be produced in bacteria while retaining their ability to interact with FcR polypeptides and thereby recruit immune affecter cells. Furthermore, Fc receptors may be selected for a particular FcR binding affinity thereby allowing therapeutics to be tailored for recruitment or targeting of specific cell types. Finally, the instant invention provided new media and methods that may be used to enhance prokaryotic interaction screening techniques. Further embodiments and advantages of the invention are described below.

I. PERIPLASMIC EXPRESSION

In some aspects of the invention a polypeptide comprising an antibody Fc domain is expressed in the periplasmic space of a gram negative bacteria. Furthermore, in some aspects an antibody Fc domain may be anchored to the periplasmic face of the inner membrane. For example, an Fc domain may be directly fused to a membrane spanning or membrane bound polypeptide or may interact (e.g., via protein-protein interactions) with a membrane spanning or membrane bound polypeptide. Such a technique may be termed "Anchored Periplasmic Expression" or "APEx".

The periplasmic compartment is contained between the inner and outer membranes of Gram negative cells (see, e.g., Oliver, 1996). As a sub-cellular compartment, it is subject to variations in size, shape and content that accompany the growth and division of the cell. Within a framework of peptidoglycan heteroploymer is a dense mileau of periplasmic proteins and little water, lending a gel-like consistency to the compartment (Hobot et al., 1984; van Wielink and Duine, 1990). The peptidoglycan is polymerized to different extents depending on the proximity to the outer membrane, close-up it forms the murein sacculus that affords cell shape and resistance to osmotic lysis.

The outer membrane (see Nikaido, 1996) is composed of phospholipids, porin proteins and, extending into the medium, lipopolysaccharide (LPS). The molecular basis of outer membrane integrity resides with LPS ability to bind divalent cations ($Mg^{2+}$ and $Ca^{2+}$) and link each other electrostatically to form a highly ordered quasi-crystalline ordered "tiled roof" on the surface (Labischinski et al., 1985). The membrane forms a very strict permeability barrier allowing passage of molecules no greater than around 650 Da (Burman et al., 1972; Decad and Nikaido, 1976) via the porins. The large water filled porin channels are primarily responsible for allowing free passage of mono and disaccharides, ions and amino acids in to the periplasm compartment (Nikaido and Nakae, 1979; Nikaido and Vaara, 1985). With such strict physiological regulation of access by molecules to the periplasm it may appear, at first glance, inconceivable that large ligands (i.e., larger than the 650 Da exclusion limit) could be employed in screening methods. However, the inventors have shown that ligands greater than 2000 Da in size can diffuse into the periplasm without disruption of the periplasmic membrane. Such diffusion can be aided by one or more treatments of a bacterial cell, thereby rendering the outer membrane more permeable, as is described herein below.

II. PERMEABILIZATION OF THE OUTER MEMBRANE

In one embodiment of the invention, methods are employed for increasing the permeability of the outer membrane to one or more labeled ligand. This can allow screening access of labeled ligands otherwise unable to cross the outer membrane. However, certain classes of molecules, for example, hydrophobic antibiotics larger than the 650 Da exclusion limit, can diffuse through the bacterial outer membrane itself, independent of membrane porins (Farmer et al., 1999). The process may actually permeabilize the membrane on so doing (Jouenne and Junter, 1990). Such a mechanism has been adopted to selectively label the periplasmic loops of a cytoplasmic membrane protein in vivo with a polymyxin B nonapeptide (Wada et al., 1999). Also, certain long chain phosphate polymers (100 Pi) appear to bypass the normal molecular sieving activity of the outer membrane altogether (Rao and Torriani, 1988).

Conditions have been identified that lead to the permeation of ligands into the periplasm without loss of viability or release of the expressed proteins from the cells, but the invention may be carried out without maintenance of the outer membrane. As demonstrated herein Fc domains expressed or anchored candidate binding polypeptides in the periplasmic space the need for maintenance of the outer membrane (as a barrier to prevent the leakage of the biding protein from the cell) to detect bound labeled ligand is removed. As a result, cells expressing binding proteins anchored to the outer (periplasmic) face of the cytoplasmic membrane can be fluorescently labeled simply by incubating with a solution of fluorescently labeled ligand in cells that either have a partially permeabilized membrane or a nearly completely removed outer membrane.

The permeability of the outer membrane of different strains of bacterial hosts can vary widely. It has been shown previously that increased permeability due to OmpF overexpression was caused by the absence of a histone like protein resulting in a decrease in the amount of a negative regulatory mRNA for OmpF translation (Painbeni et al., 1997). Also, DNA replication and chromosomal segregation is known to rely on intimate contact of the replisome with the inner membrane, which itself contacts the outer membrane at numerous points. A preferred host for library screening applications is *E. coli* ABLEC strain, which additionally has mutations that reduce plasmid copy number.

Treatments such as hyperosmotic shock can improve labeling significantly. It is known that many agents including, calcium ions (Bukau et al., 1985) and even Tris buffer (Irvin et al., 1981) alter the permeability of the outer-membrane. Further, phage infection stimulates the labeling process. Both the filamentous phage inner membrane protein pIII and the large multimeric outer membrane protein pIV can alter membrane permeability (Boeke et al., 1982) with mutants in pIV known to improve access to maltodextrins normally excluded (Marciano et al., 1999). Using the techniques of the invention, comprising a judicious combination of strain, salt and phage, a high degree of permeability may be achieved (Daugherty et al., 1999). Cells comprising anchored or periplasm-associated polypeptides bound to fluorescently labeled ligands can then be easily isolated from cells that express binding proteins without affinity for the labeled ligand using flow cytometry or other related techniques. However, in some cases, it will be desired to use less disruptive techniques in order to maintain the viability of cells. EDTA and Lysozyme treatments may also be useful in this regard.

III. ANTIBODY-BINDING POLYPEPTIDES

In certain aspects the invention concerns methods for identifying antibody Fc domains with a specific affinity for antibody-binding polypeptide such as an Fc receptor. A variety of Fc receptors are well known in the art and some examples of receptors are listed below in Table 1.

TABLE 1

Selected FcR Polypeptides

| Protein name | Gene name | Description | Organisms | Length (aa) | Reference |
|---|---|---|---|---|---|
| Fc-gamma RII-a (CD32) | FCGR2A | Low affinity immunoglobulin gamma Fc region receptor II-a precursor | *Homo sapiens* (Human) | 317 | (Stuart et al., 1987) |
| Fc-gamma RII-a | FCGR2A | Low affinity immunoglobulin gamma Fc region receptor II-a precursor | *Pan troglodytes* (Chimpanzee) | 316 | |
| Fc-gamma RII-b | FCGR2B | Low affinity immunoglobulin gamma Fc region receptor II-b precursor | *Homo sapiens* (Human) | 310 | (Stuart et al., 1989) |
| Fc-gamma RII-c | FCGR2C | Low affinity immunoglobulin gamma Fc region receptor II-c precursor | *Homo sapiens* (Human) | 323 | (Stuart et al., 1989) |
| Fc-gamma RIIIa | FCGR3A | Low affinity immunoglobulin gamma Fc region receptor III-A precursor | *Homo sapiens* (Human) | 254 | (Ravetch and Perussia, 1989) |
| Fc-gamma RIIIb | FCGR3B | Low affinity immunoglobulin gamma Fc region receptor III-B precursor | *Homo sapiens* (Human) | 233 | (Ravetch and Perussia, 1989) |
| Fc-gamma RI (CD64) | FCGR1A | High affinity immunoglobulin gamma Fc receptor I precursor | *Homo sapiens* (Human) | 374 | (Allen and Seed, 1988) |
| Fc-gamma RI | Fcgr1 | High affinity immunoglobulin gamma Fc receptor I precursor | *Mus musculus* (Mouse) | 404 | (Sears et al., 1990) |
| Fc-gamma RII | FCGR2 | Low affinity immunoglobulin gamma Fc region receptor II precursor | *Bos taurus* (Bovine) | 296 | (Zhang et al., 1994) |
| Fc-gamma RII | FCGR2 | Low affinity immunoglobulin gamma Fc region receptor II precursor | *Cavia porcellus* (Guinea pig) | 341 | (Tominaga et al., 1990) |
| Fc-gamma RII | Fcgr2 | Low affinity immunoglobulin gamma Fc region receptor II precursor | *Mus musculus* (Mouse) | 330 | (Ravetch et al., 1986) |
| Fc-gamma RII | Fcgr2 | Low affinity immunoglobulin gamma Fc region receptor II precursor | *Rattus norvegicus* (Rat) | 285 | (Bocek and Pecht, 1993) |
| Fc-gamma RIII | FCGR3 | Low affinity immunoglobulin gamma Fc region receptor III precursor | *Bos taurus* (Bovine) | 250 | (Collins et al., 1997) |
| Fc-gamma RIII | FCGR3 | Low affinity immunoglobulin gamma Fc region receptor | *Macaca fascicularis* (Crab eating macaque) | 254 | |

TABLE 1-continued

Selected FcR Polypeptides

| Protein name | Gene name | Description | Organisms | Length (aa) | Reference |
|---|---|---|---|---|---|
| | | III precursor | (Cynomolgus monkey) | | |
| Fc-gamma RIII | Fcgr3 | Low affinity immunoglobulin gamma Fc region receptor III precursor | Mus musculus (Mouse) | 261 | (Ravetch et al., 1986) |
| Fc-gamma RIII | FCGR3 | Low affinity immunoglobulin gamma Fc region receptor III precursor | Sus scrofa (Pig) | 257 | (Halloran et al., 1994) |
| Fc-gamma RIII | Fcgr3 | Low affinity immunoglobulin gamma Fc region receptor III precursor | Rattus norvegicus (Rat) | 267 | (Zeger et al., 1990) |
| FcRn | FCGRT | IgG receptor transporter FcRn large subunit p51 precursor | Homo sapiens (Human) | 365 | |
| FcRn | FCGRT | IgG receptor transporter FcRn large subunit p51 precursor | Macaca fascicularis (Crab eating macaque) (Cynomolgus monkey) | 365 | |
| FcRn | Fcgrt | IgG receptor transporter FcRn large subunit p51 precursor | Mus musculus (Mouse) | 365 | (Ahouse et al., 1993) |
| FcRn | Fcgrt | IgG receptor transporter FcRn large subunit p51 precursor | Rattus norvegicus (Rat) | 366 | (Simister and Mostov, 1989) |
| MRP protein | mrp4 | Fibrinogen- and Ig-binding protein precursor | Streptococcus pyogenes | 388 | (Stenberg et al., 1992) |
| Protein B | | cAMP factor | Streptococcus agalactiae | 226 | (Ruhlmann et al., 1988) |
| protein A | spa | Immunoglobulin G-binding protein A precursor | Staphylococcus aureus (strain NCTC 8325) | 516 | (Uhlen et al., 1984) |
| protein A | spa | Immunoglobulin G-binding protein A precursor | Staphylococcus aureus | 508 | (Shuttleworth et al., 1987) |
| protein A | spa | Immunoglobulin G-binding protein A precursor | Staphylococcus aureus (strain Mu50/ATCC 700699) | 450 | (Kuroda et al., 2001) |
| protein A | spa | Immunoglobulin G-binding protein A precursor | Staphylococcus aureus (strain N315) | 450 | (Kuroda et al., 2001) |
| protein G | spg | Immunoglobulin G-binding protein G precursor | Streptococcus sp. group G | 448 | (Fahnestock et al., 1986) |
| protein G | spg | Immunoglobulin G-binding protein G precursor | Streptococcus sp. group G | 593 | (Olsson et al., 1987) |
| protein H | | Immunoglobulin G-binding protein H precursor | Streptococcus pyogenes serotype M1 | 376 | (Gomi et al., 1990) |

TABLE 1-continued

Selected FcR Polypeptides

| Protein name | Gene name | Description | Organisms | Length (aa) | Reference |
|---|---|---|---|---|---|
| Protein sbi | sbi | Immunoglobulin G-binding protein sbi precursor | *Staphylococcus aureus* (strain NCTC 8325-4) | 436 | (Zhang et al., 1998) |
| Allergen Asp fl 1 | | Allergen Asp fl 1 causes an allergic reaction in human. Binds to IgE and IgG | *Aspergillus flavus* | 32 | |
| Allergen Asp fl 2 | | Allergen Asp fl 2 causes an allergic reaction in human. Binds to IgE and IgG | *Aspergillus flavus* | 20 | |
| Allergen Asp fl 3 | | Allergen Asp fl 3 causes an allergic reaction in human. Binds to IgE and IgG | *Aspergillus flavus* | 32 | |
| Fc-epsilon RI | | IgE receptor displayed on Mast cells, Eosinophils and Basophils | *Homo sapiens* (Human) | | |
| Fc-alpha RI (CD86) | | IgA (IgA1, IgA2) receptor displayed on Macrophages | *Homo sapiens* (Human) | | |
| C1q | C1QA NP_057075.1, C1QB NP_000482.3, C1QC NP_758957.1 | C1q is multimeric complex that binds to antibody Fc composed of 6 A chains, 6 B chains and 6 C chains | *Homo sapiens* (Human) | | |

IV. ANTIBODY FC LIBRARIES

Examples of techniques that could be employed in conjunction with the invention for creation of diverse antibody Fc domains and/or antibodies comprising such domains may employ techniques similar to those for expression of immunoglobulin heavy chain libraries described in U.S. Pat. No. 5,824,520.

V. SCREENING ANTIBODY FC DOMAINS

The present invention provides methods for identifying molecules capable of binding to a particular FcR. The binding polypeptides screened may comprise a large library of diverse candidate Fc domains, or, alternatively, may comprise particular classes of Fc domains (e.g., engineered point mutations or amino acid insertions) selected with an eye towards structural attributes that are believed to make them more likely to bind the target ligand. In one embodiment of the invention, the candidate binding protein is an intact antibody, or a fragment or portion thereof comprising an Fc domain.

To identify a candidate Fc domain capable of binding a target ligand in accordance with the invention, one may carry out the steps of: providing a population of Gram negative bacterial cells that express a distinct antibody Fc domain; admixing the bacteria or phages and at least a first labeled or immobilized target ligand (FcR polypeptide) capable of contacting the antibody and identifying at least a first bacterium expressing a molecule capable of binding the target ligand.

In some aspects of the aforementioned method, the binding between antibody Fc domain and a labeled FcR polypeptide will prevent diffusing out of a bacterial cell. In this way, molecules of the labeled ligand can be retained in the periplasm of the bacterium comprising a permeablized outer membrane. Alternatively, the periplasm can be removed, whereby the Fc domain will cause retention of the bound candidate molecule since Fc domains are shown to associate with the inner membrane. The labeling may then be used to isolate the cell expressing a binding polypeptide capable of binding the FcR polypeptide, and in this way, the gene encoding the Fc domain polypeptide isolated. The molecule capable of binding the target ligand may then be produced in large quantities using in vivo or ex vivo expression methods, and then used for any desired application, for example, for diagnostic or therapeutic applications, as described below. Furthermore, it will be understood that isolated antibody Fc domains identified may be used to construct an antibody fragment or full-length antibody comprising an antigen binding domain.

A. Cloning of Fc Domain Coding Sequences

The binding affinity of an antibody Fc or other binding protein can, for example, be determined by the Scatchard analysis of Munson & Pollard (1980). Alternatively, binding affinity can be determined by surface plasmon resonance or any other well known method for determining the kinetics and equilibrium constants for protein:protein interactions. After a bacterial cell is identified that produces molecules of the desired specificity, affinity, and/or activity, the corresponding coding sequence may be cloned. In this manner, DNA encoding the molecule can be isolated and sequenced using conventional procedures (e.g., by using oligonucleotide probes that are capable of binding specifically to genes encoding the antibody or binding protein).

Once isolated, the antibody Fc domain DNA may be placed into expression vectors, which can then transfected into host cells such as bacteria. The DNA also may be modified, for example, by the addition of sequence for human heavy and light chain variable domains, or by covalently joining to the immunoglobulin coding sequence all or part of the coding sequence for a non-immunoglobulin polypeptide. In that manner, "chimeric" or "hybrid" binding proteins are prepared to have the desired binding specificity. For instance, an identified antibody Fc domain may be fused to a therapeutic polypeptide or a toxin and used to target cells (in vitro or in vivo) that express a particular FcR.

Chimeric or hybrid Fc domains also may be prepared in vitro using known methods in synthetic protein chemistry, including those involving crosslinking agents. For example, targeted-toxins may be constructed using a disulfide exchange reaction or by forming a thioether bond. Examples of suitable reagents for this purpose include iminothiolate and methyl-4-mercaptobutyrimidate.

It will be understood by those of skill in the art that nucleic acids may be cloned from viable or inviable cells. In the case of inviable cells, for example, it may be desired to use amplification of the cloned DNA, for example, using PCR. This may also be carried out using viable cells either with or without further growth of cells.

B. Labeled Ligands

In one embodiment of the invention, an Fc domain is isolated which has affinity for a labeled FcR polypeptide. By permeabilization and/or removal of the periplasmic membrane of a Gram negative bacterium in accordance with the invention, labeled ligands of potentially any size may be screened. In the absence of removal of the periplasmic membrane, it will typically be preferable that the labeled ligand is less that 50,000 Da in size in order to allow efficient diffusion of the ligand across the bacterial periplasmic membrane.

As indicated above, it will typically be desired in accordance with the invention to provide an FcR polypeptide which has been labeled with one or more detectable agent(s). This can be carried out, for example, by linking the ligand to at least one detectable agent to form a conjugate. For example, it is conventional to link or covalently bind or complex at least one detectable molecule or moiety. A "label" or "detectable label" is a compound and/or element that can be detected due to specific functional properties, and/or chemical characteristics, the use of which allows the ligand to which it is attached to be detected, and/or further quantified if desired. Examples of labels which could be used with the invention include, but are not limited to, enzymes, radiolabels, haptens, fluorescent labels, phosphorescent molecules, chemiluminescent molecules, chromophores, luminescent molecules, photoaffinity molecules, colored particles or ligands, such as biotin.

In one embodiment of the invention, a visually-detectable marker is used such that automated screening of cells for the label can be carried out. In particular, fluorescent labels are beneficial in that they allow use of flow cytometry for isolation of cells expressing a desired binding protein or antibody. Examples of agents that may be detected by visualization with an appropriate instrument are known in the art, as are methods for their attachment to a desired ligand (see, e.g., U.S. Pat. Nos. 5,021,236; 4,938,948; and 4,472,509, each incorporated herein by reference). Such agents can include paramagnetic ions; radioactive isotopes; fluorochromes; NMR-detectable substances and substances for X-ray imaging. Types of fluorescent labels that may be used with the invention will be well known to those of skill in the art and include, for example, Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5,6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, TAMRA, TET, Tetramethylrhodamine, and/or Texas Red.

Magnetic screening techniques are well known to those of skill in the art (see, for example, U.S. Pat. Nos. 4,988,618, 5,567,326 and 5,779,907). Examples of paramagnetic ions that could be used as labels in accordance with such techniques include ions such as chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and/or erbium (III). Ions useful in other contexts include but are not limited to lanthanum (III), gold (III), lead (II), and especially bismuth (III).

Another type of FcR conjugate contemplated in the present invention are those where the ligand is linked to a secondary binding molecule and/or to an enzyme (an enzyme tag) that will generate a colored product upon contact with a chromogenic substrate. Examples of such enzymes include urease, alkaline phosphatase, (horseradish) hydrogen peroxidase or glucose oxidase. I n such instances, it will be desired that cells selected remain viable. Preferred secondary binding ligands are biotin and/or avidin and streptavidin compounds. The use of such labels is well known to those of skill in the art and are described, for example, in U.S. Pat. Nos. 3,817,837; 3,850,752; 3,939,350; 3,996,345; 4,277,437; 4,275,149 and 4,366,241; each incorporated herein by reference.

Molecules containing azido groups also may be used to form covalent bonds to proteins through reactive nitrene intermediates that are generated by low intensity ultraviolet light (Potter & Haley, 1983). In particular, 2- and 8-azido analogues of purine nucleotides have been used as site-directed photoprobes to identify nucleotide-binding proteins in crude cell extracts (Owens & Haley, 1987; Atherton et al., 1985). The 2- and 8-azido nucleotides have also been used to map nucleotide-binding domains of purified proteins (Khatoon et al., 1989; King et al., 1989; and Dholakia et al., 1989) and may be used as ligand binding agents.

Labeling can be carried out by any of the techniques well known to those of skill in the art. For instance, FcR polypeptides can be labeled by contacting the ligand with the desired label and a chemical oxidizing agent such as sodium hypochlorite, or an enzymatic oxidizing agent, such as lactoperoxidase. Similarly, a ligand exchange process could be used. Alternatively, direct labeling techniques may be used, e.g., by incubating the label, a reducing agent such as $SNCl_2$, a buffer solution such as sodium-potassium phthalate solution, and the ligand. Intermediary functional groups on the ligand could also be used, for example, to bind labels to a ligand in the presence of diethylenetriaminepentaacetic acid (DTPA) or ethylene diaminetetracetic acid (EDTA).

Other methods are also known in the art for the attachment or conjugation of a ligand to its conjugate moiety.

Some attachment methods involve the use of an organic chelating agent such as diethylenetriaminepentaacetic acid anhydride (DTPA); ethylenetriaminetetraacetic acid; N-chloro-p-toluenesulfonamide; and/or tetrachloro-3α-6α-diphenylglycouril-3 attached to the ligand (U.S. Pat. Nos. 4,472,509 and 4,938,948, each incorporated herein by reference). FcR polypeptides also may be reacted with an enzyme in the presence of a coupling agent such as glutaraldehyde or periodate. Conjugates with fluorescein markers can be prepared in the presence of these coupling agents or by reaction with an isothiocyanate. In U.S. Pat. No. 4,938,948, imaging of breast tumors is achieved using monoclonal antibodies and the detectable imaging moieties are bound to the antibody using linkers such as methyl-p-hydroxybenzimidate or N-succinimidyl-3-(4-hydroxyphenyl)propionate. In still further aspects an FcR polypeptide may be fused to a reporter protein such as an enzyme as described supra or a fluorescence protein.

The ability to specifically label periplasmic expressed proteins with appropriate fluorescent ligands also has applications other than library screening. Specifically labeling with fluorescent ligands and flow cytometry can be used for monitoring production of Fc domains during protein manufacturing.

Once an Fc domain has been isolated in accordance with the invention, it may be desired to link the molecule to at least one agent to form a conjugate to enhance the utility of that molecule. For example, in order to increase the efficacy of Fc domains or antibody molecules as diagnostic or therapeutic agents, it is conventional to link or covalently bind or complex at least one desired molecule or moiety. Such a molecule or moiety may be, but is not limited to, at least one effector or reporter molecule. Effecter molecules comprise molecules having a desired activity, e.g., cytotoxic activity. Non-limiting examples of effector molecules which have been attached to antibodies include toxins, anti-tumor agents, therapeutic enzymes, radio-labeled nucleotides, antiviral agents, chelating agents, cytokines, growth factors, and oligo- or poly-nucleotides. By contrast, a reporter molecule is defined as any moiety which may be detected using an assay. Techniques for labeling such a molecule are known to those of skill in the art and have been described herein above.

Labeled binding proteins such as Fc domains which have been prepared in accordance with the invention may also then be employed, for example, in immunodetection methods for binding, purifying, removing, quantifying and/or otherwise generally detecting biological components such as protein(s), polypeptide(s) or peptide(s). Some immunodetection methods include enzyme linked immunosorbent assay (ELISA), radioimmunoassay (RIA), immunoradiometric assay, fluoroimmunoassay, chemiluminescent assay, bioluminescent assay, and Western blot to mention a few. The steps of various useful immunodetection methods have been described in the scientific literature, such as, e.g., Doolittle and Ben-Zeev, 1999; Gulbis and Galand, 1993; and De Jager R et al., 1993, each incorporated herein by reference. Such techniques include binding assays such as the various types of enzyme linked immunosorbent assays (ELISAs) and/or radioimmunoassays (RIA) known in the art.

The Fc domain molecules, including antibodies, prepared in accordance with the present invention may also, for example, in conjunction with both fresh-frozen and/or formalin-fixed, paraffin-embedded tissue blocks prepared for study by immunohistochemistry (IHC). The method of preparing tissue blocks from these particulate specimens has been successfully used in previous IHC studies of various prognostic factors, and/or is well known to those of skill in the art (Abbondanzo et al., 1990).

VI. AUTOMATED SCREENING WITH FLOW CYTOMETRY

In one embodiment of the invention, fluorescence activated cell sorting (FACS) screening or other automated flow cytometric techniques may be used for the efficient isolation of a bacterial cell comprising a labeled ligand bound to an Fc domain. Instruments for carrying out flow cytometry are known to those of skill in the art and are commercially available to the public. Examples of such instruments include FACS Star Plus, FACScan and FACSort instruments from Becton Dickinson (Foster City, Calif.) Epics C from Coulter Epics Division (Hialeah, Fla.) and MOFLO™ from Cytomation (Colorado Springs, Co).

Flow cytometric techniques in general involve the separation of cells or other particles in a liquid sample. Typically, the purpose of flow cytometry is to analyze the separated particles for one or more characteristics thereof, for example, presence of a labeled ligand or other molecule. The basis steps of flow cytometry involve the direction of a fluid sample through an apparatus such that a liquid stream passes through a sensing region. The particles should pass one at a time by the sensor and are categorized base on size, refraction, light scattering, opacity, roughness, shape, fluorescence, etc.

Rapid quantitative analysis of cells proves useful in biomedical research and medicine. Apparati permit quantitative multiparameter analysis of cellular properties at rates of several thousand cells per second. These instruments provide the ability to differentiate among cell types. Data are often displayed in one-dimensional (histogram) or two-dimensional (contour plot, scatter plot) frequency distributions of measured variables. The partitioning of multiparameter data files involves consecutive use of the interactive one- or two-dimensional graphics programs.

Quantitative analysis of multiparameter flow cytometric data for rapid cell detection consists of two stages: cell class characterization and sample processing. In general, the process of cell class characterization partitions the cell feature into cells of interest and not of interest. Then, in sample processing, each cell is classified in one of the two categories according to the region in which it falls. Analysis of the class of cells is very important, as high detection performance may be expected only if an appropriate characteristic of the cells is obtained.

Not only is cell analysis performed by flow cytometry, but so too is sorting of cells. In U.S. Pat. No. 3,826,364, an apparatus is disclosed which physically separates particles, such as functionally different cell types. In this machine, a laser provides illumination which is focused on the stream of particles by a suitable lens or lens system so that there is highly localized scatter from the particles therein. In addition, high intensity source illumination is directed onto the stream of particles for the excitation of fluorescent particles in the stream. Certain particles in the stream may be selectively charged and then separated by deflecting them into designated receptacles. A classic form of this separation is via fluorescent-tagged antibodies, which are used to mark one or more cell types for separation.

Other examples of methods for flow cytometry that could include, but are not limited to, those described in U.S. Pat. Nos. 4,284,412; 4,989,977; 4,498,766; 5,478,722; 4,857,451; 4,774,189; 4,767,206; 4,714,682; 5,160,974; and 4,661,913, each of the disclosures of which are specifically incorporated herein by reference.

For the present invention, an important aspect of flow cytometry is that multiple rounds of screening can be carried out sequentially. Cells may be isolated from an initial round of sorting and immediately reintroduced into the flow cytometer and screened again to improve the stringency of the screen. Another advantage known to those of skill in the art is that nonviable cells can be recovered using flow cytometry. Since flow cytometry is essentially a particle sorting technology, the ability of a cell to grow or propagate is not necessary. Techniques for the recovery of nucleic acids from such non-viable cells are well known in the art and may include, for example, use of template-dependent amplification techniques including PCR.

VII. NUCLEIC ACID-BASED EXPRESSION SYSTEMS

Nucleic acid-based expression systems may find use, in certain embodiments of the invention, for the expression of recombinant proteins. For example, one embodiment of the invention involves transformation of Gram negative bacteria with the coding sequences for an antibody Fc domain, or preferably a plurality of distinct Fc domains.

A. Methods of Nucleic Acid Delivery

Certain aspects of the invention may comprise delivery of nucleic acids to target cells (e.g., gram negative bacteria). For example, bacterial host cells may be transformed with nucleic acids encoding candidate Fc domains potentially capable binding an FcR. In particular embodiments of the invention, it may be desired to target the expression to the periplasm of the bacteria. Transformation of eukaryotic host cells may similarly find use in the expression of various candidate molecules identified as capable of binding a target ligand.

Suitable methods for nucleic acid delivery for transformation of a cell are believed to include virtually any method by which a nucleic acid (e.g., DNA) can be introduced into such a cell, or even an organelle thereof. Such methods include, but are not limited to, direct delivery of DNA such as by injection (U.S. Pat. Nos. 5,994,624, 5,981,274, 5,945, 100, 5,780,448, 5,736,524, 5,702,932, 5,656,610, 5,589,466 and 5,580,859, each incorporated herein by reference), including microinjection (Harland and Weintraub, 1985; U.S. Pat. No. 5,789,215, incorporated herein by reference); by electroporation (U.S. Pat. No. 5,384,253, incorporated herein by reference); by calcium phosphate precipitation (Graham and Van Der Eb, 1973; Chen and Okayama, 1987; Rippe et al., 1990); by using DEAE-dextran followed by polyethylene glycol (Gopal, 1985); by direct sonic loading (Fechheimer et al., 1987); by liposome mediated transfection (Nicolau and Sene, 1982; Fraley et al., 1979; Nicolau et al., 1987; Wong et al., 1980; Kaneda et al., 1989; Kato et al., 1991); by microprojectile bombardment (PCT Application Nos. WO 94/09699 and 95/06128; U.S. Pat. Nos. 5,610,042; 5,322,783, 5,563,055, 5,550,318, 5,538,877 and 5,538,880, and each incorporated herein by reference); or by agitation with silicon carbide fibers (Kaeppler et al., 1990; U.S. Pat. Nos. 5,302,523 and 5,464,765, each incorporated herein by reference); by desiccation/inhibition-mediated DNA uptake (Potrykus et al., 1985). Through the application of techniques such as these, cells may be stably or transiently transformed.

1. Electroporation

In certain embodiments of the present invention, a nucleic acid is introduced into a cell via electroporation. Electroporation involves the exposure of a suspension of cells and DNA to a high-voltage electric discharge. In some variants of this method, certain cell wall-degrading enzymes, such as pectin-degrading enzymes, are employed to render the target recipient cells more susceptible to transformation by electroporation than untreated cells (U.S. Pat. No. 5,384,253, incorporated herein by reference). Alternatively, recipient cells can be made more susceptible to transformation by mechanical wounding.

2. Calcium Phosphate

In other embodiments of the present invention, a nucleic acid is introduced to the cells using calcium phosphate precipitation.

B. Vectors

Vectors may find use with the current invention, for example, in the transformation of a Gram negative bacterium with a nucleic acid sequence encoding a candidate Fc domain which one wishes to screen for ability to bind a target FcR. In one embodiment of the invention, an entire heterogeneous "library" of nucleic acid sequences encoding target polypeptides may be introduced into a population of bacteria, thereby allowing screening of the entire library. The term "vector" is used to refer to a carrier nucleic acid molecule into which a nucleic acid sequence can be inserted for introduction into a cell where it can be replicated. A nucleic acid sequence can be "exogenous," or "heterologous", which means that it is foreign to the cell into which the vector is being introduced or that the sequence is homologous to a sequence in the cell but in a position within the host cell nucleic acid in which the sequence is ordinarily not found. Vectors include plasmids, cosmids and viruses (e.g., bacteriophage). One of skill in the art may construct a vector through standard recombinant techniques, which are described in Maniatis et al., 1988 and Ausubel et al., 1994, both of which references are incorporated herein by reference.

The term "expression vector" refers to a vector containing a nucleic acid sequence coding for at least part of a gene product capable of being transcribed. In some cases, RNA molecules are then translated into a protein, polypeptide, or peptide. Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described infra.

1. Promoters and Enhancers

A "promoter" is a control sequence that is a region of a nucleic acid sequence at which initiation and rate of transcription are controlled. It may contain genetic elements at which regulatory proteins and molecules may bind such as RNA polymerase and other transcription factors. The phrases "operatively positioned," "operatively linked," "under control," and "under transcriptional control" mean that a promoter is in a correct functional location and/or orientation in relation to a nucleic acid sequence to control transcriptional initiation and/or expression of that sequence. A promoter may or may not be used in conjunction with an "enhancer," which refers to a cis-acting regulatory sequence involved in the transcriptional activation of a nucleic acid sequence.

A promoter may be one naturally associated with a gene or sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other prokaryotic cell, and promoters or enhancers not "naturally occurring," i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. Nos. 4,683,202, 5,928,906, each incorporated herein by reference).

Naturally, it will be important to employ a promoter and/or enhancer that effectively directs the expression of the DNA segment in the cell type chosen for expression. One example of such promoter that may be used with the invention is the *E. coli* arabinose or T7 promoter. Those of skill in the art of molecular biology generally are familiar with the use of promoters, enhancers, and cell type combinations for protein expression, for example, see Sambrook et al. (1989), incorporated herein by reference. The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

2. Initiation Signals and Internal Ribosome Binding Sites

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

3. Multiple Cloning Sites

Vectors can include a multiple cloning site (MCS), which is a nucleic acid region that contains multiple restriction enzyme sites, any of which can be used in conjunction with standard recombinant technology to digest the vector (see Carbonelli et al., 1999, Levenson et al., 1998, and Cocea, 1997, incorporated herein by reference.) "Restriction enzyme digestion" refers to catalytic cleavage of a nucleic acid molecule with an enzyme that functions only at specific locations in a nucleic acid molecule. Many of these restriction enzymes are commercially available. Use of such enzymes is understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

4. Termination Signals

The vectors or constructs prepared in accordance with the present invention will generally comprise at least one termination signal. A "termination signal" or "terminator" is comprised of the DNA sequences involved in specific termination of an RNA transcript by an RNA polymerase. Thus, in certain embodiments, a termination signal that ends the production of an RNA transcript is contemplated. A terminator may be necessary in vivo to achieve desirable message levels.

Terminators contemplated for use in the invention include any known terminator of transcription described herein or known to one of ordinary skill in the art, including but not limited to, for example, rhp dependent or rho independent terminators. In certain embodiments, the termination signal may be a lack of transcribable or translatable sequence, such as due to a sequence truncation.

5. Origins of Replication

In order to propagate a vector in a host cell, it may contain one or more origins of replication sites (often termed "ori"), which is a specific nucleic acid sequence at which replication is initiated.

6. Selectable and Screenable Markers

In certain embodiments of the invention, cells containing a nucleic acid construct of the present invention may be identified in vitro or in vivo by including a marker in the expression vector. Such markers would confer an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is colorimetric analysis, are also contemplated. Alternatively, screenable enzymes such as chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art.

C. Host Cells

In the context of expressing a heterologous nucleic acid sequence, "host cell" refers to a prokaryotic cell, and it includes any transformable organism that is capable of replicating a vector and/or expressing a heterologous gene encoded by a vector. A host cell can, and has been, used as a recipient for vectors. A host cell may be "transfected" or "transformed," which refers to a process by which exogenous nucleic acid is transferred or introduced into the host cell. A transformed cell includes the primary subject cell and its progeny.

In particular embodiments of the invention, a host cell is a Gram negative bacterial cell. These bacteria are suited for use with the invention in that they posses a periplasmic space between the inner and outer membrane and, particularly, the aforementioned inner membrane between the periplasm and cytoplasm, which is also known as the cytoplasmic membrane. As such, any other cell with such a periplasmic space could be used in accordance with the invention. Examples of Gram negative bacteria that may find use with the invention may include, but are not limited to, E. coli, Pseudomonas aeruginosa, Vibrio cholera, Salmonella typhimurium, Shigella flexneri, Haemophilus influenza, Bordotella pertussi, Erwinia amylovora, Rhizobium sp. The Gram negative bacterial cell may be still further defined as bacterial cell which has been transformed with the coding sequence of a fusion polypeptide comprising a candidate binding polypeptide capable of binding a selected ligand. The polypeptide is anchored to the outer face of the cytoplasmic membrane, facing the periplasmic space, and may comprise an antibody coding sequence or another sequence. One means for expression of the polypeptide is by attaching a leader sequence to the polypeptide capable of causing such directing.

Numerous prokaryotic cell lines and cultures are available for use as a host cell, and they can be obtained through the American Type Culture Collection (ATCC), which is an organization that serves as an archive for living cultures and genetic materials (www.atcc.org). An appropriate host can be determined by one of skill in the art based on the vector backbone and the desired result. A plasmid or cosmid, for example, can be introduced into a prokaryote host cell for replication of many vectors. Bacterial cells used as host cells for vector replication and/or expression include DH5α, JM109, and KC8, as well as a number of commercially available bacterial hosts such as SURE® Competent Cells and SOLOPACK™ Gold Cells (STRATAGENE®, La Jolla). Alternatively, bacterial cells such as E. coli LE392 could be used as host cells for bacteriophage.

Many host cells from various cell types and organisms are available and would be known to one of skill in the art. Similarly, a viral vector may be used in conjunction with a prokaryotic host cell, particularly one that is permissive for replication or expression of the vector. Some vectors may employ control sequences that allow it to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of vectors, as well as production of the nucleic acids encoded by vectors and their cognate polypeptides, proteins, or peptides.

D. Expression Systems

Numerous expression systems exist that comprise at least a part or all of the compositions discussed above. Such systems could be used, for example, for the production of a polypeptide product identified in accordance with the invention as capable of binding a particular ligand. Prokaryote-based systems can be employed for use with the present invention to produce nucleic acid sequences, or their cognate polypeptides, proteins and peptides. Many such systems are commercially and widely available. Other examples of expression systems comprise of vectors containing a strong prokaryotic promoter such as T7, Tac, Trc, BAD, lambda pL, Tetracycline or Lac promoters, the pET Expression System and an E. coli expression system.

E. Candidate Binding Proteins and Antibodies

In certain aspects of the invention, antibody Fc domains are expressed on the cytoplasmic or in the periplasmic space membrane of a host bacterial cell. By expression of a heterogeneous population of such Fc domains, those polypeptides having a high affinity for a target ligand (FcR) may be identified. The identified Fc domains may then be used in various diagnostic or therapeutic applications, as described herein.

As used herein, the term "Fc domain" is intended to refer broadly to any immunoglobulin Fc region such as an IgG, IgM, IgA, IgD or IgE Fc. The techniques for preparing and using various antibody-based constructs and fragments are well known in the art. Means for preparing and characterizing antibodies are also well known in the art (See, e.g., Antibodies: A Laboratory Manual, Cold Spring Harbor Laboratory, 1988; incorporated herein by reference).

Once an antibody having affinity for a target ligand is identified, the Fc domain may be purified, if desired, using filtration, centrifugation and various chromatographic methods such as HPLC or affinity chromatography. Alternatively, Fc domains encompassed by the present invention can be synthesized using an automated peptide synthesizer.

VIII. MANIPULATION AND DETECTION OF NUCLEIC ACIDS

In certain embodiments of the invention, it may be desired to employ one or more techniques for the manipulation, isolation and/or detection of nucleic acids. Such techniques may include, for example, the preparation of vectors for transformation of host cells as well as methods for cloning selected nucleic acid segments from a transgenic cell. Methodology for carrying out such manipulations will be well known to those of skill in the art in light of the instant disclosure.

Nucleic acids used as a template for amplification may be isolated from cells, tissues or other samples according to standard methodologies (Sambrook et al., 1989). In certain embodiments, analysis may be performed on whole cell or tissue homogenates or biological fluid samples without substantial purification of the template nucleic acid. The nucleic acid may be genomic DNA or fractionated or whole cell RNA. Where RNA is used, it may be desired to first convert the RNA to a complementary DNA.

The term "primer," as used herein, is meant to encompass any nucleic acid that is capable of priming the synthesis of a nascent nucleic acid in a template-dependent process. Typically, primers are oligonucleotides from ten to twenty and/or thirty base pairs in length, but longer sequences can be employed. Primers may be provided in double-stranded and/or single-stranded form, although the single-stranded form is preferred.

Pairs of primers designed to selectively hybridize to nucleic acids corresponding to a selected nucleic acid sequence are contacted with the template nucleic acid under conditions that permit selective hybridization. Depending upon the desired application, high stringency hybridization conditions may be selected that will only allow hybridization to sequences that are completely complementary to the primers. In other embodiments, hybridization may occur under reduced stringency to allow for amplification of nucleic acids comprising one or more mismatches with the primer sequences. Once hybridized, the template-primer complex is contacted with one or more enzymes that facilitate template-dependent nucleic acid synthesis. Multiple rounds of amplification, also referred to as "cycles," are conducted until a sufficient amount of amplification product is produced.

The amplification product may be detected or quantified. In certain applications, the detection may be performed by visual means. Alternatively, the detection may involve indirect identification of the product via chemiluminescence, radioactive scintigraphy of incorporated radiolabel or fluorescent label or even via a system using electrical and/or thermal impulse signals (Affymax technology; Bellus, 1994).

A number of template dependent processes are available to amplify the oligonucleotide sequences present in a given template sample. One of the best known amplification methods is the polymerase chain reaction (referred to as PCR) which is described in detail in U.S. Pat. Nos. 4,683,195, 4,683,202 and 4,800,159, and in Innis et al., 1988, each of which is incorporated herein by reference in their entirety.

A reverse transcriptase PCR™ procedure may be performed to quantify the amount of mRNA amplified. Methods of reverse transcribing RNA into cDNA are well known (see Sambrook et al., 1989). Alternative methods for reverse transcription utilize thermostable DNA polymerases. These methods are described in WO 90/07641. Polymerase chain reaction methodologies are well known in the art. Representative methods of RT-PCR are described in U.S. Pat. No. 5,882,864.

Another method for amplification is ligase chain reaction ("LCR"), disclosed in European Application 320 308, incorporated herein by reference in its entirety. U.S. Pat. No. 4,883,750 describes a method similar to LCR for binding probe pairs to a target sequence. A method based on PCR oligonucleotide ligase assay (OLA), disclosed in U.S. Pat. No. 5,912,148, may also be used.

Alternative methods for amplification of target nucleic acid sequences that may be used in the practice of the present invention are disclosed in U.S. Pat. Nos. 5,843,650, 5,846,709, 5,846,783, 5,849,546, 5,849,497, 5,849,547, 5,858,652, 5,866,366, 5,916,776, 5,922,574, 5,928,905, 5,928,906, 5,932,451, 5,935,825, 5,939,291 and 5,942,391, GB Application No. 2 202 328, and in PCT Application No. PCT/US89/01025, each of which is incorporated herein by reference in its entirety.

Qbeta Replicase, described in PCT Application No. PCT/US87/00880, may also be used as an amplification method in the present invention. In this method, a replicative sequence of RNA that has a region complementary to that of a target is added to a sample in the presence of an RNA polymerase. The polymerase will copy the replicative sequence which may then be detected.

An isothermal amplification method, in which restriction endonucleases and ligases are used to achieve the amplification of target molecules that contain nucleotide 5'-[alpha-thio]-triphosphates in one strand of a restriction site may also be useful in the amplification of nucleic acids in the present invention (Walker et al., 1992). Strand Displacement Amplification (SDA), disclosed in U.S. Pat. No. 5,916,779, is another method of carrying out isothermal amplification of nucleic acids which involves multiple rounds of strand displacement and synthesis, i.e., nick translation.

Other nucleic acid amplification procedures include transcription-based amplification systems (TAS), including nucleic acid sequence based amplification (NASBA) and 3SR (Kwoh et al., 1989; Gingeras et al., PCT Application WO 88/10315, incorporated herein by reference in their entirety). European Application No. 329 822 disclose a nucleic acid amplification process involving cyclically synthesizing single-stranded RNA ("sRNA"), ssDNA, and double-stranded DNA (dsDNA), which may be used in accordance with the present invention.

PCT Application WO 89/06700 (incorporated herein by reference in its entirety) discloses a nucleic acid sequence amplification scheme based on the hybridization of a promoter region/primer sequence to a target single-stranded DNA ("ssDNA") followed by transcription of many RNA copies of the sequence. This scheme is not cyclic, i.e., new templates are not produced from the resultant RNA transcripts. Other amplification methods include "race" and "one-sided PCR" (Frohman, 1990; Ohara et al., 1989).

IX. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Reagents for Studies

Oligonucleotides primers (Table 2) and restriction endonucleases used to construct plasmids to display homodimeric protein IgG-Fc were obtained from Integrated DNA Technologies (Coralville, Iowa) and New England Biolabs (Ipswich, Mass.), respectively. Taq Polymerase and FITC protein labeling kit were from Invitrogen (Carlsbad, Calif.). Recombinant human FcγRI/CD64 was purchased from R&D Systems (Minneapolis, Minn.). Trehalose was obtained from Fisher Scientific (Fair Lawn, N.J.). Human IgG-Fc and Rabbit anti-ECS antibody peroxidase conjugated were from Bethyl Laboratories (Montgomery, Tex.). Digoxigenin-BODIPY (Digoxigenin-4,4-difluoro-5,7-dimethyl-4-bora-3a,4a-diaza-s-indacene-3-propionyl ethylenediamine) was synthesized as described previously (Harvey et al., 2004). PA-FITC was obtained from List Biological Laboratories (Campbell, Calif.). Protein A-FITC and analytical grades of all other chemical reagents were purchased from Sigma-Aldrich (St. Louis, Mo.) unless stated otherwise.

TABLE 2

| Oligonucleotide sequences (Underlining indicates the restriction enzyme sites) | |
|---|---|
| Primer Name | Primer nucleotide sequence (5' → 3') |
| STJ#16 | TTGTGAGCGGATAACAATTTC (SEQ ID NO: 8) |
| STJ#58 | CGAACT<u>GGCCCAGCCGGCC</u>ATCGCCCGGCTAGAGGAAAAAG (SEQ ID NO: 9) |

TABLE 2-continued

Oligonucleotide sequences (Underlining indicates the restriction enzyme sites)

| Primer Name | Primer nucleotide sequence (5' → 3') |
|---|---|
| STJ#59 | CGAACTGGCCCCCGAGGCCCGGTGGTTCATGACTTTCTGTTTAAG (SEQ ID NO: 10) |
| STJ#68 | GATATCGCGGCCGCACTGACCGACACCCTGCAGG (SEQ ID NO: 11) |
| STJ#69 | TTTTAGGGGTCGACTGCGGCGTGTGCCGCCAGGATGAAC (SEQ ID NO: 12) |
| STJ#74 | CGCAGCGAGGCCCAGCCGGCCATGGCGCAAGCTGCTCCCCCAAAGGC (SEQ ID NO: 13) |
| STJ#78 | CGCAGCGAGGCCCAGCCGGCCATGGCGATCCAGCGTACTCCAAAGATTC (SEQ ID NO: 14) |
| STJ#80 | CGCAATTCGGCCCCCGAGGCCCCAATGACCCCCATTGGTGAAGAG (SEQ ID NO: 15) |
| STJ#84 | CGCAATTCGGCCCCCGAGGCCCCCATGTCTCGATCCCACTTAAC (SEQ ID NO: 16) |
| STJ#86 | CAGCGTACTCCAAAGATTCAGGTTTACTCACGTCATCCAGCAGAGAATGGAAAG (SEQ ID NO: 17) |
| STJ#87 | CAGCAGAGAATGGAAAGTCAAATTTCCTGAATTGCTATGTGTCTGGGTTTCATC (SEQ ID NO: 18) |
| STJ#88 | CTATGTGTCTGGGTTTCATCCATCCGACATTGAAGTTGACTTACTGAAGAATGG (SEQ ID NO: 19) |
| STJ#89 | GTTGACTTACTGAAGAATGGAGAGAGAATTGAAAAAGTGGAGCATTCAGACTTG (SEQ ID NO: 20) |
| STJ#90 | GTACAAGAGATAGAAAGACCAGTCCTTGCTGAAAGACAAGTCTGAATGCTCCAC (SEQ ID NO: 21) |
| STJ#91 | ACTCATCTTTTTCAGTGGGGGTGAATTCAGTGTAGTACAAGAGATAGAAAGACC (SEQ ID NO: 22) |
| STJ#92 | CTGTGACAAAGTCACATGGTTCACACGGCAGGCATACTCATCTTTTTCAGTGGG (SEQ ID NO: 23) |
| STJ#93 | CATGTCTCGATCCCACTTAACTATCTTGGGCTGTGACAAAGTCACATGG (SEQ ID NO: 24) |
| STJ#94 | CGAACTGGCCCAGCCGGCCATGGCGTGCGGCGGCATCGCCCGGCTAGAGGAAAA (SEQ ID NO: 25) |
| STJ#95 | CGAACTGGCCCCCGAGGCCCGGCAGCCGCCGTGGTTCATGACTTTCTGTTTAAG (SEQ ID NO: 26) |
| STJ#96 | GATATCGCGGCCGCATGCGGCGGCCTGACCGACACCCTGCAGG (SEQ ID NO: 27) |
| STJ#97 | TTTTAGGGGTCGACTGCGGCGCAGCGCCGTGTGCCGCCAGGATGAAC (SEQ ID NO: 28) |
| STJ#114 | GACGAACTGGCCCAGCCGGCCATGGCGGAGAGTAAACGGAATAAGCCAGGGAAG (SEQ ID NO: 29) |
| STJ#115 | GCGAACTGGCCCCCGAGGCCCCCTTACCCCGATGAATATCAATATGTCGCTTAG (SEQ ID NO: 30) |
| STJ#116 | CGAGATATCGCGGCCGCAATGGAACTGAAACATAGTATTAGTGATTATACCGAG (SEQ ID NO: 31) |
| STJ#117 | GTTTTAGGGGTCGACTGCGGCGCCCTGTTTAAATCCTGACTTACCGTTAGC (SEQ ID NO: 32) |
| STJ#118 | CTTACCCCGATGAATATCAATCGCTCGCTTAGGTGTGGTCACTCTGATATTATT (SEQ ID NO: 33) |
| STJ#119 | GCGAACTGGCCCCCGAGGCCCCCTTACCCCGATGAATATCAATCGCTCGCTTAG (SEQ ID NO: 34) |
| STJ#120 | CTTACCCCGCGCAATATCAATATGTCGCTTAGGTGTGGTCACTC (SEQ ID NO: 35) |
| STJ#121 | GCGAACTGGCCCCCGAGGCCCCCTTACCCCGCGCAATATCAATATGTCGCTTAG (SEQ ID NO: 36) |
| STJ#122 | CTTACCCCGCGCAATATCAATCGCTCGCTTAGGTGTGGTCACTCTGATATTATT (SEQ ID NO: 37) |
| STJ#123 | GCGAACTGGCCCCCGAGGCCCCCTTACCCCGCGCAATATCAATCGCTCGCTTAG (SEQ ID NO: 38) |
| STJ#136 | TTTTAGGGGTCGACCAAGCTGCTCCCCCAAAGGCTG (SEQ ID NO: 39) |
| STJ#139 | TTTAAGGGAAGCTTCTATCAATGGTGGTGGTGGTGGTGATG (SEQ ID NO: 40) |
| STJ#144 | TTTTAGGGGTCGACGACAAAACTCACACATGCCCACCGTG (SEQ ID NO: 41) |
| STJ#145 | TTTAAGGGAAGCTTCTATTAGGCGCGCCCTTTGTCATCG (SEQ ID NO: 42) |
| STJ#194 | CTAGGGAGCCGCGGGAGGAGCAGTACAACNNSNNSNNSNNSNNSNNSNNSNNSNNSAGCACGTACCGTGTGGTCAGCG (SEQ ID NO: 43) |
| STJ#195 | CTAGAGGAATTCGGCCCCCGAGGCCCCTTTAC (SEQ ID NO: 44) |
| STJ#196 | CGCAGCGAGGCCCAGCCGGCCATGGCG (SEQ ID NO: 45) |
| STJ#197 | CGCAATTCGAATTCGGCCCCCGAGGCCCC (SEQ ID NO: 46) |

TABLE 2-continued

Oligonucleotide sequences (Underlining indicates the restriction enzyme sites)

| Primer Name | Primer nucleotide sequence (5' → 3') |
|---|---|
| STJ#220 | CAATTTTGTCAGCCGCCTGAGCAGAAG (SEQ ID NO: 47) |
| STJ#283 | CTTCTATCCCAGCGACATCGCCGTGNNSTGGNNSAGCNNSGGGCAGCCGGAGAACAACTACAAG (SEQ ID NO: 48) |
| STJ#284 | GACCAAGA<u>ACCAGGT</u>CAGCCTGACCTGCCTGGTCAAAGGCTTCTATCCCAGCGACATCGCCGTG (SEQ ID NO: 49) |
| STJ#285 | AGGGAGAG<u>GCTCTTC</u>TGCGTGTAGTGGTTGTGCAGAGCWNNATGWNNCACWNNGCATGAGAAGACGTTCCCCTGCTG (SEQ ID NO: 50) |
| STJ#286 | AGGGAGAG<u>GCTCTTC</u>TGCGTGTAGTGGTTGTGCAGAGCCTCATGWNNWNNCACGGAGCATGAGAAGACGTTCCCCTGCTG (SEQ ID NO: 51) |
| STJ#287 | AGGGAGAG<u>GCTCTTC</u>TGCGTGTAGTGGTTGTGCAGAGCCTCATGWNNWNNWNNCACGGAGCATGAAGACGTTCCCCTGCTG (SEQ ID NO: 52) |
| STJ#302 | GCGGAATTC<u>CCATGG</u>CGGATATTCAAATGACCC (SEQ ID NO: 53) |
| STJ#303 | CAGACGCGCTTAAAGAAGACGGGCTTTGGGTCATTTGAATATCCGCCATG (SEQ ID NO: 54) |
| STJ#304 | CGTCTTCTTTAAGCGCGTCTGTCGGTGATCGCGTGACCATCACGTGTCGT (SEQ ID NO: 55) |
| STJ#305 | AGGCCACCGCCGTATTAACATCTTGGCTCGCACGACACGTGATGGTCACG (SEQ ID NO: 56) |
| STJ#306 | GTTAATACGGCGGTGGCCTGGTATCAACAAAAACCGGGTAAAGCCCCGAA (SEQ ID NO: 57) |
| STJ#307 | GAGTACAGAAAGCTGGCGCTGTAGATTAACAGCTTCGGGGCTTTACCCGG (SEQ ID NO: 58) |
| STJ#308 | CAGCGCCAGCTTTCTGTACTCTGGCGTCCCGAGCCGCTTTTCTGGCAGCC (SEQ ID NO: 59) |

Example 2

Construction of Plasmids to Display Homodimeric Protein IgG-Fc

All plasmids and primers used in the present examples are described in Table 3 and Table 2. Plasmid pPelBHis was generated by ligating BamHI-HindIII digested skp gene from pMopac12 into pMopac1 digested with the same restriction endonucleases. pPelBFLAG was derived from pPelBHis in which polyhistidine tag and c-myc tag were replaced by FLAG tag (DYKDDDDK; SEQ ID NO:114). Subcloning of PCR amplified and SfiI digested Fc gene encoding human IgG1-Fc fragment, hinge, CH2 and CH3 region of human IgG1 heavy chain (GeneBank Accession No. AF237583; SEQ ID NO:83) into SfiI digested pPelBHis and pPelBFLAG generated pPelBHis-Fc and pPelBFLAG-Fc, respectively. pPelBHis-beta 2 microglobulin was constructed by subcloning soluble mature human beta 2 microglobulin gene synthesized from overlap PCR amplification using 10 primers including 2 external primers (STJ #78 and STJ #84; SEQ ID NOS:14 and 16) and 8 internal primers (STJ #86-93; SEQ ID NOS:17-24) into pPelBHis using SfiI restriction endonuclease site. pPelBHis-FcγRIIa was generated by introducing SfiI digested soluble mature human FcγRIIa gene (GeneBank Accession No. P12318) (Stengelin et al., 1988) amplified from pDNR-LIB-FcγRIIa (ATCC: MGC-23887) using primers STJ #74 and STJ #80 (SEQ ID NOS:13 and 15) into pPelBHis. SfiI digested genes from pMoPacI-FLAG-M18 and pMoPacI-FLAG-2610 for M18 scFv (Harvey et al., 2006) and 26-10 scFv (Francisco et al., 1993) specific for the PA antigen of *Bacillus anthracis* and cardiac glycoside digoxin, respectively, were introduced to pPelBFLAG to generate pPelBFLAG-M18 scFv and pPelB-2610 scFv.

TABLE 3

Plasmids Used in The Present Examples

| Plasmids | Relevant characteristics | Reference or source |
|---|---|---|
| pMoPac1 | Cm'', lac promoter, tetA gene, C-terminal polyhistidine tag and c-myc tag | Hayhurst et al., 2003 |
| pMoPac12 | Ap'', lac promoter, tetA gene, skp gene, C-terminal polyhistidine tag and c-myc tag | Hayhurst et al., 2003 |
| pMoPac16 | Ap'', lac promoter, tetA gene, HuCκ gene, skp gene, C-terminal polyhistidine tag and c-myc tag | Hayhurst et al., 2003 |
| pMoPac1-FLAG-M18 | NlpA fused M18 scFv gene, C-terminal FLAG tag in pMoPac1 | Jung et al., 2007 |
| pMoPac1-FLAG-2610 | NlpA fused 26-10 scFv gene, C-terminal FLAG in pMoPac1 | Jung et al., 2007 |
| pPelBHis | Cm'', lac promoter, tetA gene, skp gene, C-terminal polyhistidine tag and c-myc tag | The Present Examples |

TABLE 3-continued

Plasmids Used in The Present Examples

| Plasmids | Relevant characteristics | Reference or source |
|---|---|---|
| pPelBHis-Fc | IgG1-Fc gene in pPelBHis | The Present Examples |
| pPelBHis-beta 2 microglobulin | Human beta 2 microglobulin gene in pPelBHis | The Present Examples |
| pPelBHis-FcγRIIa | FcγRIIa gene in pPelBHis | The Present Examples |
| pPelBHis-Fc-cFos | IgG1-Fc gene fused to C-terminal cFos gene in pPelBHis | The Present Examples |
| pPelBHis-Fc-cFos(Cys) | IgG1-Fc gene fused to C-terminal cFos(Cys) gene in pPelBHis | The Present Examples |
| pPelBFLAG | $Cm^r$, lac promoter, tetA gene, skp gene, C-terminal FLAG tag | The Present Examples |
| pPelBFLAG-Fc | IgG1-Fc gene in pPelBFLAG | The Present Examples |
| pPelBFLAG-M18 scFv | M18 scFv gene in pPelBFLAG | The Present Examples |
| pPelBFLAG-2610 scFv | 26-10 scFv gene in pPelBFLAG | The Present Examples |
| pPelBFLAG-Fc-Im2 | IgG1-Fc gene fused to C-terminal Im2 gene in pPelBFLAG | The Present Examples |
| pPelBFLAG-M18 scFv-Im2 | M18 scFv gene fused to C-terminal Im2 gene in pPelBFLAG | The Present Examples |
| pPelBFLAG-2610 scFv-Im2 | 26-10 scFv gene fused to C-terminal Im2 gene in pPelBFLAG | The Present Examples |
| pMopac12-M18.1 hum scFv | M18.1 humanized scFv gene in pMoPac12 | The Present Examples |
| pMopac12-2610 scFv | 26-10 scFv gene in pMoPac12 | The Present Examples |
| pMopac16-M18.1 hum scab | M18.1 humanized scAb gene in pMoPac16 | The Present Examples |
| pMopac16-2610 scAb | 26-10 scAb gene in pMoPac16 | The Present Examples |
| pMAZ360-M18.1-Hum-IgG | M18.1 humanized IgG1 gene in pMAZ360 | Mazor et al., 2007 |
| pMAZ360-26.10 IgG | 26-10 IgG1 gene in pMAZ360 | Mazor et al., 2007 |
| pNlpAFLAG-M18 | NlpA fused M18 scFv gene in pPelBFLAG | The Present Examples |
| pNlpAHis-Fc | NlpA fused IgG-Fc gene in pPelBHis | The Present Examples |
| pBAD30 | $Ap^r$, BAD promoter | Guzman et al., 1995 |
| pBADNlpAFLAG-M18 | NlpA fused M18 scFv gene, C-terminal FLAG tag in pBAD30 | The Present Examples |
| pBADNlpAFLAG-cJun | NlpA fused cJun gene, C-terminal FLAG tag in pBAD30 | The Present Examples |
| pBADNlpAFLAG-cJun(Cys) | NlpA fused cJun(Cys) gene, C-terminal FLAG in pBAD30 | The Present Examples |
| pBADNlpAHis-Fc | NlpA fused IgG-Fc gene, C-terminal polyhistidine tag in pBAD30 | The Present Examples |
| pBADNlpAHis-ColE2(H574A) | NlpA fused ColE2(H574A) gene, C-terminal polyhistidine tag in pBAD30 | The Present Examples |
| pBADNlpAHis-ColE2(H578A) | NlpA fused ColE2(H578A) gene, C-terminal polyhistidine tag in pBAD30 | The Present Examples |
| pBADNlpAHis-ColE2(H574A/H578A) | NlpA fused ColE2(H574A/H578A) gene, C-terminal polyhistidine tag in pBAD30 | The Present Examples |
| pTrc99A | $Ap^r$, trc promoter, $lacI^q$ | Amersham Biosci., (Piscataway, NJ) |
| pTrcdsbAHis-Fc | dsbA fused IgG-Fc gene, C-terminal FLAG tag in pTrc99A | The Present Examples |
| pTrcdsbAHis-FcγRIIa | dsbA fused FcγRIIa gene, C-terminal polyhistidine tag in pTrc99A | The Present Examples |
| pSTJ4-Herceptin IgG1 | Herceptin IgG1 gene in pMAZ360-M18.1-Hum-IgG1 | The Present Examples | pNlpAFLAG-M18 was constructed by ligating XbaI-HindIII digested fragments for NlpA and 6 amino acid residues (CDQSSS; SEQ ID NO:84) fused M18 scFv gene from pMopac1-FLAG-M18 into pPelBFLAG-M18. pNlpAHis-Fc was generated by subcloning SfiI digested Fc gene into pNlpAFLAG-M18 and by replacing FLAG with polyhistidine tag and c-myc tag. pBADNlpAFLAG-M18 and pBADNlpAHis-Fc were generated by ligating XbaI-HindIII digested M18 scFv gene and Fc gene from pNlpAFLAG-M18 and pNlpAHis-Fc, respectively, into pBAD30 digested with same restriction endonucleases.

To display Fc domain using leucine zipper pair of cJun-cFos interaction, NotI-SalI digested cFos fragments amplified using two primers (STJ #68 and STJ #69; SEQs ID NO:11 and 12) and the cFos(Cys) fragments encoding additional three amino acids including internal two Gly residues and external Cys residue at both ends of C-terminus and N-terminus amplified using two primers (STJ #96 and STJ #97; SEQ ID NOS:27 and 28) were cloned into pPel- BHis-Fc to make pPelBHis-Fc-cFos for non-covalent bonding of cJun-cFos interaction pair and pPelBHis-Fc-cFos (Cys) for covalent disulfide bonding of both N terminal and C terminal ends of cJun-cFos pair in *E. coli* periplasmic space. For anchoring periplasmic expressed Fc domain fused to cFos or cFos(Cys), pBADNlpAFLAG-cJun and pBADNlpAFLAG-cJun(Cys) were generated by subcloning SfiI digested cJun fragments amplified with primers (STJ #58 and STJ #59; SEQ ID NOS:11 and 12) and cJun(Cys) fragments amplified with primers (STJ #94 and STJ #95; SEQ ID NOS:25 and 26) into SfiI digested pBADNlpA-FLAG-M18.

For the display of Fc using tight ColE2-Im2 interaction, Im2 gene that is PCR amplified using two primers (ST #116 and STJ #117; SEQ ID NOS:31 and 32) and template *E. coli* WTZ1011 ColE2 harboring plasmid ColE2-P9 (The Coli Genetic Stock Center, Yale Univ. CGSC No. 8203) (Masaki et al., 1985) was NotI-SalI digested and ligated into pPelB-FLAG-Fc, pPelBFLAG-M18, and pPelBFLAG-2610 to generate pPelBFLAG-Fc-Im2, pPelBFLAG-M18-Im2, and pPe1bFLAG-2610-Im2. To construct plasmids encoding NlpA fused ColE2 mutants binding to Im2 with strong protein protein interaction, the catalytic domains of three ColE2 mutants were amplified by overlap PCR with the template plasmid used for Im2 gene amplification and with four primers including two common external primers (STJ #114 and STJ #115; SEQ ID NOS:29 and 30) and two internal reverse primers (STJ #120 and STJ #121; SEQ ID NOS:35 and 36) for ColE2(H574A), internal primers (STJ #118 and STJ #119; SEQ ID NOS:33 and 34) for ColE2 (H578A), and internal primers (STJ #122 and STJ #123; SEQ ID NOS:37 and 38) for ColE2(H574A/H578A), respectively. The amplified PCR products were SfiI digested and introduced into pBADNlpAHis to generate pBADNlpAHis-ColE2(H574A), pBADNlpAHis-ColE2(H578A), and pBADNlpAHis-ColE2(H574A/H578A).

Subcloning of SfiI digested M18.1 hum scFv (1) and 26-10 scFv gene into pMopac12 generated pMopac12-M18.1 hum scFv and pMopac12-2610 scFv. Also, subcloning of the SfiI digested M18.1 hum scFv and 26-10 scFv into pMopac16 generated pMopac16-M18 scAb and pMopac16-2610 scAb. For pTrcdsabAHis-Fc and pTrcdsbAHis-FcγRIIa, Fc and FcγRIIa gene fragments were PCR amplified using primers (STJ #144 and STJ #139; SEQ ID NOS:41 and 40) with the templates pPelBHis-Fc for Fc gene and primers (STJ #136 and STJ #139; SEQ ID NOS:39 and 40) with the template pPelB-FcγRIIa for FcγRIIa gene, respectively, SalI-HindIII digested, and ligated into dsbA signal sequence (Schierle et al., 2003) inserted pTrc99A.

All plasmids were transformed into *E. coli* Jude-1 (F′ [Tn10(Tetr) proAB+lacIq Δ(lacZ)M15] mcrA Δ(mrr-hs-dRMS-mcrBC) φ80dlacZΔM15 ΔlacX74 deoR recA1 araD139 Δ(ara leu)7697 galU galK rpsL endA1 nupG) (Kawarasaki et al., 2003).

Example 3

Culture Conditions

Culture Conditions for Two Plasmids System

For the periplasmic display using leucine zippers, cJun-cFos, pPelBHis-Fc-cFos and pPelBHis-Fc-cFos(Cys) were co-transformed with pBADNlpAFLAG-cJun or pBADNlpAFLAG-cJun(Cys) into *E. coli* Jude-1. To display Fc using the interaction of ColE2-Im2, pPelBFLAG-Fc-Im2, pPelB-M18 scFv-Im2, and pPelBFLAG-2610 scFv-Im2 were co-transformed with pBADNlpAHis-ColE2(H574A), pBADNlpAHis-ColE2(H578A), or pBADNlpAHis-ColE2(H574/578) containing single or double mutations at C-terminal ColE2 DNase catalytic domain. The transformants harboring two plasmids were grown overnight at 37° C. with 250 rpm shaking in Terrific Broth (TB) (Becton Dickinson Diagnostic Systems DIFCO™, Sparks, Md.) supplemented with 2% (wt/vol) glucose, chloramphenicol (40 µg/ml) and ampicillin (50 µg/ml). After overnight culture, the cells were diluted 1:100 in fresh TB medium without glucose, incubated at 37° C. for 2 h and then cooled at 25° C. for 20 min. Firstly, PelB signal sequence fused proteins were induced with 1 mM of isopropyl-1-thio-β-D-galactopyranoside (IPTG) to allow time for correct folding in periplasmic space prior to binding to inner membrane anchored ColE2 mutants. And 2 h after IPTG induction, 0.2% (wt/vol) arabinose was added to induce expression of inner membrane anchored cJun, cJun(Cys), ColE2(H574A), ColE2 (H578A), or ColE2(H574A/H578A).

Culture Conditions for One Plasmid System

*E. coli* transformed with various plasmids, pPelBHis-Fc, pPelBHis-beta 2 microglobulin, pPelBFLAG-M18 scFv, pMopac12-M18.1 hum scFv, pMopac12-2610 scFv, pMopac16-M18.1 hum scAb, pMopac16-2610 scAb, pMAZ360-M18.1-Hum-IgG, pMAZ360-26.10 IgG, pNlpA-His-Fc, pTrcdsbAHis-Fc, and pTrcdsbAHis-FcγRIIa were cultured overnight at 37° C. with 250 rpm shaking in Terrific Broth (TB) with 2% (wt/vol) glucose. Antibiotics, chloramphenicol (40 µg/ml) or ampicillin (50 µg/ml) appropriate for antibiotic resistance gene of each plasmid, were added for overnight culture. The overnight cultured cells were diluted 1:50 in fresh TB medium with 0.5M trehalose and the supplement of appropriate antibiotics, chloramphenicol (40 µg/ml) or ampicillin (50 µg/ml). After incubation at 37° C. for 3 h and cooling at 25° C. for 20 min with 250 rpm shaking, the protein expression was induced with 1 mM of isopropyl-1-thio-β-D-galactopyranoside (IPTG).

For the culture of various *E. coli* transformants in the media without trehalose was performed as same as above culture condition for one plasmid cultured in the media with trehalose except 1:100 dilution after overnight culture and incubation for 2 h instead of 3 h before IPTG induction.

Example 4

Flow Cytometry Analysis for Screening of Fc Libraries

Spheroplasts Preparation and Flow Cytometry Analysis 5 h after IPTG induction, an aliquot of the culture broth equivalent to 8 ml/OD600 was harvested by centrifugation and washed two times in 1 ml of cold 10 mM Tris-HCl (pH 8.0). After resuspension in 1 ml of cold STE solution (0.5 M Sucrose, 10 mM Tris-HCl, 10 mM EDTA, pH 8.0), the cells were incubated with rotating mixing at 37° C. for 30 min, pelleted by centrifugation at 12,000×g for 1 min and washed in 1 ml of cold Solution A (0.5 M Sucrose, 20 mM MgCl$_2$, 10 mM MOPS, pH 6.8). The washed cells were incubated in 1 ml of Solution A with 1 mg/ml of hen egg lysozyme at 37° C. for 15 min. After centrifugation at 12,000×g for 1 min and the resulting spheroplasts pellet were resuspended in 1 ml of cold PBS. 200 µl of the spheroplasts further diluted in 800 µl of PBS was mixed with each fluorescent labeled probes, 0.5 ul of Protein A-FITC (5 mg/ml), 2 ul of PA-FITC (0.25 mg/ml), 2.5 ul of FcγRIa-FITC (0.6 mg/ml), or 200 nM Digoxin-BODIPY. After incubation for 1 h with vigorous shaking at 25° C. in dark condition, the mixture was pelleted by centrifugation at centrifuged at 12,000×g for 1 min and resuspended in 1 ml of PBS. The 100 μl of the resuspension was diluted in 1 ml of PBS and analyzed on BD FACSort (BD Bioscience, San Jose, Calif.).

Screening of Fc Libraries Using Flow Cytometry

To construct random peptide loop inserted Fc library, 10 degenerate codons (NNS: N=A, T, G, or C; S=G or C) encoding 10 random amino acid residues were introduced between 297Asn and 298Ser. Fc partial gene fragments amplified using primers (STJ #194 and STJ195 (SEQ ID NOS:43 and 44) were digested with SacII and EcoRI restriction endonucleases and subcloned into SacII-EcoRI digested pPelBFLAG-Fc to generate random peptide loop inserted Fc library. For the error prone PCR library for full Fc region, standard error prone PCR methods (Fromant et al., 1995) were employed using primers STJ #196 and STJ #197 (SEQ ID NOS:45 and 46). The amplified PCR fragments were digested with SfiI and cloned into SfiI digested pPelBFLAG-Fc to generate error prone PCR Fc library. Two kinds of libraries were mixed at a 1:1 volume ratio and cultured in TB with 0.5M trehalose and chloramphenicol (40 μg/ml). After 2 h incubation at 37° C. and cooling at 25° C. for 20 min, the protein expression was induced with 1 mM of isopropyl-1-thio-β-D-galactopyranoside (IPTG). After spheroplasting and incubation with glycosylated human FcγRIa-FITC, spheroplasts were sorted on a MoFlo droplet deflection flow cytometry (Dako Cytomation, Fort Collins, Colo.) equipped with a 488 nm Argon laser for excitation. By gating spheroplasts exhibiting the approximately high 3% of FL2 signal, high fluorescent spheroplasts were sorted and resorted immediately after the initial sorting. The Fc genes in the spheroplasts were rescued by PCR amplification using two specific primers (STJ #16 and STJ #220; SEQ ID NOS:8 and 47), ligated into pPelBFLAG-Fc using SfiI restriction enzyme site, and transformed in electrocompetent *E. coli* Jude-1 cells. The resulting transformants were employed for the next round sorting.

Example 5

Bacterial Display System for Homo-Multimeric Proteins

In the bacterial display of homomultimeric protein including dimeric protein Fc, three factors should be made a consideration. Firstly, for efficient construction of libraries encompassing random peptide loop library or error prone PCR library, the multimeric protein should be encoded by single gene to make the homomultimer. Fc encoded by two separate genes generates heterodimeric Fc. Secondly, the homomultimeric proteins should be expressed in the space enabling correct folding and assembly. In bacterial expression system, *E. coli* periplasmic space provides oxidative environment for disulfide bonds and is suitable for the production of correct folded heterologous protein with the use of cellular folding machinery (Georgiou and Segatori, 2005). Finally, the expressed and folded multimeric proteins should be tightly anchored to bacterial cells during high throughput Fluorescent Activated Cell Sorting (FACS).

Figure 2A:
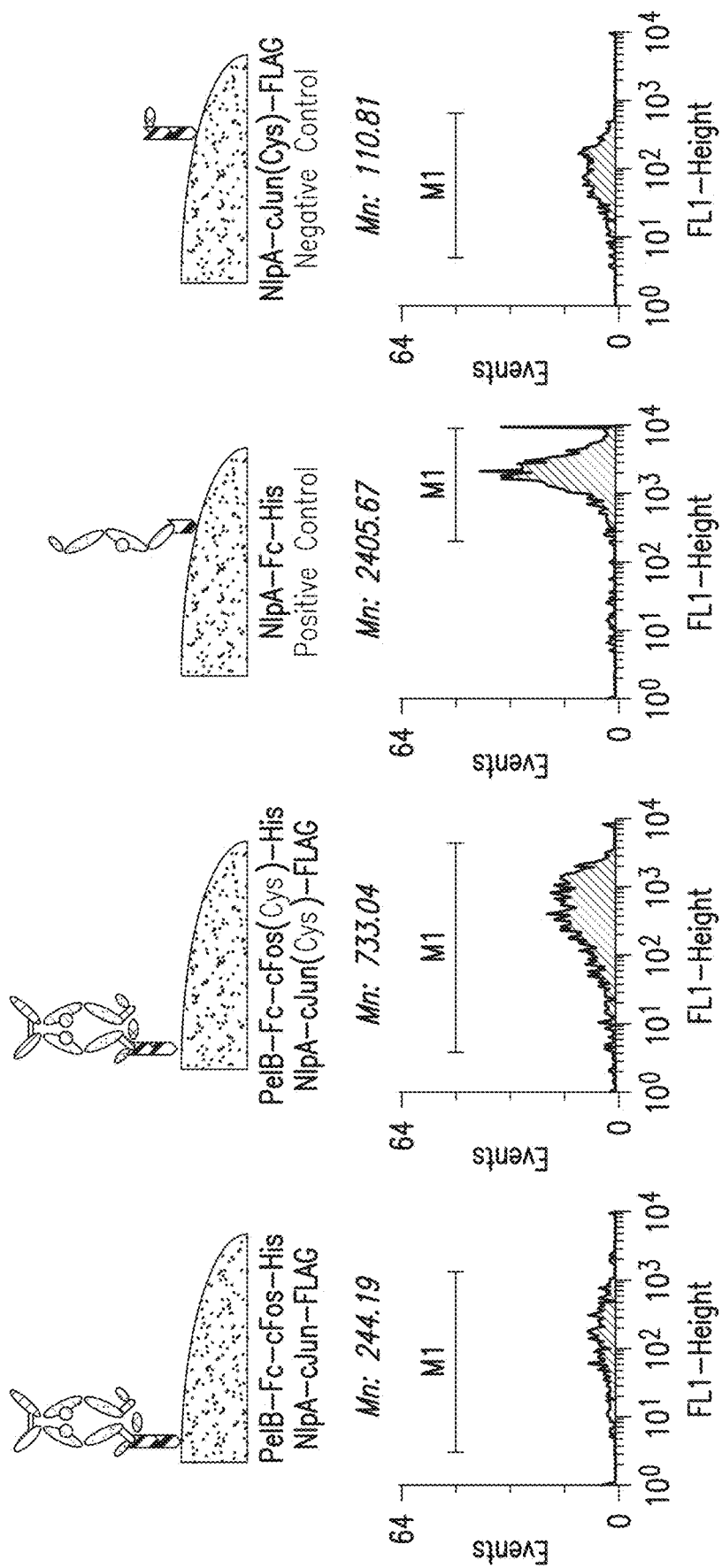
FIG. 2a-b: FACS analysis results of periplasmic displayed Fc homodimer using cJun-cFos and cJun(Cys)-cFos(Cys) interaction pairs.
Figure 2B:
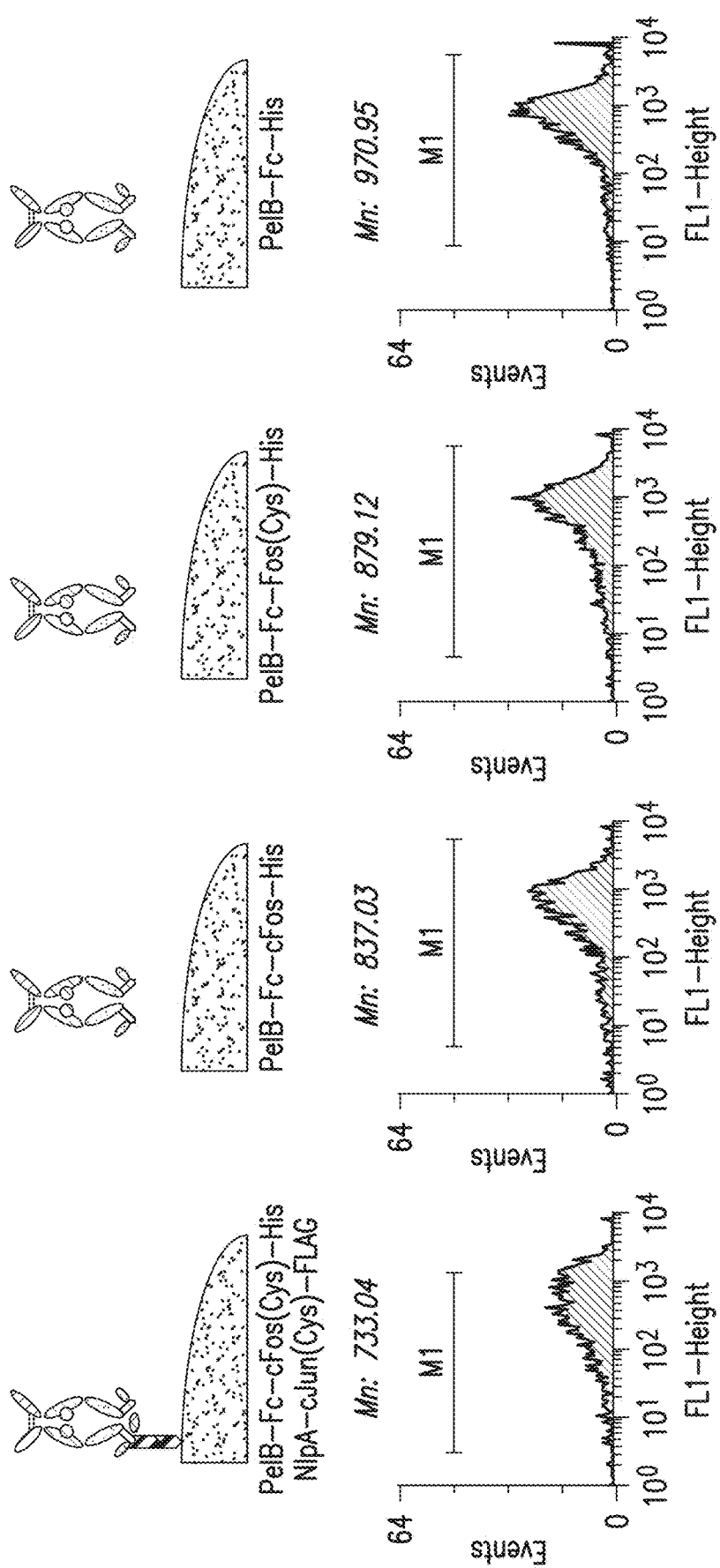

The first attempted system was leucine zippers cJun-cFos interaction pair. The repetitive leucine residues at every seven amino acid of cJun and cFos allow strong non-covalent interaction (Landschulz et al., 1988; Kouzarides and Ziff, 1988). Expression of cFos fused Fc from pPelBHis-Fc-cFos was firstly induced for periplasmic expression and then pBADNlpAFLAG-cJun for cJun fused to NlpA leader sequence and six amino acid residues (CDQSSS; SEQ ID NO:84) for inner membrane anchoring was induced for binding to the periplasmic assembled Fc homodimer (FIG. 1). Also, for another Fc display system, three amino acid residues including one external Cys and two internal Gly were introduced to N and C terminal ends of both cJun and cFos for more tight anchoring of periplasmic expressed Fc for the purpose of inhibiting the dissociation of cJun-cFos non-covalent bond. The resulting cJun(Cys)-cFos(Cys) enables disulfide covalent bond between the two leucine zippers in the periplasmic space (de Kruif and Logtenberg, 1996). With the APEx displayed pNlpAHis-Fc as a positive control and the pNlpAFLAG-cJun(Cys) not anchoring Fc domains as a negative control, the two Fc display systems were analyzed on flow cytometry after spheroplasting and incubation with Protein A-FITC (FIG. 2a). As expected, the periplasmic Fc display system employing engineered cJun(Cys)-cFos(Cys) showed higher fluorescence signal compared with native cJun-cFos, suggesting improved anchoring of Fc domains to inner membrane. However, when the system was compared with other negative controls that express only periplasmic Fc domains without co-expression of anchoring partner cJun or cJun(Cys), it did not show selective high signals. The spheroplasts harboring pPelB-FLAG-Fc for PelB leader peptide fused Fc without additional inner membrane anchoring motif showed very high fluorescence signal suggesting that most of the periplasmic expressed Fc proteins are remained binding to the cells without additional inner membrane anchoring motif even after spheroplasting (FIG. 2b).

Figure 3:
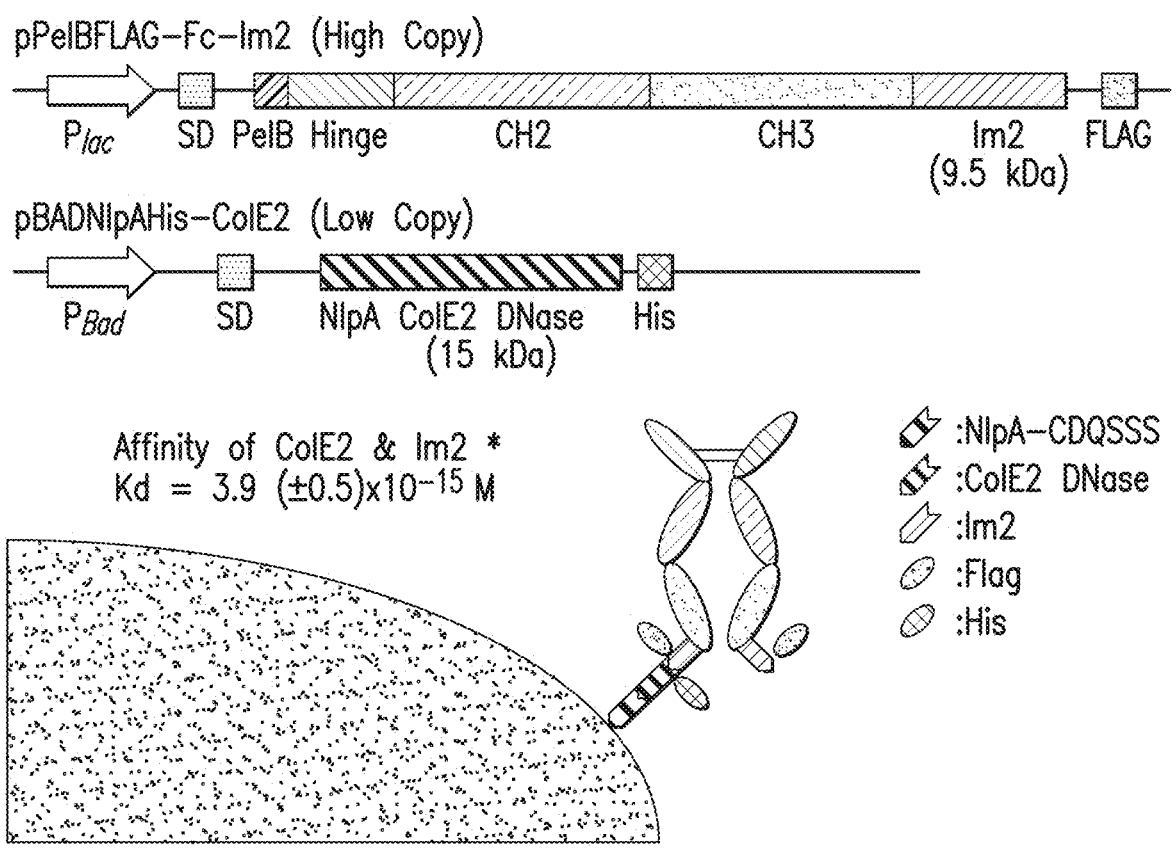
FIG. 3: Two plasmids system for the periplasmic display of Fc using ColE2-Im2 interaction.
Figure 4A:
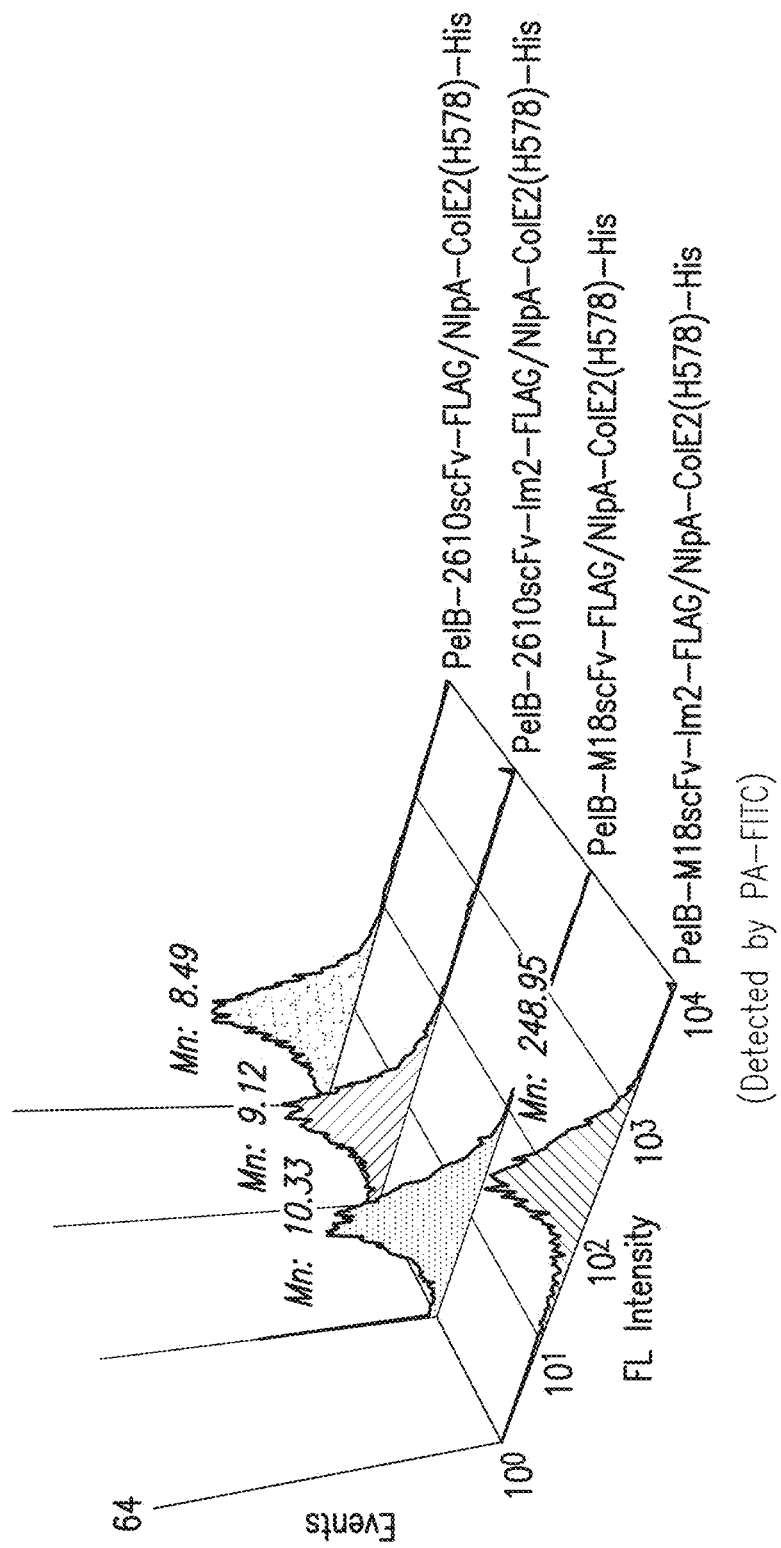
FIG. 4a-b: FACS analysis results for the periplasmic display of Fc homodimer using ColE2-Im2 interaction pairs.
Figure 4B:
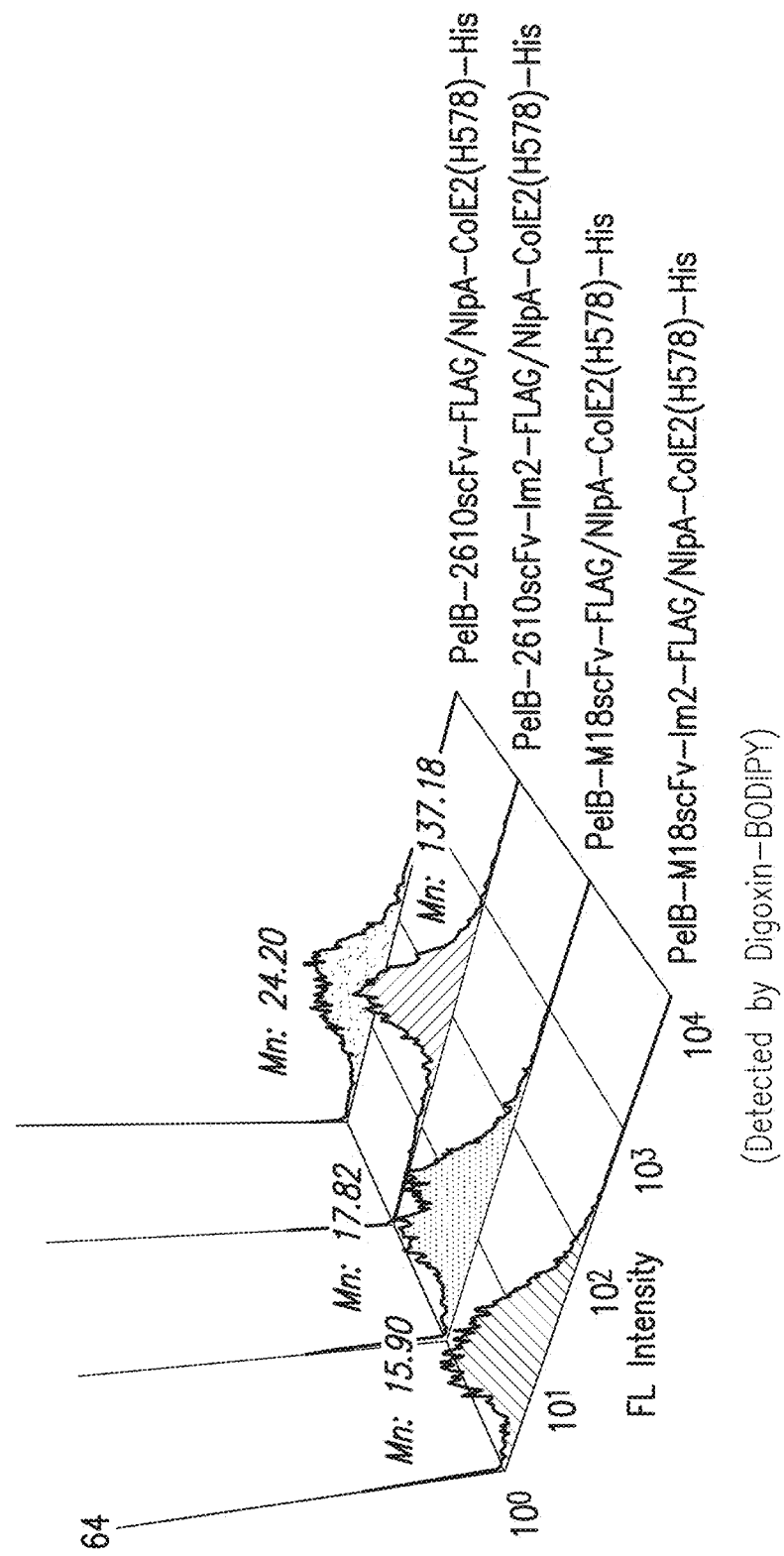
Figure 5:
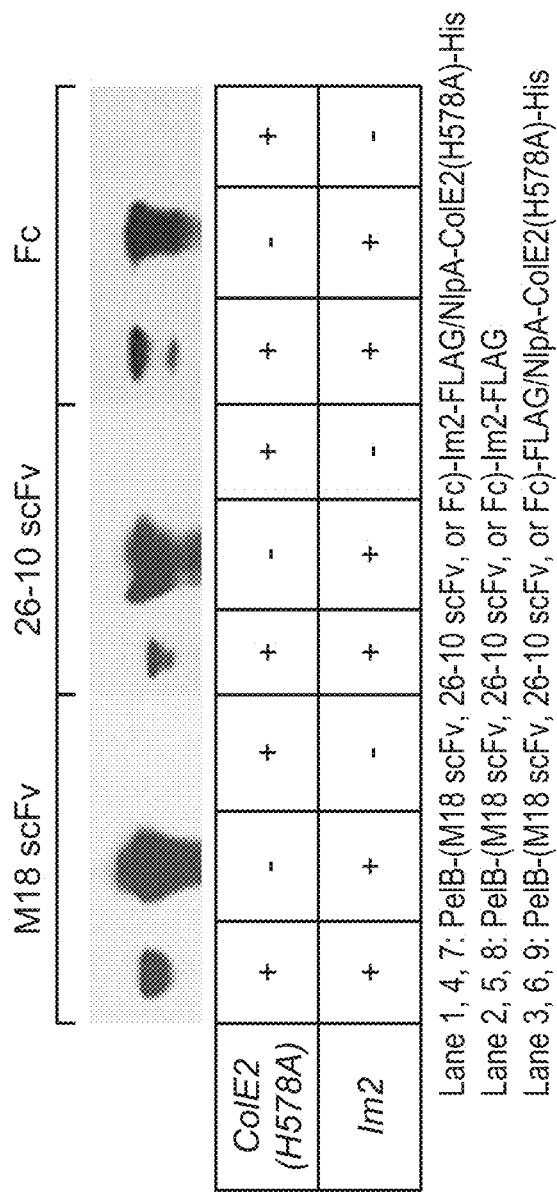
FIG. 5: Effect of ColE2 for the expression of target proteins, M18 scFv (Lane 1-3), 26-10 scFv (Lane 4-6), and Fc (Lane 7-9). In lane 1, 4 and 7, Im2 fused proteins were co-expressed with APEx displayed ColE2(H578A). In lane 2, 5 and 7, Im2 fused proteins were expressed without APEx displayed ColE2(H578A). In lane 3, 6 and 9, proteins without Im2 fusions were co-expressed APEx displayed ColE2(H578A). Anti-ECS antibody peroxidase conjugated was used as a detection antibody for Western blot.

As an alternative display system, stronger protein-protein interaction pair than leucine zippers can be considered. For example, the ColE2-Im2 interaction pair, one of the tightest protein-protein interaction pair in nature ($Kd=10^{-15}$) may be used (Li et al., 2004). To display homodimeric Fc using the tight ColE2-Im2 interaction, Im2 fused Fc was firstly induced for periplasmic Fc assembly and then the expression of ColE2 mutants fused to NlpA leader sequence and six amino acids (CDQSSS; SEQ ID NO:84) was induced for inner membrane anchoring (FIG. 3). To prevent auto degradation of host DNA, zinc binding histidines (H574, H578) were substituted to Ala by site directed mutagenesis (Garinot-Schneider et al., 1996). The resulting three mutants (H574A, H578A, or H574A/H578A) could inhibit host DNase activity with retaining Im2 binding property. Of the three ColE2 mutants, the single mutant, ColE2(H578A) showed the best result for the display of Im2 fused 26-10 scFv on the FACS analysis detected by digoxin BODIPY. The feasibility of the display system using ColE2(H578A)-Im2 interaction was further investigated with M18 scFv, 26-10 scFv, and homodimeric Fc. Although Im2 fused antibodies, M18 scFv-Im2 and 26-10 scFv-Im2 showed selectively higher fluorescence signal comparing negative controls, M18 scFv and 26-10 scFv not fused to Im2, respectively (FIG. 4), this selective high signals were derived from the deviation in expression levels. When ColE2 was not expressed, M18 scFv, 26.10 scFv, and Fc were well expressed. However, the expression of ColE2 with Im2 or without Im2 inhibited the expression of M18 scFv, 26-10 scFv and Fc partially or completely, respectively (FIG. 5).

In cJun-cFos or cJun(Cys)-cFos(Cys) system, it was found that periplasmic expressed Fc proteins are not clearly removed even in harsh spheroplasting conditions and keep bound strongly to the spheroplasts with enabling access of fluorescent dye labeled ligands. PelB fused small globular protein such as human beta 2 microglobulin was well removed after spheroplasting. On the contrary, PelB fused larger proteins including antibody domains or full antibody including Fc, scFv, scAb, and full IgG remained bound to the cells after spheroplasting.

Example 6

Trehalose Effect in Periplasmic Display

Figure 6:
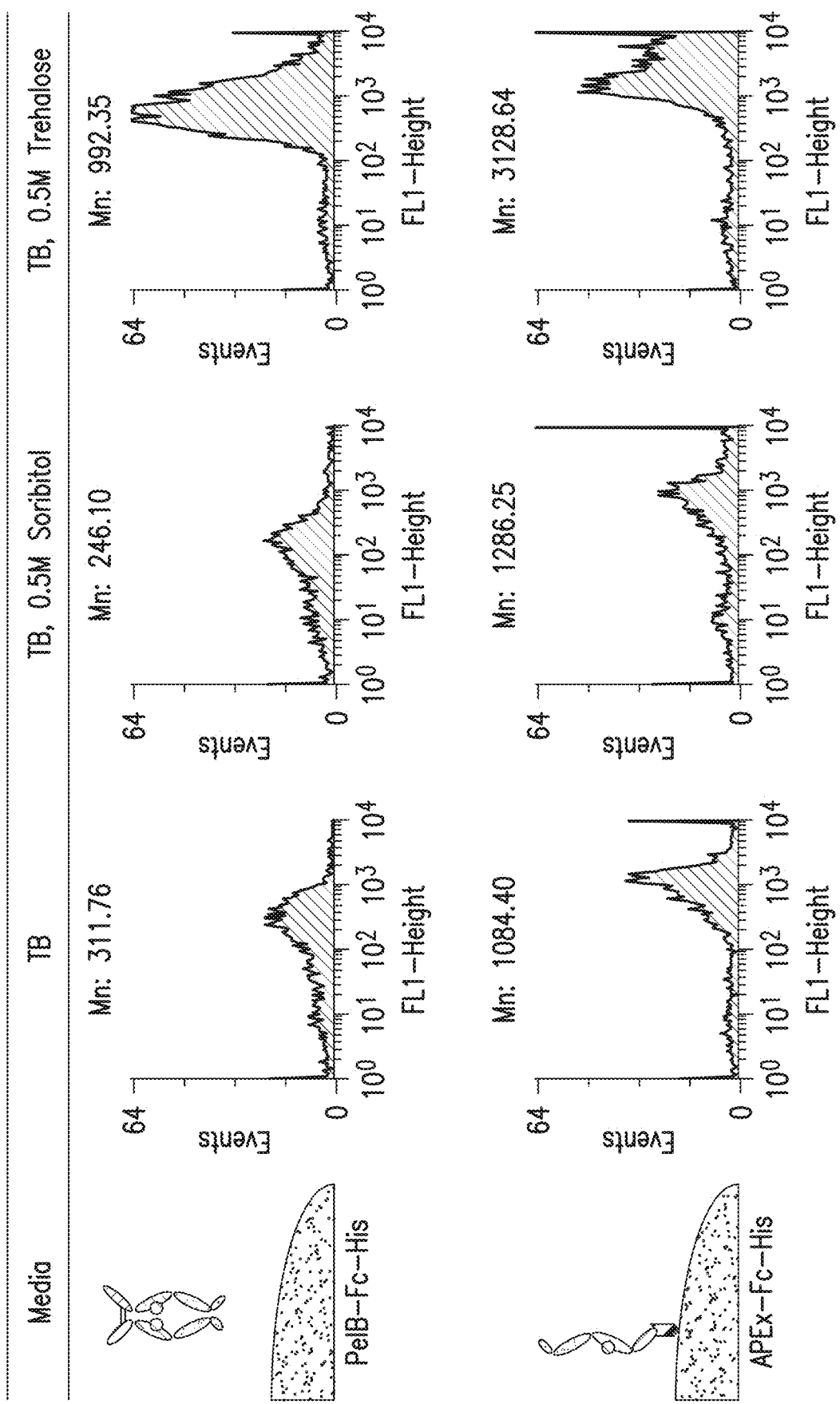
FIG. 6: Effect of sugars (sorbitol and trehalose) on the FACS analysis for periplasmic displayed Fc or APEx displayed Fc. Spheroplasts were incubated with Protein A-FITC probe for detection. Mn: Mean fluorescence intensity.
Figure 7:
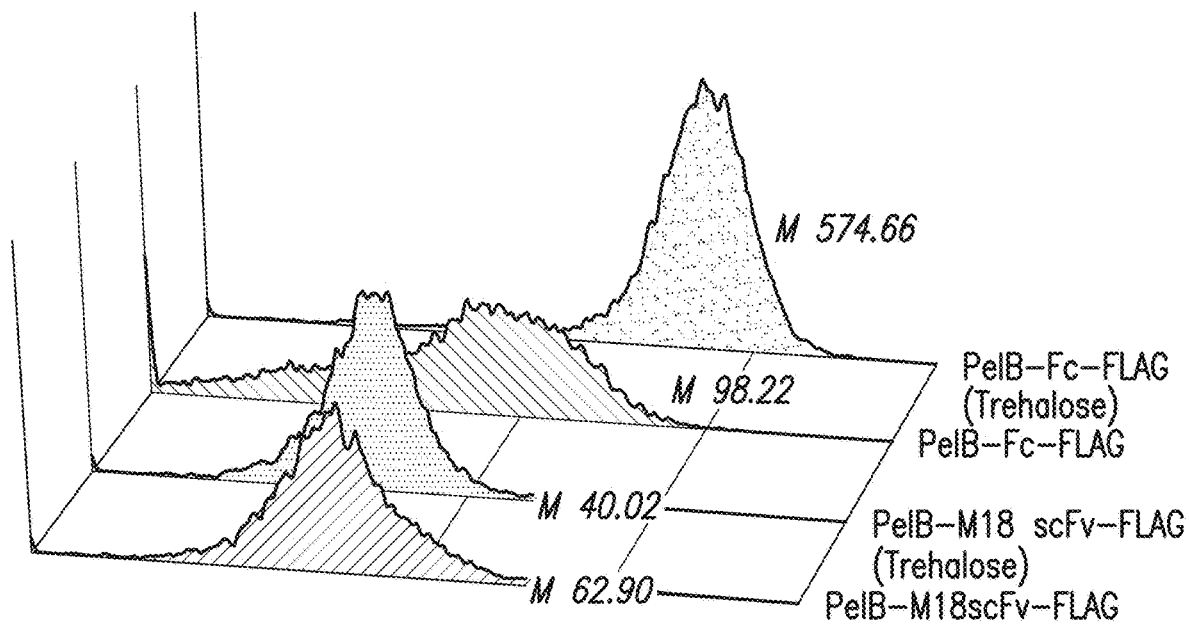
FIG. 7: Effect of trehalose on the periplasmic display of Fc. As a negative control, M18 scFv was used. Spheroplasts were incubated with Protein A-FITC probe for detection. Mn: Mean fluorescence intensity.
Figure 8:
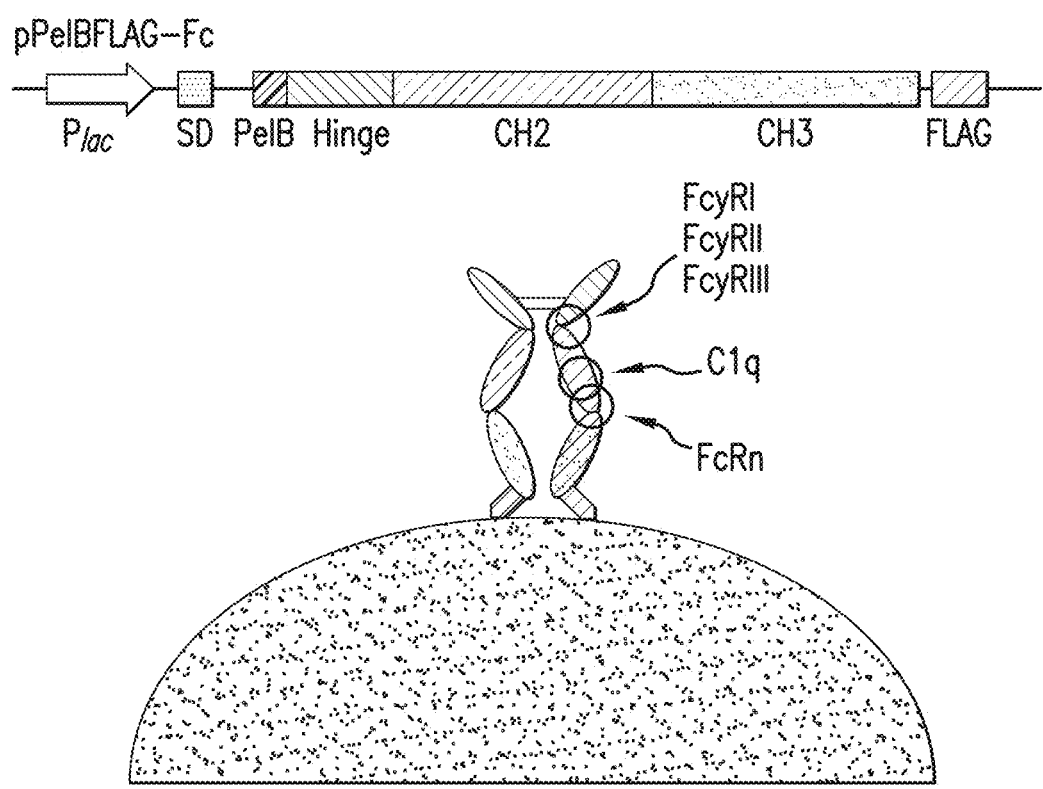
FIG. 8: One plasmid system for the periplasmic display of trapped Fc with trehalose.

For affinity maturation using FACS sorting method based on gating selective fluorescence and scattering regions, it is required to get distinguishable high or low fluorescence signal comparing a negative control with low coefficient of variation (CV=[Standard Deviation/Mean Value]×100). Some carbohydrates such as sucrose, sorbitol, mannitol, and trehalose are widely used sugars for protein stabilization at protein drug formulation or long term storage (Jung et al., 2003; Elbein et al., 2003; Purvis et al., 2005). Sugars have been used to enhance periplasmic folding and stabilize protein (Bowden and Georgiou, 1990). The fluorescence signal for the PelB fused Fc was tested when cultured in media comprising sorbitol or trehalose. Surprisingly, 0.5M trehalose greatly increased fluorescence signal intensity in the FACS analysis for both the APEx displayed Fc and the PelB leader peptide fused Fc (FIG. 6). Also, in comparison with other negative controls, PelB fused M18 scFv cultured in the media with or without 0.5M trehalose, the PelB fused Fc clearly exhibited dramatically improved signal intensity and CV value (FIG. 7) providing a selective display system for real affinity maturation of homodimeric Fc (FIG. 8).

Figure 9A:
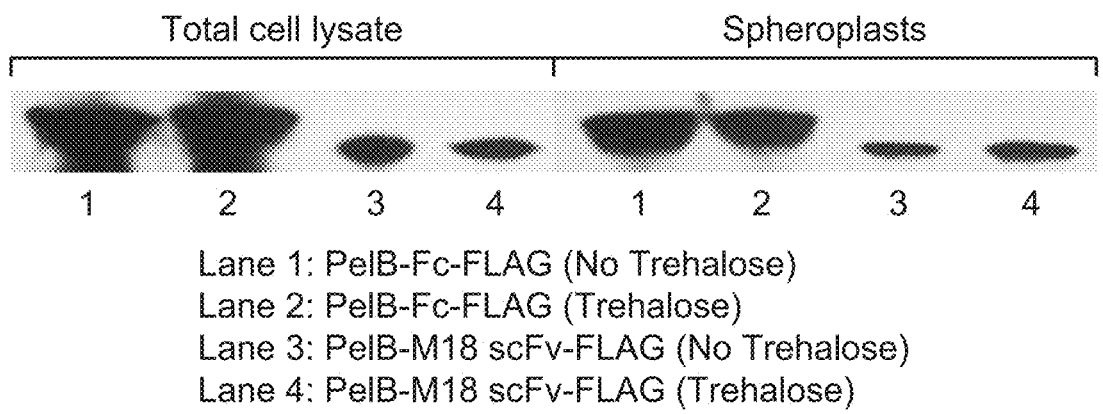
FIG. 9a-b: Effect of trehalose on the expression level and the rentention after spheroplasting for homodimeric Fc.
Figure 9B:
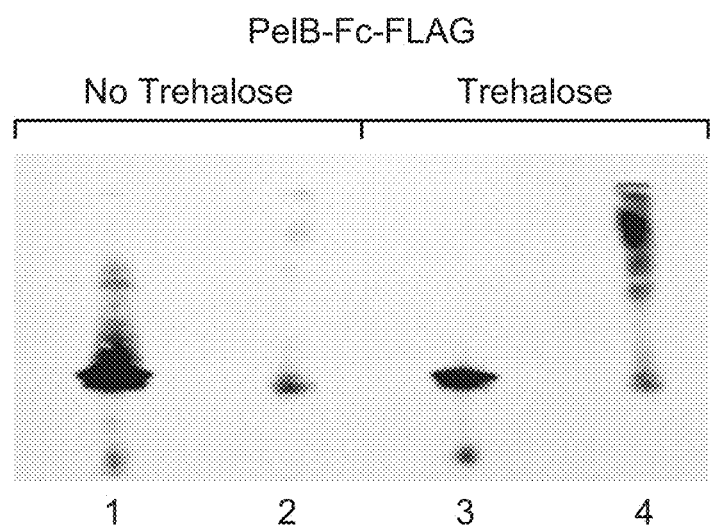
Figure 10A:
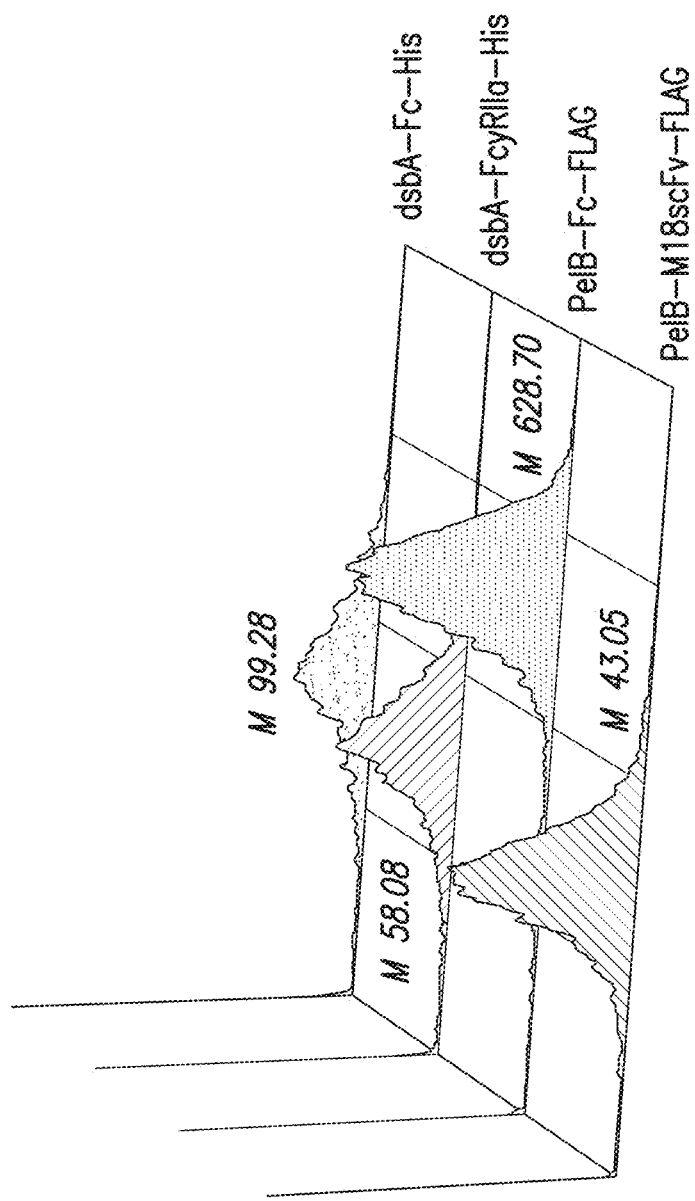
FIG. 10a-b: Effect of signal leader peptides (PelB and dsbA) on the periplasmic display of Fc.
Figure 10B:
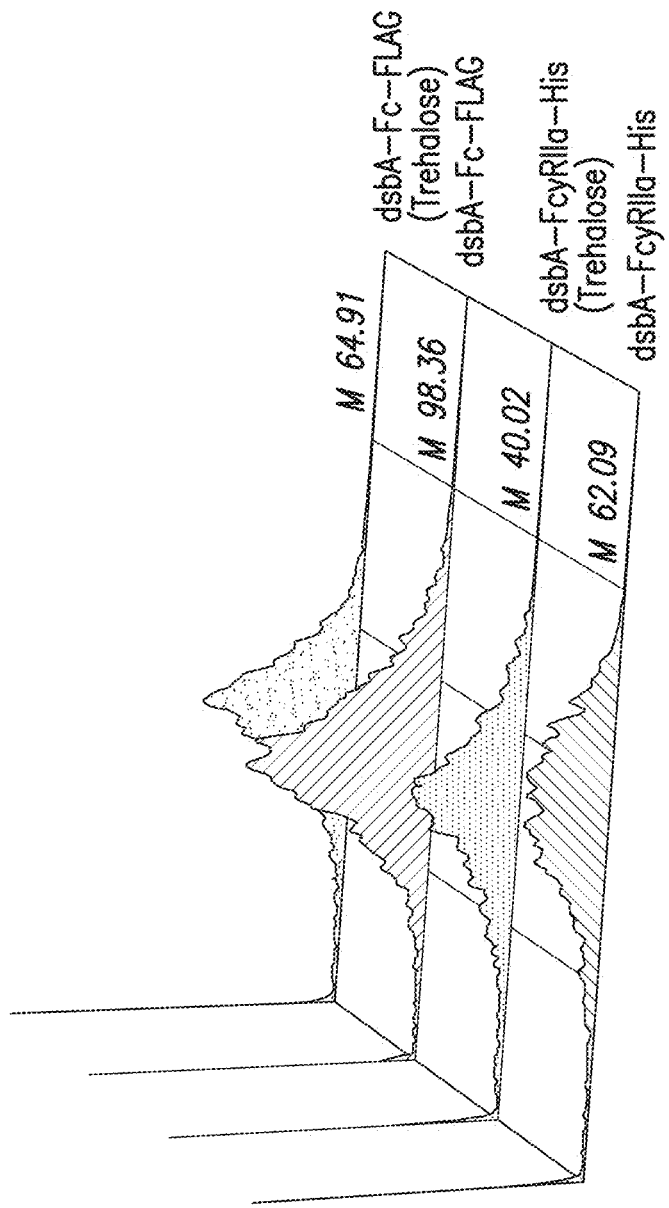
Figure 11:
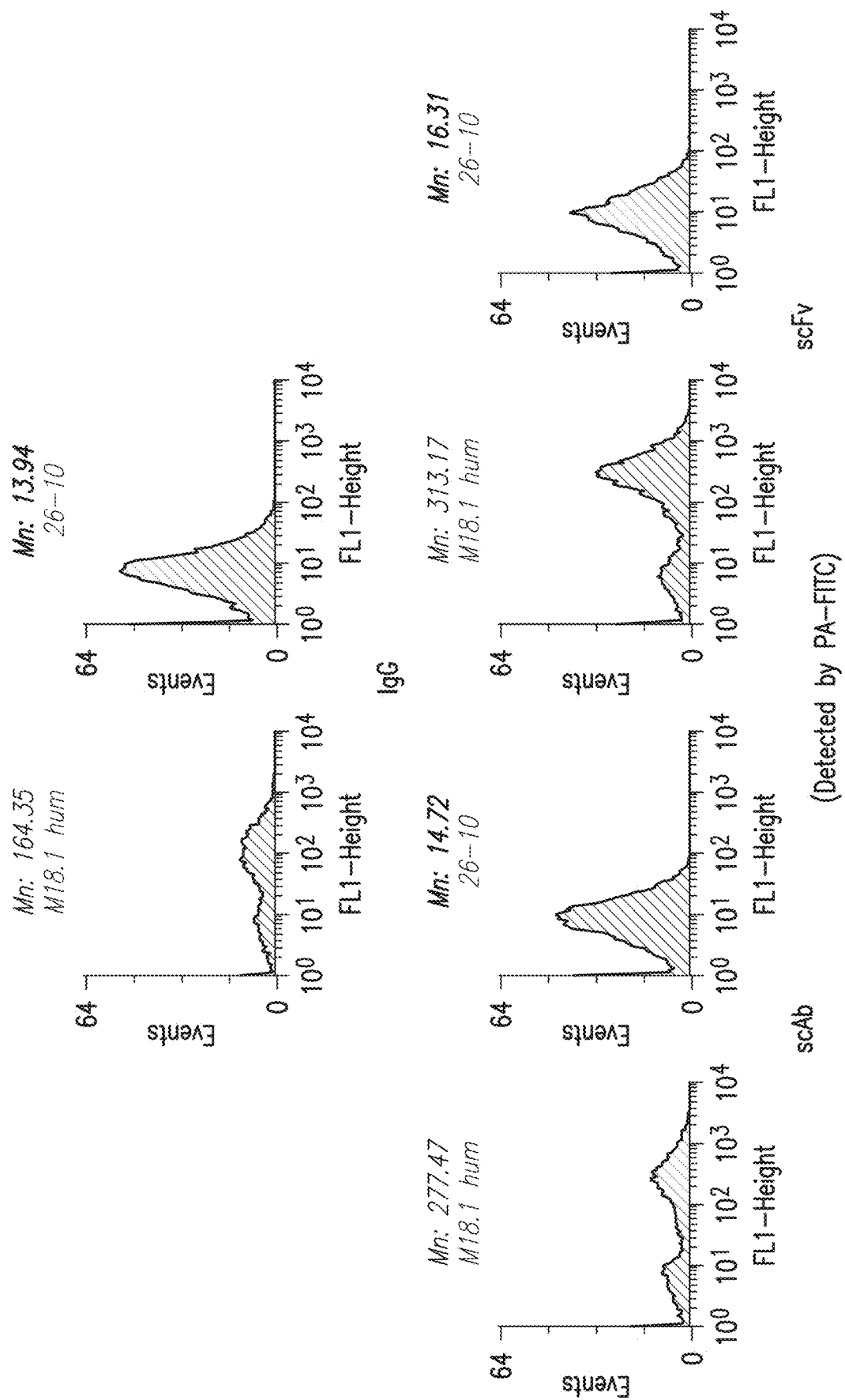
FIG. 11: FACS analysis for the periplasmic displayed antibodies. M18.1 humanized antibodies and 26-10 antibodies with various formats, scFv, scAb, and IgG., were periplasmic displayed and detected by PA-FITC. Mn: Mean fluorescence intensity.

Culture with trehalose did not significantly change the expression levels in total cell lysate and spheroplasts fraction (FIG. 9a). However, on the Western blot result of non-reduced samples, it clearly shows that trehalose increases the rentention of dimeric Fc after spheroplasting (FIG. 9b). When PelB signal peptide was replaced by dsbA signal sequence depending on SRP (Signal recognition pathway), culture with trehalose did not significantly change fluorescence signal (FIG. 10). The display system using periplasmic expression with trehalose and spheroplasting has been tested for various formats of antibodies, full IgG1, scAb, and scFv. In the FACS analysis with PA-FITC probe, periplasmic expressed M18.1 antibodies showed significantly higher fluorescence signal than negative control, periplasmic expressed 26.10 antibodies (FIG. 11).

Example 7

Fc Library Construction and Screening Using High Throughput Flow Cytometry

The native human IgG has two N-linked biantennary complex type oligosaccharide chains at the Asn297 amino acid residue of each CH2 domain. The two chains are located between the CH2 domains and interact with hydrophobic parts of the domains. Effector functions are largely dependent on the presence of the oligosaccharide chains (Wright and Morrison, 1997; Jefferis, 2005) to keep open structure of heavy chains for immune ligands binding (Sondermann et al., 2001). Aglycosylation causes great reduction or complete loss of effector functions (Jefferis, 2005). In the first library, 10 random amino acids were introduced between N-linked glycosylation site 297Asn and 298Ser using random degenerate codons (NNS) to find random peptide loop showing similar function with the oligosaccharide chains of mammalian IgG molecules. The gene encoding the Fc domain was used as a template for random mutagenesis by error-prone PCR (Fromant et al., 1995) with primers STJ #196 and STJ #197; SEQ ID NOS:45 and 46. The random 10 a.a. insertion library was constructed by PCR amplification using forward primer STJ #194 (SEQ ID NO:43) containing 10 degenerate codons encoded by the NNS randomization scheme and reverse primer STJ #195 (SEQ ID NO:44) with the same template. The amplified PCR fragments were ligated into pPelBFLAG cut with SfiI restriction sites for the error prone PCR library and with SacII/EcoRI for random 10 a.a. insertion library, respectively. The transformation of the resulting library generated $2.8 \times 10^7$ transformants. In the second library, error prone PCR was used to generate random mutation for full Fc region. The resulting library was $9.2 \times 10^8$ individual transformants with 0.49% error rate per gene based on the sequence of 20 library clones randomly selected.

Figure 12A:
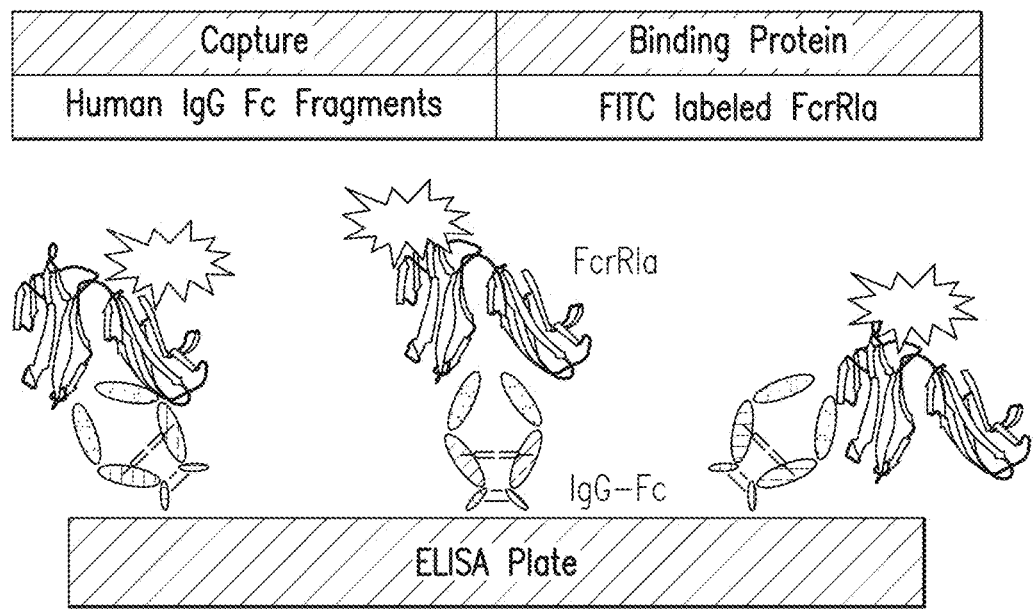
FIG. 12a-b: Fluorescence ELISA to detect affinity of FITC labeled FcγRIa for IgG-Fc.
Figure 12B:
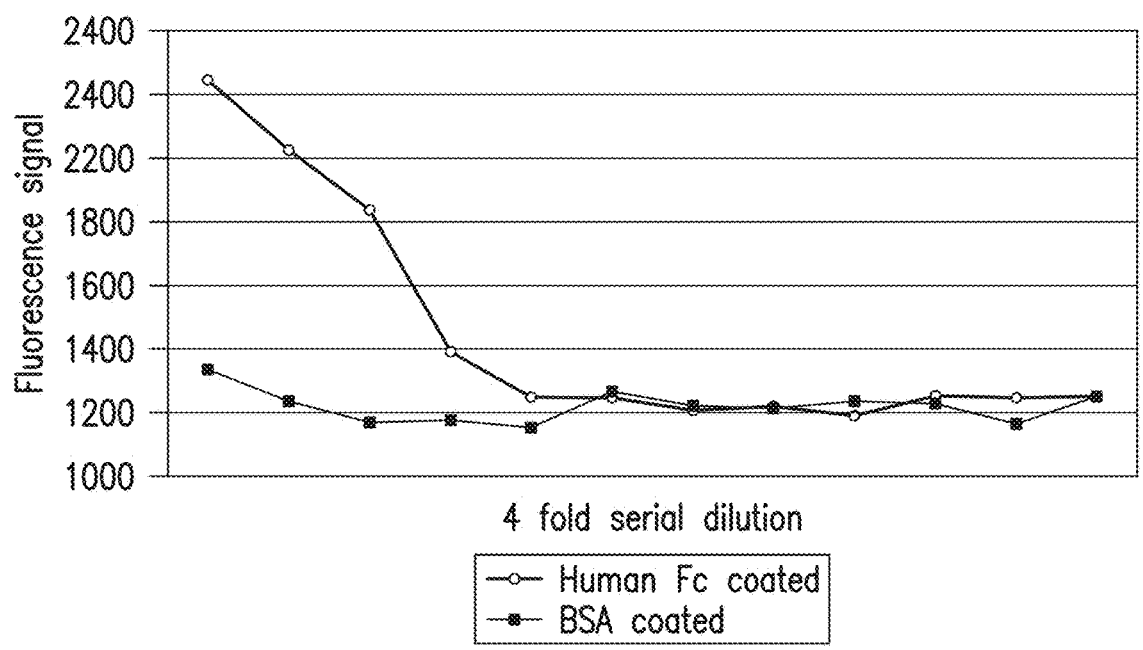
Figure 13A:
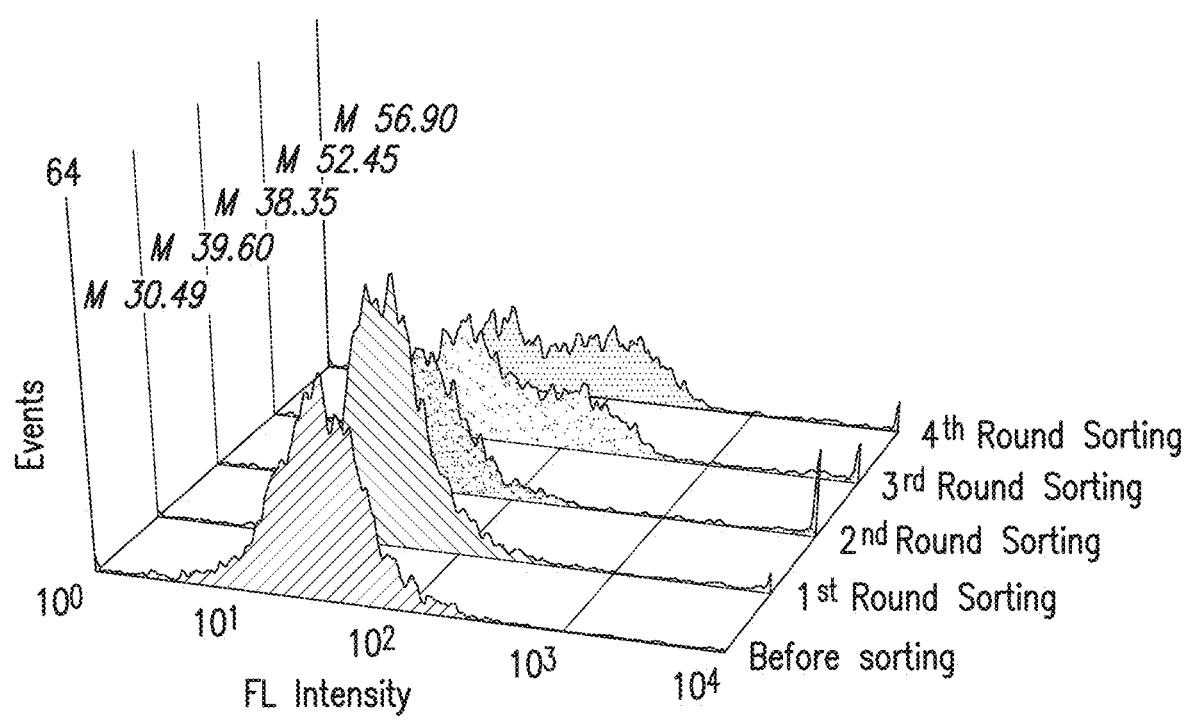
FIG. 13*a-b*: Fc library screening using FACS sorting.
Figure 13B:
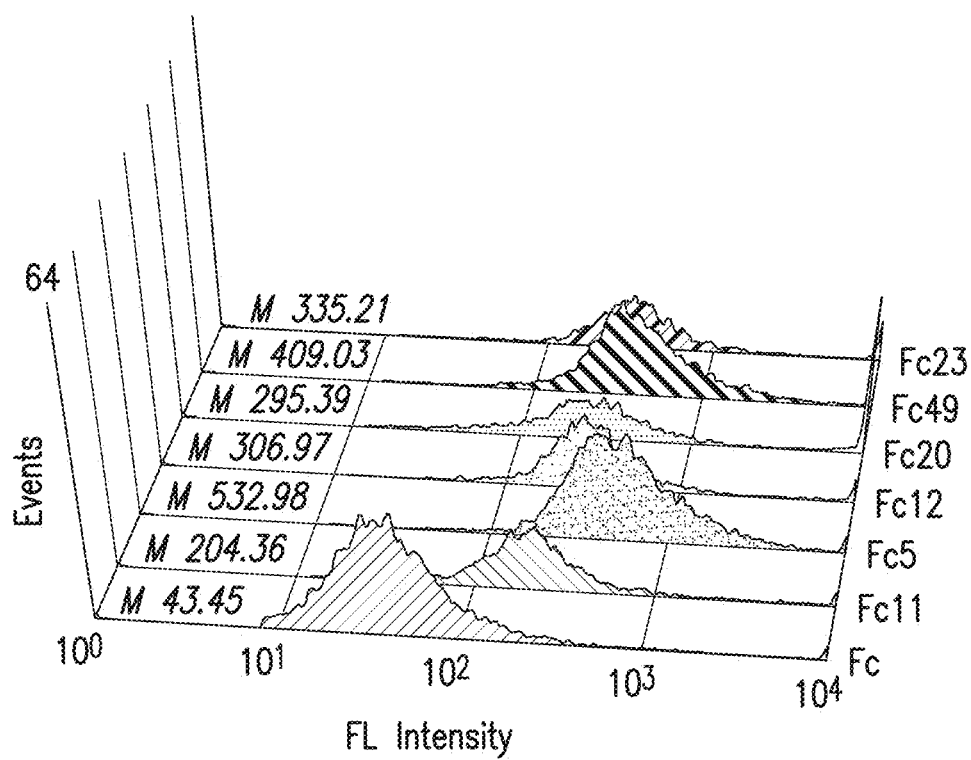
Figure 14:
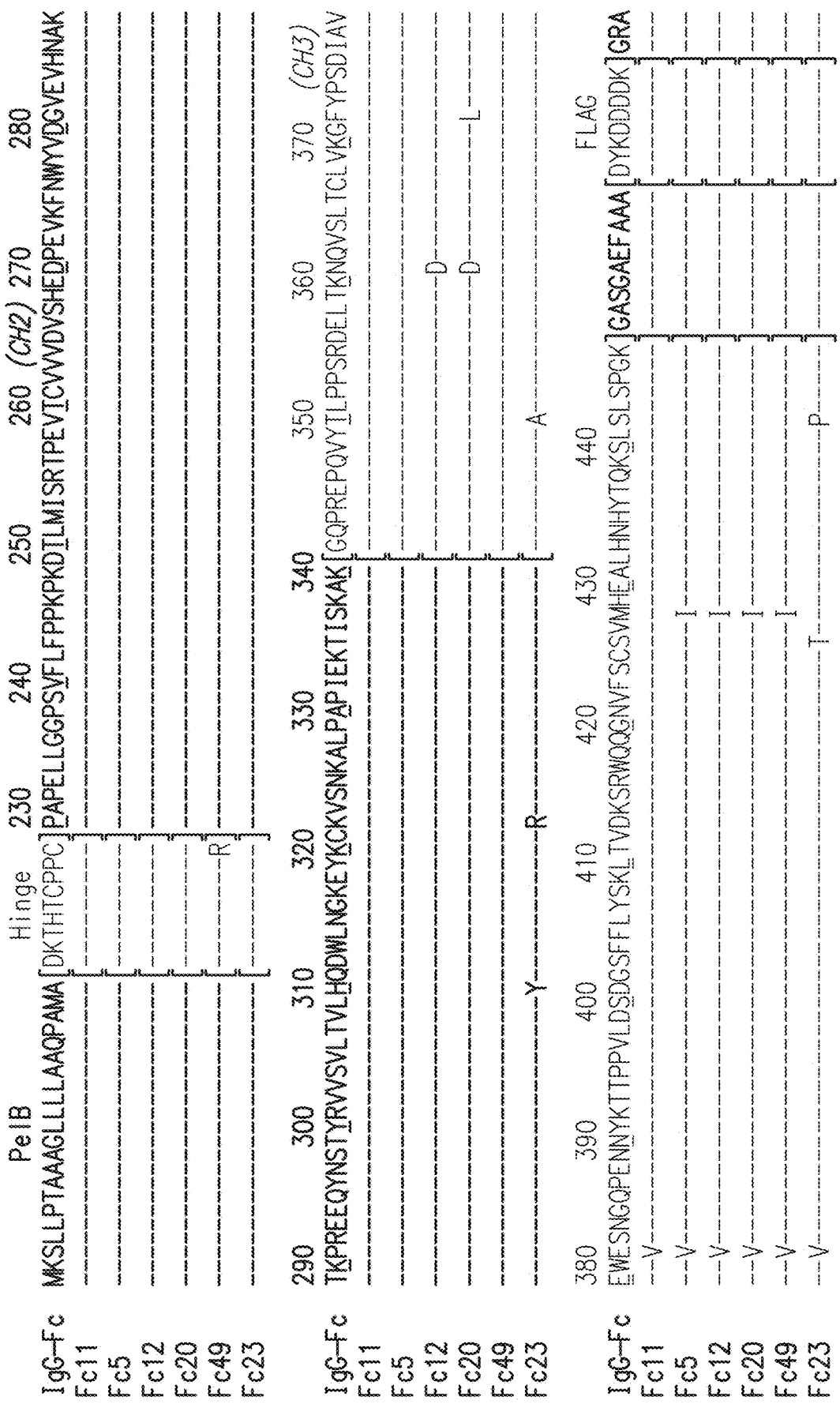
FIG. 14: Sequences of isolated Fc mutant clones exhibiting high affinity to FcγRIa. Depicted sequences are as follows used in the experiment with a FLAG tag attached to the C-terminal end, wt-IgG1 Fc, SEQ ID NO:1, Fc11, SEQ ID NO:2; Fc5, SEQ ID NO:3; Fc12, SEQ ID NO:4; Fc20, SEQ ID NO:5; Fc49, SEQ ID NO:6; and Fc23, SEQ ID NO:7.
Figure 15A:
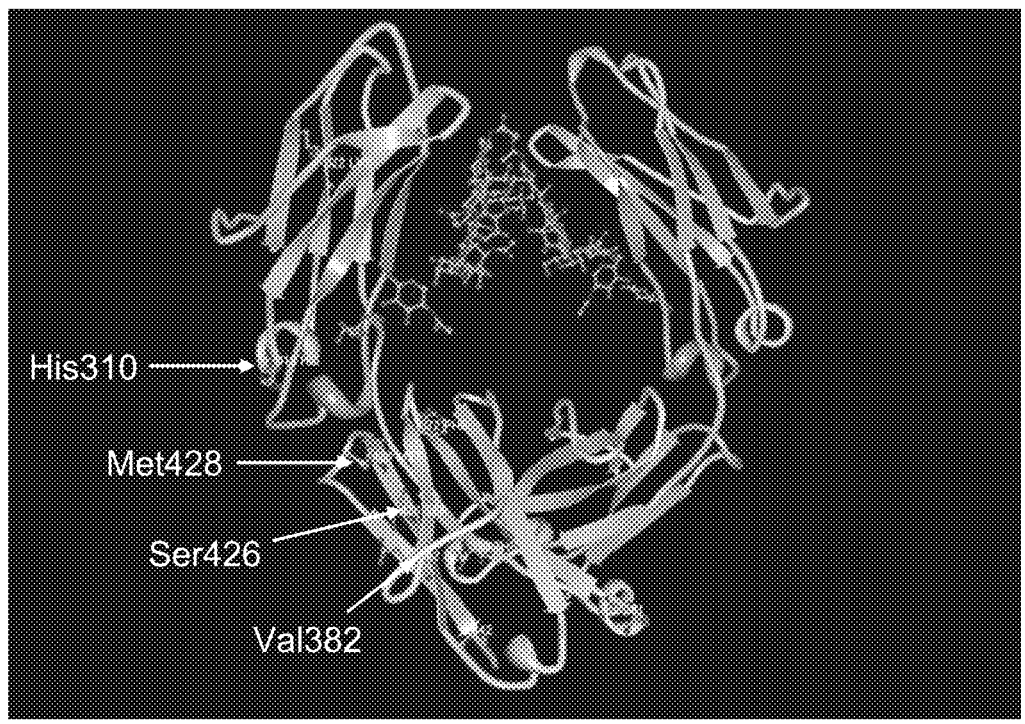
FIG. 15*a-b*: Mutation points of isolated aglycosylated Fcs in 3D structure of glycosylated IgG (PBD Code: 1FC1).
Figure 15B:
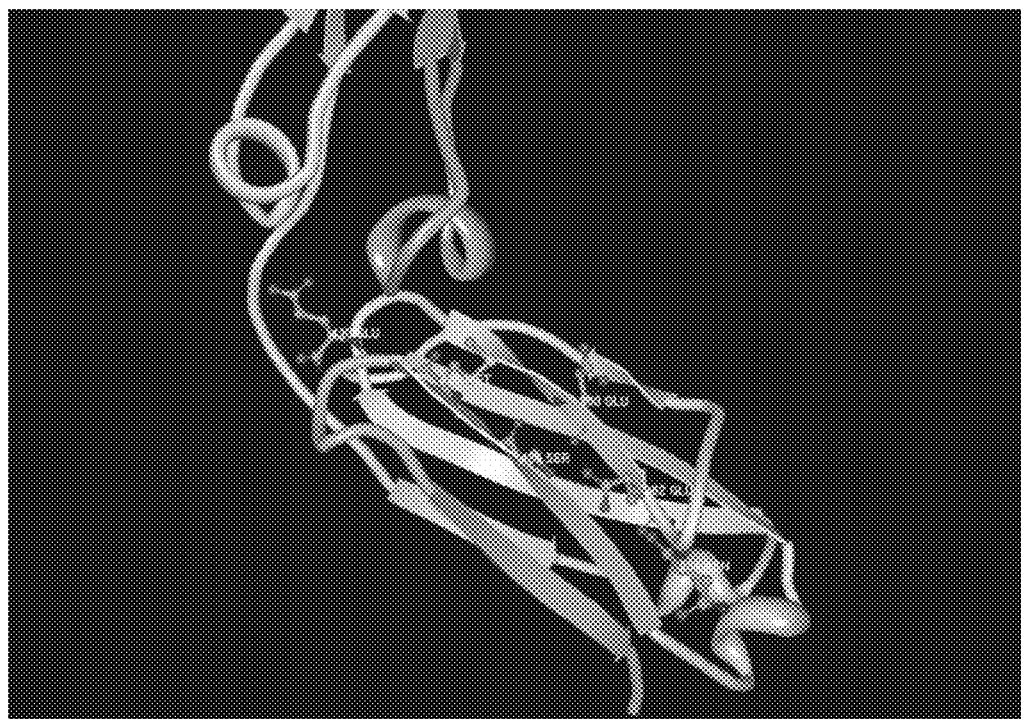

For library screening, extracellular domain of glycosylated FcγRIa was labeled with FITC as manufacturer's instruction. After the labeling reaction, the affinity of FITC labeled FcγRIa for human IgG Fc was confirmed by fluorescent ELISA displaying high fluorescence in the Fc glycosylated human IgG-Fc coated well comparing in the BSA coated well (FIG. 12). Total $1 \times 10^8$ spheroplasts were sorted and high fluorescent clones were enriched as sorting rounds go on (FIG. 13a). After the 4th round sorting, six individual clones showing high affinity to FcγRIa were isolated (FIG. 13b). All the six clones were from error prone PCR Fc library. The Fc5 showing the highest affinity to FcγRIa had two mutations E382V and M428I in CH3 region. The other five clones contained consensus mutations in E382V as well as M428I or S426T (FIG. 14) suggesting a critical role of two interacting beta sheets including the major mutation points in CH3 region for the binding of aglycosylated Fc to FcγRIa (FIGS. 15a and 15b).

Example 8

Randomization of Residues Around the Amino Acid Substitutions 382E and 428M

Figure 16:
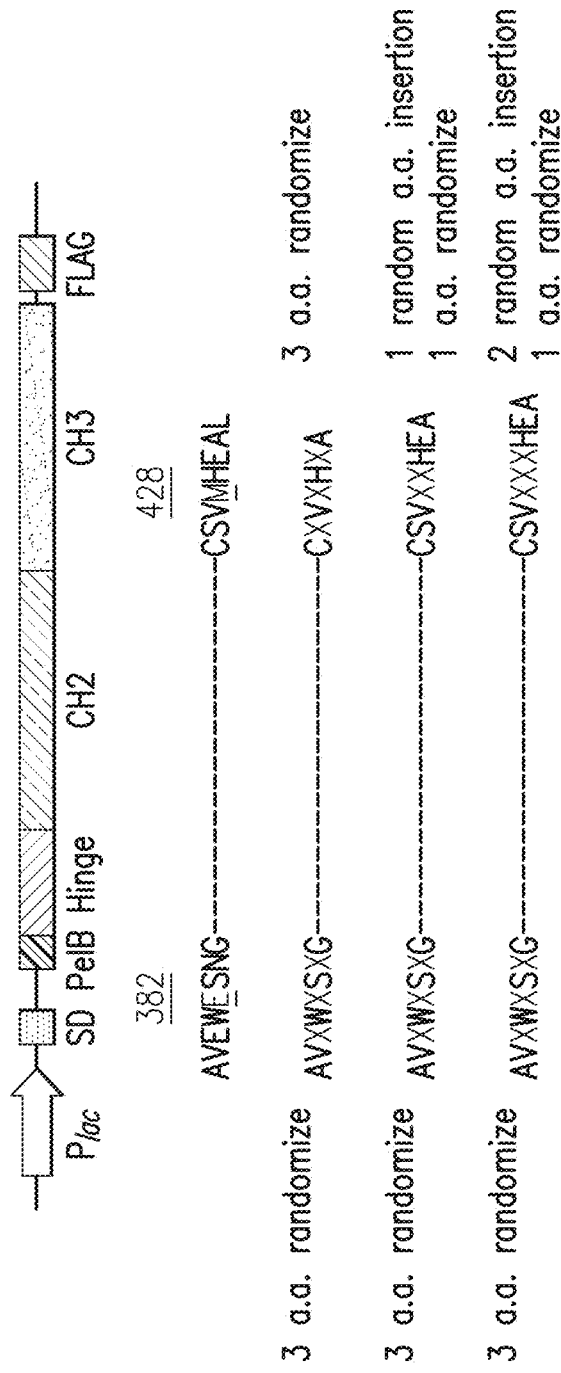
FIG. 16: Fc library comprising 3 kinds of sub-libraries randomized and inserted around 382E and 428M (AVEWESNG (Seq ID NO:123); CSVMHEAL (Seq ID NO:124); AVXWXSXG (Seq ID NO:125); CXVXHXA (Seq ID NO:126); CSVXXHEA (Seq ID NO:127); CSVXXXHEA (Seq ID NO:128)).

For the screening of Fc exhibiting high affinity to FcγRIa by randomization around the two critical mutation points 382E and 428M, a new library comprising three kinds of sub-libraries was constructed from the PelB leader peptide fused Fc (FIG. 16). In the first sub-library, three amino acids (380E, 382E, and 384N) around 382E interacting with the beta sheet containing 482M, were replaced by three random amino acid residues using random degenerate codons (NNS) (Kabat et al., 1991). Also, for the combinatorial library of beta sheet around 428M, three amino acids (426S, 428M, and 420E) interacting with the beta sheet including of 382E, were replaced by three random amino acids. In the second and third sub-libraries, to increase the interaction of the two beta sheets containing 382E and 428M in CH3 region with the alpha helix of CH2 region and possibly increase accessibility of FcγRIa (FIG. 15b), one or two random amino acids were inserted between 428M and 429H with the randomization of 428M and three amino acid residues (380E, 382E, and 384N) around 382E. The three sublibraries randomized around E382V and M428I, were generated using PCR products amplified using forward primers STJ #283 and STJ #284 (SEQ ID NOS:48 and 49) and reverse primers STJ #285, STJ #286, or STJ #287 (SEQ ID NOS: 50, 51 or 52). Each of the three sublibraries was subcloned into SexAI/SapI digested pPelBFLAG.-Fc. The resulting plasmids were transformed into E. coli Jude-1(F′ [Tn10 (Tet$^r$) proAB$^+$lacI$^q$ Δ(lacZ)M15] mcrA Δ(mrr-hsdRMSmcrBC) φ80d/acZΔM15 ΔlacX74 deoR recA1 araD139 Δ(ara leu)7697 galU galKrpsL endA1 nupG) (Kawarasaki et al., 2003).

Figure 17:
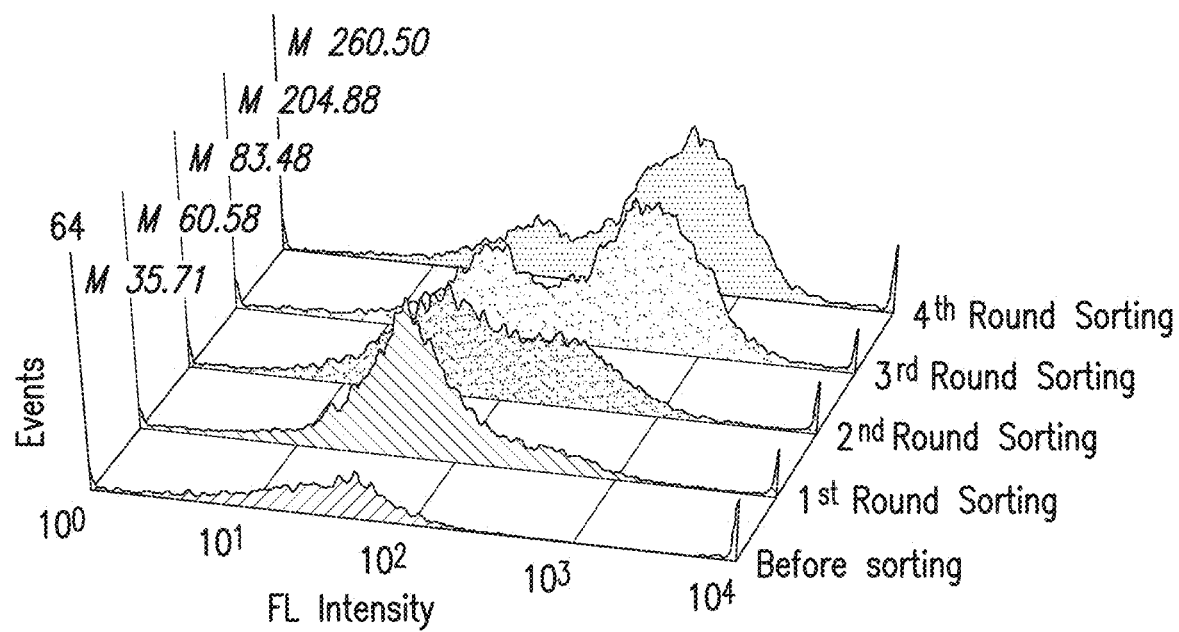
FIG. 17: Histogram showing enrichment of clones showing high affinity to FcγRIa by FACS sorting from the library randomized around 382E and 428M in FIG. 16.
Figure 18A:
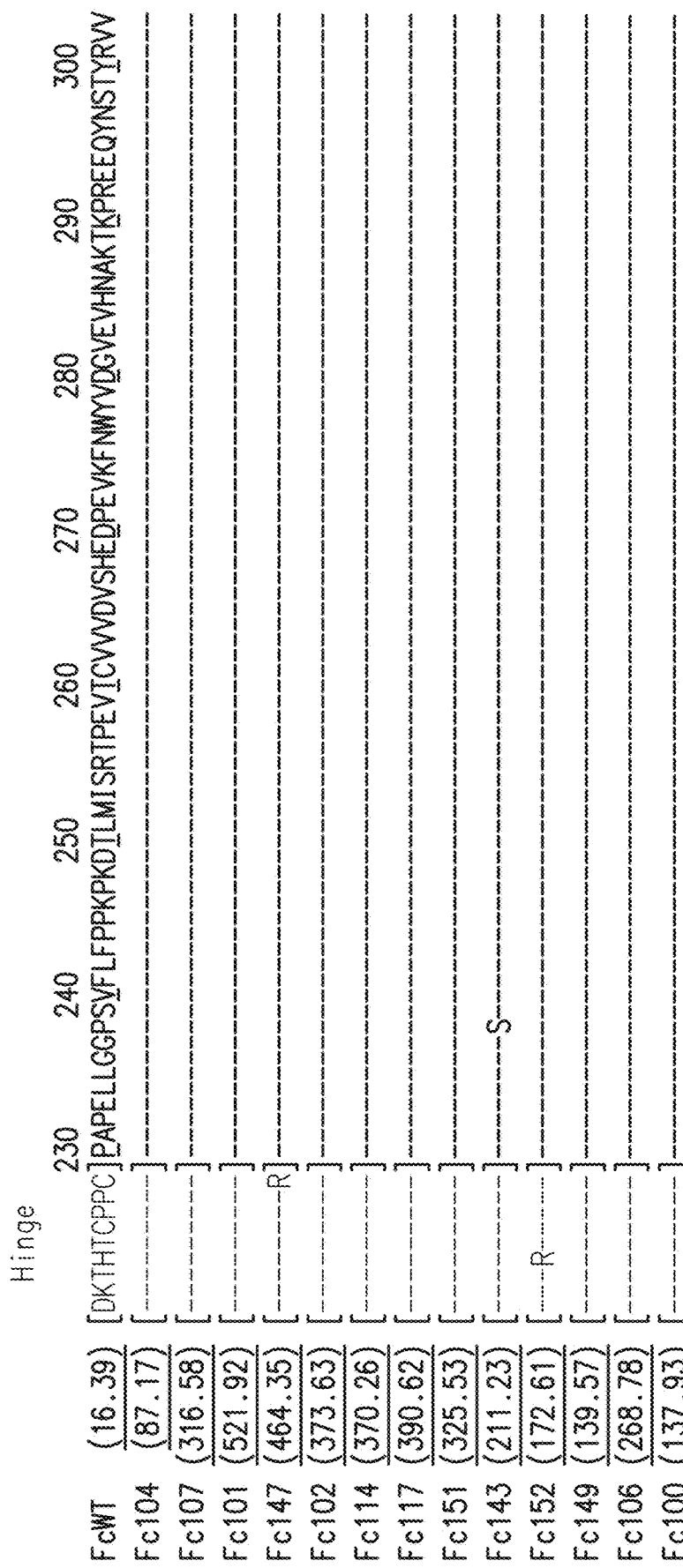
Figure 18B:
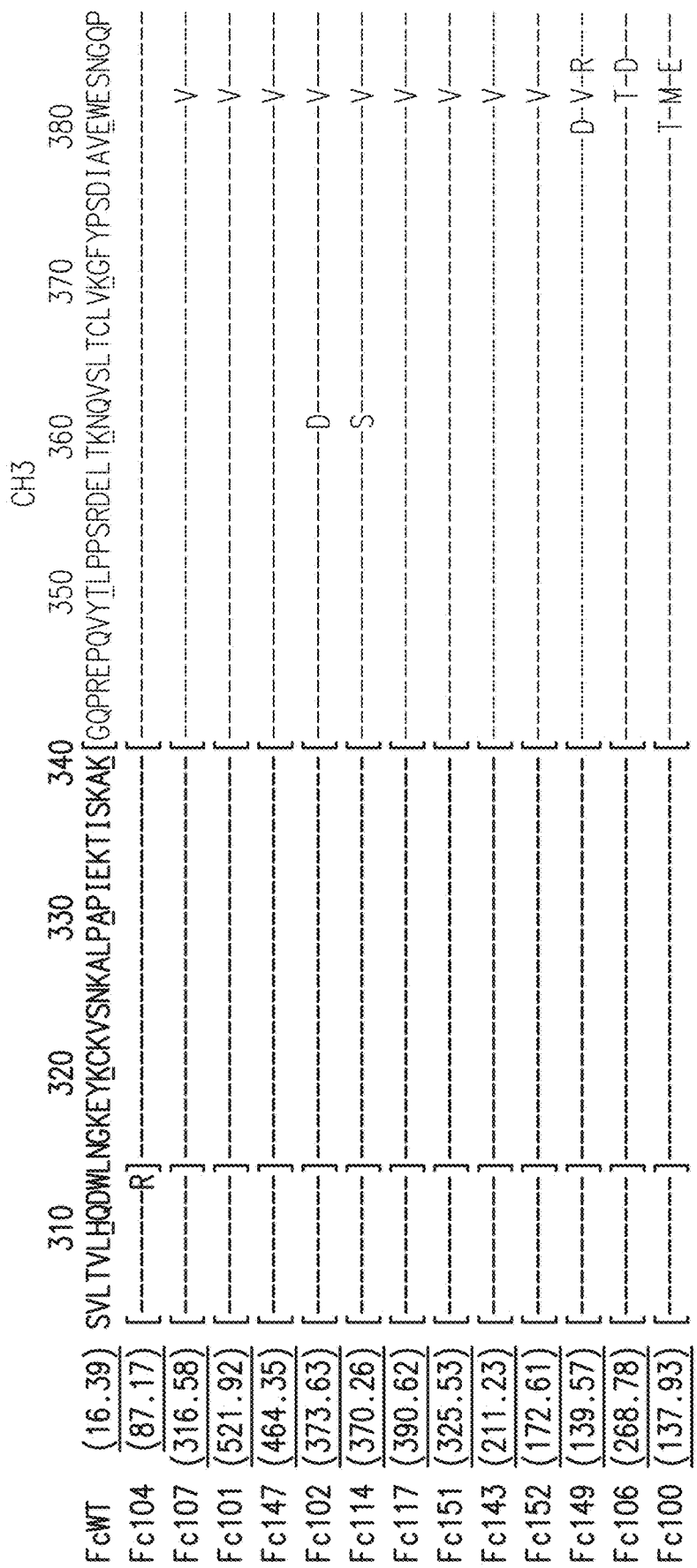
Figure 19:
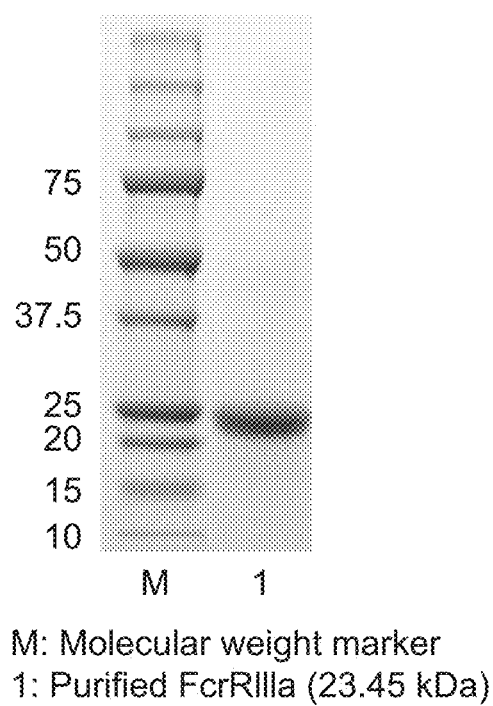
FIG. 19: SDS-PAGE of purified and refoled FcγRIIIa from *E. coli* inclusion bodies.

The transformation of the resulting library, mixture of three sub-libraries, generated over $10^7$ transformants. Table 4 shows the sequencing results of 10 randomly picked clones indicating that the expected sequence diversity had been obtained. The library cells were cultured in media containing trehalose, protein synthesis was induced with 1 mM IPTG and after 5 hours the cells were harvested and converted into spheroplasts as described in Example 4. Following labeling, spheroplasts were sorted by FACS. In each round the top 3% of the population showing the highest fluorescence due to FcγRIa-FITC binding labeling was isolated (~1×10$^8$ spheroplasts were sorted in each round of sorting). The Fc encoding genes were recovered by PCR ligated into vector and the ligation mix was transformed into E. coli Jude-1. Transformants were selected on chloramphenicol containing media and then grown, spheroplasted as above in preparation for the next round of sorting (FIG. 17). After the 4$^{th}$ round of sorting, 14 individual clones exhibiting high fluorescence were isolated (FIG. 18a-c). However, the parental Fc5 clone (E382V/M428I) showed the highest fluorescence; importantly most of the selected mutants contained the mutations E382V and/or M428I or M428L, again suggesting the importance of these two amino acid substitutions.

phosphate buffer, pH 8.2) and solubilized in U8 KP buffer (8M urea, 10 mM potassium phosphate buffer, pH 8.2). The solubilized and denatured FcγRIIIa protein was purified using Ni-NTA affinity chromatography and refolded by consecutive dialysis (FIG. 19) (Jung et al., 2003). The purified FcγRIIIa was labeled with FITC using a commercial FITC labeling kit (Molecular Probes) as described in the manufacurer's instructions. 1.5 µl of FITC labeled FcγRIIIa (0.8 mg/ml) per 1 ml reaction was used for the labeling of spheroplasts.

Example 10

Selection of FcγRIIIa Binders

In order to select candidate Fc mutants having the ability to bind FcγRIIIa polypeptides, a technique similar to that described above for FcγRIa binders was employed, with the exception FcγRIIIa polypeptides were employed in place of the FcγRIa polypeptides. In the context of FcγRIIIa binders, however, the approach has not been uniformly reproducible. That is, mutants so identified demonstrate FcγRIIIa binding capability in some studies and fail to demonstrate binding capability in other studies. At the time of the present filing, the inventors are confirming that this technique can indeed be used to identify reproducible FcγRIIIa binders. In this technique, to isolate binders to FcγRIIIa two libraries were

TABLE 4

Sequence of randomly picked up 10 clones from library randomized around 382E and 428M

| Wild type | 378-AVEWESNG-385 | 425-CSVMHE~~AL-432 |
|---|---|---|
| 1 | AV<u>AWDSR</u>G (SEQ ID NO: 85) | CSV<u>AL</u>HE~AL (SEQ ID NO: 95) |
| 2 | AV<u>YWSSL</u>G (SEQ ID NO: 86) | C<u>LVCH</u>S~~AL (SEQ ID NO: 96) |
| 3 | AV<u>LWGSL</u>G (SEQ ID NO: 87) | C<u>LVLH</u>G~~AL (SEQ ID NO: 97) |
| 4 | AV<u>VCYS</u>YG (SEQ ID NO: 88) | C<u>RV*HP</u>~~AL (SEQ ID NO: 98) |
| 5 | AV<u>SWISQ</u>G (SEQ ID NO: 89) | CSV<u>GG</u>HE~AL (SEQ ID NO: 99) |
| 6 | AV<u>NWESK</u>G (SEQ ID NO: 90) | CSV<u>LLS</u>HEAL (SEQ ID NO: 100) |
| 7 | AV<u>TWRSW</u>G (SEQ ID NO: 91) | CSV<u>P</u>VHE~AL (SEQ ID NO: 101) |
| 8 | AV<u>*WSSQ</u>G (SEQ ID NO: 92) | CSV<u>H</u>LHE~AL (SEQ ID NO: 102) |
| 9 | AV<u>NWNSW</u>G (SEQ ID NO: 93) | CSV<u>R</u>DHE~AL (SEQ ID NO: 103) |
| 10 | AV<u>DWRSV</u>G (SEQ ID NO: 94) | C<u>TVCH</u>I~~AL (SEQ ID NO: 104) |

Underlining indicates mutated or inserted amino acids; *: Stop codon; ~: Blank

Example 9

Preparation and Labeling of the Extracellular Domain of the FcγRIIIa Protein

Figure 20:
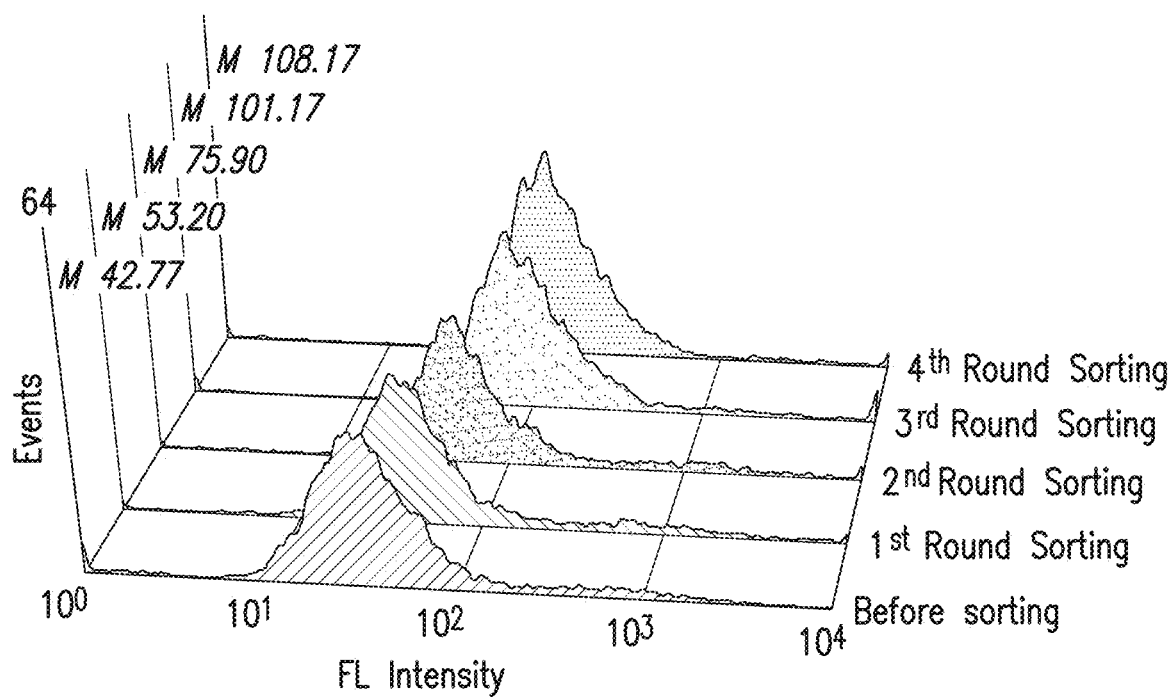
FIG. 20: Histogram showing enrichment of high affinity clones sorted by FcγRIIIa-FITC.
Figure 21:
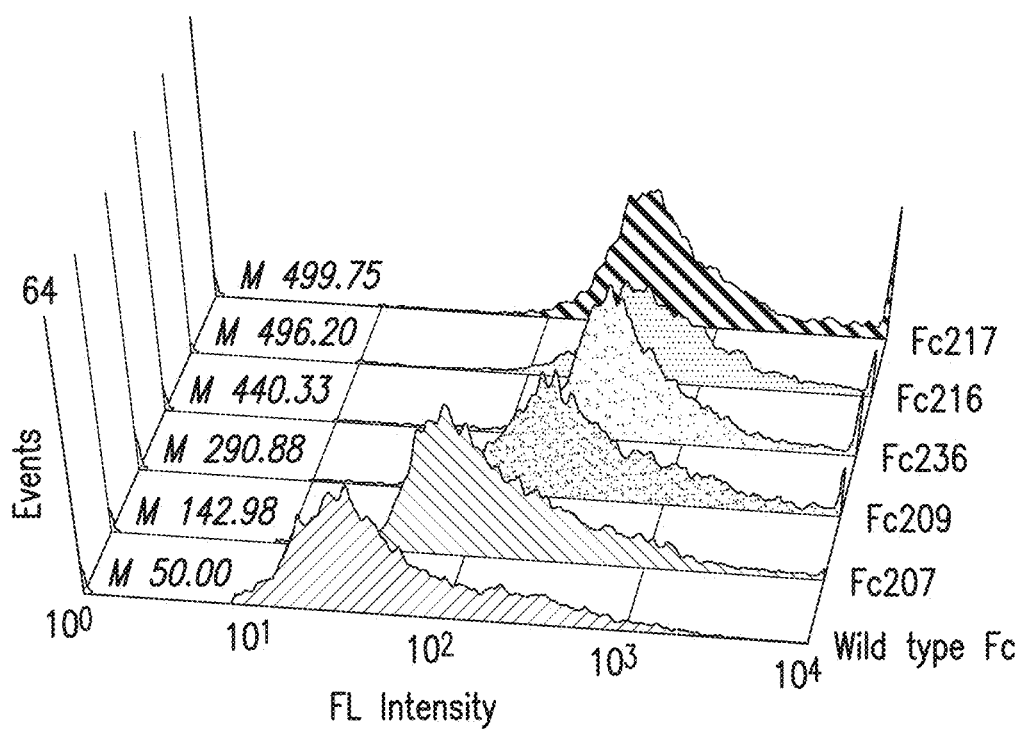
FIG. 21: Histogram showing fluorescence signals of Fc mutants comparing with wild type Fc. Spheroplasts were incubated with FcγRIIIa-FITC for detection. M: Mean fluorescence intensity.
Figure 22:
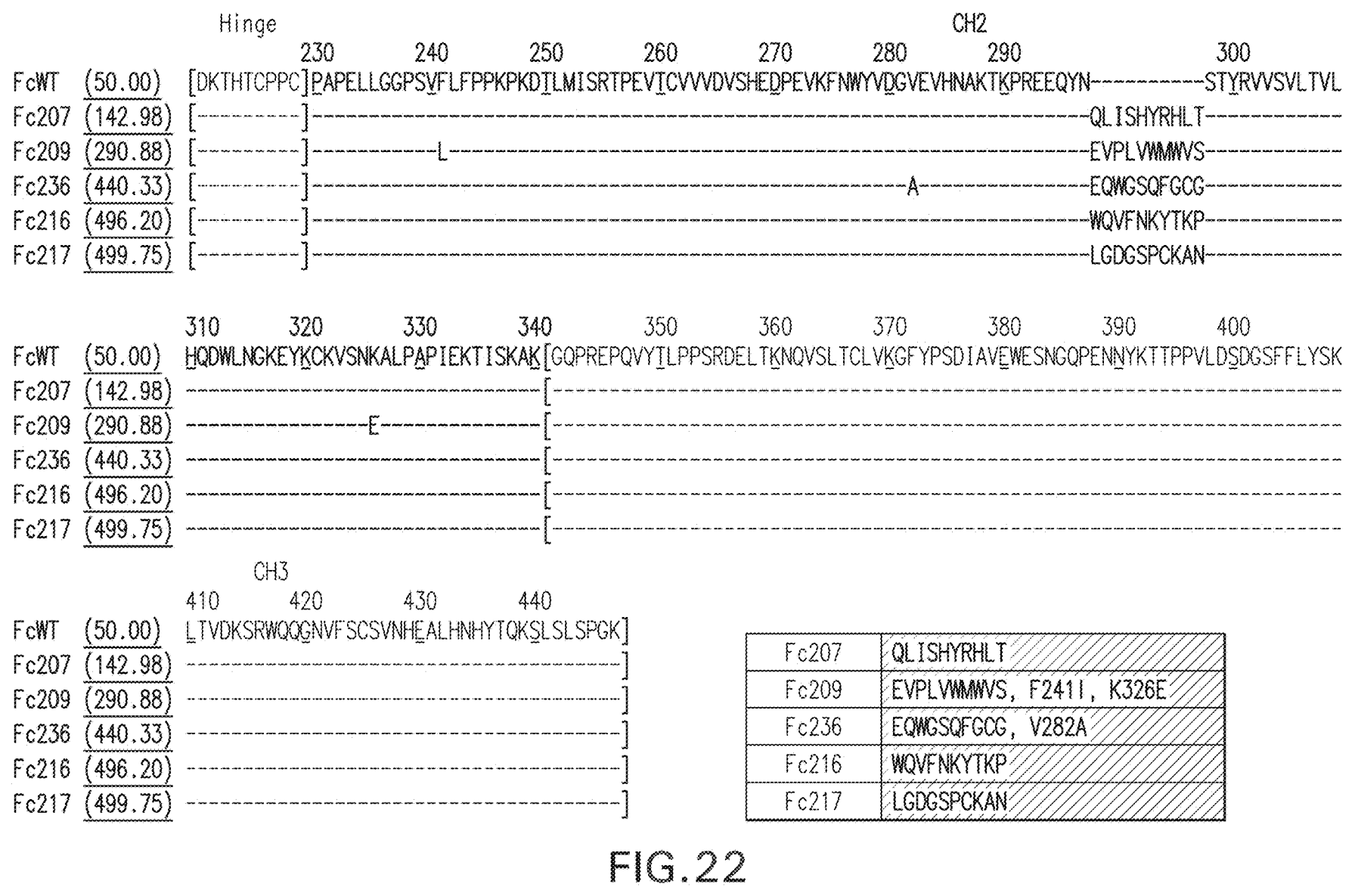

For library screening, the extracellular domain of aglycosylated FcγRIIIa was first purified from E. coli inclusion bodies. First an E. coli codon optimized FcγRIIIa synthetic gene (Nucleotide Sequence #1 (SEQ ID NO:105)) was subcloned into pET21a (Novagen) and transformed into E. coli BL21(DE3). After 5 hr induction with 1 mM IPTG induction, Western blot analysis revealed that the majority of the FcγRIIIa protein was present as inclusion bodies. Inclusion bodies were harvested by centrifugation of cell lysates, washed with U2 KP buffer (2M urea in 10 mM potassium constructed: First, the Fc gene was subjected to random mutagenesis by error prone PCR. Second, a 10 random amino acids insertion library was employed. The library cells were cultured in media containing trehalose, protein synthesis was induced with 1 mM IPTG and after 5 hours the cells were harvested and converted into spheroplasts as described in Example 4. Following labeling, spheroplasts were sorted by FACS. In each round the top 3% of the population showing the highest fluorescence due to FcγRIIIa-FITC binding labeling was isolated (1×10$^8$ spheroplasts were sorted in each round of sorting). The Fc encoding genes were recovered by PCR ligated into vector and the ligation mix was transformed into E. coli Jude-1. Transformants were selected on chloramphenicol containing media and then grown, spheroplasted as above in preparation for the next round of sorting (FIG. 20). After the 4th round sorting, five individual clones exhibiting high affinity to FcγRIIIa were isolated (FIG. 21). All five clones contained 10 random amino acid insertions. Two of these clones had additional mutations that presumably resulted from PCR amplification (FIG. 22). Although these mutant clones are generally considered to be high affinity binders, as noted above they have been found to exhibit certain variability in different tests.

Example 11

Selection of FcγRIIa Binders from a Library of Random Mutants of Fc5

Figure 23:
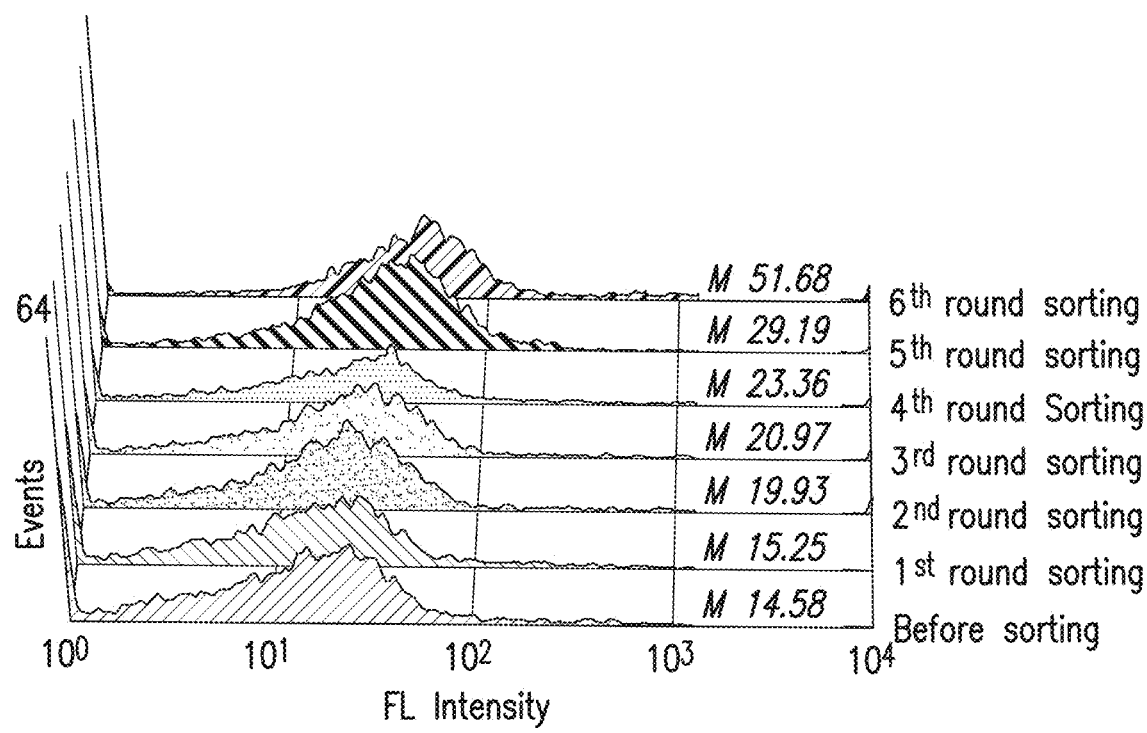
FIG. 23: Histogram showing enrichment of high affinity clones sorted by FcγRIIa-FITC
Figure 24:
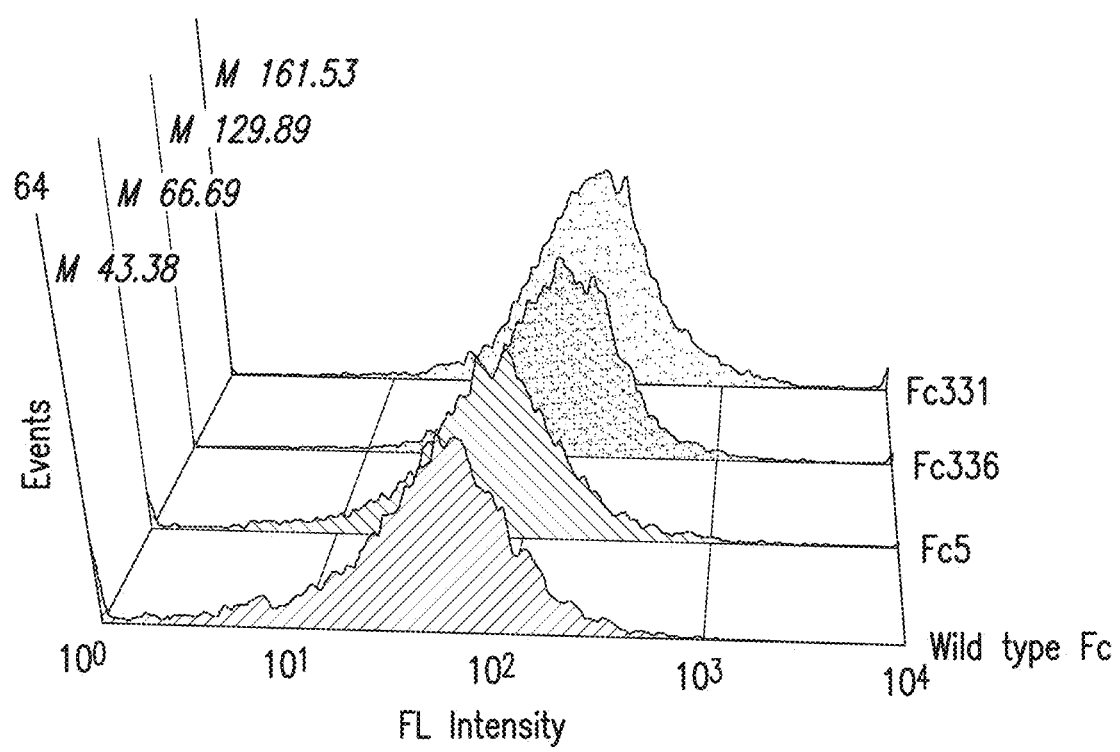
FIG. 24: Histogram showing fluorescence signals of Fc mutants comparing with wild type Fc. Spheroplasts were incubated with FcγRIIa-FITC for detection. M: Mean fluorescence intensity.
Figure 25:
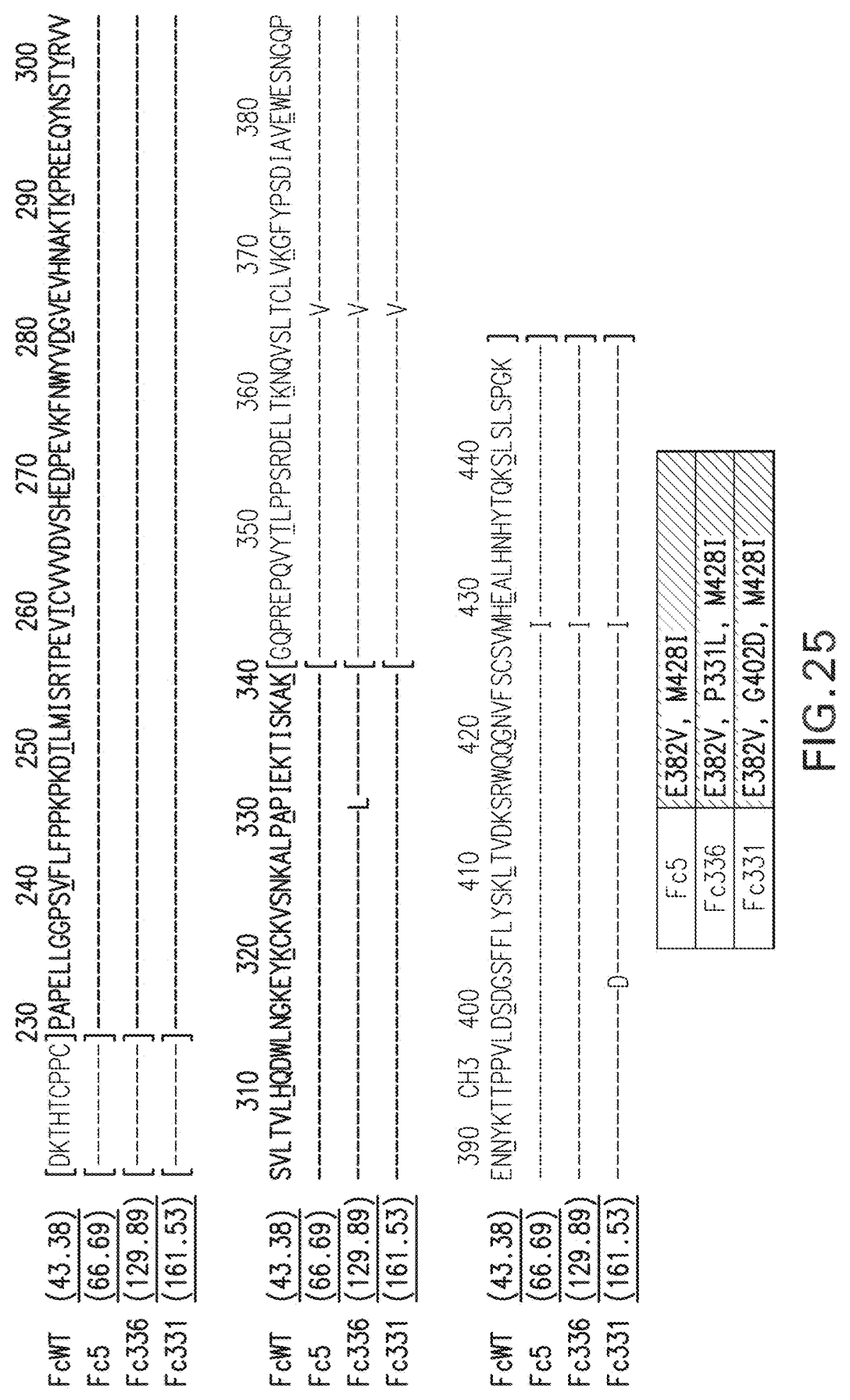

For the selection of FcγRIIa binders, either the same mixture of library including 10 a.a. insertion library and an error prone PCR library described in Example 7 or the Fc5 error prone PCR library using the template Fc5 (Fc: E382V, M428I) are used. The library size of Fc5 error prone PCR library was $1.1 \times 10^7$ and the error rate was 0.131% as determined by the sequencing of 20 randomly selected clones. For library screening, the extracellular domain of glycosylated FcγRIIa (R&D systems) was conjugated to FITC using a FITC labeling kit (Molecular Probes) as described in the manufacturer's instruction. For the labeling of spheroplasts, 2 μl of FITC labeled FcγRIIa (0.975 mg/ml) per 1 ml reaction was used. The library cells were cultured in media containing trehalose, protein synthesis was induced with 1 mM IPTG and after 5 hours the cells were harvested and converted into spheroplasts as described in Example 4. Following labeling spheroplasts were sorted by FACS. In each round the top 3% of the population showing the highest fluorescence due to FcγRIIa-FITC binding labeling was isolated ($1 \times 10^8$ spheroplasts were sorted in each round of sorting) (FIG. 23). The Fc encoding genes were recovered by PCR ligated into vector and the ligation mix was transformed into *E. coli* Jude-1. Transformants were selected on chloramphenicol containing media and then grown, spheroplasted as above in preparation for the next round of sorting. After the 6$^{th}$ round sorting from the Fc5 error prone PCR library, two individual clones showing high affinity to FcγRIIa were isolated (FIG. 24). In addition to the two mutations encoded by the Fc5 parental gene (E382V/M428I), the two isolated clones Fc331 and Fc336 had the mutations G402D and P331L, respectively (FIG. 25). Although these mutant clones are generally considered to be high affinity binders, they may exhibit certain variability in different tests.

Figure 26:
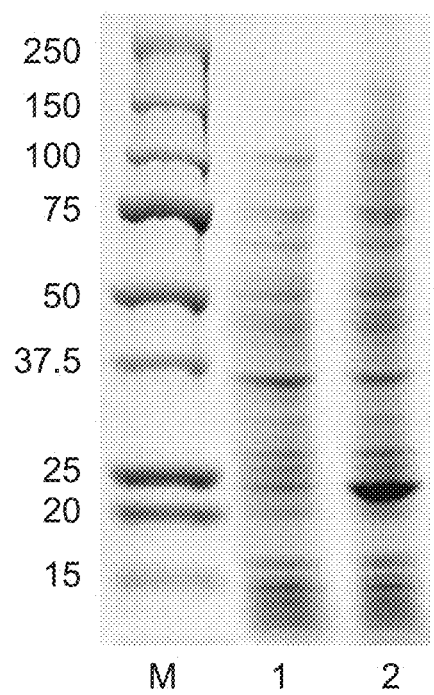
FIG. 26. SDS-PAGE showing the expression of wild type FcγRIIa and codon optimized FcγRIIa, Lane 1: Wild type FcγRIIa; Lane 2: codon optimized FcγRIIa.
Figure 27:
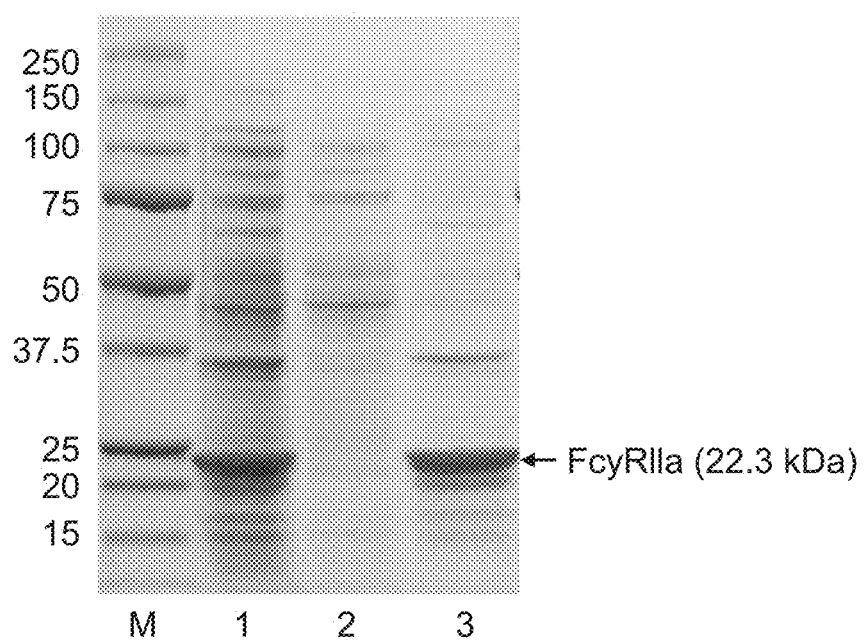
FIG. 27. SDS-PAGE showing the localization of codon optimized FcγRIIa, Lane 1: Total fraction; Lane 2: soluble fraction; Lane 3: insoluble fraction.
Figure 28:
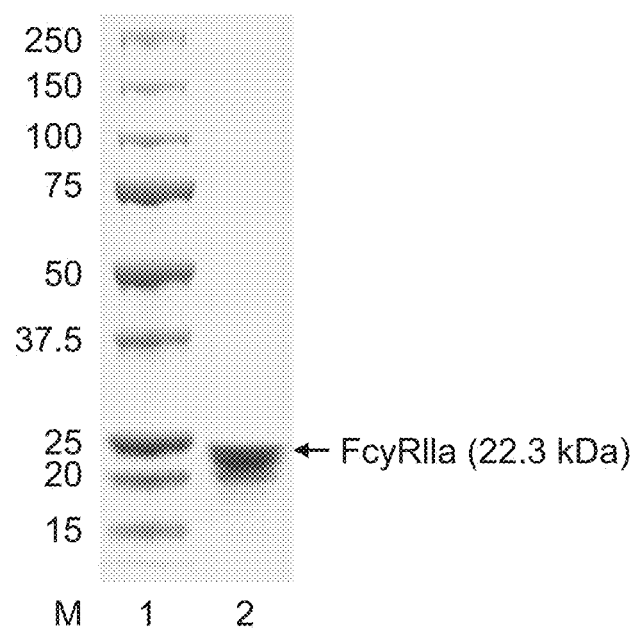
FIG. 28. SDS-PAGE showing the purified FcγRIIa. Lane 1: purified FcγRIIa.
Figure 29:
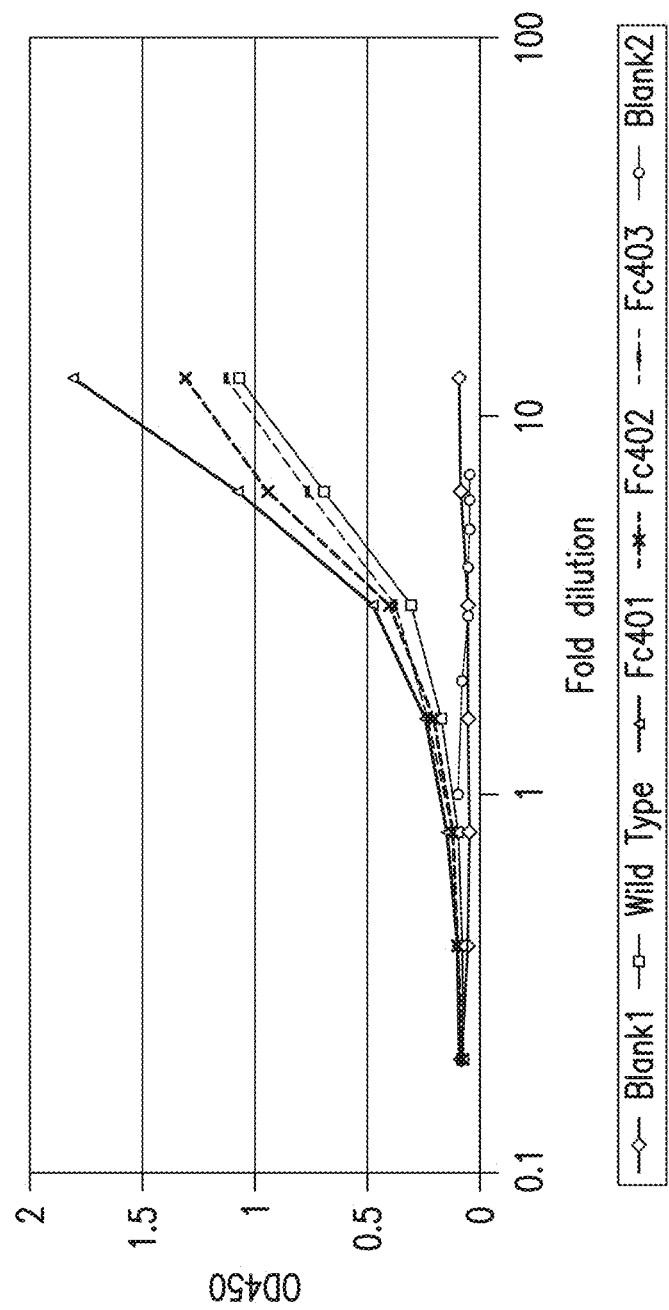
FIG. 29. ELISA result of Fc mutants to FcγRIIa from the media fraction of cultured Jude-1 cells harboring pDsbA-FLAG-Fc mutant plasmids.

Alternatively, after the 5$^{th}$ round sorting from the same mixture of library including 10 a.a. insertion library and error prone PCR library described in Example 7, Fc fragment genes were subcloned into SaiI/HindIII digested pDsbAFLAG plasmid and 192 individual colony harboring pDsbAFLAG-Fc mutant genes were cultured in 96 well plates with 200 μl working volume. The culture supernatant from the induced cells was separated by centrifugation at 4000 rpm for 30 min. For ELISA analysis, the extracellular domain of aglycosylated FcγRIIa was purified from *E. coli* inclusion bodies. First an *E. coli* codon optimized FcγRIIa synthetic gene (Nucleotide Sequence #2 SEQ ID NO:106)) was subcloned into pET21a (Novagen) and transformed into *E. coli* BL21(DE3). After 5 hr induction with 1 mM IPTG induction, SDS-PAGE analysis revealed that codon optimized FcγRIIa synthetic gene shows dramatically increased expression level comparing with wild type FcγRIIa gene (FIG. 26) and the majority of the FcγRIIa protein was present as inclusion bodies (FIG. 27). Inclusion bodies were harvested by centrifugation of cell lysates, washed with U2KP buffer (2M urea in 10 mM potassium phosphate buffer, pH 8.2) and solubilized in U8KP buffer (8M urea, 10 mM potassium phosphate buffer, pH 8.2). The solubilized and denatured FcγRIIa protein was purified using Ni-NTA affinity chromatography and refolded by consecutive dialysis (FIG. 28) (Jung et al., 2003). 100 μl of the culture supernatants were transferred to 96 well ELISA plates and incubated at 4° C. for overnight. After coating with PBS, 0.5% BSA for 2 h at room temperature, the plate was washed 4 times with PBS, 0.05% Tween20 and then added with 12.5 μg/ml of aglycosylated FcγRIIa purified from *E. coli*. After 1 h incubation at room temperature and washing with PBS, 0.05% Tween20, 1:10000 diluted Anti-His antibody HRP conjugate (Sigma-Aldrich) was added. After additional 1 h incubation at room temperature and washing, TMB was added for detection and 2M $H_2SO_4$ was added to quench the reaction. The plate was read at 450 nm with 96 well plate reader (Bio-Tek). Three Fc mutants, (Fc401, 402, and Fc403) showed higher ELISA signal comparing with wild type Fc (FIG. 29).

Example 12

Sequences of Selected Clones

Isolated Fc mutants have substitution or insertion mutations in the sequence of wild type Fc (Nucleotide Sequence #3 (SEQ ID NO: 107) and Protein Sequence #1 (SEQ ID NO:1)). Mutation points of the isolated clones showing high affinity to FcγR5 are summarized in Table 5. Fc mutants (Protein Sequence #2, 3, 4, 5, 6, 7, 8, 9, 10, 11, 12, 13, 14, 15, 16, and 17; SEQ ID NOS:3, 2, 4, 5, 7, 6 and SEQ ID NOS:65-73) show high affinity to FcγRIa. Fc mutants (Protein Sequences #18, 19, 20, 21, and 22; SEQ ID NOS:74-78) show high affinity to FcγRIIIa. Fc mutants (Protein Sequence #23, 24, 25, 26, 27; SEQ ID NOS:79, 80, 122, 81 and 82) show high affinity to FcγRIIa. Although these mutant clones binding to FcγRIIIa and FcγRIIa are generally considered to be high affinity binders, some of them have been found to exhibit certain variability in different tests.

TABLE 5

Mutations in Fc showing high affinity to FcγRs

| Fc mutants | Binding FcγR | Mutations |
|---|---|---|
| Fc5 | FcγRIa | E382V, M428I |
| Fc11 | | E382V |
| Fc12 | | N361D, E382V, M428I |
| Fc20 | | N361D, F372L, E382V, M428I |
| Fc23 | | H310Y, K322R, T350A, E382V, S426T, S442P |

TABLE 5-continued

Mutations in Fc showing high affinity to FcγRs

| Fc mutants | Binding FcγR | Mutations |
|---|---|---|
| Fc49 | | C229R, E382V, M428I |
| Fc104 | | W313R, M428I |
| Fc106 | | E382T, N384D, M428I |
| Fc110 | | E380R, E382M, N384E |
| Fc114 | | N361S, E382V, M428I |
| Fc117 | | E382V, M428I, Y436A |
| Fc143 | | P238S, E382V, S426V, M428L, E430H |
| Fc149 | | E380D, E382V, N384R, S426V, M428L, E430D |
| Fc151 | | E382V, S426I, M428L, E430S |
| Fc152 | | H224R, E382V, S426T, M428S, E430P |
| Fc207 | FcγRIIIa | QLISHYRHLT (SEQ ID NO: 108) insertion between N297 and S298 |
| Fc209 | | F241L, K326E, EVPLVWMWVS (SEQ ID NO: 63) insertion between N297 and S298 |
| Fc216 | | WQVFNKYTKP (SEQ ID NO: 61) insertion between N297 and S298 |
| Fc217 | | LGDGSPCKAN (SEQ ID NO: 62) insertion between N297 and S298 |
| Fc236 | | V282A, EQWGSQFGCG (SEQ ID NO: 64) insertion between N297 and S298 |
| Fc331 | FcγRIIa | E382V, G402D, M428I |
| Fc336 | | E382V, P331L, M428I |
| Fc401 | | RTETPVYMVM (SEQ ID NO: 60), 10 a.a. insertion between N297 and S298 |
| Fc402 | | P331L |
| Fc403 | | S239L, I253T, Q347L, E382V |

Example 13

Soluble Expression and Purification of Wild Type Fc and Fc Mutants

For the expression of correctly assembled, homodimeric Fc in the periplasmic space of *E. coli*, two different signal peptides were examined: The PelB signal peptide which is directed to the general secretory pathway post-translationally (Lei et al., 1987; Better et al., 1988) and the DsbA signal peptide which is exported co-translationally in an SRP (signal recognition particle)-dependent fashion (Schierle et al., 2003). For the former, the Fc gene was cloned into the pPelBFLAG-Fc plasmid described in Example 2. The plasmid pDsbAFLAG-Fc was constructed for the export of Fc via the DsbA signal peptide. To construct pDsbALAG-Fc first, a synthetic DNA fragment encoding the 53 by DsbA signal peptide gene (ATGAAAAAGATTTGGCTG-GCGCTGGCTGGTTTAGTTTTAGCGTTTAGCG-CATCGGCG (SEQ ID NO:109)) was introduced into pTrc99A following cleavage with FatI which is compatible with the NcoI in pTrc99A (Amersham Pharmacia) and also with SalI. The resulting plasmid was named pDsbA. The parental Fc or Fc mutant genes were amplified using he primers STJ #144 (TTTTAGGGGTCGACGACAAAACT-CACACATGCCCACCGTG (SEQ ID NO:41)) and STJ #145 (TTTAAGGGAAGCTTCTATTAGGCGCGCCCTTT-GTCATCG (SEQ ID NO:42), ligated into pDsbA plasmid using SalI and HindIII restriction enzyme sites giving rise to pDsbAFLAG-Fc.

Figure 30:
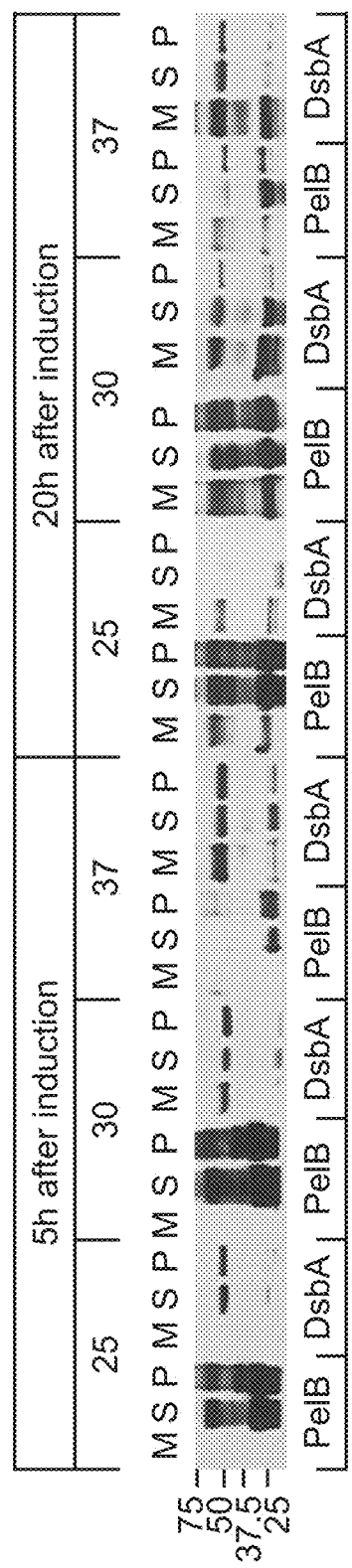
FIG. 30: Soluble expression of homodimeric wild type Fc and Fc mutants (5 ml tube culture). Wild type Fc with two different signal peptides (PelB and DsbA) was expressed at different culture temperatures after induction and was harvested at different times. The localization of the protein was also analyzed.

The effect of growth temperature, following induction of protein synthesis on the localization of Fc proteins was examined in *E. coli* Jude-1 cells harboring pPelBFLAG-Fc and on pDsbAFLAG-Fc was examined as follows: Cells were grown at 37° C. and then growth temperature was either changed to 25° C. or 30° C. or kept 37° C. 15 minutes before induction. The cells were induced with 1 mM IPTG at mid-exponential growth phase ($OD_{600}$=0.6) and harvested either 5 h or 20 h after induction. Cells were fractionated by the periplasmic osmotic shock procedure (Osborn et al., 1972) and the level of Fc protein in the extracellular fluid (growth medium) periplasmic (osmotic shock) and cytoplasmic fractions was determined by SDS-PAGE and Western bloting (O'Brien et al., 2002) (FIG. 30). Export via the DsbA leader peptide showed a substantially higher amount of correctly assembled Fc both in the periplasmic fraction and in the growth media.

Figure 31:
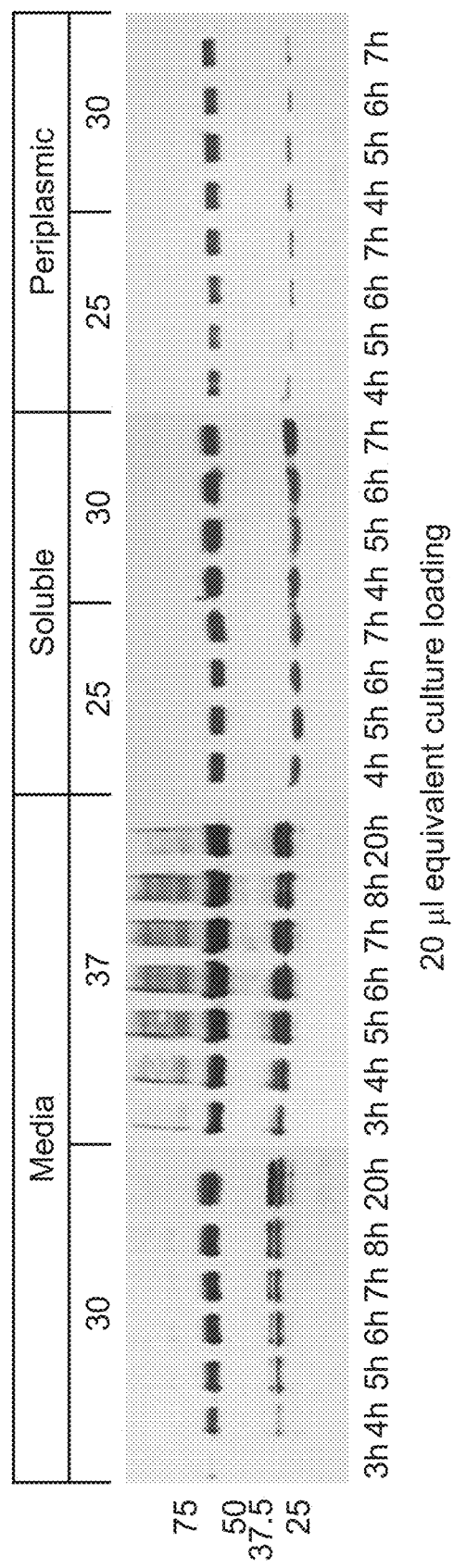
FIG. 31: Soluble expression of homodimeric wild type Fc and Fc mutants (500 ml flask culture). DsbA leader peptide fused wild type Fc was expressed at different culture temperatures and culture time after induction. The localization of the protein was also analyzed.

The effect of growth temperature and harvest time after induction, were tested in 500 ml shake flask cultures. Optimal expression of Fc in the media (thus alleviating further purification) was obtained in cultured incubated for 8 h after induction at 30° C. with 1 mM IPTG (FIG. 31).

Figure 32:
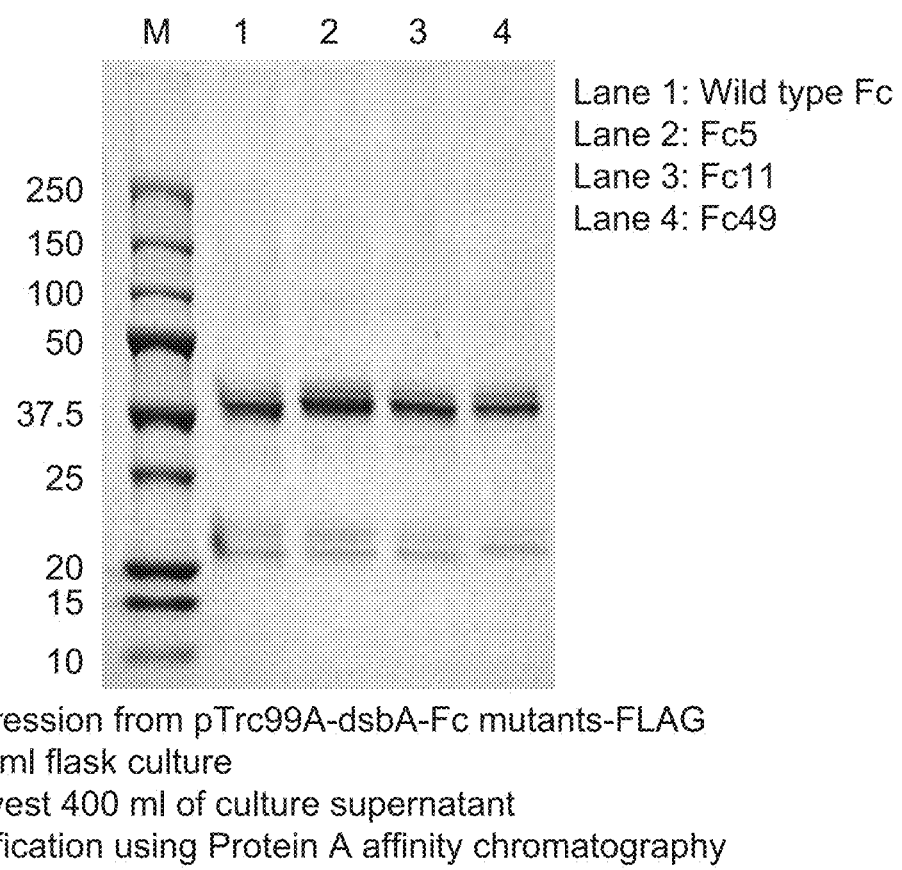
FIG. 32: SDS-PAGE of wild type Fc and Fc mutants purified with Protein A affinity chromatography.
Figure 33A:
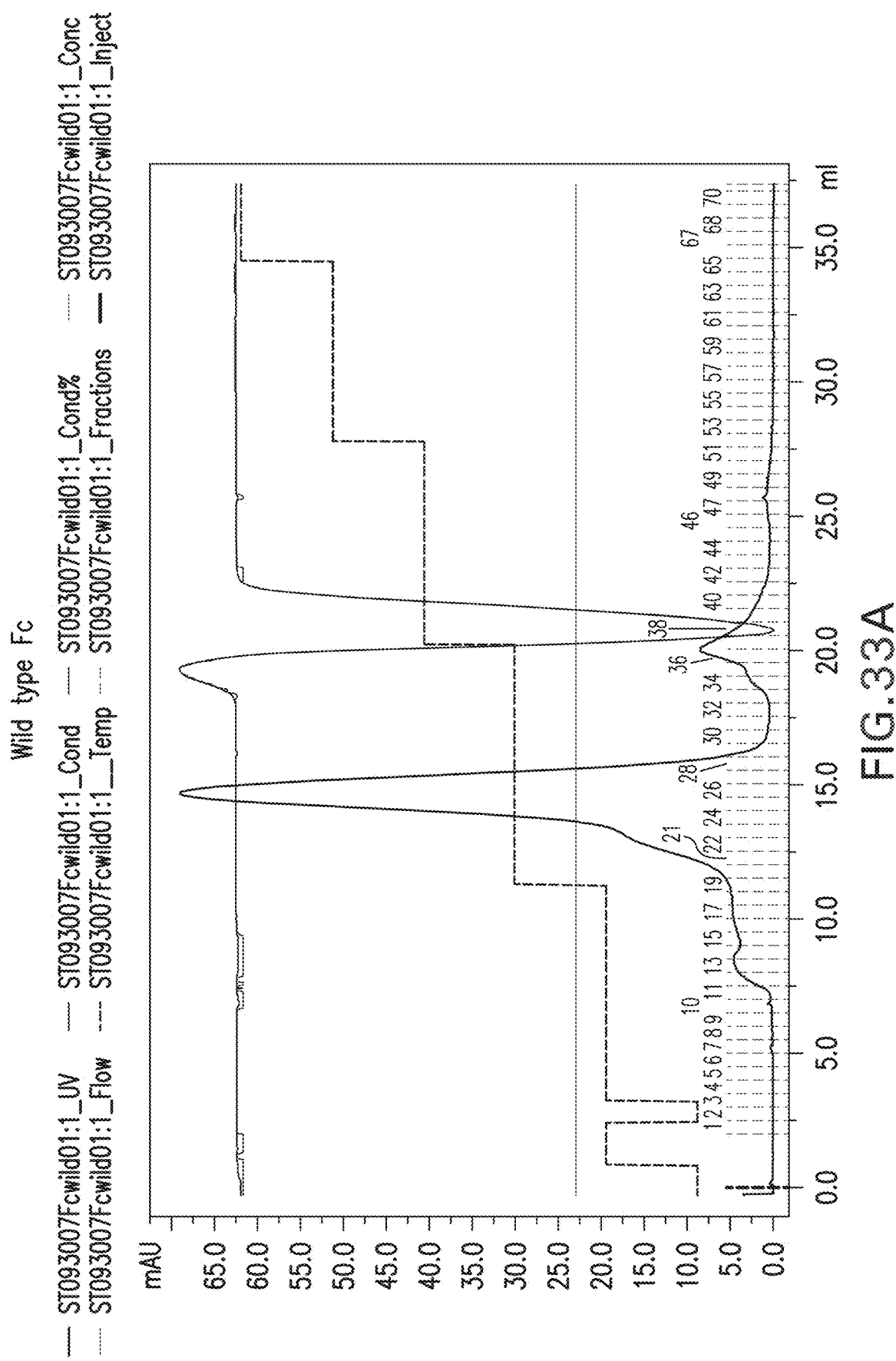
FIG. 33*a-d*: Chromatogram of wild type Fc (FIG. 33*a*) and Fc mutants using Supedex 200 gel filtration chromatography, including Fc5 (FIG. 33*b*), Fc11 (FIG. 33*c*) and Fc49 (FIG. 33*d*).
Figure 33B:
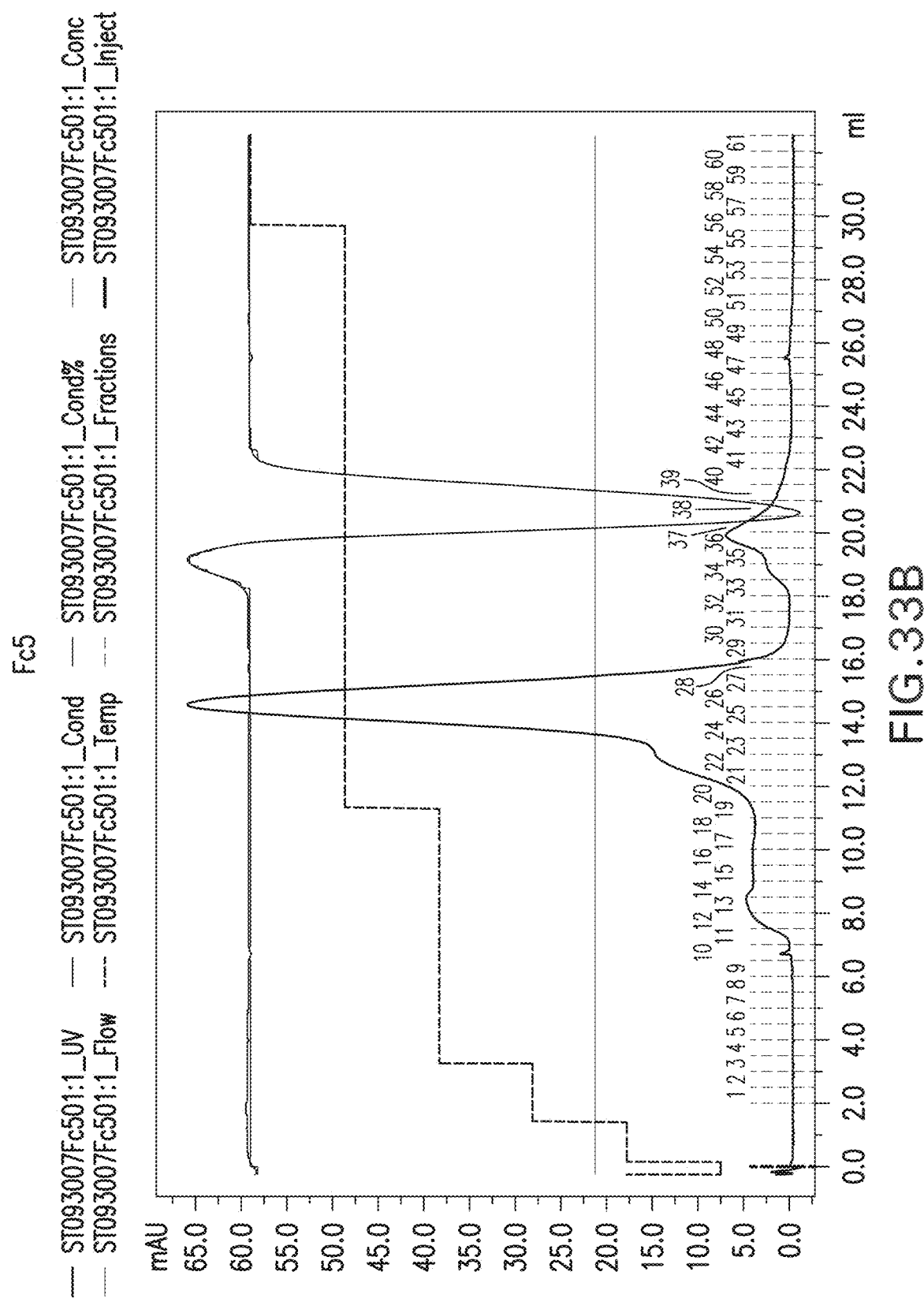
Figure 33C:
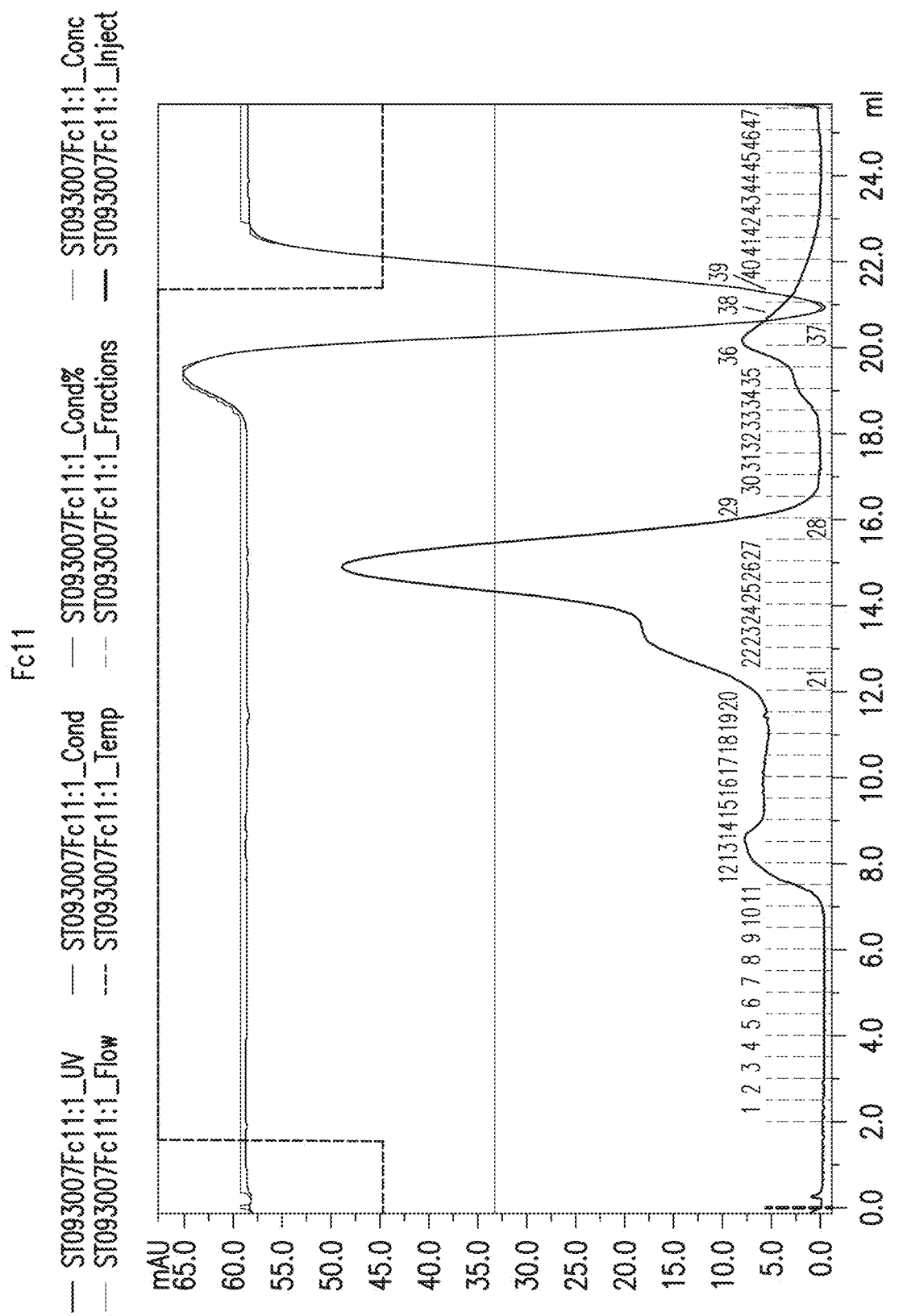
Figure 33D:
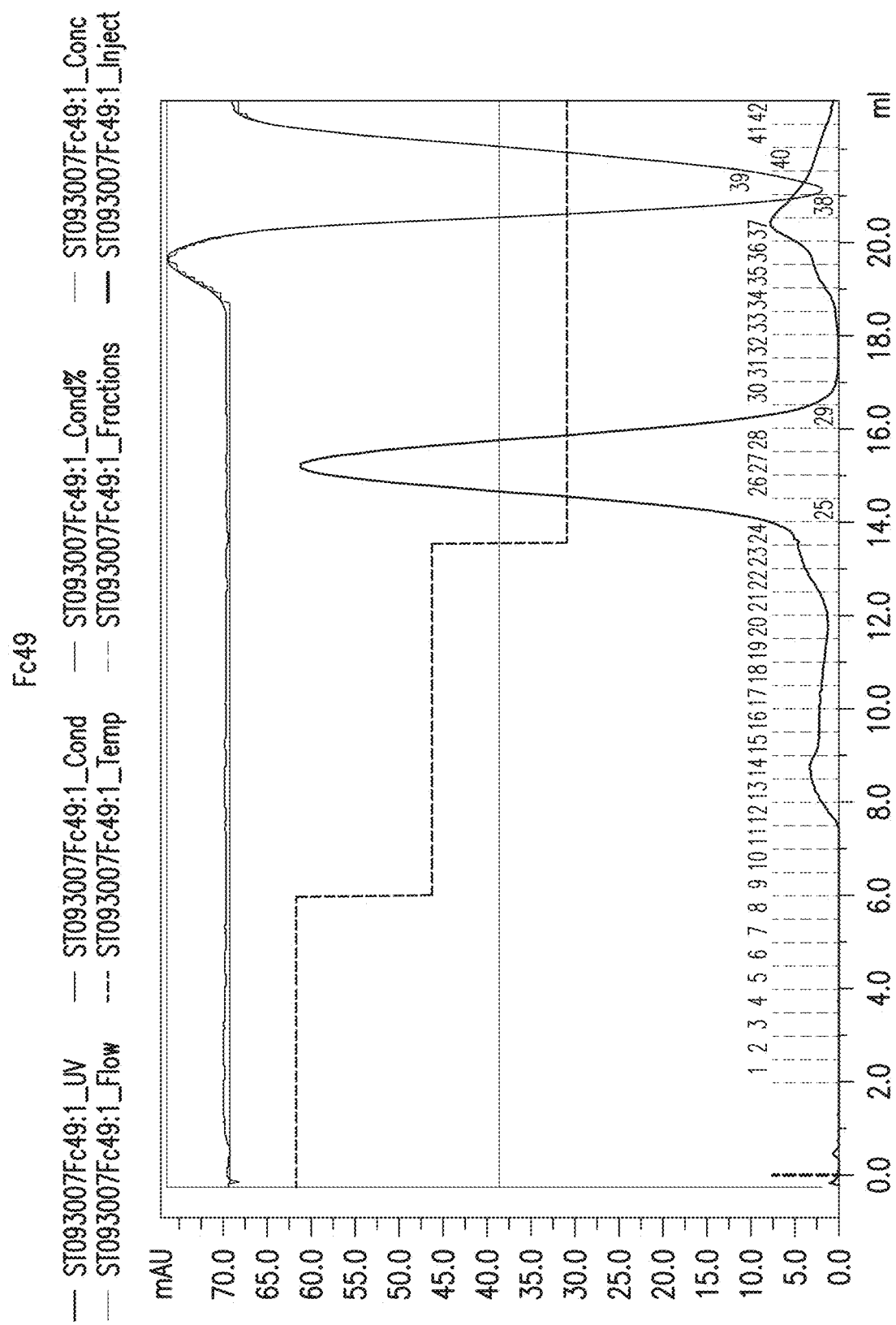
Figure 34:
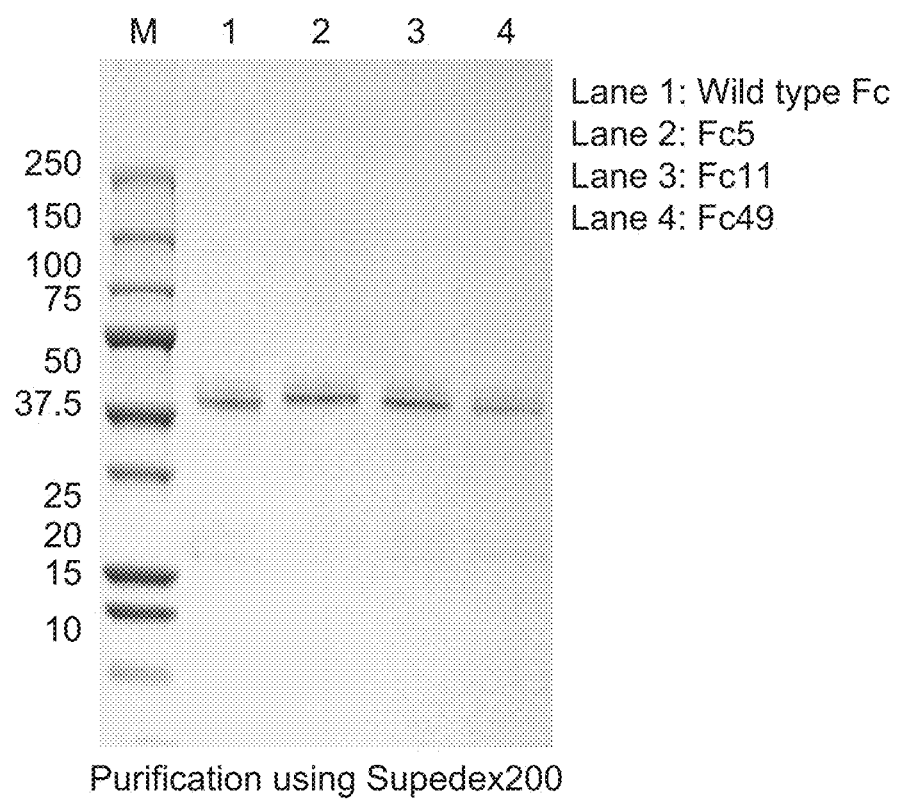
FIG. 34: SDS-PAGE of wild type Fc and Fc mutants purified with Superdex 200 gel filtration chromatography.

For purification, *E. coli* Jude-1 cells harboring pDsbA-FLAG-Fc or Fc mutants were cultured in 2 L flask with 500 ml working volume. The culture supernatant from the induced cells was separated by centrifugation at 7000 rpm for 30 min. The supernatant was filtered using 0.22 μm bottle top filters (Corning) and loaded onto a column packed with 1 ml of Immobilized Protein A agarose (Pierce). After loading of 400 ml of supernatants by gravity flow, the columns were washed with 75 ml of 20 mM sodium phosphate buffer (pH 7.0) and with 50 ml of 40 mM sodium citrate (pH 5.0). Wild type Fc and Fc mutants were eluted using 0.1M glycine (pH 2.5) and neutralized immediately with 1M Tris (pH 8.0) solution. The eluted wild type Fc and Fc mutants were analyzed by SDS-PAGE (FIG. 32). To collect dimeric Fc, the eluted samples from Protein A affinity chromatography column were concentrated with an ultrafiltration unit (10 kDa Mw cutoff: Millipore) and purified using Superdex 200 (Amersham Pharmacia) gel filtration chromatography (FIG. 33). Most of the purified wild type Fc and Fc mutants were dimeric forms (FIG. 34). The final yield of purified dimeric Fc and Fc mutants was approximately 800 µg/ml.

Example 14

Quantification of Fc Binding to FcγR5 by ELISA

Figure 35:
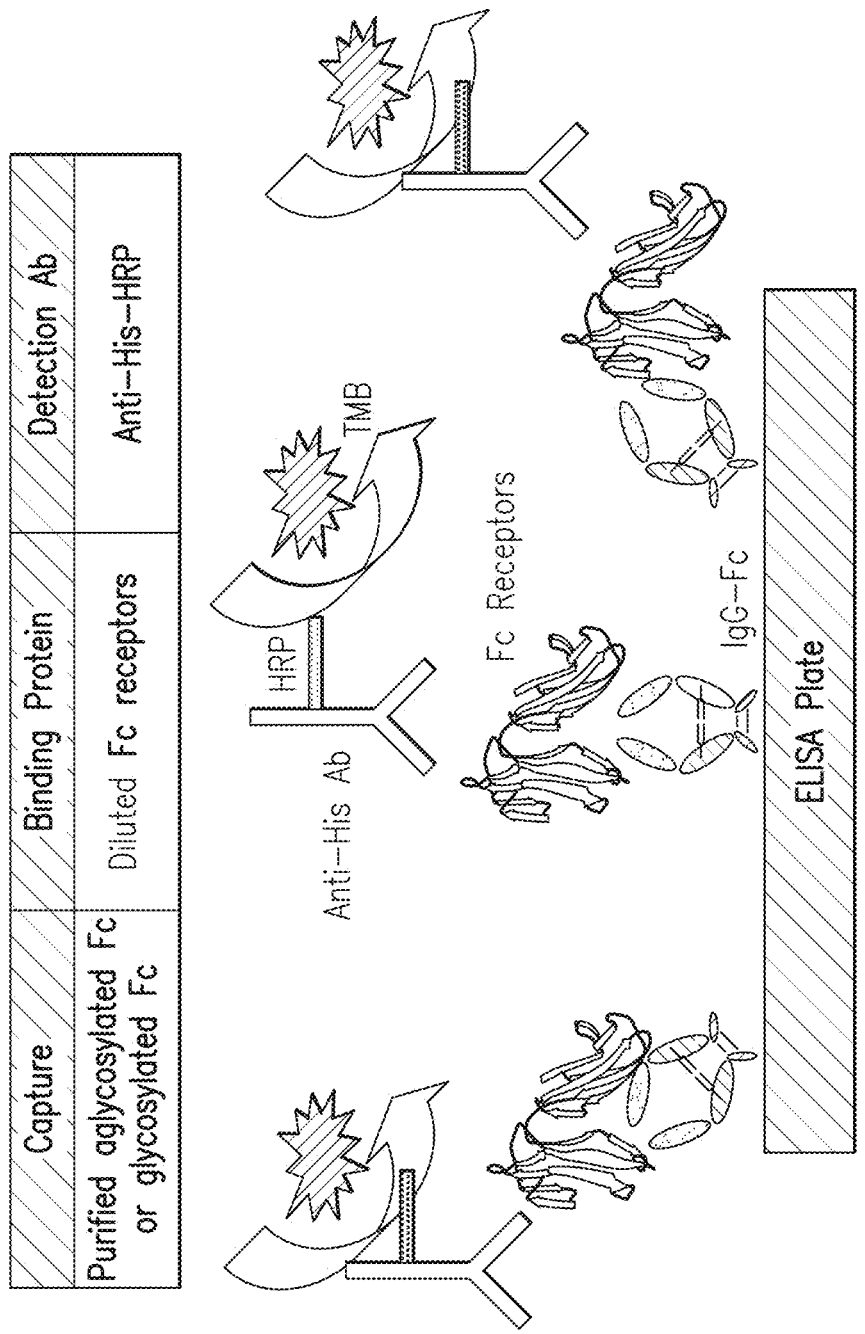
FIG. 35: Direct coating ELISA for the detection of affinity of Fc mutants to FcγRs FIG. 36. ELISA result of Fc mutants to FcγRI.
Figure 36:
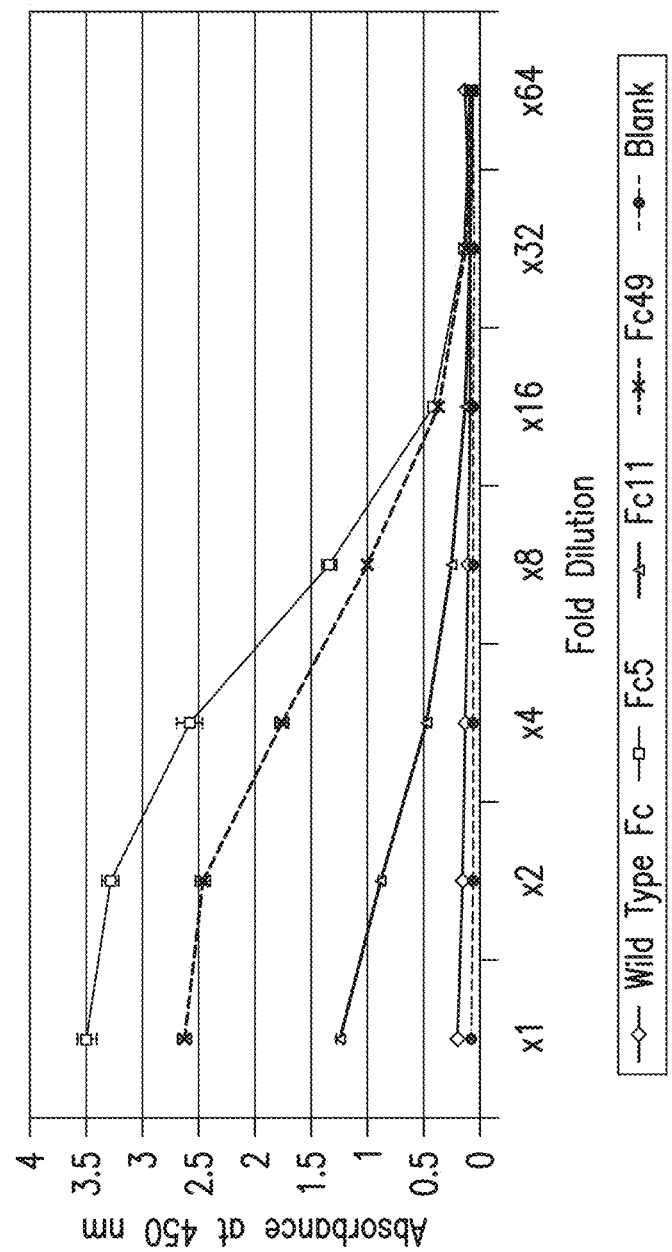

The affinity of purified Fc or Fc mutant proteins for FcγRIa, FcγRIIa or FcγRIIIa was analyzed by ELISA (FIG. 35). 50 µl of 5 µg/ml purified wild type Fc, Fc mutants (Fc5, Fc11, Fc49), or glycosylated IgG-Fc (Bethyl laboratories) diluted in 0.05 M $Na_2CO_3$ (pH 9.6) buffer were coated on 96 well polystyrene ELISA plate (Corning) by overnight incubation at 4° C. After coating with PBS, 0.5% BSA for 3 h at room temperature, the plate was washed 4 times with PBS, 0.05% Tween20 and then added with 2 fold-diluted FcγRIa from 4 µg/ml of initial concentration. After 1 h incubation at room temperature and washing with PBS, 0.05% Tween20, 1:10000 diluted Anti-His antibody HRP conjugate (Sigma-Aldrich) was added. After additional 1 h incubation at room temperature and washing, TMB was added for detection and 2M $H_2SO_4$ was added to quench the reaction. The plate was read at 450 nm with 96 well plate reader (Bio-Tek). Soluble Fc mutants, (Fc5 and Fc49) showed higher affinity comparing with glycosylated IgG-Fc (FIG. 36).

Example 15

Quantification of Fc Binding to FcγRs by BIAcore

Figure 37A:
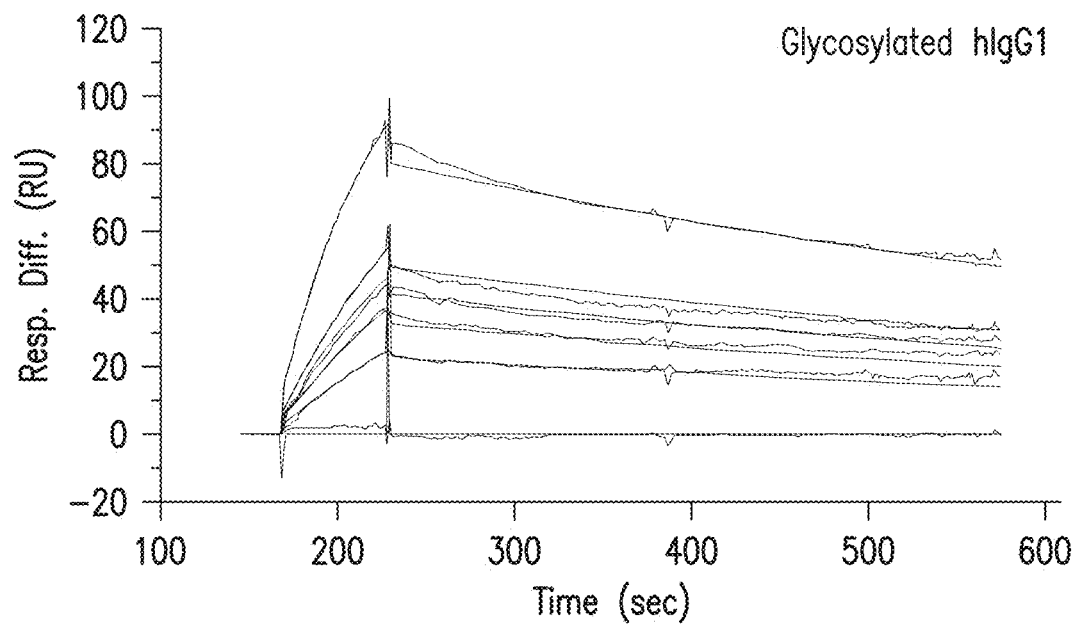
FIG. 37*a-b*. SPR Sensorgrams of Fc protein binding onto immobilized FcγRI.
Figure 37B:
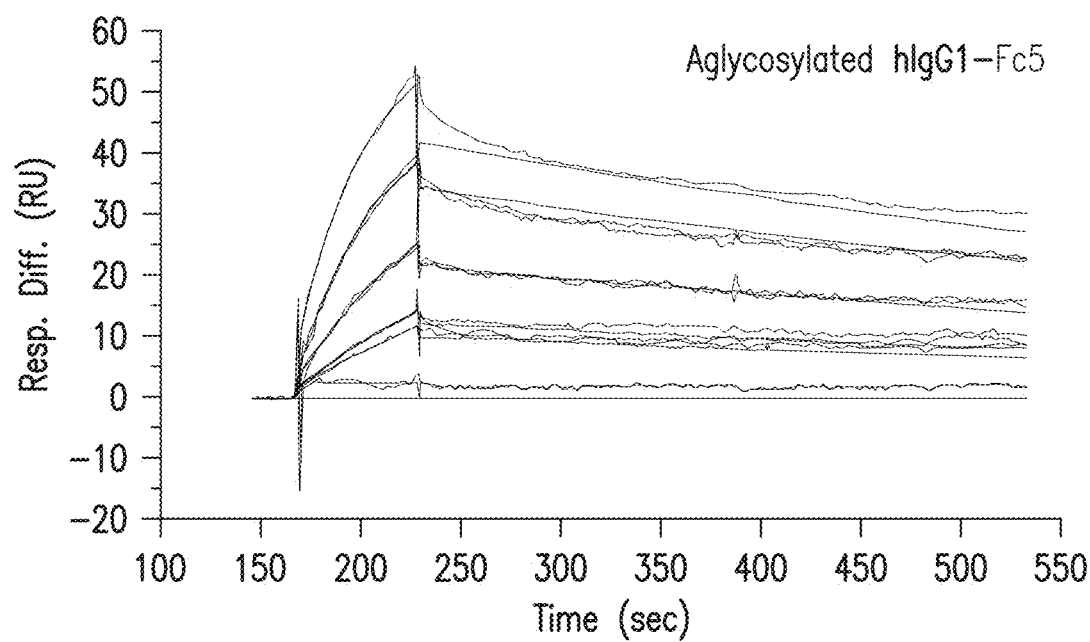

Binding of IgG1-Fc domains to the human FcγRI was analyzed by surface plasmon resonance using a BIAcore 3000 biosensor (BIAcore). The soluble monomeric FcγRIa was immobilized on the CM-5 sensor chip by the amine coupling kit as recommended by the manufacturer. Binding experiments were performed in HBS-EP buffer (10 mM HEPES pH 7.4, 150 mM NaCl, 3.4 mM EDTA, and 0.005% P20 surfactant). Aglycosylated IgG1-Fc fragments, aglycosylated Fc mutants (Fc5, Fc49), or glycosylated IgG1 were injected at flow rate of 100 ul/min for 30 s with dissociation time 300 s. Regeneration was performed by a single injection of 100 mM citric acid, pH 3.0. Fc5 and Fc49 were injected in duplicate at concentrations 0, 80, 100, 200, 400, 600 nM and 0, 200, 400, 600, 800, and 1,000 nM. BIAcore analysis revealed that wt Fc does not bind to FcγRI ($K_D$>50 µM). In contrast, Fc5 and Fc49 exhibited $K_D$ values of 31 and 92 nM respectively. For comparison, the equilibrium dissociation constant of commercially available, glycosylated IgG1 was 18 nM. Notably, the aglycosylated Fc5 mutant and the glycosylated human Fc exhibited experimentally indistinguishable dissociation rate constants, $k_{off}$ and a 2-fold lower association rate constant, $k_{on}$ (Table 6) (FIG. 37a-b).

TABLE 6

Kinetic rates and equilibrium dissociation constants of isolated Fc mutants determined by BIACore.

| | $k_{on}$ (M$^{-1}$ sec$^{-1}$) | $k_{off}$ (sec$^{-1}$) | $K_D$ (nM) |
|---|---|---|---|
| Glycosylated-hIgG1 | $8.0 \times 10^4$ | $1.4 \times 10^{-3}$ | 18 |
| aglycosylated-Fc | Undetectable | Undetectable | (a) |
| aglycosylated-Fc49 | $2.5 \times 10^4$ | $2.3 \times 10^{-3}$ | 92 |
| aglycosylated-Fc5 | $4.5 \times 10^4$ | $1.4 \times 10^{-3}$ | 31 |

(a) $K_D$ > 50 µM

Example 16

Plasmid Construction for the Expression of Aglycosylated Wild Type and Fc5 Trastuzumab For the construction of pSTJ4-Herceptin™ IgG1, *E. coli* codon-optimized (Hoover and Lubkowski, 2002) $V_L$ and $V_H$ domains of humanized 4D5-8 (anti-p185HER2) (Eigenbrot et al., 1993) were synthesized by total gene synthesis with overlap extension PCR using 12 oligonucleotides that included 2 external primers (STJ #302 and STJ #313) and 10 internal primers (STJ #303-312) for $V_L$ and 14 primers total 2 external primers (STJ #314 and STJ #327) and 12 internal primers (STJ #315-326) for $V_H$, respectively. The ligation of the amplified $V_L$ and $V_H$ into pMAZ360-M18.1-Hum-IgG1 using NcoI/NotI for $V_L$ and NheI/HindIII restriction endonuclease sites generated pSTJ4-Herceptin™ IgG1.

Example 17

Expression of Aglycosylated Wild Type and Fc5 Trastuzumab in *E. coli*

Figure 38:
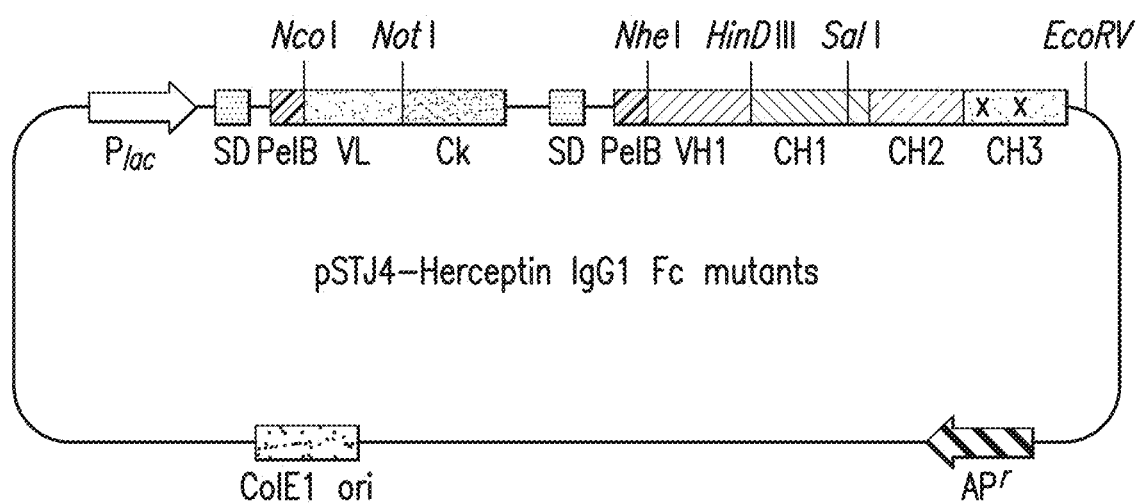
FIG. 38. Map of plasmid pSTJ4-Herceptin™ IgG1.
Figure 39:
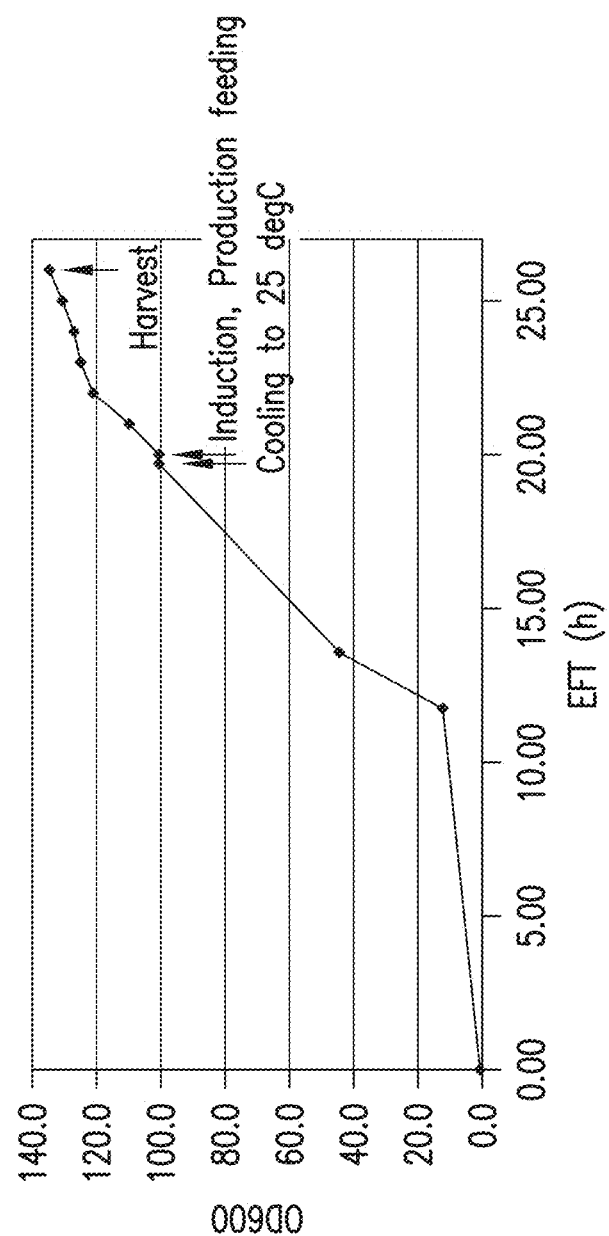
FIG. 39. Fed batch fermentation for the production of aglycosylated trastuzumab or trastuzumab-Fc5 in a 3.3 L fermenter with 1.2 liter working volume. The $OD_{600}$ is shown as a function of time after inoculation during the expression of trastuzumab in *E. coli*
Figure 40:
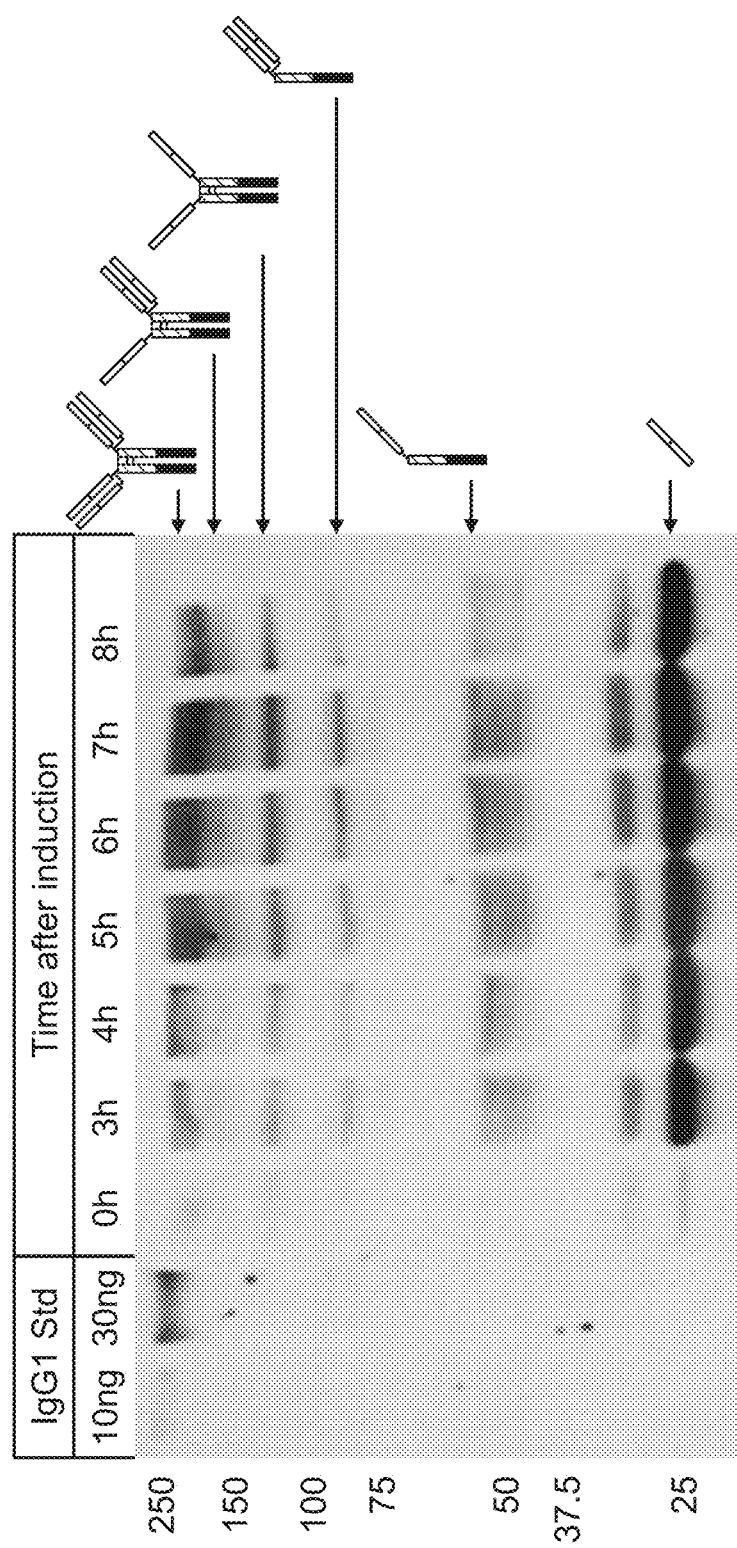
FIG. 40. Fully assembled IgG as detected by non-denaturing gel electrophoresis and Western bloting with goat anti-human IgG (H+L) antibodies. Results are shown for cells expressing wild type trasuzumab; similar results were obtained for cells expressing trastuzumab-Fc5.
Figure 41:
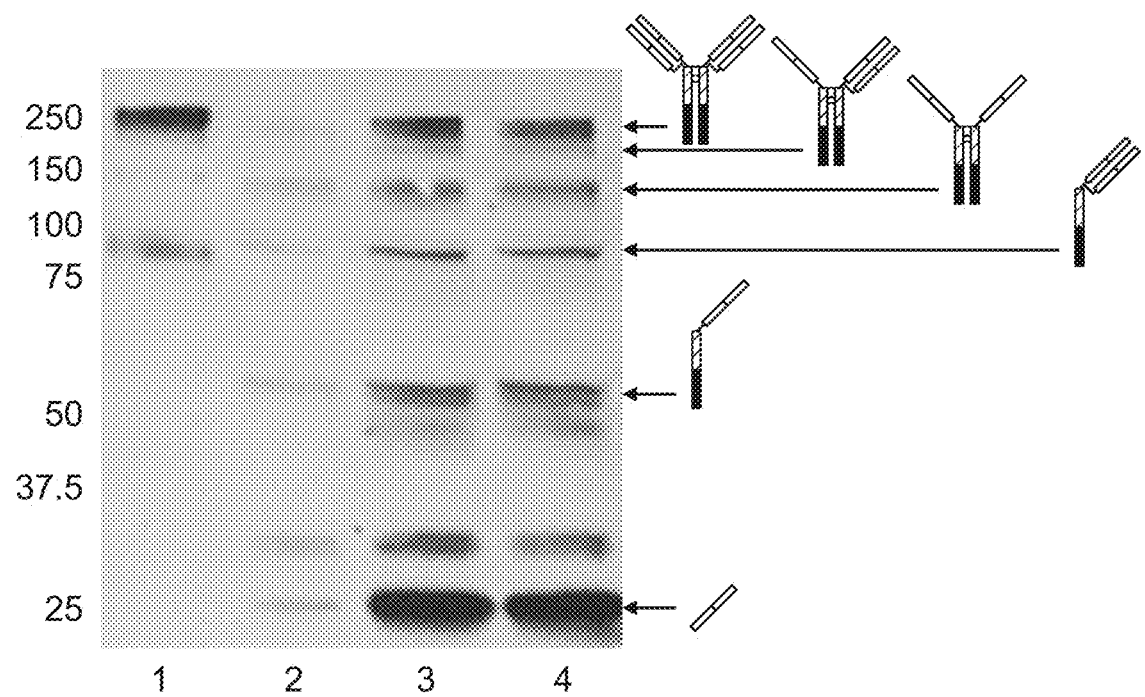
FIG. 41. Expression of aglycosylated trastuzumab and trastuzumab-Fc5, Lane 1: IgG1 standard; Lane 2: Before induction; Lane 3: aglycosylated trastuzumab; Lane 4: trastuzumab-Fc5.

Trastuzumab (Herceptin™) recognizes HER2/neu (Erb2) which is overexpressed in about 30% of breast carcinomas (Sergina and Moasser, 2007). Extensive evidence indicates that recruitment of innate immune cells via interactions with Fcγ receptors plays an important role in the therapeutic action of trastuzumab (Sergina and Moasser, 2007; Lazar et al., 2006). For preparative production of aglycosylated trastuzumab and trastuzumab-Fc5 in *E. coli* the heavy and light chains were fused to the PelB signal peptide and placed downstream from the lac promoter in a dicistronic operon (FIG. 38). Preparative expression was performed by fed-batch fermentation using a 3.3 L jar fermentor (New Brunswick Scientific Co., Edison, N.J.) with 1.2 L working volume. BL21(DE3) cells were grown at 30° C. in R/2 medium (Jeong and Lee, 2003) consisting of: 2 g of $(NH_4)_2HPO_4$, 6.75 g of $KH_2PO_4$, 0.93 g of citric acid $H_2O$, 0.34 g of $MgSO_4$, 20 g of glucose, 0.05 g of ampicillin and 5 ml of trace metal solution dissolved in 2 N HCl (10 g of $FeSO_4$-$7H_2O$, 2.25 g $ZnSO_4$-$7H_2O$, 1 g of $CuSO_4$-$5H_2O$, 0.35 g of $MnSO_4$—$H_2O$, 0.23 g of $Na_2B_4O_7$-$10H_2O$, 1.5 g of $CaCl_2$, and 0.1 g of $(NH_4)_6Mo_7O_{24}$) per L). *E. coli* BL21(DE3) (EMD Chemicals, Gibbstown, N.J.) harboring pSTJ4-Herceptin™ IgG1 or pSTJ4-Herceptin™ IgG1-Fc5 were cultured in 500 mL baffled-flask with 120 ml R/2 media at 30° C. at 250 rpm for 8 h and used to inoculate the fermenter. The dissolved oxygen (DO) concentration was maintained at 40% of air saturation using automatic cascade control by increasing agitation speed from 100 rpm to 1000 rpm, air flow rate from 1 to 3 SLPM (Standard liquid per minute) and pure oxygen flow rate from 0 to 1.5 SLPM when required. Fed-batch fermentation were performed using pH-stat glucose feed control (FIG. 39). The initial pH was adjusted to 6.8 and controlled by the addition of 30% (v/v) ammonium hydroxide when it decreased to less than 6.75 and by the supply of feeding solutions, (700 g/L of glucose and 10 g/L of $MgSO_47H_2O$; before induction) and (500 g/L glucose, 10 g/L of $MgSO_47H_2O$, and 100 g/L of yeast extract; after induction), when it increased to more than 6.9. When $OD_{600}$ reached 100, the culture temperature was reduced to 25° C. and 30 min later, protein expression was induced with 1 mM of isopropyl-1-thio-β-D-galactopyranoside (IPTG). The culture broth was harvested 7 h after induction. The yield of aglycosylated tertameric IgG was 40 mg/L; a significant amount of light chain and minor amounts of incompletely assembled antibody molecules were also observed (FIG. 40 and FIG. 41).

Figure 42:
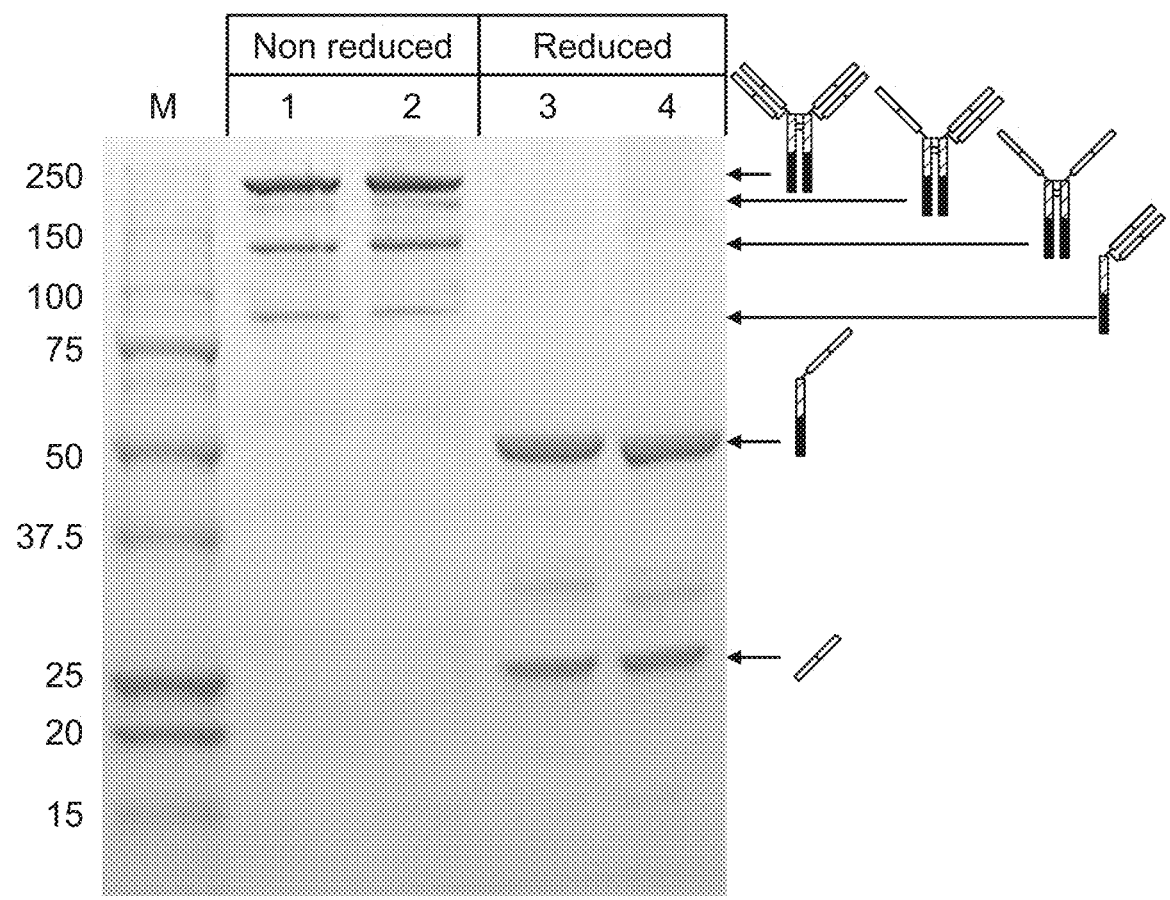
FIG. 42. SDS-PAGE showing the purified aglycosylated trastuzumab and trastuzumab-Fc5, Lane 1, 3: Wild type Fc aglycosylated trastuzumab; Lane 2, 4: trastuzumab-Fc5.

Cells were pelleted by centrifugation at 11,000×g for 30 min, suspended in 1.2 L 100 mM Tris, 10 mM EDTA (pH 7.4), 4 mg of lysozyme (per g of dry cell weight), and 1 mM PMSF and were incubated with shaking at 250 rpm at 30° C. for 16 h to release periplasmic proteins. After centrifugation at 14,000×g for 30 min, the supernatant was mixed with polyethyleneimine (MP Biomedical, Solon, Ohio) to a final concentration of 0.2% (w/v) recentrifuged at 14,000×g for 30 min, and filtered through 0.2 μm filter. Immobilized Protein A agarose resin pre-equilibrated in 20 mM sodium phosphate buffer (pH 7.0) was added to the supernatant and incubated at 4° C. for 16 h. After washing with 200 ml of 20 mM sodium phosphate buffer (pH 7.0) and 200 ml of 40 mM sodium citrate (pH 5.0), IgG1 was eluted from the resin using 15 ml of 0.1 M glycine (pH 3.0) and neutralized immediately with 1M Tris (pH 8.0) solution. The eluted samples were concentrated by ultrafiltration through a 10 kDa Mw cutoff membrane and the retentate was applied to a Superdex 200 gel filtration column developed with PBS (pH 7.4) (FIG. 42).

Example 18

Figure 43:
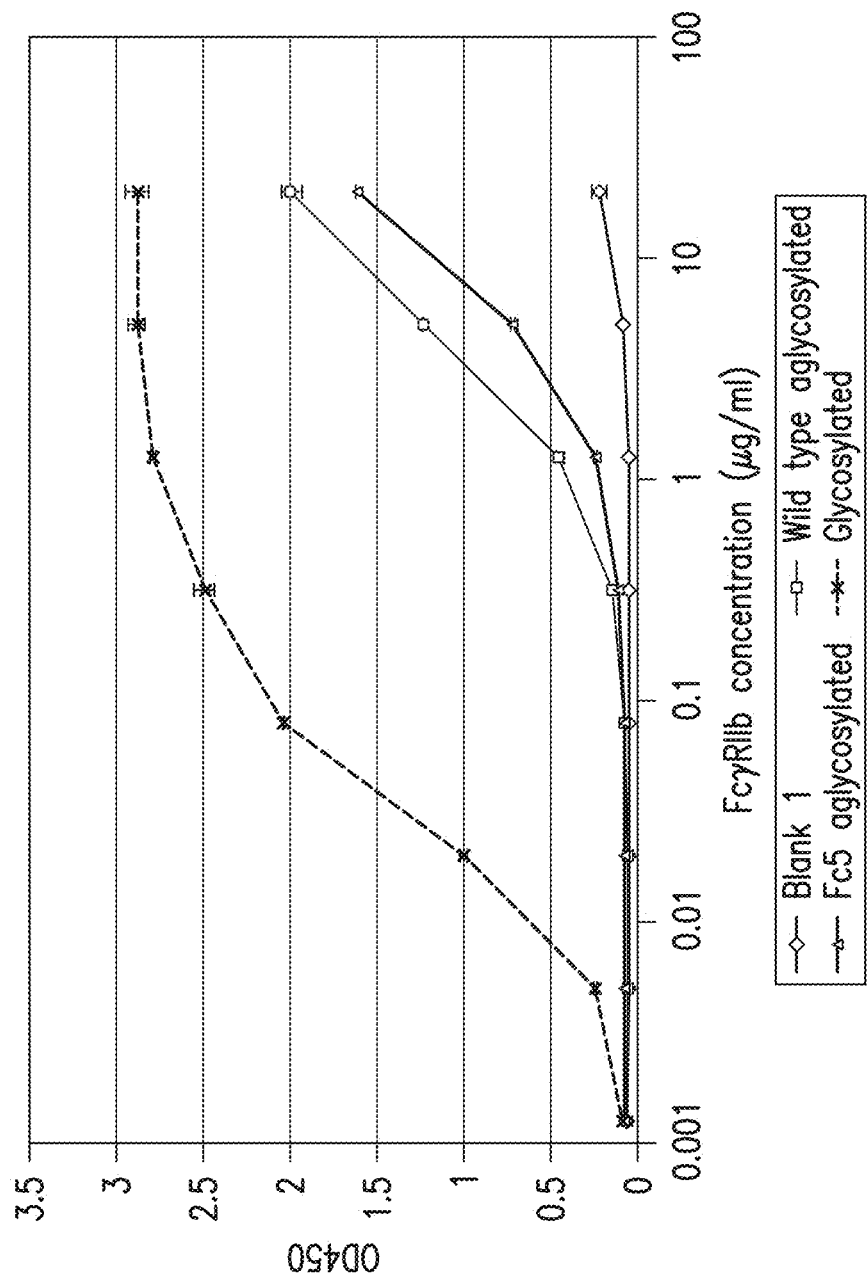
FIG. 43. ELISA assays for binding to FcγRIIa. Plates were coated with purified trastuzumab or trastuzumab-Fc5 and the binding of FcγR was detected using anti-GST-HRP.
Figure 44:
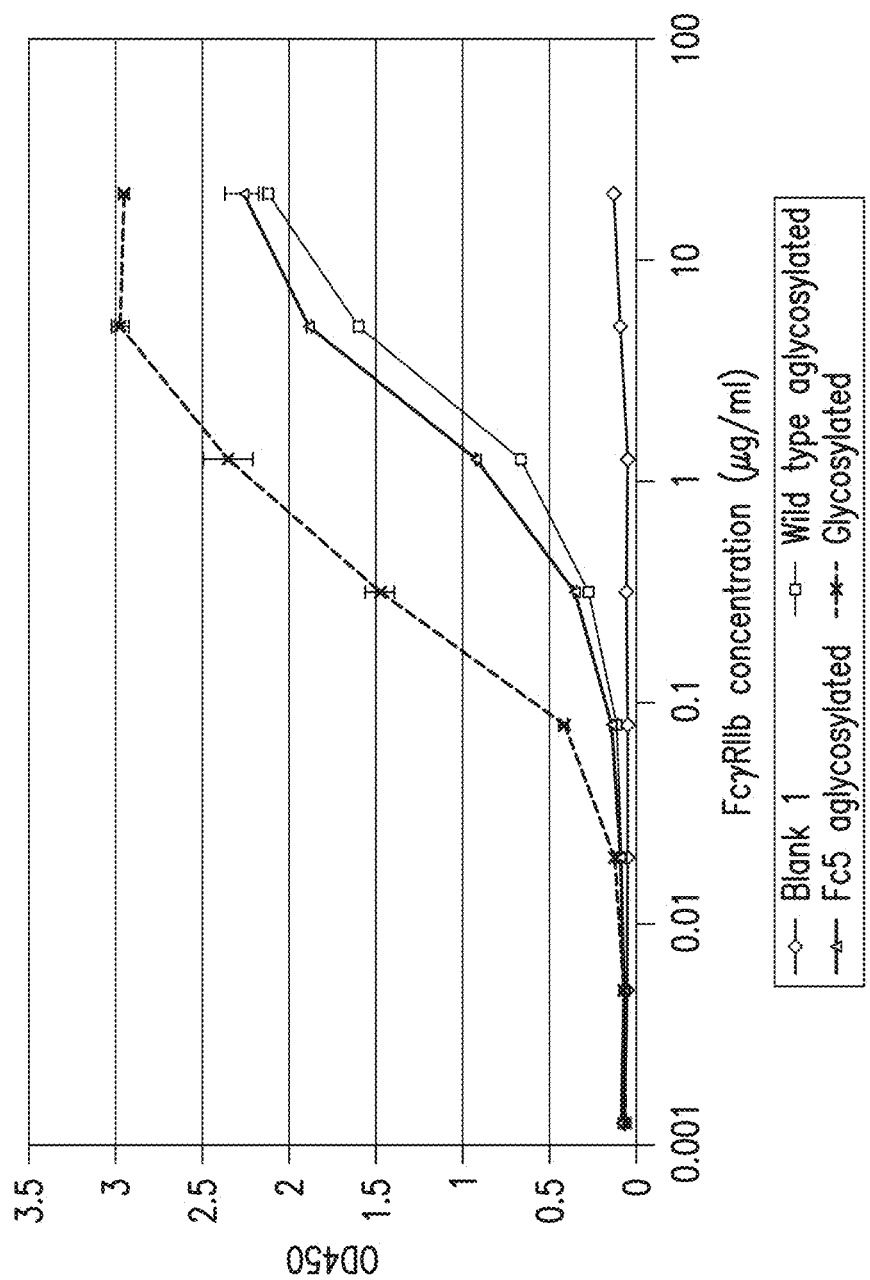
FIG. 44. ELISA assays for binding to FcγRIIb. Plates were coated with purified trastuzumab or trastuzumab-Fc5 and the binding of FcγR was detected using either anti-polyhistidine-HRP or anti-GST-HRP.
Figure 45:
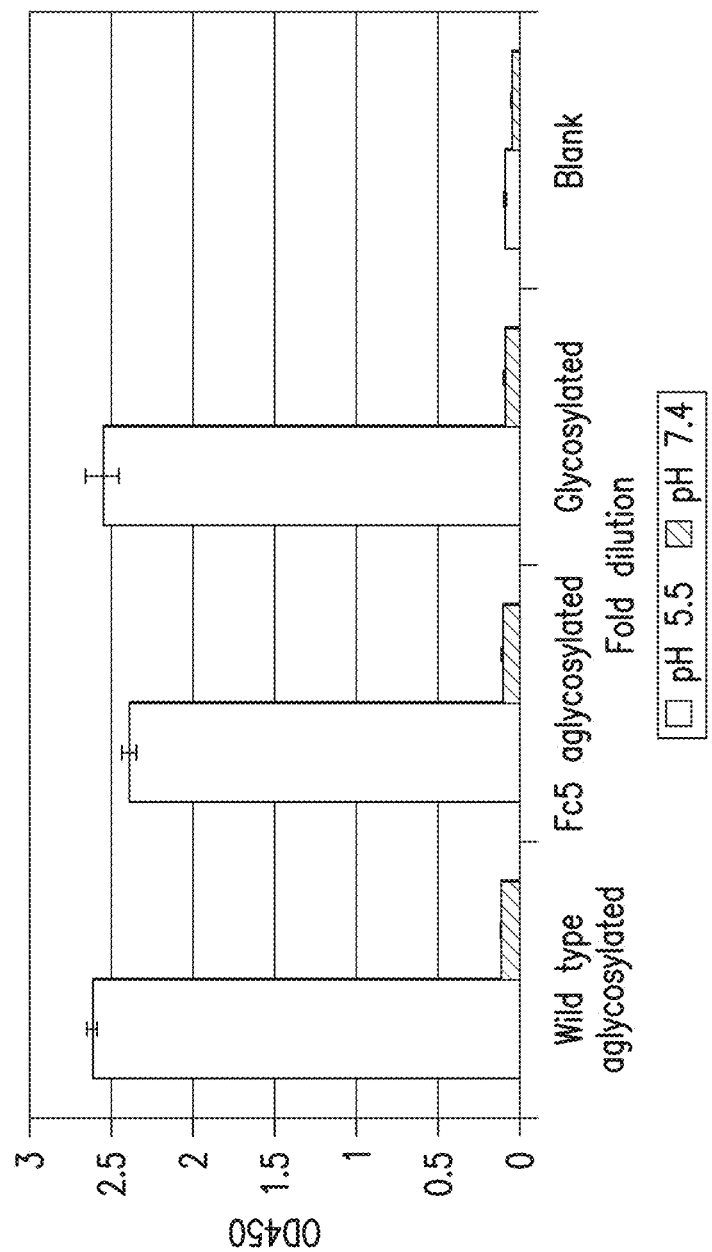
FIG. 45. ELISA assays for binding to FcRn at pH 7.4 and 5.5. Plates were coated with purified trastuzumab or trastuzumab-Fc5 and the binding of FcγR was detected using anti-GST-HRP.
Figure 46:
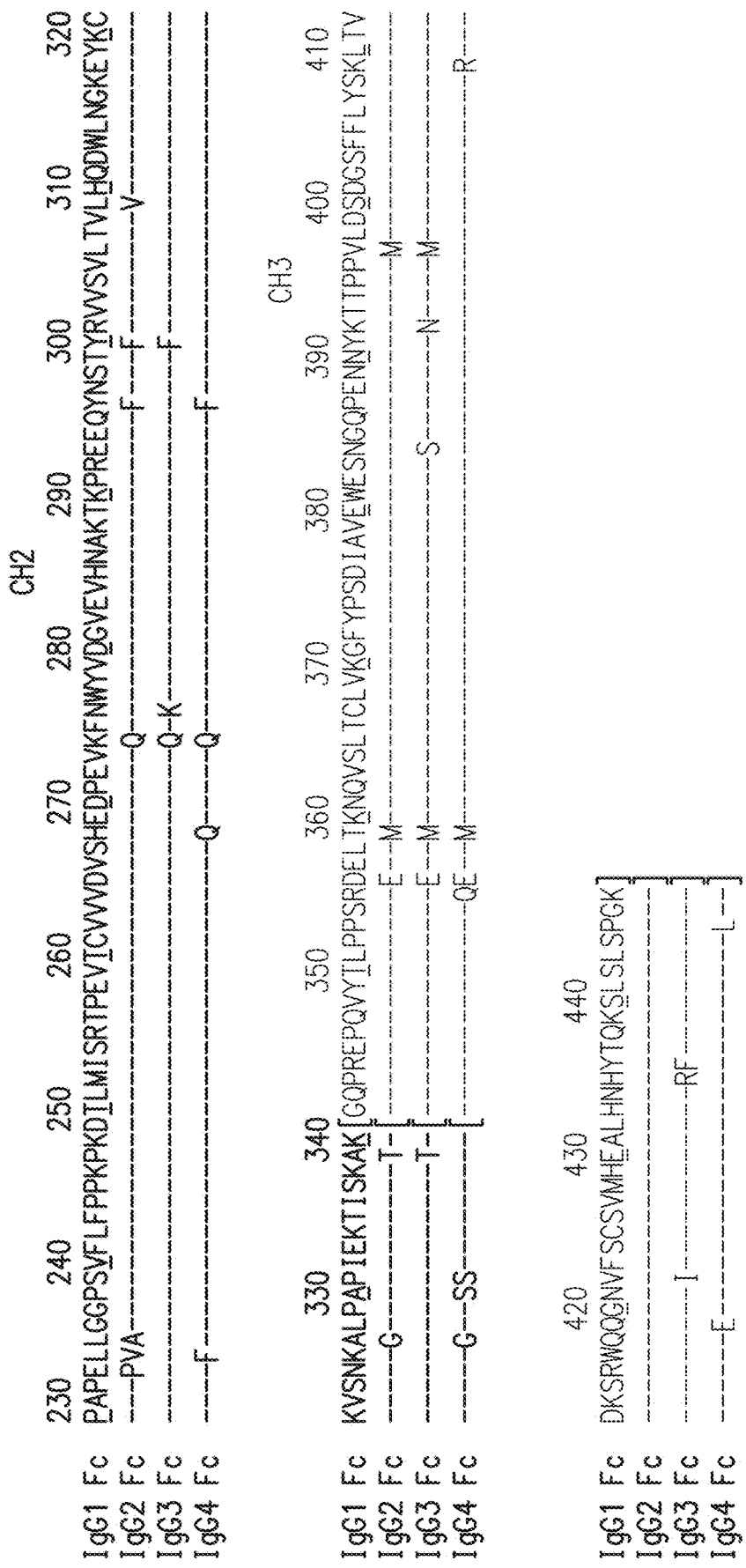
FIG. 46. Alignment of sequences for human IgG subclasses (IgG1 (Seq ID NO:110); IgG2 (Seq ID NO:111); IgG3 (Seq ID NO:112); IgG4 (Seq ID NO:113)).

ELISA and BIAcore Analysis of Aglycosylated Wild Type and Fc5 Trastuzumab for FcγRs The affinity of the purified IgGs for the extracellular domain of FcγRIIa and FcγRIIb expressed as an N-terminal fusion to GST in 293E cells (Berntzen et al., 2005) was determined by ELISA. 50 μl of 4 μg/ml of wild type Fc, Fc mutants, aglycosylated trastuzumab, or trastuzumab-Fc5 purified from E. coli, glycosylated IgG trastuzumab (Clinical grade, Fox Chase Cancer Center Pharmacy) or glycosylated IgG1 (Sigma-Aldrich, St. Louis, Mo.), or were diluted in 0.05 M Na$_2$CO$_3$ (pH 9.6) buffer and used to coat 96 well polystyrene ELISA wells (Corning, Corning, N.Y.) overnight at 4° C. After blocking with 1×PBS (pH 7.4), 0.5% BSA for 2 hr at room temperature, the plate was washed 4 times with PBS containing 0.05% Tween20, and incubated with serially diluted FcγRIIa, FcγRIIb C-terminal fused to GST (Berntzen et al., 2005), FcγRIa or FcγRIIIb (R&D Systems, Minneapolis, Minn.) at room temperature for 1 h. After washing 4 times with the same buffer, 1:10,000 diluted anti-polyhistidine antibody HRP conjugate (Sigma-Aldrich, St. Louis, Mo.) for FcγRIIIb or 1:5,000 diluted anti-GST antibody HRP conjugate (Amersham Pharmacia, Piscataway, N.J.) for FcγRIIa and FcγRIIb was added and plates were washed and developed as described previously (Mazor et al., 2007). To determine the binding of IgG to FcRn at pH 7.4, 2 μg/ml FcRn preincubated with 1:5,000 diluted anti-GST-HRP for 1 h as previously described (Andersen et al., 2006) was added to plates coated with IgG. To evaluate binding at pH 5.5, ELISAs were carried out as above except that the washing buffer and sample dilution buffers were adjusted to pH 5.5. As expected, the aglycosylated trastuzumab exhibited low affinity to FcγRIIa or FcγRIIb (FIG. 43 and FIG. 44). Trastuzumab-Fc5 antibody exhibited only slightly higher affinity for FcγRIIb. The neonatal FcγRn receptor binds to the CH3 domain and is responsible for the endosomal recycling of IgG in plasma (Ghetie and Ward, 2000). Glycosylated, aglycosylated and trastuzumab-Fc5 exhibited near identical binding to FcRn at pH 5.5 and low binding at pH 7.5 suggesting that the E382V and M42I substitutions are not likely to affect the circulation half-life of this antibody (FIG. 45).

Binding of FcγRI to the full assembled IgG trastuzumab was also analyzed by immobilizing glycosylated trastuzumab, aglycosylated trastuzumab, and aglycosylated trastuzumab-Fc5 individually on the CM-5 sensor chip. Binding experiments were done in the same HBS-EP buffer. For trastuzumab or trastuzumab-Fc5 FcγRIa was injected in duplicate at concentrations 0, 10, 20, 30, 50, and 100 nM for 60 s at a flow rate of 10 μl/min. For aglycosylated trastuzumab FcγRIa was injected at concentrations 0, 100, 200, 300, 500, and 1,000. Regeneration was performed by single injection of 100 mM H$_3$PO$_4$. Data were analyzed using the BIAevaluation 3.0 software. On the other hand consistent with the results shown in Table 6 for the Fc domains alone, trastuzumab-Fc5 bound strongly to FcγRIa. Specifically, the equilibrium dissociation constants for glycosylated trastuzumab from CHO cells, the E. coli expressed trastuzumab and trastuzumab-Fc5 were 1.7 nM, 0.8 μM and 3.6 nM respectively. (glycosylated trastuzumab: $k_{on}$=2.1×10$^5$M$^{-1}$ sec$^{-1}$ $k_{off}$=3.5×10$^{-4}$ sec$^{-1}$; E. coli, aglycosylated trastuzumab $k_{on}$=4.6×10$^5$ M$^{-1}$ sec$^{-1}$ $k_{off}$=3.7×10$^{-2}$ sec$^{-1}$; trastuzumab Fc5: $k_{on}$=1.4×10$^4$M$^{-1}$ sec$^{-1}$, $k_{off}$=5×10$^{-5}$ sec$^{-1}$). Thus, trastuzumab-Fc5 exhibits selective binding only to the FcγRIa receptor.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 3,817,837
U.S. Pat. No. 3,826,364
U.S. Pat. No. 3,850,752
U.S. Pat. No. 3,939,350
U.S. Pat. No. 3,996,345
U.S. Pat. No. 4,275,149
U.S. Pat. No. 4,277,437
U.S. Pat. No. 4,284,412
U.S. Pat. No. 4,366,241
U.S. Pat. No. 4,472,509
U.S. Pat. No. 4,498,766
U.S. Pat. No. 4,661,913
U.S. Pat. No. 4,683,195
U.S. Pat. No. 4,683,202
U.S. Pat. No. 4,714,682
U.S. Pat. No. 4,767,206
U.S. Pat. No. 4,774,189
U.S. Pat. No. 4,800,159
U.S. Pat. No. 4,857,451
U.S. Pat. No. 4,883,750
U.S. Pat. No. 4,938,948

U.S. Pat. No. 4,988,618
U.S. Pat. No. 4,989,977
U.S. Pat. No. 5,021,236
U.S. Pat. No. 5,160,974
U.S. Pat. No. 5,302,523
U.S. Pat. No. 5,322,783
U.S. Pat. No. 5,384,253
U.S. Pat. No. 5,464,765
U.S. Pat. No. 5,478,722
U.S. Pat. No. 5,538,877
U.S. Pat. No. 5,538,880
U.S. Pat. No. 5,550,318
U.S. Pat. No. 5,563,055
U.S. Pat. No. 5,567,326
U.S. Pat. No. 5,580,859
U.S. Pat. No. 5,589,466
U.S. Pat. No. 5,610,042
U.S. Pat. No. 5,656,610
U.S. Pat. No. 5,702,932
U.S. Pat. No. 5,736,524
U.S. Pat. No. 5,779,907
U.S. Pat. No. 5,780,448
U.S. Pat. No. 5,789,215
U.S. Pat. No. 5,824,520
U.S. Pat. No. 5,843,650
U.S. Pat. No. 5,846,709
U.S. Pat. No. 5,846,783
U.S. Pat. No. 5,849,497
U.S. Pat. No. 5,849,546
U.S. Pat. No. 5,849,547
U.S. Pat. No. 5,858,652
U.S. Pat. No. 5,866,366
U.S. Pat. No. 5,882,864
U.S. Pat. No. 5,912,148
U.S. Pat. No. 5,916,776
U.S. Pat. No. 5,916,779
U.S. Pat. No. 5,922,574
U.S. Pat. No. 5,928,905
U.S. Pat. No. 5,928,906
U.S. Pat. No. 5,932,451
U.S. Pat. No. 5,935,825
U.S. Pat. No. 5,939,291
U.S. Pat. No. 5,942,391
U.S. Pat. No. 5,945,100
U.S. Pat. No. 5,981,274
U.S. Pat. No. 5,994,624
U.S. Pat. No. 7,094,571
U.S. Pat. No. 7,094,571
U.S. Patent Publ. 20030180937
U.S. Patent Publ. 20030219870
U.S. Patent Publ. 20050260736
U.S. Patent Publ. 20060173170
Abbondanzo et al., *Breast Cancer Res. Treat.*, 16:182(151), 1990.
Ahouse et al., *J. Immunol.*, 151:6076-6088, 1993.
Allen and Seed, *Nucleic Acids Res.*, 16:11824, 1988.
Andersen et al., *Eur. J. Immunol.*, 36:3044-3051, 2006.
Antibodies: A Laboratory Manual, Cold Spring Harbor Laboratory, 1988
Atherton et al., *Biol. Reprod.*, 32(1):155-171, 1985.
Ausubel et al., In: *Current Protocols in Molecular Biology*, John, Wiley & Sons, Inc, NY, 1994.
Baneyx and Mujacic, *Nat. Biotechnol.*, 22:1399-1408, 2004.
Bellus, *J. Macromol. Sci. Pure Appl. Chem.*, A31(1): 1355-1376, 1994.
Berntzen et al., *J. Immunol. Methods*, 298:93-104, 2005.
Better et al., *Science*, 240: 1041-10433, 1988.
Bocek and Pecht, *FEBS Lett.*, 331, 86-90, 1993.
Boeke et al., *Mol. Gen. Genet.*, 186, 1982.
Boss et al., *Nucleic Acids Res.*, 12:3791-3806, 1984.
Bowden and Georgiou, *J. Biol. Chem.*, 265:16760-16766, 1990.
Bukau et al., *J. Bacteriol.*, 163:61, 1985.
Burman et al., *J. Bacteriol.*, 112:1364, 1972.
Cabilly et al., *Proc. Natl. Acad. Sci. USA*, 81:3273-3277, 1984.
Carbonelli et al., *FEMS Microbiol Lett.*, 177:75-82. 1999
Chames et al., *Proc. Natl. Acad. Sci. USA*, 97:7969-7974, 2000.
Chen and Okayama, *Mol. Cell. Biol.*, 7(8):2745-2752, 1987.
Cocea, *Biotechniques*, 23(5):814-816, 1997.
Collins et al., *Immunogenetics*, 45:440-443, 1997.
Daugherty et al., *Protein Eng.*, 12:613 621, 1999.
De Jager et al., *Semin. Nucl. Med.*, 23(2):165-179, 1993.
de Kruif and Logtenberg, *J. Biol. Chem.*, 271:7630-7634, 1996.
Decad and Nikaido, *J. Bacteriol.*, 128:325, 1976.
Desai et al., *Cancer Res.*, 58:2417-2425, 1998.
Dholakia et al., *J. Biol. Chem.*, 264(34):20638-20642, 1989.
Doolittle and Ben-Zeev, *Methods Mol Biol*, 109:215-237, 1999.
Eigenbrot et al., *J. Molec. Biol.*, 229:969-995, 1993.
Elbein et al., *Glycobiology*, 13:17 R-27, 2003.
European Appln. 320 308
European Appln. 329 822
Fahnestock et al., *J. Bacteriol.*, 167:870-880, 1986.
Farmer et al., *FEMS Microbiol. Lett.*, 176:11, 1999.
Fechheimer, et al., *Proc Natl. Acad. Sci. USA*, 84:8463-8467, 1987.
Fraley et al., *Proc. Natl. Acad. Sci. USA*, 76:3348-3352, 1979.
Francisco et al., *Proc. Natl. Acad. Sci. USA*, 90:10444-10448, 1993.
Frohman, In: *PCR Protocols: A Guide To Methods And Applications*, Academic Press, N.Y., 1990.
Fromant et al., *Analytical Biochemistry*, 224:347-353, 1995.
Garinot-Schneider et al., *J. Mol. Biol.*, 260:731-742, 1996.
GB Appln. 2 202 328
Georgiou and Segatori, *Current Opin. Biotech.*, 16:538-545, 2005.
Ghetie and Ward, *Annu. Rev. Immunol.*, 18:739-766, 2000.
Gomi et al., *J. Immunol.*, 144:4046-4052, 1990.
Gopal, *Mol. Cell. Biol.*, 5:1188-1190, 1985.
Graham and Van Der Eb, *Virology*, 52:456-467, 1973.
Griffiths and Duncan, *Curr. Opin. Biotechnol.*, 9:102-108, 1998.
Gulbis and Galand, *Hum. Pathol.*, 24(12):1271-1285, 1993.
Guzman et al., *J. Bacteriol.*, 177:4121-30, 1995.
Halloran et al., *J. Immunol.*, 153:2631-2641, 1994.
Harland and Weintraub, *J. Cell Biol.*, 101(3):1094-1099, 1985.
Harvey et al., *J. Immunol. Methods*, 308:43-52, 2006.
Harvey et al., *Proc. Natl. Acad. Sci. USA*, 101, 9193-9198, 2004.
Hayhurst et al., *J. Immunol. Methods*, 276:185-196, 2003.
Hobot et al., *J. Bacteriol.*, 160:143, 1984.
Hoogenboom and Winter, *J. Mol. Biol.*, 227:381-388, 1992.
Hoogenboom et al., *Immunotechnology.*, 4:1-20, 1998.
Hoover and Lubkowski, *Nucl. Acids Res.*, 30:e43, 2002.
Innis et al., *Proc. Natl. Acad. Sci. USA*, 85(24):9436-9440, 1988.
Irvin et al., *J. Bacteriol.*, 145:1397, 1981.
Jefferis, *Biotechnol. Prog.*, 21:11-16, 2005.

Jeong and Lee, *Appl. Environ. Microbiol.*, 69:1295-1298, 2003.
Jouenne and Junter, *FEMS Microbiol. Lett.*, 56:313, 1990.
Jung et al., *Biotechnol Bioeng*, 98:39-47, 2007
Jung et al., *Protein Expr. Purif.*, 31:240-246, 2003.
Kabat et al., In: *Sequences of Proteins of Immunological Interest*, U.S. Dept. Health and Hum. Serv., Bethesda, Md., 1991.
Kaeppler et al., *Plant Cell Reports*, 9:415-418, 1990.
Kaneda et al., *Science*, 243:375-378, 1989.
Kato et al, *J. Biol. Chem.*, 266:3361-3364, 1991.
Kawarasaki et al., *Nucleic Acids Res.*, 31:e126, 2003.
Khatoon et al., *Ann. Neurol*, 26(2):210-215, 1989.
King et al., *J. Biol. Chem.*, 264(17):10210-10218, 1989.
Kipriyanov and Little, *Mol. Biotechnol.*, 12:173-201, 1999.
Kjaer et al., *FEBS Lett.*, 431:448-452, 1998.
Knight et al., *Mol. Immunol.*, 32:1271-1281, 1995.
Kohler and Milstein, *Nature*, 256:495-497, 1975.
Kouzarides and Ziff, *Nature*, 336:646-6451, 1988.
Kuroda et al., *Lancet.*, 357:1225-1240, 2001.
Kwoh et al., *Proc. Natl. Acad. Sci. USA*, 86:1173, 1989.
Labischinski et al., *J. Bacteriol.*, 162:9, 1985.
Landschulz et al., *Science*, 240:1759-1764, 1988.
Lazar et al., *Proc. Natl. Acad. Sci. USA*, 103:4005-4010, 2006.
Lei et al., *J. Bacteriol.*, 169:4379-4383, 1987.
Levenson et al., *Hum. Gene Ther.*, 9(8):1233-1236, 1998.
Li et al., *J. Mol. Biol.*, 337:743-759, 2004.
Maniatis, et al., Molecular Cloning, A Laboratory Manual, Cold Spring Harbor Press, Cold Spring Harbor, N.Y., 1988.
Marciano et al., *Science*, 284:1516, 1999.
Masaki et al., *Nucleic Acids Res.*, 13:1623-1635, 1985.
Mazor et al., *Nat. Biotech.*, 25:563-5, 2007.
Munson and Pollard, *Anal. Biochem.*, 107:220, 1980.
Nagaoka and Akaike, Protein Engineering, 16: 243-245, 2003.
Nicolau and Sene, *Biochim. Biophys. Acta*, 721:185-190, 1982.
Nicolau et al., *Methods Enzymol.*, 149:157-176, 1987.
Nikaido and Nakae, *Adv. Microb. Physiol.*, 20:163, 1979.
Nikaido and Vaara, *Microbiol. Rev.*, 49:1, 1985.
Nikaido, *J. Bacteriology*, 178(20):5853-5859, 1996.
O'Brien et al., *Protein Expr. Purif.*, 24:43-50, 2002.
Olsson et al., *Eur. J. Biochem.*, 168:319-324, 1987.
Orlandi et al., *Proc. Natl. Acad. Sci. USA*, 86:3833-3837, 1989.
Osborn et al., *J. Biol. Chem.*, 247:3973-3986, 1972.
Owens and Haley, *Biochem. Biophys. Res. Commun.*, 142(3):964-971, 1987.
Painbeni et al., *Proc Natl. Acad. Sci. USA*, 94:6712, 1997.
Pavlou and Belsey, *Eur. J. Pharm. Biopharm.*, 59:389-396, 2005.
PCT Appln. PCT/US87/00880
PCT Appln. PCT/US89/01025
PCT Appln. WO 88/10315
PCT Appln. WO 89/06700
PCT Appln. WO 90/07641
PCT Appln. WO 93/06213
PCT Appln. WO 94/09699
PCT Appln. WO 95/06128
Potrykus et al., *Mol. Gen. Genet.*, 199(2):169-177, 1985.
Potter and Haley, *Methods Enzymol*, 91:613-633, 1983.
Purvis et al., *Appl. Environ. Microbiol.*, 71:3761-3769, 2005.
Rao and Torriani, *J. Bacteriol.*, 170, 5216, 1988.
Ravetch and Perussia et al., *J. Exp. Med.*, 170:481-497, 1989.
Ravetch et al., *Science*, 234:718-725, 1986.
Rippe, et al., *Mol. Cell. Biol.*, 10:689-695, 1990.
Ruhlmann et al., *FEBS Lett.*, 235:262-266, 1988.
Sambrook et al., In: *Molecular cloning: a laboratory manual*, $2^{nd}$ Ed., Cold Spring Harbor Laboratory Press, Cold Spring Harbor, N.Y., 1989.
Schierle et al., *J. Bacteriol.*, 185:5706-5713, 2003.
Sears et al., *J. Immunol.*, 144:371-378, 1990.
Sergina, and Moasser, *Trends in Molec. Med.*, 13:527-534, 2007.
Shuttleworth et al., *Gene*, 58(2-3):283-295, 1987.
Simister and Mostov, *Nature*, 337(6203):184-187, 1989.
Sondermann et al., *J. Mol. Biol.*, 309:737-749, 2001.
Stenberg et al., *Mol. Microbiol.*, 6:1185-1194, 1992.
Stengelin et al., *Embo J*, 7:1053-1059, 1988.
Stuart et al., *Embo J.*, 8:3657-3666, 1989.
Stuart et al., *J. Exp. Med.*, 166:1668-1684, 1987.
Tominaga et al., *Biochem. Biophys. Res. Commun.*, 168:683-689, 1990.
Uhlen et al., *J. Biol. Chem.*, 259:1695-702, 1984.
Van Wielink and Duine, *Trends Biochem Sci.*, 15:136, 1990.
Wada et al., *J. Biol. Chem.*, 274:17353-17357, 1999.
Walker et al., *Nucleic Acids Res.*, 20(7):1691-1696, 1992.
Wong et al., *Gene*, 10:87-94, 1980.
Wright and Morrison, *Trends Biotech.*, 15:26-32, 1997.
Zeger et al., *Proc. Natl. Acad. Sci. USA*, 87:3425-3429, 1990.
Zhang et al., *Immunogenetics*, 39:423-437, 1994.
Zhang et al., *Microbiology*, 144(Pt 4):985-991, 1998.

What is claimed is:

1. A method of selecting a bacterial cell comprising an aglycosylated antibody Fc domain having specific affinity for an Fc receptor (FcR) polypeptide comprising the steps of:
   a) obtaining a population of Gram negative bacterial cells, cells of which population express an aglycosylated antibody Fc domain in their periplasm, wherein the population expresses a plurality of different Fc domains;
   b) contacting the bacterial cells with an FcR polypeptide under conditions wherein the FcR polypeptide contacts the aglycosylated Fc domains; and
   c) selecting at least one bacterial cell based on binding of the aglycosylated Fc domain to the FcR polypeptide.

2. The method of claim 1, wherein the bacterial cells are *E. coli* cells.

3. The method of claim 1, wherein the Fc domain is an IgG, IgA or IgE Fc domain.

4. The method of claim 3, wherein the IgG Fc domain is an IgG1 Fc domain.

5. The method of claim 4, wherein the IgG1 Fc domain is the Fc domain of an anti-HER2 antibody.

6. The method of claim 5, wherein the IgG1 Fc domain is the Fc domain of the Fc domain of trastuzumab.

7. The method of claim 1, wherein the population of Gram negative bacterial cells comprise a plurality of nucleic acids encoding said plurality of aglycosylated Fc domains.

8. The method of claim 7, wherein the plurality of nucleic acids further encodes a membrane secretion signal fused to said plurality of aglycosylated Fc domains.

9. The method of claim 8, wherein the membrane secretion signal is PelB.

10. The method of claim 8, wherein the membrane secretion signal is DsbA.

11. The method of claim 1, wherein the aglycosylated Fc domain comprises a hinge, CH2 and CH3 region.

12. The method of claim 1, wherein the FcR polypeptide comprises an eukaryotic FcR domain.

13. The method of claim 1, wherein the FcR polypeptide comprises a prokaryotic or synthetic FcR domain.

14. The method of claim 12, wherein the FcR polypeptide comprises an antibody-binding domain from one or more of the following polypeptides: Fc-gamma FCGR2A (CD32), FCGR2B, Fc-gamma FCGR2C, Fc-gamma FCGR3A, Fc-gamma FCGR3B, Fc-gamma FCGR1A, Fc-gamma Fcgr1, Fc-gamma FCGR2, Fc-gamma FCGR3, FcRn FCGRT, Protein B, Protein A spa, protein G spg, protein H, Protein sbi, Allergen Asp fl 1, Allergen Asp fl 2, Allergen fl 3, Fc-epsilon R1, Fc-alpha R1 (CD86) and C1q.

15. The method of claim 14, wherein the FcR polypeptide comprises an antibody-binding domain from human FcγRIa, FcγRIIa, FcγRIIb, FcγRIIc, FcγRIIIa, FcγRIIIb, FcαRI or C1q.

16. The method of claim 15, wherein the FcR polypeptide comprises an antibody-binding domain from human FcγRIa.

17. The method of claim 1, wherein the FcR polypeptide is labeled.

18. The method of claim 17, wherein the FcR polypeptide is labeled with a fluorophore, a radioisotope or an enzyme.

19. The method of claim 18, wherein the FcR polypeptide is labeled with a fluorophore.

20. The method of claim 17, wherein the FcR polypeptide is fused to a fluorescence protein or an enzyme.

21. The method of claim 20, wherein the FcR polypeptide is fused to a green fluorescence protein.

22. The method of claim 1, wherein the FcR polypeptide is immobilized on a solid support.

23. The method of claim 1, wherein the selecting of step (c) is further defined as comprising at least two rounds of selection wherein the sub-population of bacterial cells obtained in the first round of selection is subjected to at least a second round of selection based on the binding of the Fc polypeptide to FcR polypeptide.

24. The method of claim 23, comprising two to ten rounds of selection.

25. The method of claim 24, wherein the selecting is carried out by FACS or magnetic separation.

26. The method of claim 1, further comprising contacting the bacterial cells with at least two FcR polypeptides.

27. The method of claim 26, wherein the at least two FcR polypeptides comprise distinct labels.

28. The method of claim 27, further comprising selecting bacterial cells based on binding of the aglycosylated Fc domain to the at least two FcR polypeptides.

29. The method of claim 27, further comprising selecting bacterial cells based on binding of the aglycosylated Fc domain to at least one FcR polypeptide and based on the aglycosylated Fc domain not binding to at least one other FcR polypeptide.

30. The method of claim 1, further comprising disrupting the outer membrane of the bacterial cells before contacting the bacterial cells with an FcR polypeptide.

31. The method of claim 30, wherein disrupting the outer membrane of the bacterial cell comprises treatment with hyperosmotic conditions, treatment with physical stress, infecting the bacterium with a phage, treatment with lysozyme, treatment with EDTA, treatment with a digestive enzyme or treatment with a chemical that disrupts the outer membrane.

32. The method of claim 30, wherein disrupting the outer membrane of the bacterial cell comprises heating the bacterial cell with a combination of physical, chemical and enzyme disruption of the outer membrane.

33. The method of claim 30, wherein disrupting the outer membrane of the bacterial cell further comprises removing the outer membrane of said bacterium.

34. The method of claim 1, further comprising removing FcR polypeptide not bound to the aglycosylated Fc domain.

35. The method of claim 1, wherein the bacteria are grown in a media comprising sucrose, sorbitol, mannitol or trehalose.

36. The method of claim 1, wherein the bacteria are grown in a media comprising trehalose.

37. The method of claim 1, further comprising the step of cloning a nucleic acid sequence encoding the Fc polypeptide from the bacterial cell to produce a nucleic acid sequence encoding an antibody Fc polypeptide having a specific affinity for an FcR polypeptide.

38. The method of claim 37, wherein cloning comprises amplification of the nucleic acid sequence.

39. The method of claim 37, further comprising the step of expressing a nucleic acid sequence encoding the antibody Fc polypeptide to produce an antibody Fc polypeptide having a specific affinity for an FcR polypeptide.

* * * * *